US011566066B2

(12) United States Patent
Beaumont et al.

(10) Patent No.: US 11,566,066 B2
(45) Date of Patent: Jan. 31, 2023

(54) ANTI-GDF15 ANTIBODIES, COMPOSITIONS AND METHODS OF USE

(71) Applicant: Pfizer Inc., New York, NY (US)

(72) Inventors: Kevin Charles Beaumont, Littleton, MA (US); Danna M. Breen, Stow, MA (US); Matthew Allister Lambert, Dublin (IE); Jeffrey Raymond Chabot, Medford, MA (US); Tao He, Acton, MA (US); Ksenya Shchors, San Mateo, CA (US); James R. Apgar, Medford, MA (US)

(73) Assignee: Pfizer Inc., New York, NY (US)

( * ) Notice: Subject to any disclaimer, the term of this patent is extended or adjusted under 35 U.S.C. 154(b) by 78 days.

(21) Appl. No.: 16/541,817

(22) Filed: Aug. 15, 2019

(65) Prior Publication Data

US 2020/0055930 A1 Feb. 20, 2020

Related U.S. Application Data

(60) Provisional application No. 62/881,064, filed on Jul. 31, 2019, provisional application No. 62/750,393, filed on Oct. 25, 2018, provisional application No. 62/750,479, filed on Oct. 25, 2018, provisional application No. 62/765,289, filed on Aug. 20, 2018.

(51) Int. Cl.
| | |
|---|---|
| *C07K 16/22* | (2006.01) |
| *C12N 5/10* | (2006.01) |
| *C12N 15/63* | (2006.01) |
| *A61P 35/00* | (2006.01) |
| *C07K 16/28* | (2006.01) |
| *C07K 16/24* | (2006.01) |

(52) U.S. Cl.
CPC .............. *C07K 16/22* (2013.01); *A61P 35/00* (2018.01); *C07K 16/244* (2013.01); *C07K 16/2818* (2013.01); *C07K 16/2875* (2013.01); *C07K 16/2878* (2013.01); *C07K 2317/565* (2013.01); *C07K 2317/76* (2013.01); *C07K 2317/92* (2013.01); *C07K 2317/94* (2013.01); *C12N 5/10* (2013.01); *C12N 15/63* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,754,065 A | 6/1988 | Levenson et al. | |
| 4,800,159 A | 1/1989 | Mullis et al. | |
| 9,334,331 B2 * | 5/2016 | Igawa .................... | C07K 16/36 |
| 10,421,807 B2 * | 9/2019 | Gonzales ................ | A61P 17/08 |
| 2017/0073395 A1 | 3/2017 | Finlay et al. | |

FOREIGN PATENT DOCUMENTS

| | | |
|---|---|---|
| WO | 198704462 | 7/1987 |
| WO | 2003040170 | 5/2003 |
| WO | 2003048731 | 6/2003 |
| WO | 2004058184 | 7/2004 |
| WO | 2005099746 | 10/2005 |
| WO | 2009021293 | 2/2009 |
| WO | 2010027827 | 3/2010 |
| WO | 2011066342 | 6/2011 |
| WO | 2013079174 | 6/2013 |
| WO | 2014100689 | 6/2014 |
| WO | 2015144855 | 10/2015 |
| WO | 2015196142 | 12/2015 |
| WO | 2016049470 | 3/2016 |
| WO | 2016092419 | 6/2016 |
| WO | 2020039321 | 2/2020 |

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Rabia, et al. (2018, Biochemical Engineering Journal 137:365-374).*
Ahmadzadeh et al, Blood 2009 114(8): 1537.
Baert, et al., 2003, New Engl. J. Med. 348:601-608.
Barbas et al., 1994, Proc Nat. Acad. Sci, USA 91:3809-3813.
Beniaminovitz, et al., 2000, New Engl. J. Med. 342:613-619.
Bird et al. Science 242:423-426 (1988).
Bootcov et al., 1997, PNAS 94(21): 11514-11519.
Chothia et al., 1989, Nature 342:877-883.
Cox et al., Eur. J. Immunol. 24:827-836, 1994.
Edelman et al., 1969, Proc. Natl. Acad. Sci. USA 63(1):78-85.
Eisenhauer et al., Eur J of Cancer 2009; 45(2):228-47.
Emmerson et al., 2017, Nature Med. 23(10):1215.
Ghosh, et al., 2003, New Engl. J. Med. 348:24-32.
Hawkins et al., 1992, J. Mol. Biol., 226:889-896.
Holliger et al., 1993, Proc. Natl. Acad. Sci. USA 90:6444-6448.
Hsu et al., 2017, Nature 550:255-259.
Huston et al., 1988, Proc. Natl. Acad. Sci. USA 85:5879-5883.
Jackson et al., 1995, J. Immunol., 154(7):3310-9.
Keir et al., 2008 Annu. Rev. Immunol. 26:677.
Kratochvill, 2015, Cell Reports 12(11): 1902-1914.
Lipsky, et al., 2000, New Engl. J. Med. 343:1594-1602.
MacCallum et al., 1996, J. Mol. Biol., 262:732-745.
Makabe et al.,2008, J. Biol. Chem., 283:1156-1166.
Marks et al., 1992, Bio/Technology, 10:779-783.
Milgrom, et al., 1999, New Engl. J. Med. 341:1966-1973.
North et al., 2011, J. Mol. Biol. 406: 228-256.
Okazaki T et al., Intern. Immun. 2007 19(7):813.

(Continued)

*Primary Examiner* — Elizabeth C. Kemmerer

(57) ABSTRACT

The invention provides antibodies, and antigen-binding fragments thereof, that specifically bind to GDF15, as well as methods and uses for the antibodies.

11 Claims, 34 Drawing Sheets

Specification includes a Sequence Listing.

(56) References Cited

OTHER PUBLICATIONS

Poljak et al., 1994, Structure 2:1121-1123.
Rafei et al., Anticancer Research 37: 377-388 (2017).
Ratnam et al., 2017, J. Clin. Invest. 127(10): 3796-38.
Ribas et al., Science, 359, 1350-1355, 2018.
Roth et al., Clin Cancer Res; 16(15), 2010.
Scher et al., J Clin Oncol Apr. 20, 2016; 34(12):1402-18.
Schier et al., 1996, Gene, 169:147-155.
Slamon, et al., 2001, New Engl. J. Med. 344:783-792.
Thompson RH et al., Cancer Res 2006, 66(7):3381.
Tomlinson et al., J. Mol. Biol. 227:776-798, 1992.
Townsend et al., 2015, Proc. Natl. Acad. Sci. USA. 112(50):15354-15359.
Ward et al., 1989 Nature 341:544-546.
Yang et al., 2017, Nature Med. 23(10): 1158.
Yelton et al., 1995, J. Immunol., 155:1994-2004.
International Search Report and Written Opinion, dated Mar. 30, 2020, 14 pages.

\* cited by examiner

FIG. 28

| Antibody | Heavy Chain | | | | | | | | | | | | | Light Chain | | | | | | |
|---|---|---|---|---|---|---|---|---|---|---|---|---|---|---|---|---|---|---|---|---|
| | CDR_H1 | CDR_H2 | CDR_H3 | JH | FV_H | FW_H1 | FW_H2 | FW_H3 | CH1 | HINGE | CH2 | CH3 | HC | CDR_L1 | CDR_L2 | CDR_L3 | JK | FV_L | CL | LC |
| GDF15_200 | 17 | 18 | 19 | 25 | 21 | 22 | 23 | 24 | 20 | 13 | 14 | 15 | 16 | 7 | 8 | 9 | 12 | 11 | 10 | 6 |
| GDF15_100 | 32 | 33 | 19 | 25 | 34 | 22 | 23 | 24 | 20 | 13 | 14 | 15 | 31 | 27 | 28 | 29 | 12 | 30 | 10 | 26 |
| GDF15_022 | 41 | 42 | 43 | 25 | 44 | 22 | 23 | 24 | 20 | 13 | 14 | 15 | 40 | 36 | 37 | 38 | 12 | 39 | 10 | 35 |
| GDF15_021 | 32 | 51 | 52 | 25 | 53 | 22 | 23 | 24 | 20 | 13 | 14 | 15 | 50 | 46 | 47 | 48 | 12 | 49 | 10 | 45 |
| GDF15_020 | 58 | 59 | 19 | 25 | 60 | 22 | 23 | 24 | 20 | 13 | 14 | 15 | 57 | 55 | 28 | 48 | 12 | 56 | 10 | 54 |
| GDF15_018 | 66 | 67 | 19 | 25 | 68 | 22 | 23 | 24 | 20 | 13 | 14 | 15 | 65 | 62 | 28 | 63 | 12 | 64 | 10 | 61 |
| GDF15_017 | 66 | 33 | 19 | 25 | 73 | 22 | 23 | 24 | 20 | 13 | 14 | 15 | 72 | 36 | 70 | 38 | 12 | 71 | 10 | 69 |
| GDF15_015 | 58 | 33 | 79 | 25 | 80 | 22 | 23 | 24 | 20 | 13 | 14 | 15 | 78 | 27 | 47 | 76 | 12 | 77 | 10 | 75 |
| GDF15_014 | 32 | 85 | 19 | 25 | 86 | 22 | 23 | 24 | 20 | 13 | 14 | 15 | 84 | 82 | 8 | 48 | 12 | 83 | 10 | 81 |
| GDF15_013 | 58 | 92 | 19 | 25 | 93 | 22 | 23 | 24 | 20 | 13 | 14 | 15 | 91 | 88 | 8 | 89 | 12 | 90 | 10 | 87 |
| GDF15_012 | 58 | 98 | 43 | 25 | 99 | 22 | 23 | 24 | 20 | 13 | 14 | 15 | 97 | 95 | 28 | 38 | 12 | 96 | 10 | 94 |
| GDF15_010 | 41 | 105 | 19 | 25 | 106 | 22 | 23 | 24 | 20 | 13 | 14 | 15 | 104 | 101 | 8 | 102 | 12 | 103 | 10 | 100 |
| GDF15_009 | 17 | 33 | 111 | 25 | 112 | 22 | 23 | 24 | 20 | 13 | 14 | 15 | 110 | 27 | 108 | 48 | 12 | 109 | 10 | 107 |
| GDF15_008 | 117 | 118 | 119 | 25 | 120 | 22 | 23 | 24 | 20 | 13 | 14 | 15 | 116 | 27 | 114 | 63 | 12 | 115 | 10 | 113 |
| GDF15_007 | 125 | 126 | 19 | 25 | 127 | 22 | 23 | 24 | 20 | 13 | 14 | 15 | 124 | 46 | 122 | 9 | 12 | 123 | 10 | 121 |
| GDF15_006 | 133 | 134 | 135 | 25 | 136 | 22 | 23 | 24 | 20 | 13 | 14 | 15 | 132 | 129 | 130 | 102 | 12 | 131 | 10 | 128 |
| GDF15_005 | 58 | 141 | 119 | 25 | 142 | 22 | 23 | 24 | 20 | 13 | 14 | 15 | 140 | 138 | 37 | 9 | 12 | 139 | 10 | 137 |
| GDF15_004 | 32 | 146 | 147 | 25 | 148 | 22 | 23 | 24 | 20 | 13 | 14 | 15 | 145 | 88 | 28 | 48 | 12 | 144 | 10 | 143 |
| GDF15_003 | 153 | 33 | 154 | 25 | 155 | 22 | 23 | 24 | 20 | 13 | 14 | 15 | 152 | 150 | 108 | 38 | 12 | 151 | 10 | 149 |
| GDF15_002 | 32 | 126 | 160 | 25 | 161 | 22 | 23 | 24 | 20 | 13 | 14 | 15 | 159 | 157 | 114 | 9 | 12 | 158 | 10 | 156 |
| GDF15_001 | 32 | 165 | 52 | 25 | 166 | 22 | 23 | 24 | 20 | 13 | 14 | 15 | 164 | 95 | 28 | 9 | 12 | 163 | 10 | 162 |

ANTI-GDF15 ANTIBODIES, COMPOSITIONS AND METHODS OF USE

CROSS-REFERENCE TO RELATED APPLICATIONS

This application claims the benefit of U.S. Provisional Patent Application No. 62/881,064, filed on Jul. 31, 2019, U.S. Provisional Patent Application No. 62/750,393, filed on Oct. 25, 2018, U.S. Provisional Patent Application No. 62/750,479, filed on Oct. 25, 2018, and U.S. Provisional Patent Application No. 62/765,289, filed on Aug. 20, 2018, all of which are incorporated herein by reference in their entireties.

SEQUENCE LISTING INCORPORATED BY REFERENCE

This application contains a Sequence Listing submitted as an electronic text file named "PC72348A_Seq_Listing_ST25.txt", having a size in bytes of 275,047, and created on Aug. 13, 2019. The information contained in this electronic file is hereby incorporated by reference in its entirety.

BACKGROUND

GDF15, also known as macrophage inhibiting cytokine 1 (MIC-1), prostate derived factor (PDF), placental bone morphogenetic protein (PLAB), NSAID-activated gene 1 (NAG-1), and placental transforming growth factor β (PTGFB), is a 12-kDa secreted protein that forms a 25 kDa disulfide-linked homodimer that is a member of the transforming growth factor beta (TGFβ) superfamily. Normally, GDF15 is weakly expressed or not expressed at all in tissues and plasma concentrations are low. GDF15 expression is upregulated during inflammation and malignancy, limiting inflammation and tumor growth. This elevated expression results in markedly elevated circulating concentrations of GDF15 (>1-100 ng/mL) in cancer (e.g. prostate, pancreas, colorectal, and gastric), heart failure, chronic kidney disease (CKD), sarcopenia, and chronic obstructive pulmonary disease (COPD).

GDF15-related weight loss has been shown in preclinical models. Exogenous GDF15 administration decreases food intake and body weight under physiological and pathophysiological conditions. Increased plasma GDF15 is associated with weight loss in cancer patients with cachexia (WO2005/099746; WO2009/021293, WO2014/100689, WO2016/049470). Although evidence is strongest in cancer patients, an association between GDF15 and weight loss in cachexia associated with heart failure has also been reported (WO/2015/196142). Consistent with human data, elevated plasma GDF15 is associated with cachexia in mouse tumor models. Further, multiple studies using multivariate analysis have identified GDF15 as an independent prognostic biomarker associated with poor survival in many cancer types (e.g. NSCLC, pancreatic, and sarcoma, among others), and in heart failure, CKD, and COPD.

More recently, in October of 2017, it was reported that GDF15 activity, e.g., its metabolic effects, is mediated by GDF15 binding to its cognate receptor GDNF-family receptor α-like (GFRAL), an orphan member of the GFR-α family. See, e.g., Hsu et al., 2017, Nature 550:255-259; Yang et al., 2017, Nature Med. 23(10): 1158; and Emmerson et al., 2017, Nature Med. 23(10):1215. These studies demonstrated that GDF15 binding GFRAL activates a GFRAL-mediated signaling pathway whereby a receptor tyrosine kinase, RET, is activated and acts as a coreceptor of GFRAL, and RET, in turn, mediates downstream phosphorylation of ERK (pERK), ribosomal protein S6 (pS6), AKT, MAPK, and phospholipase C gamma 1 (PLC-γ1) among others. Further, these studies demonstrated that activation of GFRAL by GDF15 occurs in regions of the brainstem, the area postrema and nucleus tractus solitarius, which contain chemosensory neurons and receptors for neuropeptides that control appetite and emesis. The area postrema senses chemical messengers in the blood and controls autonomic physiological systems, including systems that control metabolism and appetite. In addition, these regions of the brainstem are outside the blood-brain barrier (BBB) making them accessible to, among other things, large molecules, including antibodies, that can bind GFRAL or GDF15 and prevent GFRAL-GDF15 interaction to modulate the metabolic effects of GDF15 related to appetite, body mass, weight, fat mass, and food intake. Thus, the GDF15-GFRAL pathway present in the brainstem is a potential target for modulating diseases, conditions and disorders mediated by GDF15 activity.

There remains a significant need for therapeutic options for weight loss caused by or associated with cachexia that is mediated by or associated with elevated GDF15 levels. The present invention provides novel potential therapeutic antibodies that meet this need.

PD-L1 (programmed death-ligand 1; also known as CD274 and B7 homolog 1 [B7-H1]) is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood. PD-1 (programmed cell death protein 1), the cognate receptor of PD-L1 on tumor-reactive T cells, can contribute to impaired antitumor immune responses (Ahmadzadeh et al, Blood 2009 1 14(8): 1537). This may be due to exploitation of PD-L1 signaling mediated by PD-L1 expressing tumor cells interacting with PD-1 expressing T cells to result in attenuation of T cell activation and evasion of immune surveillance (Sharpe et al., Nat Rev 2002) (Keir M E et al., 2008 Annu. Rev. Immunol. 26:677). Therefore, inhibition of the PD-L1/PD-1 interaction and signaling pathway (also referred to as "the PD-1 axis") may enhance CD8+ T cell-mediated killing of tumors.

The inhibition of PD-1 axis signaling through its direct ligands (e.g., PD-L1, PD-L2 [programmed cell death 1 ligand 2 and B7-DC]) has been proposed to enhance T cell immunity for the treatment of cancer (e.g., tumor immunity). Moreover, similar enhancements to T cell immunity have been observed by inhibiting the binding of PD-L1 to another binding partner, i.e., B7-1 (also known as CD80).

There are currently at least five PD-1 axis binding antagonists approved by the FDA in more than 10 cancer indications (A Ribas et al, Science, 359, 1350-1355, 2018) as well as others known in the art. Among these, nivolumab (OPDIVO), pembrolizumab (KEYTRUDA), spartalizumab, pidilizumab, tislelizumab, AMP-224, AMP-514, cemiplimab, PF-06801591 (sasanlimab, RN888), are each anti-PD-1 antibodies, while avelumab (BAVENCIO), atezolizumab (TECENTRIQ) durvalumab (IMFINZI), BMS-936559 (MDX-1105), MEDI4736, MPDL3280A (YW243.55.570) are each anti PD-L1 antibodies.

The combination therapy of a PD-1 axis binding antagonist with one or more anti-cancer agents have been investigated, with the first clinical trial started in 2009. New clinical trials directed to such combinations increased dramatically; since then, 467 new trials registered in 2017 (C. Schmidt, Nature, Vol 552, 21/28 Dec. 2017). While the combination therapy of nivolumab (anti-PD-1) and ipilimumab (anti-CTLA-4) to treat melanoma, and the combination therapy of pembrolizumab (anti-PD-1) with chemotherapy to treat non-small cell lung cancer was approved by the FDA in 2015 and 2017, respectively, there is a continued need of finding optimal therapeutic treatment that combines a PD-1 axis binding antagonist with one or more other anti-cancer agents, for treating, stabilizing, preventing, and/or delaying development of various cancers.

GDF15 was shown to be induced by a number of pro-inflammatory factors and lipopolysaccharide (LPS) and is involved in feedback mechanism imposing the breaks on macrophage activation by suppressing tumor necrosis factor alpha (TNFα) production via inhibition of NF-kB signaling pathway (Bootcov et al., 1997, PNAS 94(21): 11514-11519, Ratnam et al., 2017, J. Clin. Invest. 127(10): 3796-3809). Decreased expression of TNFα is associated with a drift of macrophage population towards the pro-tumorigenic M2 phenotype (Kratochvill, 2015, Cell Reports 12(11): 1902-1914). Targeting the M2 phenotype in tumor associated macrophages is a potential strategy to enhance response to cancer therapies focused on activation of host immune response.

There remains a significant need for therapeutic options for cancer, particularly for solid tumors. The present invention provides novel potential therapeutic GDF15 antibodies, with or without one or more other anti-cancer agents, that meet these needs. There also remains a need of finding optimal therapeutic treatment that combines a PD-1 axis binding antagonist with another therapeutic agent, such as a GDF15 inhibitor, with or without one or more other anti-cancer agents, for treating, stabilizing, preventing, and/or delaying development of various cancers. The present invention provides novel potential useful therapeutic combinations of the GDF15 antibodies of the invention with a PD-1 axis binding antagonist that meet this need.

BRIEF SUMMARY OF THE INVENTION

The invention provides antibodies, and antigen-binding fragments thereof, that specifically bind to GDF15, as well as uses, and associated methods. Those skilled in the art will recognize or be able to ascertain using no more than routine experimentation, many equivalents to the specific embodiments of the invention described herein. Such equivalents are intended to be encompassed by the following embodiments (E).

E1. An isolated antibody or antigen-binding fragment thereof that specifically binds to GDF15.

E2. The antibody, or antigen-binding fragment thereof, of E1, comprising the HCDR-1, HCDR-2, and HCDR-3 sequences of one of the group consisting of SEQ ID NO:21, 34, 44, 53, 60, 68, 73, 80, 86, 93, 99, 106, 112, 120, 127, 136, 142, 148, 155, 161 and 166.

E3. The antibody, or antigen-binding fragment thereof, of any one of E1-E2, comprising the LCDR-1LCDR-1, LCDR-2, and LCDR-3 sequences of one of the group consisting of SEQ ID NO:11, 30, 39, 49, 56, 64, 71, 77, 83, 90, 96, 103, 109, 115, 123, 131, 139, 144, 151, 158 and 163.

E4. The antibody, or antigen binding fragment thereof, as in any one of E1-E3 comprising one or more of (a)-(f)
    a) a LCDR-1LCDR-1 selected from the group consisting of SEQ ID NO:7, 27, 36, 46, 55, 62, 82, 88, 95, 101, 129, 138, 150 and 157,
    b) a LCDR-2 selected from the group consisting of SEQ ID NO:8, 28, 37, 47, 70, 108, 114, 122, and 130,
    c) a LCDR-3 selected from the group consisting of SEQ ID NO:9, 29, 38, 48, 63, 76, 89, and 102,
    d) a HCDR-1 selected from the group consisting of SEQ ID NO:17, 32, 41, 58, 66, 117, 125, 133, and 153,
    e) a HCDR-2 selected from the group consisting of SEQ ID NO:18, 33, 42, 51, 59, 67, 85, 92, 98, 105, 118, 126, 134, 141, 146 and 165,
    f) a HCDR-3 selected from the group consisting of SEQ ID NO:1, 19, 43, 52, 79, 111, 119, 135, 147, 154, and 160.

E5. The antibody or antigen-binding fragment thereof, according to E1-E4 comprising: i) a HCDR-1 comprising the amino acid sequence $GYTFX_1X_2YNID$, wherein $X_1$ is S or T and $X_2$ is S or D; ii) a HCDR-2 comprising the amino acid sequence $X_3INPX_4X_5GX_6AX_7X_8X_9QKFQG$, wherein $X_3$ is G or Q; $X_4$ is I or N; $X_6$ is F or N; $X_6$ is T or L; $X_7$ is F or N; $X_8$ is Y or F and $X_9$ is N or A; and iii) a HCDR-3 comprising the amino acid sequence $EX_{10}ITTX_{11}GAMDX_{12}$, wherein $X_{10}$ is A or Q; $X_{11}$ is V or I; and $X_{12}$ is H or Y.

E6. The antibody or antigen-binding fragment thereof, according to E1-E5 comprising: i) a LCDR-1LCDR-1 comprising the amino acid sequence $RX_1SQX_2X_3X_4X_5YLA$, wherein $X_1$ is T or A, $X_2$ is S or N, $X_3$ is V or L, $X_4$ is H or S, and $X_5$ is N or S; ii) a LCDR-2 comprising the amino acid sequence $DAX_6X_7RAX_8$, wherein $X_6$ is S or K; $X_7$ is T or N; and $X_8$ is D or T; and iii) a LCDR-3 comprising the amino acid sequence $QQFX_9X_{10}X_{11}PX_{12}T$, wherein $X_9$ is W or S; $X_{10}$ is S or N; $X_{11}$ is W or D; and $X_{12}$ is W or Y.

E7. The antibody, or antigen binding fragment thereof, as in any one of E1-E6 comprising one or more of the following:
    a) a LCDR-1LCDR-1 comprising the amino acid sequence of SEQ ID NO:174,
    b) a LCDR-2 comprising the amino acid sequence of SEQ ID NO:175,
    c) a LCDR-3 comprising the amino acid sequence of SEQ ID NO:176,
    d) a HCDR-1 comprising the amino acid sequence of SEQ ID NO:171,
    e) a HCDR-2 comprising the amino acid sequence of SEQ ID NO:172,
    f) a HCDR-3 comprising the amino acid sequence of SEQ ID NO:173.

E8. The antibody, or antigen-binding fragment thereof, of any one of E1-E7, comprising the HCDR-1, HCDR-2, and HCDR-3 sequences of one at least one sequence selected from the group consisting of SEQ ID NO:34, 106, 148, 155, and 166.

E9. The antibody, or antigen-binding fragment thereof, of any one of E1-E8, comprising the LCDR-1LCDR-1, LCDR-2, and LCDR-3 sequences of at least one sequence selected from the group consisting of SEQ ID NO:30, 103, 144, 151, and 163.

E10. The antibody, or antigen binding fragment thereof, as in any one of E1-E9 comprising one or more of (a)-(f)
    a) a LCDR-1LCDR-1 selected from the group consisting of SEQ ID NO:27, 88, 95, 101 and 150.
    b) a LCDR-2 selected from the group consisting of SEQ ID NO:8, 28 and 108.
    c) a LCDR-3 selected from the group consisting of SEQ ID NO:9, 29, 38, 48 and 102.
    d) a HCDR-1 selected from the group consisting of SEQ ID NO:32, 41, and 153.
    e) a HCDR-2 selected from the group consisting of SEQ ID NO:33, 105, 146 and 165.

f) a HCDR-3 selected from the group consisting of SEQ ID NO:19, 52, 147, and 154.

E11. The antibody, or antigen-binding fragment thereof, of any one of E1-E10, comprising the HCDR-1, HCDR-2, and HCDR-3 sequences of SEQ ID NO:166.

E12. The antibody, or antigen-binding fragment thereof, of any one of E1-E11, comprising the LCDR-1LCDR-1, LCDR-2, and LCDR-3 sequences of SEQ ID NO:163.

E13. The antibody, or antigen binding fragment thereof, as in any one of E1-E12 comprising one or more of the following:
a) a LCDR-1 comprising the sequence of SEQ ID NO:95,
b) a LCDR-2LCDR-2 comprising the sequence of SEQ ID NO:28,
c) a LCDR-3 comprising the sequence of SEQ ID NO:9,
d) a HCDR-1 comprising the sequence of SEQ ID NO:32,
e) a HCDR-2 comprising the sequence of SEQ ID NO:165, and
f) a HCDR-3 comprising the sequence of SEQ ID NO:52.

E14. The antibody, or antigen-binding fragment thereof, of any one of E1-E13, comprising a LCDR-1 comprising the amino acid sequence of SEQ ID NO:95, a LCDR-2LCDR-2 comprising the amino acid sequence of SEQ ID NO:28, a LCDR-3 comprising the amino acid sequence of SEQ ID NO:9, a HCDR-1 comprising the amino acid sequence of SEQ ID NO:32, a HCDR-2 comprising the amino acid sequence of SEQ ID NO:165, and a HCDR-3 comprising the amino acid sequence of SEQ ID NO:52.

E15. The antibody, or antigen-binding fragment thereof, of any one of E1-E14, comprising one or more of the following substitutions:
a) 1, 2, 3, 4, 5, or 6 substitutions in LCDR-1 to the corresponding residue of a human germline VL sequence,
b) 1, 2, 3, 4, or 5 substitutions in LCDR-2 to the corresponding residue of a human VL germline sequence,
c) 1, 2, 3, 4, 5, or 6 substitutions in LCDR-3 to the corresponding residue of a human germline VL sequence,
d) 1 substitution in HCDR-1 to the corresponding residue of a human germline VH sequence,
e) 1, 2, 3, 4, 5, 6, 7, or 8 substitutions in HCDR-2 to the corresponding residue of a human germline VH sequence,
wherein the human germline VL sequence is selected from the group consisting of IGKV1-12*01, IGKV1-13*02, IGKV1-33*01, IGKV1-39*01, IGKV1-5*01, IGKV3-11*01, IGKV3-15*01, IGKV3-20*01, IGKV3D-20*02, and IGKV4-1*01, and the human germline VH is selected from the group consisting of IGHV1-2*02, IGHV1-3*01, IGHV1-46*01, IGHV1-69*01, IGHV1-69*02, IGHV1-8*01, IGHV3-13*01, IGHV3-23*01, IGHV3-23*04, IGHV3-30*01, IGHV3-30*18, IGHV5-10-1*01, IGHV5-10-1*04, and IGHV5-51*01.

E16. The antibody, or antigen-binding fragment thereof, of any one of E1-E15, comprising a VH framework sequence derived from a human germline VH sequence selected from the group consisting of IGHV1-2*02, IGHV1-3*01, IGHV1-46*01, IGHV1-69*01, IGHV1-69*02, IGHV1-8*01, IGHV3-13*01, IGHV3-23*01, IGHV3-23*04, IGHV3-30*01, IGHV3-30*18, IGHV5-10-1*01, IGHV5-10-1*04, and IGHV5-51*01.

E17. The antibody, or antigen-binding fragment thereof, of any one of E1-E16, comprising an IGHV1-69*01 VH framework sequence.

E18. The antibody, or antigen-binding fragment thereof, of any one of E1-E17, comprising a VL framework sequence derived from a human germline VL sequence selected from the group consisting of IGKV1-12*01, IGKV1-13*02, IGKV1-33*01, IGKV1-39*01, IGKV1-5*01, IGKV3-11*01, IGKV3-15*01, IGKV3-20*01, IGKV3D-20*02, and IGKV4-1*01.

E19. The antibody, or antigen-binding fragment thereof, of any one of E1-E18, comprising an IGKV3-11*01 VL framework sequence.

E20. The antibody, or antigen-binding fragment thereof, of any one of E1-E19, comprising a VL framework sequence and a VH framework sequence, and wherein the VL framework sequence is at least 72% identical to the human germline sequence from which it was derived.

E21. The antibody, or antigen-binding fragment thereof, of any one of E1-E20, comprising a VL framework sequence and a VH framework sequence, and wherein the VL framework sequence is at least 72%, 74%, 75%, 77%, 90%, 91%, 92%, 93%, 94%, 95%, 96%, 97%, 98%, or 99% identical to the human germline sequence from which it was derived.

E22. The antibody, or antigen-binding fragment thereof, of any one of E1-E21, comprising a VL framework sequence and a VH framework sequence, and wherein the VH framework sequence is at least 53% identical to the human germline sequence from which it was derived.

E23. The antibody, or antigen-binding fragment thereof, of any one of E1-E22, comprising a VL framework sequence and a VH framework sequence, and wherein the VH framework sequence is at least 53%, 58%, 60%, 63%, 71%, 72%, 90%, 91%, 92%, 93%, 94%, 95%, 96%, 97%, 98%, or 99% identical to the human germline sequence from which it was derived.

E24. The antibody, or antigen-binding fragment thereof, of any one of E1-E23, comprising a VH comprising an amino acid sequence at least 90% identical to SEQ ID NO:166.

E25. The antibody, or antigen-binding fragment thereof, of any one of E1-E24, comprising a VH comprising an amino acid sequence at least 91%, 92%, 93%, 94%, 95%, 96%, 97%, 98%, or 99% identical to SEQ ID NO:166.

E26. The antibody, or antigen-binding fragment thereof, of any one of E1-E25, comprising a VH comprising the amino acid sequence of SEQ ID NO:166.

E27. The antibody, or antigen-binding fragment thereof, of any one of E1-E26, comprising a VL comprising an amino acid sequence at least 90% identical to SEQ ID NO:163.

E28. The antibody, or antigen-binding fragment thereof, of any one of E1-E27, comprising a VL comprising an amino acid sequence at least 91%, 92%, 93%, 94%, 95%, 96%, 97%, 98%, or 99%, identical to SEQ ID NO:163.

E29. The antibody, or antigen-binding fragment thereof, of any one of E1-E28, comprising a VL comprising the amino acid sequence of SEQ ID NO:163.

E30. The antibody, or antigen-binding fragment thereof, of any of E1-E29, comprising a VH comprising the amino acid sequence of SEQ ID NO:166 and the VL amino acid sequence of SEQ ID NO:163.

E31. The antibody, or antigen-binding fragment thereof, of any one of E1-E30, comprising an Fc domain.

E32. The antibody, or antigen-binding fragment thereof, of E31, wherein the Fc domain is the Fc domain of an IgA (for example IgA$_1$ or IgA$_2$), IgD, IgE, IgM, or IgG (for example IgG$_1$, IgG$_2$, IgG$_3$, or IgG$_4$).

E33. The antibody, or antigen-binding fragment thereof, of E32 wherein the Fc domain is the Fc domain of an IgG.

E34. The antibody, or antigen-binding fragment thereof, of E33, wherein the IgG is selected from the group consisting of $IgG_1$, $IgG_2$, $IgG_3$, or $IgG_4$.

E35. The antibody, or antigen-binding fragment thereof, of E34 wherein the IgG is $IgG_1$.

E36. The antibody, or antigen-binding fragment thereof, of any one of E1-E35, comprising a heavy chain comprising an amino acid sequence at least 90% identical to SEQ ID NO:164.

E37. The antibody, or antigen-binding fragment thereof, of any one of E1-E36, comprising a heavy chain comprising an amino acid sequence at least 91%, 92%, 93%, 94%, 95%, 96%, 97%, 98%, or 99%, identical to SEQ ID NO:164.

E38. The antibody, or antigen-binding fragment thereof, of any one of E1-E37, comprising a heavy chain comprising the amino acid sequence of SEQ ID NO:164.

E39. The antibody, or antigen-binding fragment thereof, of any one of E1-E38, comprising a LC comprising an amino acid sequence at least 90% identical to SEQ ID NO:162.

E40. The antibody, or antigen-binding fragment thereof, of any one of E1-E39, comprising a LC comprising an amino acid sequence at least 91%, 92%, 93%, 94%, 95%, 96%, 97%, 98%, or 99%, identical to SEQ ID NO:162

E41. The antibody, or antigen-binding fragment thereof, of any one of E1-E40, comprising a LC comprising the amino acid sequence of SEQ ID NO:162.

E42. An antibody, or antigen-binding fragment thereof, of any one of E1-E41, comprising a heavy chain comprising the amino acid sequence of SEQ ID NO:164 and a light chain comprising the amino acid sequence of SEQ ID NO:162.

E43. The antibody, or antigen-binding fragment thereof, of any one of E1-E42, comprising the CDR1, CDR2 and CDR3 encoded by the insert of the plasmid deposited at the ATCC and having ATCC Accession No. PTA-125038.

E44. The antibody, or antigen-binding fragment thereof, of any one of E1-E43, comprising the CDR1, CDR2 and CDR3 encoded by the insert of the plasmid deposited at the ATCC and having ATCC Accession No. PTA-125039.

E45. The antibody, or antigen-binding fragment thereof, of any one of E1-E44, encoded by the insert in the plasmid deposited at the ATCC and having ATCC Accession No. PTA-125038.

E46. The antibody, or antigen-binding fragment thereof, of any one of E1-E45, encoded by the insert in the plasmid deposited at the ATCC and having ATCC Accession No. PTA-125039.

E47. The antibody, or antigen-binding fragment thereof, of any one of E1-E46, comprising the amino acid sequence encoded by the insert in the plasmid deposited at the ATCC and having ATCC Accession No. PTA-125038 and the amino acid sequence encoded by the insert in the plasmid deposited at the ATCC and having ATCC Accession No. PTA-125039.

E48. The antibody, or antigen-binding fragment thereof, of any one of E1-E47, wherein the antibody or antigen-binding fragment is an Fc fusion protein, a monobody, a maxibody, a bifunctional antibody, an scFab, an scFv, a peptibody.

E49. The antibody, or antigen-binding fragment thereof, of E1-E48, wherein the antibody, or antigen binding fragment thereof, binds human GDF15 with a $K_D$ about or less than a value selected from the group consisting of about 10 nM, 5 nM, 2 nM, 1 nM, 900 pM, 800 pM, 700 pM, 600 pM, 500 pM, 400 pM, 300 pM, 250 pM, 200 pM, 150 pM, 100 pM, 50 pM, 40 pM, 30 pM, 25 pM, 20 pM, 15 pM, and 10 pM.

E50. The antibody, or antigen-binding fragment thereof, of E1-E49, wherein the antibody, or antigen binding fragment thereof, binds cynomolgus monkey GDF15 with a $K_D$ about or less than a value selected from the group consisting of about 10 nM, 5 nM, 2 nM, 1 nM, 900 pM, 800 pM, 700 pM, 600 pM, 500 pM, 400 pM, 300 pM, 250 pM, 200 pM, 150 pM, 100 pM, 50 pM, 40 pM, 30 pM, 25 pM, 20 pM, 15 pM, 13 pM, 10 pM, and 9 pM.

E51. The antibody, or antigen-binding fragment thereof, of E1-E50, wherein the antibody, or antigen binding fragment thereof, binds cynomolgus monkey GDF15 with a $K_D$ of about 8 pM or 9 pM.

E52. The antibody, or antigen-binding fragment thereof, of E1-E51, wherein the antibody, or antigen binding fragment thereof, binds cynomolgus monkey GDF15 with a $K_D$ of about 8.28 pM.

E53. The antibody, or antigen-binding fragment thereof, of any one of E1-E52, wherein the terminal half-life in humans is at least about 16 days.

E54. The antibody, or antigen-binding fragment thereof, of any one of E1-E53, wherein the terminal half-life in humans is at least 17 days.

E55. The antibody, or antigen-binding fragment thereof, of E1-E54, wherein the predicted immunogenic potential of the antibody, as indicated by the t-regitope (tReg) adjusted score, is less than about −24.

E56. The antibody, or antigen-binding fragment thereof, of E1-E55, wherein the predicted immunogenic potential of the antibody, as indicated by the tReg adjusted score, is less than the tReg adjusted score selected from the group consisting of about −24, −26, −27, −30, −32, −33, −34, −35, −36, −37, −38, −39, −40, −41, −42, −43, −50 and −51.

E57. The antibody, or antigen-binding fragment thereof, of E1-E56, wherein the predicted immunogenic potential of the antibody, as indicated by the tReg adjusted score, is selected from the group consisting of about −26, −34, −36, −41, and −42.

E58. The antibody, or antigen-binding fragment thereof, of E1-E57, wherein the predicted immunogenic potential of the antibody, as indicated by tReg adjusted score, is about −41 or −42.

E59. The antibody, or antigen-binding fragment thereof according to E1-E58, wherein the antibody or antigen-binding fragment has a viscosity selected from the group consisting of at least about 10 centipoise (cP), at least about 15 cP, at least about 20 cP, at least about 40 cP, and at least about 70 cP, when measured at 25° C.

E60. The antibody, or antigen-binding fragment thereof according to E1-E59, wherein the antibody or antigen-binding fragment has a viscosity of about 20 cP when measured at 25° C.

E61. The antibody, or antigen-binding fragment thereof according to E1-E60, wherein the antibody or antigen-binding fragment has a viscosity of 20 cP when measured at 25° C.

E62. The antibody, or antigen-binding fragment thereof, of E1-E61, wherein the ratio of binding $K_D$ of the antibody or antigen binding fragment to human GDF15 compared with the binding to murine GDF15 is between about 0.05 and about 0.10.

E63. The antibody, or antigen-binding fragment thereof, of E1-E62, wherein the ratio of binding $K_D$ of the antibody or antigen binding fragment to human GDF15 compared with the binding to murine GDF15 is about 0.07.

E64. The antibody, or antigen-binding fragment thereof, of E1-E63, wherein the ratio of binding $K_D$ of the antibody or antigen binding fragment to human GDF15 compared with the binding to murine GDF15 is 0.07.

E65. The antibody, or antigen-binding fragment thereof, of E1-E64, wherein the ratio of binding $K_D$ of the antibody or antigen binding fragment to human GDF15 compared with the binding to cynomolgus GDF15 is between about 1.0 and about 1.5.

E66. The antibody, or antigen-binding fragment thereof, of E1-E65, wherein the ratio of binding $K_D$ of the antibody or antigen binding fragment to human GDF15 compared with the binding to cynomolgus GDF15 is about 1.2.

E67. The antibody, or antigen-binding fragment thereof, of E1-E66, wherein the ratio of binding $K_D$ of the antibody or antigen binding fragment to human GDF15 compared with the binding to cynomolgus GDF15 is 1.21.

E68. The antibody, or antigen-binding fragment thereof, of E1-E67, wherein the ratio of binding $K_D$ of the antibody or antigen binding fragment to cynomolgus GDF15 compared with the binding to murine GDF15 is between about 0.03 and about 0.09.

E69. The antibody, or antigen-binding fragment thereof, of E1-E68, wherein the ratio of binding $K_D$ of the antibody or antigen binding fragment to cynomolgus GDF15 compared with the binding to murine GDF15 is between about 0.04 and 0.08.

E70. The antibody, or antigen-binding fragment thereof, of E1-E69, wherein the ratio of binding $K_D$ of the antibody or antigen binding fragment to cynomolgus GDF15 compared with the binding to murine GDF15 is between 0.05 and 0.06.

E71. The antibody, or antigen-binding fragment thereof, of E1-E70, wherein the ratio of binding $K_D$ of the antibody or antigen binding fragment to cynomolgus GDF15 compared with the binding to murine GDF15 is 0.05.

E72. The antibody according to E1-E71, wherein the antibody has a thermal stability with a melting temperature ($T_m1$), or the temperature at which the $C_H2$ of the antibody is 50% unfolded, of about 71° C. or greater, as measured by Differential Scanning calorimetry.

E73. The antibody according to E1-E72, wherein the antibody has a thermal stability with a melting temperature ($T_m1$), or the temperature at which the $C_H2$ of the antibody is 50% unfolded, between 71° C. and 72° C., as measured by Differential Scanning calorimetry.

E74. The antibody according to E1-E73, wherein the antibody has a thermal stability with a melting temperature ($T_m1$), or the temperature at which the $C_H2$ of the antibody is 50% unfolded, between 71° C. and 72° C., as measured by Differential Scanning calorimetry.

E75. The antibody according to E1-E74, wherein the antibody has a thermal stability with a melting temperature ($T_m2$), or the temperature at which the Fab of the antibody is 50% unfolded, of about 80° C. or greater, as measured by Differential Scanning calorimetry.

E76. The antibody according to E1-E75, wherein the antibody has a thermal stability with a melting temperature ($T_m2$), or the temperature at which the Fab of the antibody is 50% unfolded, between 80° C. and 86° C., as measured by Differential Scanning calorimetry.

E77. The antibody according to E1-E76, wherein the antibody has a thermal stability with a melting temperature ($T_m2$), or the temperature at which the Fab of the antibody is 50% unfolded, between 84° C. and 85° C., as measured by Differential Scanning calorimetry.

E78. The antibody according to E1-E77, wherein the antibody has a thermal stability with a melting temperature ($T_m3$), or the temperature at which the $C_H3$ of the antibody is 50% unfolded, of about 82° C. or greater, as measured by Differential Scanning calorimetry.

E79. The antibody according to E1-E78, wherein the antibody has a thermal stability with a melting temperature ($T_m3$), or the temperature at which the $C_H3$ of the antibody is 50% unfolded, between 83° C. and 91° C., as measured by Differential Scanning calorimetry.

E80. The antibody according to E1-79 wherein the antibody has a thermal stability with a melting temperature ($T_m3$), or the temperature at which the $C_H3$ of the antibody is 50% unfolded, between 87° C. and 89° C., as measured by Differential Scanning calorimetry.

E81. An isolated nucleic acid molecule comprising a nucleic acid sequence encoding the antibody, or antigen binding fragment thereof, of any one of E1-E80.

E82. An isolated nucleic acid molecule comprising at least one nucleic acid sequence encoding the antibody, or antigen binding fragment thereof, of any one of E1-E81.

E83. An isolated nucleic acid molecule encoding the VL, VH, or both, of an antibody, or an antigen-binding portion thereof, that specifically binds human GDF15, wherein said nucleic acid molecule comprises the nucleic acid sequence of SEQ ID NO:167, the nucleic acid sequence of SEQ ID NO:168, or both.

E84. An isolated nucleic acid molecule comprising the nucleic acid sequence of SEQ ID NO:167, the nucleic acid sequence of SEQ ID NO:168, or both.

E85. An isolated nucleic acid molecule encoding the light chain, heavy chain, or both, of an antibody, or an antigen-binding portion thereof, that specifically binds human GDF15, wherein said nucleic acid molecule comprises the nucleic acid sequence of SEQ ID NO:169, the nucleic acid sequence of SEQ ID NO:170, or both.

E86. An isolated nucleic acid molecule comprising the nucleic acid sequence of SEQ ID NO:169, the nucleic acid sequence of SEQ ID NO:170, or both.

E87. An isolated nucleic acid molecule comprising at least one nucleic acid sequence selected from the group consisting of the sequence set forth as SEQ ID NO:167, 168, 169, or 170.

E88. An isolated nucleic acid molecule comprising the nucleic acid sequence as set forth as SEQ ID NO:167.

E89. An isolated nucleic acid molecule comprising the nucleic acid sequence as set forth as SEQ ID NO:168.

E90. An isolated nucleic acid molecule comprising the nucleic acid sequence as set forth as SEQ ID NO:169.

E91. An isolated nucleic acid molecule comprising the nucleic acid sequence as set forth as SEQ ID NO:170.

E92. An isolated nucleic acid molecule encoding an antibody, or an antigen-binding portion thereof, that specifically binds human GDF15, wherein said nucleic acid molecule comprises the nucleic acid sequence of the insert of the plasmid deposited with the ATCC and having the Accession Number PTA-125038.

E93. An isolated nucleic acid molecule encoding an antibody, or an antigen-binding portion thereof, that specifically binds human GDF15, wherein said nucleic acid molecule comprises the nucleic acid sequence of the insert of the plasmid deposited with the ATCC and having the Accession Number PTA-125039.

E94. An isolated nucleic acid molecule encoding an antibody, or an antigen-binding portion thereof, that specifically binds human GDF15, wherein said nucleic acid comprises the nucleic acid sequence of the insert of the plasmid deposited with the ATCC and having the Accession Number PTA-125038 and the nucleic acid sequence of the insert of the plasmid deposited with the ATCC and having the Accession Number PTA-125039.

E95. An isolated nucleic acid molecule comprising the nucleic acid sequence of the insert of the plasmid deposited with the ATCC and having the Accession Number PTA-125038.

E96. An isolated nucleic acid molecule comprising the nucleic acid sequence of the insert of the plasmid deposited with the ATCC and having the Accession Number PTA-125039.

E97. An isolated nucleic acid molecule comprising the nucleic acid sequence of the insert of the plasmid deposited with the ATCC and having the Accession Number PTA-125038, and the nucleic acid sequence of the insert of the plasmid deposited with the ATCC and having the Accession Number PTA-125039.

E98. A vector comprising the nucleic acid molecule of any one of E81-E97.

E99. A host cell comprising the nucleic acid molecule of any one of E81-E98, or the vector of E98.

E100. The host cell of E99, wherein said cell is a mammalian cell.

E101. The host cell of E100, wherein said host cell is a CHO cell, a HEK-293 cell, an NS0 cell, a PER.C6® cell, or an Sp2.0 cell.

E102. A method of making an antibody or antigen-binding fragment thereof, comprising culturing the host cell of any one of E99-E101, under a condition wherein said antibody or antigen-binding fragment is expressed by said host cell.

E103. The method of E102, further comprising isolating said antibody or antigen-binding fragment thereof.

E104. A pharmaceutical composition comprising an antibody or antigen-binding fragment thereof of any one of E1-E103, and a pharmaceutically acceptable carrier or excipient.

E105. The composition of E104, comprising thiotepa, cyclophosphamide (CYTOXAN), busulfan, improsulfan, piposulfan, benzodopa, carboquone, meturedopa, uredopa, altretamine, triethylenemelamine, trietylenephosphoramide, triethiylenethiophosphoramide, trimethylolomelamine; bullatacin, bullatacinone), delta-9-tetrahydrocannabinol (dronabinol, MARINOL), beta-lapachone, lapachol, colchicines, betulinic acid, topotecan (HYCAMTIN), CPT-11 (irinotecan, CAMPTOSAR), acetylcamptothecin, scopolectin, 9-aminocamptothecin, bryostatin, pemetrexed, callystatin, CC-1065 (including its adozelesin, carzelesin and bizelesin synthetic analogues), podophyllotoxin, podophyllinic acid, teniposide, cryptophycins, dolastatin, duocarmycin (including the synthetic analogues, KW-2189 and CB1-TM1), eleutherobin, pancratistatin, TLK-286, CDP323, an oral alpha-4 integrin inhibitor, a sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimnustine, enediyne antibiotics (including calicheamicin, calicheamicin gamma and calicheamicin omegal, dynemicin, dynemicin A, an esperamicin, neocarzinostatin chromophore and related chromoprotein enediyne antibiotic chromophores, aclacinomysins, actinomycin, authramycin, azaserine, bleomycins, cactinomycins, carabicin, carminomycin, carzinophilin, chromomycinis, dactinomycin, daunorubicin, detorubicin, 6-diazo-5-oxo-L-norleucine, doxorubicin (including ADRIAMYCIN, morpholino-doxorubicin, cyanomorpholino-doxorubicin, 2-pyrrolino-doxorubicin, doxorubicin HCl liposome injection (DOXIL) and deoxydoxorubicin), epirubicin, esorubicin, idarubicin, marcellomycin, mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, methotrexate, gemcitabine (GEMZAR), tegafur (UFTORAL), capecitabine (XELODA), an epothilone, 5-fluorouracil (5-FU), denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, imatinib, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, PSK polysaccharide complex, razoxane, rhizoxin, sizofiran, spirogermanium, tenuazonic acid, triaziquone, 2,2',2"-trichlorotriethylamine, T-2 toxin, verracurin A, roridin A, anguidine, urethan, vindesine (ELDISINE, FILDESIN), dacarbazine, mannomustine, mitobronitol, mitolactol, pipobroman, gacytosine, arabinoside ("Ara-C"), thiotepa, paclitaxel (TAXOL), albumin-engineered nanoparticle formulation of paclitaxel (ABRAXANE), doxetaxel (TAXOTERE), chlorambucil, 6-thioguanine, mercaptopurine, methotrexate, cisplatin, carboplatin, vinblastine (VELBAN), platinum, etoposide (VP-16), ifosfamide, mitoxantrone, vincristine (ONCOVIN), oxaliplatin, leucovovin, vinorelbine (NAVELBINE), novantrone, edatraxate, daunomycin, aminopterin, ibandronate, topoisomerase inhibitor RFS 2000, difluorometlhylomithine (DMFO), anti-estrogens and selective estrogen receptor modulators (SERMs) (including, for example, tamoxifen (including NOLVADEX tamoxifen), raloxifene (EVISTA), droloxifene, 4-hydroxytamoxifen, trioxifene, keoxifene, LY 1 1 7018, onapristone, and toremifene (FARESTON), anti-progesterones, estrogen receptor down-regulators (ERDs), fulvestrant (FASLODEX), leutinizing hormone-releasing hormone (LHRFI) agonists (including leuprolide acetate (LUPRON and ELIGARD), goserelin acetate, buserelin acetate and tripterelin), anti-androgens (including fiutamide, nilutamide and bicalutamide); aromatase inhibitors (including 4(5)-imidazoles, aminoglutethimide, megestrol acetate (MEGASE), exemestane (AROMASIN), formestanie, fadrozole, vorozole (RJVISOR), letrozole (FEMARA), and anastrozole (ARIMIDEX), bisphosphonates (including clodronate (BONEFOS or OSTAC), etidronate (DIDROCAL), NE-58095, zoledronic acid/zoledronate (ZOMETA), alendronate (FOSAMAX), pamidronate (AREDIA), tiludronate (SKELID), and risedronate (ACTONEL), troxacitabine, anti-sense oligonucleotides (including PKC-alpha, Raf, H-Ras, and epidermal growth factor receptor (EGF-R)), THERATOPE vaccine, gene therapy vaccines (including ALLOVECTIN vaccine, LEUVECTIN vaccine, and VAXID® vaccine; topoisomerase 1 inhibitor (e.g., LURTOTECAN)), fulvestrant; imatinib, EXEL-0862, erlotinib, cetuximab, bevacizumab, arinotecan, rmRH (e.g., ABARELIX), lapatinib, lapatinib ditosylate (also known as GW572016), 17AAG, inotuzumab ozogamicin (BESPONSA), bosutinib (BOSULIF), palbociclib (IBRANCE), axitinib (INLYTA), sunitinib malate (SUTENT), crizotinib (XALKORI), enzalutamide (XTANDI) and combinations of two or more of, pharmaceutically acceptable salts of, and/or acids or derivatives of, any of the above.

E106. A method of reducing the activity of GDF15, comprising administering to a subject in need thereof a therapeutically effective amount of the antibody, or antigen-binding fragment thereof, of any one of embodiments E1-E80, or the pharmaceutical composition of E104 or E105, and comparing the activity of GDF15 before administration with the level of GDF15 activity after administration of the antibody, thereby reducing the activity of GDF15.

E107. The method of E106, wherein the activity of GDF15 is selected from the group consisting of:
(a) binding of GFRAL;
(b) decreasing food intake;
(c) decreasing body mass;
(d) decreasing muscle mass;
(e) decreasing fat mass;
(f) activating RET;
(g) increasing phosphorylation of ERK (pERK); and
(h) increasing phosphorylation of ribosomal protein S6 (S6)
(i) increasing phosphorylation of AKT;
(j) increasing phosphorylation of MAPK; and
(k) increasing phosphorylation of PLC-γ1.

E108. A method of reducing the level of free GDF15 in a subject in need thereof, the method comprising administering to a subject in need thereof a therapeutically effective amount of the antibody, or antigen-binding fragment thereof, of any one of embodiments E1-E80, or the pharmaceutical composition of E104 or E105.

E109. The method of E108, wherein the level of free GDF15 before administration is compared with the level of free GDF15 after administration, and the dose and dosing regimen is adjusted to reduce to level of free GDF15 below 1 ng/ml.

E110. The method of E108, wherein the level of free GDF15 before administration is compared with the level of free GDF15 after administration, and the dose and dosing regimen is adjusted to reduce to level of free GDF15 below 0.9 ng/ml.

E111. The method of E108, wherein the level of free GDF15 before administration is compared with the level of free GDF15 after administration, and the dose and dosing regimen is adjusted to reduce to level of free GDF15 below 0.8 ng/ml.

E112. The method of E108, wherein the level of free GDF15 before administration is compared with the level of free GDF15 after administration, and the dose and dosing regimen is adjusted to reduce to level of free GDF15 below 0.7 ng/ml.

E113. The method of E108, wherein the level of free GDF15 before administration is compared with the level of free GDF15 after administration, and the dose and dosing regimen is adjusted to reduce to level of free GDF15 below 0.6 ng/ml.

E114. The method of E108, wherein the level of free GDF15 before administration is compared with the level of free GDF15 after administration, and the dose and dosing regimen is adjusted to reduce to level of free GDF15 below 0.5 ng/ml.

E115. The method of E108, wherein the level of free GDF15 before administration is compared with the level of free GDF15 after administration, and the dose and dosing regimen is adjusted to reduce to level of free GDF15 below 0.4 ng/ml.

E116. A method of treating cachexia, comprising administering to a subject in need thereof a therapeutically effective amount of the antibody, or antigen-binding fragment thereof, of any one of E1-E80, or the pharmaceutical composition of E104 or E105.

E117. The method of E116, wherein is cachexia associated with cancer, chemotherapy, chemotherapy in combination with an immuno-oncology therapy, chronic obstructive pulmonary disease, chronic kidney disease, chronic heart failure, congestive heart failure, or sarcopenia.

E118. The method of E117, wherein cancer is a solid tumor cancer, pancreatic cancer, lung cancer, non-small cell lung cancer, colorectal cancer, prostate cancer, ovarian cancer, cervical cancer, or testicular cancer.

E119. The method E117 or E118, where in the chemotherapy is thiotepa, cyclophosphamide (CYTOXAN), busulfan, improsulfan, piposulfan, benzodopa, carboquone, meturedopa, uredopa, altretamine, triethylenemelamine, trietylenephosphoramide, triethiylenethiophosphoramide, trimethylolomelamine; bullatacin, bullatacinone), delta-9-tetrahydrocannabinol (dronabinol, MARINOL), beta-lapachone, lapachol, colchicines, betulinic acid, topotecan (HYCAMTIN), CPT-11 (irinotecan, CAMPTOSAR), acetylcamptothecin, scopolectin, 9-aminocamptothecin, bryostatin, pemetrexed, callystatin, CC-1065 (including its adozelesin, carzelesin and bizelesin synthetic analogues), podophyllotoxin, podophyllinic acid, teniposide, cryptophycins, dolastatin, duocarmycin (including the synthetic analogues, KW-2189 and CB1-TM1), eleutherobin, pancratistatin, TLK-286, CDP323, an oral alpha-4 integrin inhibitor, a sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimnustine, enediyne antibiotics (including calicheamicin, calicheamicin gamma and calicheamicin omegal, dynemicin, dynemicin A, an esperamicin, neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN, morpholino-doxorubicin, cyanomorpholino-doxorubicin, 2-pyrrolino-doxorubicin, doxorubicin HCl liposome injection (DOXIL) and deoxydoxorubicin), epirubicin, esorubicin, idarubicin, marcellomycin, mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, methotrexate, gemcitabine (GEMZAR), tegafur (UFTORAL), capecitabine (XELODA), an epothilone, 5-fluorouracil (5-FU), denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, imatinib, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, PSK polysaccharide complex, razoxane, rhizoxin, sizofiran, spirogermanium, tenuazonic acid, triaziquone, 2,2',2"-trichlorotriethylamine, T-2 toxin, verracurin A, roridin A, anguidine, urethan, vindesine (ELDISINE, FILDESIN), dacarbazine, mannomustine, mitobronitol, mitolactol, pipobroman, gacytosine, arabinoside ("Ara-C"), thiotepa, paclitaxel (TAXOL), albumin-engineered nanoparticle formulation of paclitaxel (ABRAXANE), doxetaxel (TAXOTERE), chlorambucil, 6-thioguanine, mercaptopurine, methotrexate, cisplatin, carboplatin, vinblastine (VELBAN), platinum, etoposide (VP-16), ifosfamide, mitoxantrone, vincristine (ONCOVIN), oxaliplatin, leucovovin, vinorelbine (NAVELBINE), novantrone, edatraxate, daunomycin, aminopterin, ibandronate, topoisomerase inhibitor RFS 2000, difluorometlhylomithine (DMFO), anti-estrogens and selective estrogen receptor modulators (SERMs) (including, for example, tamoxifen (including NOLVADEX tamoxifen), raloxifene (EVISTA), droloxifene, 4-hydroxytamoxifen, trioxifene, keoxifene, LY 1 1 7018, onapristone, and toremifene (FARESTON), anti-progesterones, estrogen receptor down-regulators (ERDs), fulvestrant (FASLODEX), leutinizing hormone-releasing hormone (LHRFI) agonists (including leuprolide acetate (LUPRON and ELIGARD), goserelin acetate, buserelin acetate and tripterelin), anti-androgens (including fiutamide, nilutamide and bicalutamide); aromatase inhibitors (including 4(5)-imidazoles, aminoglutethimide, megestrol acetate (MEGASE), exemestane (AROMASIN), formestanie, fadrozole, vorozole (RJVISOR), letrozole (FEMARA), and anastrozole (ARIMIDEX), bisphosphonates (including clodronate (BONEFOS or OSTAC), etidronate (DIDROCAL), NE-58095, zoledronic acid/zoledronate (ZOMETA), alendronate (FOSAMAX), pamidronate (AREDIA), tiludronate (SKELID), and risedronate (ACTONEL), troxacitabine, anti-sense oligonucleotides (including PKC-alpha, Raf, H-Ras, and epidermal growth factor receptor (EGF-R)), THERATOPE vaccine, gene therapy vaccines (including ALLOVECTIN vaccine, LEUVECTIN vaccine, and VAXID® vaccine; topoisomerase 1 inhibitor (e.g., LURTOTECAN)), fulvestrant; imatinib, EXEL-0862, erlotinib, cetuximab, bevacizumab, arinotecan, rmRH (e.g., ABARELIX), lapatinib, lapatinib ditosylate (also known as GW572016), 17AAG, inotuzumab ozogamicin (BESPONSA), bosutinib (BOSULIF), palbociclib (IBRANCE), axitinib (INLYTA), sunitinib malate (SUTENT), crizotinib (XALKORI), enzalutamide (XTANDI) and combinations of two or more of, pharmaceutically acceptable salts of, and/or acids or derivatives of, any of the above.

E120. The method of E119, wherein the chemotherapy is platin-based chemotherapy.

E121. The method of any one of E106-E120, wherein said subject is a human.

E122. The method of any one of E106-E121, comprising administering said antibody or antigen-binding fragment thereof, or pharmaceutical composition, subcutaneously.

E123. The method of any one of E106-E122, comprising administering said antibody or antigen-binding fragment thereof, or pharmaceutical composition, intravenously.

E124. The method of any one of E106-E123, wherein said antibody or antigen-binding fragment thereof, or pharmaceutical composition, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, or once every four months once every five months, once every six months, once every seven months, once every eight months, once every nine months, once every ten months, once every eleven months or once every twelve months.

E125. The method of any one of E106-E124, wherein said antibody or antigen-binding fragment thereof, or pharmaceutical composition, is administered once a week at a dose between about 0.1 mg and about 60 mg.

E126. The method of any one of E106-E125, wherein said antibody or antigen-binding fragment thereof, or pharmaceutical composition, is administered once a week at a dose between about 2 mg and about 50 mg.

E127. The method of any one of E106-E126, wherein said antibody or antigen-binding fragment thereof, or pharmaceutical composition, is administered once a week at a dose selected from the group consisting of about 2 mg, about 5 mg, about 7 mg, about 10 mg, about 12 mg, about 15 mg, about 25 mg, about 40 mg, and about 50 mg.

E128. The method of any one of E106-E124, wherein said antibody or antigen-binding fragment thereof, or pharmaceutical composition, is administered once every two weeks at a dose between about 0.1 mg and about 130 mg.

E129. The method of any one of E106-E124 or E128, wherein said antibody or antigen-binding fragment thereof, or pharmaceutical composition, is administered once every two weeks at a dose between about 5 mg and about 125 mg.

E130. The method of any one of E106-E124 or E128-E129, wherein said antibody or antigen-binding fragment thereof, or pharmaceutical composition, is administered once every two weeks at a dose selected from the group consisting of about 5 mg, about 12 mg, about 20 mg, about 25 mg, about 30 mg, about 40 mg, about 60 mg, about 90 mg, and about 125 mg.

E131. The method of any one of E106-E124, wherein said antibody or antigen-binding fragment thereof, or pharmaceutical composition, is administered once every four weeks at a dose between about 0.1 mg and about 400 mg.

E132. The method of any one of E106-E124 or E131, wherein said antibody or antigen-binding fragment thereof, or pharmaceutical composition, is administered once every four weeks at a dose between about 15 mg and about 385 mg.

E133. The method of any one of E106-E124 or E131-E132, wherein said antibody or antigen-binding fragment thereof, or pharmaceutical composition, is administered once every four weeks at a dose selected from the group consisting of about 15 mg, about 40 mg, about 60 mg, about 75 mg, about 100 mg, about 115 mg, about 200 mg, about 300 mg, and about 385 mg.

E134. The antibody, or antigen-binding fragment thereof, of any one of E1-E80, or the pharmaceutical composition of E104 or E105, for use as a medicament.

E135. The antibody, or antigen-binding fragment thereof, of any one of E1-80, or the pharmaceutical composition of E104 or E105, for use in reducing the activity of GDF15 in a subject.

E136. A method of reducing the activity of GDF15, comprising administering to a subject in need thereof a therapeutically effective amount an antibody, or antigen-binding fragment thereof, comprising
  a) the HCDR-1, HCDR-2, and HCDR-3 sequences of SEQ ID NO:177 and the LCDR-1, LCDR-2LCDR-2, and LCDR-3 sequences of SEQ ID NO:178, or
  b) the VH comprising the amino acid sequence of SEQ ID NO:177 and the VL comprising the amino acid sequence of SEQ ID NO:178
  and comparing the activity of GDF15 before administration with the level of GDF15 activity after administration of the antibody, thereby reducing the activity of GDF15.

E137. A method of reducing the activity of GDF15, comprising administering to a subject in need thereof a therapeutically effective amount an antibody, or antigen-binding fragment thereof, comprising
- a) a pharmaceutical composition comprising an antibody, or antigen-binding fragment thereof, comprising the HCDR-1, HCDR-2, and HCDR-3 sequences of SEQ ID NO:177; the LCDR-1, LCDR-2, and LCDR-3 sequences of SEQ ID NO:178; and a pharmaceutically acceptable carrier or excipient, or
- b) a pharmaceutical composition comprising an antibody, or antigen-binding fragment thereof, comprising the VH comprising the amino acid sequence of SEQ ID NO:177; the VL comprising the amino acid sequence of SEQ ID NO:178; and a pharmaceutically acceptable carrier or excipient, thereby reducing the activity of GDF15.

E138. The method of E137, wherein the activity of GDF15 is selected from the group consisting of:
- (a) binding of GFRAL;
- (b) decreasing food intake;
- (c) decreasing body mass;
- (d) decreasing muscle mass;
- (e) decreasing fat mass;
- (f) activating RET;
- (g) increasing phosphorylation of ERK (pERK); and
- (h) increasing phosphorylation of ribosomal protein S6 (S6)
- (i) increasing phosphorylation of AKT;
- (j) increasing phosphorylation of MAPK; and
- (k) increasing phosphorylation of PLC-☐1.

E139. A method of treating cachexia, comprising administering to a subject in need thereof a therapeutically effective amount an antibody, or antigen-binding fragment thereof, comprising
- a) the HCDR-1, HCDR-2, and HCDR-3 sequences of SEQ ID NO:177 and the LCDR-1, LCDR-2, and LCDR-3 sequences of SEQ ID NO:178, or
- b) the VH comprising the amino acid sequence of SEQ ID NO:177 and the VL comprising the amino acid sequence of SEQ ID NO:178.

E140. A method of treating cachexia, comprising administering to a subject in need thereof a therapeutically effective amount an antibody, or antigen-binding fragment thereof, comprising
- a) a pharmaceutical composition comprising an antibody, or antigen-binding fragment thereof, comprising the HCDR-1, HCDR-2, and HCDR-3 sequences of SEQ ID NO:177; the LCDR-1, LCDR-2, and LCDR-3 sequences of SEQ ID NO:178; and a pharmaceutically acceptable carrier or excipient, or
- b) a pharmaceutical composition comprising an antibody, or antigen-binding fragment thereof, comprising the VH comprising the amino acid sequence of SEQ ID NO:177; the VL comprising the amino acid sequence of SEQ ID NO:178;

and a pharmaceutically acceptable carrier or excipient.

E141. The method of E139 or E140, wherein is cachexia associated with cancer, chemotherapy, chemotherapy in combination with an immuno-oncology therapy, chronic obstructive pulmonary disease, chronic kidney disease, chronic heart failure, congestive heart failure, or sarcopenia.

E142. The method of E141, wherein cancer is a solid tumor cancer, pancreatic cancer, lung cancer, non-small cell lung cancer, colorectal cancer, prostate cancer, ovarian cancer, cervical cancer, or testicular cancer.

E143. The method E141 or E142, where in the chemotherapy is thiotepa, cyclophosphamide (CYTOXAN), busulfan, improsulfan, piposulfan, benzodopa, carboquone, meturedopa, uredopa, altretamine, triethylenemelamine, trietylenephosphoramide, triethiylenethiophosphoramide, trimethylolomelamine; bullatacin, bullatacinone), delta-9-tetrahydrocannabinol (dronabinol, MARINOL), beta-lapachone, lapachol, colchicines, betulinic acid, topotecan (HYCAMTIN), CPT-11 (irinotecan, CAMPTOSAR), acetylcamptothecin, scopolectin, 9-aminocamptothecin, bryostatin, pemetrexed, callystatin, CC-1065 (including its adozelesin, carzelesin and bizelesin synthetic analogues), podophyllotoxin, podophyllinic acid, teniposide, cryptophycins, dolastatin, duocarmycin (including the synthetic analogues, KW-2189 and CB1-TM1), eleutherobin, pancratistatin, TLK-286, CDP323, an oral alpha-4 integrin inhibitor, a sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimnustine, enediyne antibiotics (including calicheamicin, calicheamicin gamma and calicheamicin omegal, dynemicin, dynemicin A, an esperamicin, neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN, morpholino-doxorubicin, cyanomorpholino-doxorubicin, 2-pyrrolino-doxorubicin, doxorubicin HCl liposome injection (DOXIL) and deoxydoxorubicin), epirubicin, esorubicin, idarubicin, marcellomycin, mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, methotrexate, gemcitabine (GEMZAR), tegafur (UFTORAL), capecitabine (XELODA), an epothilone, 5-fluorouracil (5-FU), denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, imatinib, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, PSK polysaccharide complex, razoxane, rhizoxin, sizofiran, spirogermanium, tenuazonic acid, triaziquone, 2,2',2"-trichlorotriethylamine, T-2 toxin, verracurin A, roridin A, anguidine, urethan, vindesine (ELDISINE, FILDESIN), dacarbazine, mannomustine, mitobronitol, mitolactol, pipobroman, gacytosine, arabinoside ("Ara-C"), thiotepa, paclitaxel (TAXOL), albumin-engineered nanoparticle formulation of paclitaxel (ABRAXANE), doxetaxel (TAXOTERE), chlorambucil, 6-thioguanine, mercaptopurine, methotrexate, cisplatin, carboplatin, vinblastine (VELBAN), platinum, etoposide (VP-16), ifosfamide, mitoxantrone, vincristine (ONCOVIN), oxaliplatin, leucovovin, vinorelbine (NAVELBINE), novantrone, edatraxate, daunomycin, aminopterin, ibandronate, topoisomerase inhibitor RFS 2000, difluorometlhylomithine (DMFO), anti-estrogens and selective estrogen receptor modulators (SERMs) (including, for example, tamoxifen (including NOLVADEX tamoxifen), raloxifene (EVISTA), droloxifene, 4-hydroxytamoxifen, trioxifene, keoxifene, LY 1 1 7018, onapristone, and toremifene (FARESTON), anti-progesterones, estrogen receptor down-regulators (ERDs), fulvestrant (FASLODEX), leutinizing hormone-releasing hormone (LHRFI) agonists (including leuprolide acetate (LUPRON and ELIGARD), goserelin acetate, buserelin acetate and tripterelin), anti-androgens (including flutamide, nilutamide and bicalutamide); aromatase inhibitors (including 4(5)-imidazoles, aminoglutethimide, megestrol acetate (MEGASE), exemestane (AROMASIN), formestanie, fadrozole, vorozole (RJVISOR), letrozole (FEMARA), and anastrozole (ARIMIDEX), bisphosphonates (including clodronate (BONEFOS or OSTAC), etidronate (DIDROCAL), NE-58095, zoledronic acid/zoledronate (ZOMETA), alendronate (FOSAMAX), pamidronate (AREDIA), tiludronate (SKELID), and risedronate (ACTONEL), troxacitabine, anti-sense oligonucleotides (including PKC-alpha, Raf, H-Ras, and epidermal growth factor receptor (EGF-R)), THERATOPE vaccine, gene therapy vaccines (including ALLOVECTIN vaccine, LEUVECTIN vaccine, and VAXID® vaccine; topoisomerase 1 inhibitor (e.g., LURTOTECAN)), fulvestrant; imatinib, EXEL-0862, erlotinib, cetuximab, bevacizumab, arinotecan, rmRH (e.g., ABARELIX), lapatinib, lapatinib ditosylate (also known as GW572016), 17AAG, inotuzumab ozogamicin (BESPONSA), bosutinib (BOSULIF), palbociclib (IBRANCE), axitinib (INLYTA), sunitinib malate (SUTENT), crizotinib (XALKORI), enzalutamide (XTANDI) and combinations of two or more of, pharmaceutically acceptable salts of, and/or acids or derivatives of, any of the above.

E144. The method of E141, wherein the chemotherapy is platin-based chemotherapy.

E145. The method of any one of E136-E144, wherein said subject is a human.

E146. The method of any one of E136-E145, comprising administering said antibody or antigen-binding fragment thereof, or pharmaceutical composition, subcutaneously.

E147. The method of any one of E136-E146, comprising administering said antibody or antigen-binding fragment thereof, or pharmaceutical composition, intravenously.

E148. The method of any one of E136-E147, wherein said antibody or antigen-binding fragment thereof, or pharmaceutical composition, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, or once every four months.

E149. The method of any one of E136-E148, wherein said antibody or antigen-binding fragment thereof, or pharmaceutical composition, is administered once a week at a dose between about 0.1 mg and about 60 mg.

E150. The method of any one of E136-E149, wherein said antibody or antigen-binding fragment thereof, or pharmaceutical composition, is administered once a week at a dose between about 2 mg and about 50 mg.

E151. The method of any one of E136-E150, wherein said antibody or antigen-binding fragment thereof, or pharmaceutical composition, is administered once a week at a dose selected from the group consisting of about 2 mg, about 5 mg, about 7 mg, about 10 mg, about 12 mg, about 15 mg, about 25 mg, about 40 mg, and about 50 mg.

E152. The method of any one of E136-E148, wherein said antibody or antigen-binding fragment thereof, or pharmaceutical composition, is administered once every two weeks at a dose between about 0.1 mg and about 130 mg.

E153. The method of any one of E136-E148 or E152, wherein said antibody or antigen-binding fragment thereof, or pharmaceutical composition, is administered once every two weeks at a dose between about 5 mg and about 125 mg.

E154. The method of any one of E136-E148 or E152-E153, wherein said antibody or antigen-binding fragment thereof, or pharmaceutical composition, is administered once every two weeks at a dose selected from the group consisting of about 5 mg, about 12 mg, about 20 mg, about 25 mg, about 30 mg, about 40 mg, about 60 mg, about 90 mg, and about 125 mg.

E155. The method of any one of E136-E148, wherein said antibody or antigen-binding fragment thereof, or pharmaceutical composition, is administered once every four weeks at a dose between about 0.1 mg and about 400 mg.

E156. The method of any one of E136-E148 or E155, wherein said antibody or antigen-binding fragment thereof, or pharmaceutical composition, is administered once every four weeks at a dose between about 15 mg and about 385 mg.

E157. The method of any one of E136-E148 or E155-E156, wherein said antibody or antigen-binding fragment thereof, or pharmaceutical composition, is administered once every four weeks at a dose selected from the group consisting of about 15 mg, about 40 mg, about 60 mg, about 75 mg, about 100 mg, about 115 mg, about 200 mg, about 300 mg, and about 385 mg.

E158. A method of reducing the level of free GDF15 in the plasma of a subject in need thereof, said method comprising administering the antibody of any one of E1-E80 or the composition of any one of E104-E105.

E159. The method of any one of E106-E108 or E116-E158, wherein the level of free GDF15 in the plasma of the subject is reduced to within from about 0.05 ng/mL to about 3 ng/mL.

E160. The method of any one of E106-E108 or E116-E159, wherein the level of free GDF15 in the plasma of the subject is reduced to within from about 0.1 ng/mL to about 1 ng/mL.

E161. The method of any one of E106-E108 or E116-E160, wherein the level of free GDF15 in the plasma of the subject is reduced to within from about 0.4 ng/mL to about 0.8 ng/mL.

E162. The method of any one of E106-E114 or E116-E158, wherein the level of free GDF15 in the plasma of the subject is reduced to below 0.5 ng/ml.

E163. The method of any one of E106-E158 or E162, wherein the level of free GDF15 in the plasma of the subject is reduced to below 0.4 ng/ml.

E164. The method of any one of E106-E108 or E116-E158, where the level of free GDF15 in the plasma of the subject is reduced to a range whose lower value is selected from the group consisting of 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 ng/mL and whose upper value is selected from the group consisting of 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, and 3.0 ng/mL.

E165. The method of E106-E114 or E116-E158, where the level of free GDF15 in the plasma of the subject is reduced to less than about 0.5 ng/mL.

E166. The method of any one of E106-E165, wherein the level of free GDF15 in the plasma of the subject is reduced beyond the lowest level of detection using an assay known in the art to detect free GDF15 in plasma.

E167. A pharmaceutical composition comprising an antibody, or antigen binding fragment thereof, of E1-E80, a PD-1 axis binding antagonist, and a pharmaceutically acceptable carrier or excipient.

E168. A pharmaceutical composition comprising an antibody, or antigen binding fragment thereof, of E1-E80, a PD-1 axis binding antagonist, and a pharmaceutically acceptable carrier or excipient, with the proviso that the PD-1 axis binding antagonist is not avelumab.

E169. A method for treating cancer comprising administering to a patient in need thereof an amount of a PD-1 axis binding antagonist, and an amount of an antibody, or antigen binding fragment thereof, of any one of E1-E80, or an amount of the pharmaceutical composition of E167-E168, wherein the amounts together are effective in treating cancer.

E170. A method of treating cancer comprising administering to a patient in need thereof an amount of a PD-1 axis binding antagonist, and an amount of an antibody, or antigen binding fragment thereof, of any one of E1-E80, or an amount of the pharmaceutical composition of E167-169, wherein the amounts together are effective in treating cancer, and wherein the PD-1 axis binding antagonist is not avelumab.

E171. The method of E169-E170, wherein the amounts together provide a synergistic therapeutic effect in treating cancer.

E172. The method of E169, wherein the PD-1 axis binding antagonist is an anti PD-L1 antibody.

E173. The method of E169, wherein the PD-1 axis binding antagonist is an anti PD-L1 antibody, with the proviso that the anti PD-L1 antibody is not avelumab.

E174. The method of E172, wherein the PD-L1 antibody is selected from the group consisting of avelumab, atezolizumab or durvalumab.

E175. The method of E172, wherein the PD-L1 antibody is atezolizumab or durvalumab.

E176. The method of E172, wherein the PD-1 axis binding antagonist is avelumab and is administered intravenously in the amount of about 10 mg/kg Q2W or about 800 mg Q2W.

E177. The method of claim E168, wherein the PD-1 axis binding antagonist is an anti PD-1 antibody.

E178. The method of claim E177, wherein the anti PD-1 antibody is selected from the group consisting of nivolumab, pembrolizumab, spartalizumab, tislelizumab, pidilizumab, AMP-224, AMP-514, cemiplimab and sasanlimab (PF-06801591, RN888, mAb7).

E179. The method of claim E178, wherein the PD-1 axis binding antagonist is sasanlimab and is administered subcutaneously in the amount of about 300 mg Q4W or about 600 mg Q6W.

E180. The method of any one of E170-E180, wherein the cancer is selected from the group consisting of melanoma, non-small cell lung cancer, renal cell carcinoma, Merkel cell carcinoma, ovarian cancer, breast cancer, pancreatic cancer, urothelial cancer and castration-resistant prostate cancer.

E181. The method of E180, wherein the cancer is renal cell carcinoma.

E182. The method of E1181, wherein the cancer is pancreatic cancer.

E183. A method of detecting GDF15 in a sample, tissue, or cell using the antibody, or antigen binding portion thereof, of any one of E1-E80, comprising contacting the sample, tissue or cell with the antibody and detecting the antibody.

E184. A method for treating cancer in a patient in need thereof, comprising administering to the patient a combination therapy comprising a synergistic therapeutically effective amount of a PD-1 axis binding antagonist, and a synergistic therapeutically effective amount of a GDF15 inhibitor, wherein the amounts together provide a synergistic therapeutic effect thereby treating cancer.

E185. A method of treating cancer in a patient in need thereof, comprising administering to the patient a combination therapy comprising a synergistic therapeutically effective amount of a PD-1 axis binding antagonist, and a synergistic therapeutically effective amount of a GDF15 inhibitor, wherein the amounts together provide a synergistic therapeutic effect thereby treating cancer, and wherein the PD-1 axis binding antagonist is not avelumab.

E186. The method of E184-E185, wherein the GDF15 inhibitor is an anti-GDF15 antibody, or an antigen binding fragment thereof, of any of E1-E80.

E187. The method of E186, wherein the anti-GDF15 antibody, or antigen binding fragment therein, comprises:
  a) a LCDR-1 comprising the amino acid sequence of SEQ ID NO:95;
  b) a LCDR-2 comprising the aa sequence of SEQ ID NO:28;
  c) a LCDR-3 comprising the aa sequence of SEQ ID NO:9;
  d) a HCDR-1 comprising the aa sequence of SEQ ID NO:32;
  e) a HCDR-2 comprising the aa sequence of SEQ ID NO:165; and
  f) a HCDR-3 comprising the aa sequence of SEQ ID NO:52.

E188. The method of E187, wherein the PD-1 axis binding antagonist is an antibody that specifically binds PD-1 and comprises:
  a) a LCDR-1 comprising the amino acid sequence of SEQ ID NO:216;
  b) a LCDR-2 comprising the aa sequence of SEQ ID NO:217;
  c) a LCDR-3 comprising the aa sequence of SEQ ID NO:218;
  d) a HCDR-1 comprising the aa sequence of SEQ ID NO:210;
  e) a HCDR-2 comprising the aa sequence of SEQ ID NO:213; and
  f) a HCDR-3 comprising the aa sequence of SEQ ID NO:215.

E189. The method of E186, wherein the PD-1 axis binding antagonist is an anti-PD-1 antibody selected from the group consisting of nivolumab, pembrolizumab, spartalizumab, pidilizumab, tislelizumab, AMP-224, AMP-514, cemiplimab, and sasanlimab (PF-06801591).

E190. The method of claim E188-E189, wherein the anti-PD-1 antibody is sasanlimab (PF-06801591).

E191. The method of claim 186, wherein the PD-1 axis binding antagonist is an anti-PD-L1 antibody.

E192. The method of claim 190, wherein sasanlimab is administered subcutaneously in the amount of about 300 mg Q4W or about 600 mg Q6W.

E.193. The method of claim 191, wherein the PD-L1 antibody is selected from the group consisting of atezolizumab, durvalumab, BMS-936559, MED14736, and MPDL3280A.

E194. The method of claim 187, wherein the anti-GDF15 antibody, or an antigen binding fragment thereof, comprises a VH comprising the amino acid sequence of SEQ ID NO:166 and a VL comprising the amino acid sequence of SEQ ID NO:163.

E195. The method of E194, wherein the anti-GDF15 antibody comprises a HC comprising the amino acid sequence of SEQ ID NO:164, and a LC comprising the amino acid sequence of SEQ ID NO:162.

E196. The method of E195, wherein the anti-PD-1 antibody comprises a HC comprising the amino acid sequence of SEQ ID NO:197, and a LC comprising the amino acid sequence of SEQ ID NO:199.

E197. The method of claim 31, wherein the cancer is selected from the group consisting of melanoma, non-small cell lung cancer, renal cell carcinoma, Merkel cell carcinoma, ovarian cancer, breast cancer, pancreatic cancer, urothelial cancer and castration-resistant prostate cancer.

E198. The method of E184-E197, wherein the cancer is renal cell carcinoma or pancreatic cancer.

E199. A kit for the treatment of cancer, comprising a synergistic therapeutically effective amount of an anti-PD-1 antibody, and a synergistic therapeutically effective amount of an anti-GDF15 antibody.

E200. A method of treating cancer, comprising administering to a subject in need thereof a therapeutically effective amount of the antibody, or antigen-binding fragment thereof, of any one of E1-E80, or the pharmaceutical composition of E104 or E105.

E201. The method of E200, wherein the cancer is, for example without limitation, bladder cancer, breast cancer, cervical cancer, choriocarcinoma, colon cancer, esophageal cancer, gastric cancer, glioblastoma, glioma, brain tumor, head and neck cancer, kidney cancer, lung cancer, oral cancer, ovarian cancer, pancreatic cancer, prostate cancer, liver cancer, uterine cancer, bone cancer, leukemia, lymphoma, sarcoma, blood cancer, thyroid cancer, thymic cancer, eye cancer, and skin cancer.

E202. The method of E200 or E201, wherein method further comprises administering one or more additional therapeutic agent(s).

E203. The method of E202, wherein the additional therapeutic agent(s) is selected from a chemotherapy, a vaccine, a CAR-T cell-based therapy, radiotherapy, a cytokine therapy, a vaccine, a bispecific antibody, an inhibitor of other immunosuppressive pathways, an inhibitors of angiogenesis, a T cell activator, an inhibitor of a metabolic pathway, an mTOR inhibitor, an inhibitor of an adenosine pathway, a tyrosine kinase inhibitor including but not limited to INLYTA, ALK inhibitors and sunitinib, a BRAF inhibitor, an epigenetic modifier, an inhibitors or depletor of Treg cells and/or of myeloid-derived suppressor cells, a JAK inhibitor, a STAT inhibitor, a cyclin-dependent kinase inhibitor, a biotherapeutic agent (including but not limited to antibodies to VEGF, VEGFR, EGFR, Her2/neu, other growth factor receptors, CD20, CD40, CD-40L, CTLA-4, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), cells transfected with genes encoding immune stimulating cytokines such as but not limited to GM-CSF), a STING agonist, and a toll-like receptor (e.g., TLR3, TLR7, TLR8, TLR9) agonist.

E204. The method of E202, wherein the additional therapeutic agent is an anti-CD40 antibody.

E205. The method of E203, where in the chemotherapy is thiotepa, cyclophosphamide (CYTOXAN), busulfan, improsulfan, piposulfan, benzodopa, carboquone, meturedopa, uredopa, altretamine, triethylenemelamine, trietylenephosphoramide, triethiylenethiophosphoramide, trimethylolomelamine; bullatacin, bullatacinone), delta-9-tetrahydrocannabinol (dronabinol, MARINOL), beta-lapachone, lapachol, colchicines, betulinic acid, topotecan (HYCAMTIN), CPT-11 (irinotecan, CAMPTOSAR), acetylcamptothecin, scopolectin, 9-aminocamptothecin, bryostatin, pemetrexed, callystatin, CC-1065 (including its adozelesin, carzelesin and bizelesin synthetic analogues), podophyllotoxin, podophyllinic acid, teniposide, cryptophycins, dolastatin, duocarmycin (including the synthetic analogues, KW-2189 and CB1-TM1), eleutherobin, pancratistatin, TLK-286, CDP323, an oral alpha-4 integrin inhibitor, a sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimnustine, enediyne antibiotics (including calicheamicin, calicheamicin gamma and calicheamicin omegal, dynemicin, dynemicin A, an esperamicin, neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN, morpholinodoxorubicin, cyanomorpholino-doxorubicin, 2-pyrrolinodoxorubicin, doxorubicin HCl liposome injection (DOXIL) and deoxydoxorubicin), epirubicin, esorubicin, idarubicin, marcellomycin, mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, methotrexate, gemcitabine (GEMZAR), tegafur (UFTORAL), capecitabine (XELODA), an epothilone, 5-fluorouracil (5-FU), denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, imatinib, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, PSK polysaccharide complex, razoxane, rhizoxin, sizofiran, spirogermanium, tenuazonic acid, triazi-quone, 2,2',2"-trichlorotriethylamine, T-2 toxin, verracurin A, roridin A, anguidine, urethan, vindesine (ELDISINE, FILDESIN), dacarbazine, mannomustine, mitobronitol, mitolactol, pipobroman, gacytosine, arabinoside ("Ara-C"), thiotepa, paclitaxel (TAXOL), albumin-engineered nanoparticle formulation of paclitaxel (ABRAXANE), doxetaxel (TAXOTERE), chlorambucil, 6-thioguanine, mercaptopurine, methotrexate, cisplatin, carboplatin, vinblastine (VELBAN), platinum, etoposide (VP-16), ifosfamide, mitoxantrone, vincristine (ONCOVIN), oxaliplatin, leucovovin, vinorelbine (NAVELBINE), novantrone, edatraxate, daunomycin, aminopterin, ibandronate, topoisomerase inhibitor RFS 2000, difluorometlhylomithine (DMFO), anti-estrogens and selective estrogen receptor modulators (SERMs) (including, for example, tamoxifen (including NOLVADEX tamoxifen), raloxifene (EVISTA), droloxifene, 4-hydroxytamoxifen, trioxifene, keoxifene, LY 1 1 7018, onapristone, and toremifene (FARESTON), anti-progesterones, estrogen receptor down-regulators (ERDs), fulvestrant (FASLODEX), leutinizing hormone-releasing hormone (LHRFI) agonists (including leuprolide acetate (LUPRON and ELIGARD), goserelin acetate, buserelin acetate and tripterelin), anti-androgens (including fiutamide, nilutamide and bicalutamide); aromatase inhibitors (including 4(5)-imidazoles, aminoglutethimide, megestrol acetate (MEGASE), exemestane (AROMASIN), formestanie, fadrozole, vorozole (RJVISOR), letrozole (FEMARA), and anastrozole (ARIMIDEX), bisphosphonates (including clodronate (BONEFOS or OSTAC), etidronate (DIDROCAL), NE-58095, zoledronic acid/zoledronate (ZOMETA), alendronate (FOSAMAX), pamidronate (AREDIA), tiludronate (SKELID), and risedronate (ACTONEL), troxacitabine, anti-sense oligonucleotides (including PKC-alpha, Raf, H-Ras, and epidermal growth factor receptor (EGF-R)), THERATOPE vaccine, gene therapy vaccines (including ALLOVECTIN vaccine, LEUVECTIN vaccine, and VAXID® vaccine; topoisomerase 1 inhibitor (e.g., LURTOTECAN)), fulvestrant; imatinib, EXEL-0862, erlotinib, cetuximab, bevacizumab, arinotecan, rmRH (e.g., ABARELIX), lapatinib, lapatinib ditosylate (also known as GW572016), 17AAG, inotuzumab ozogamicin (BESPONSA), bosutinib (BOSULIF), palbociclib (IBRANCE), axitinib (INLYTA), sunitinib malate (SUTENT), crizotinib (XALKORI), enzalutamide (XTANDI) and combinations of two or more of, pharmaceutically acceptable salts of, and/or acids or derivatives of, any of the above.

E206. The method E203, wherein the chemotherapy is platin-based chemotherapy.

E207. The method of any one of E200-E206, wherein said subject is a human.

E208. The method of any one of E200-E207, comprising administering said antibody or antigen-binding fragment thereof, or pharmaceutical composition, subcutaneously.

E209. The method of any one of E200-E206, comprising administering said antibody or antigen-binding fragment thereof, or pharmaceutical composition, intravenously.

E210. The method of any one of E200-E206, wherein said antibody or antigen-binding fragment thereof, or pharmaceutical composition, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, or once every four months.

E211. The method of any one of E200-E206, wherein said antibody or antigen-binding fragment thereof, or pharmaceutical composition, is administered once a week at a dose between about 0.1 mg and about 60 mg.

E212. The method of any one of E200-E206, wherein said antibody or antigen-binding fragment thereof, or pharmaceutical composition, is administered once a week at a dose between about 2 mg and about 50 mg.

E213. The method of any one of E200-E206, wherein said antibody or antigen-binding fragment thereof, or pharmaceutical composition, is administered once a week at a dose selected from the group consisting of about 2 mg, about 5 mg, about 7 mg, about 10 mg, about 12 mg, about 15 mg, about 25 mg, about 40 mg, and about 50 mg.

E214. The method of any one of E200-E206, wherein said antibody or antigen-binding fragment thereof, or pharmaceutical composition, is administered once every two weeks at a dose between about 0.1 mg and about 130 mg.

E215. The method of any one of E200-E206, wherein said antibody or antigen-binding fragment thereof, or pharmaceutical composition, is administered once every two weeks at a dose between about 5 mg and about 125 mg.

E216. The method of any one of E200-E206, wherein said antibody or antigen-binding fragment thereof, or pharmaceutical composition, is administered once every two weeks at a dose selected from the group consisting of about 5 mg, about 12 mg, about 20 mg, about 25 mg, about 30 mg, about 40 mg, about 60 mg, about 90 mg, and about 125 mg.

E217. The method of any one of E200-E206, wherein said antibody or antigen-binding fragment thereof, or pharmaceutical composition, is administered once every four weeks at a dose between about 0.1 mg and about 400 mg.

E218. The method of any one of E200-E206, wherein said antibody or antigen-binding fragment thereof, or pharmaceutical composition, is administered once every four weeks at a dose between about 15 mg and about 385 mg.

E219. The method of any one of E200-E206, wherein said antibody or antigen-binding fragment thereof, or pharmaceutical composition, is administered once every four weeks at a dose selected from the group consisting of about 15 mg, about 40 mg, about 60 mg, about 75 mg, about 100 mg, about 115 mg, about 200 mg, about 300 mg, and about 385 mg.

E220. A method of treating cancer in a subject in need thereof, the method comprising administering a therapeutically effective amount of the anti-GDF15 antibody, or antigen binding fragment thereof, of E1-E80, or the pharmaceutical composition of E104 or E105.

E221. The method of E220, wherein the method further comprises administering to the subject an effective amount of one or more additional therapeutic agents.

E222. The method of E221, wherein the additional therapeutic agent is an anti-CD40 antibody, or antigen binding fragment thereof.

E223. The method of any one of E220-E222, wherein the cancer is selected from the group consisting of gastric cancer, sarcoma, lymphoma, Hodgkin's lymphoma, leukemia, head and neck cancer, squamous cell head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, renal cell carcinoma, bladder cancer, cervical cancer, choriocarcinoma, colon cancer, oral cancer, skin cancer, and melanoma.

E224. The method of any one of E220-223, wherein the subject is a human.

E225. A method for enhancing the therapeutic effect of an immune modulator administered to a subject for the treatment of cancer, the method comprising administering to the subject receiving the immune modulator an effective amount of the anti-GDF15 antibody, or antigen binding fragment thereof, of E1-E80, or the pharmaceutical composition of E104 or E105.

E226. The method of E225, wherein the cancer is selected from the group consisting of breast cancer, gastric cancer, liver cancer, lung cancer, ovarian cancer, pancreatic cancer, prostate cancer, glioma, glioblastoma, renal cancer, endometrial cancer, and colorectal cancer.

E227. A method for treating or preventing cytokine release syndrome (CRS) in a subject in need thereof, the method comprising administering to the subject an effective amount of the anti-GDF15 antibody, or antigen binding fragment thereof, of E1-E80, or the pharmaceutical composition of E104 or E105, thereby treating or prevent CRS in the subject.

E228. A method of decreasing or inhibiting toxicity in a subject experiencing cytokine release syndrome (CRS) or cytokine storm or vulnerable to cytokine release syndrome or cytokine storm, comprising administering the step of administering a composition comprising administering to the subject an effective amount of the anti-GDF15 antibody, or antigen binding fragment thereof, of E1-E80, or the pharmaceutical composition of E104 or E105.

E229. The method of claim E227 or E228, wherein production of at least one pro-inflammatory cytokine is decreased or inhibited in said subject compared with a subject experiencing cytokine release syndrome or cytokine storm or vulnerable to cytokine release syndrome or cytokine storm and not administered the anti-GDF15 antibody, or antigen binding fragment thereof, of E1-E80, or the pharmaceutical composition of E104 or E105.

E230. The method of any one of E227-E229, wherein the subject is undergoing cancer therapy and said method does not reduce the efficacy of the cancer therapy.

E231. The method of E230, wherein the cancer therapy comprises an immune modulator.

E232. The method of E230 or E231, wherein administration of the anti-GDF15 antibody, or antigen binding fragment thereof, occurs prior to, concurrent with, or following the cancer therapy.

E233. The method of any one of E231-E232, wherein the immune modulator is: an anti-CD40 antibody, an anti-CD47 antibody, an anti-CTLA4 antibody, an anti-4-1BB/CD137 antibody, interleukin 12 (IL-12), or IL-15.

E234. The method of any one of E228-E233, wherein the cause of the CRS or cytokine storm comprises an infectious stimuli, condition, or syndrome, or wherein the cause of said cytokine release syndrome or cytokine storm comprises a non-infectious stimuli, condition, or syndrome, or any combination thereof.

E235. The method of E234, wherein said infectious stimuli, condition, or syndrome comprises influenza, bird flu, severe acute respiratory syndrome (SARS), Epstein-Barr virus-associated hemophagocytic lymphohistiocytosis (HLH), sepsis, gram-negative sepsis, malaria, an Ebola virus, a variola virus, a systemic Gram-negative bacterial infection, or Jarisch-Herxheimer syndrome, or wherein said non-infectious stimuli, condition, or syndrome comprises is hemophagocytic lymphohistiocytosis (HLH), sporadic HLH, macrophage activation syndrome (MAS), chronic arthritis, systemic Juvenile idiopathic Arthritis (sJIA), Still's Disease, a Cryopyrin-associated Periodic Syndrome (CAPS), Familial Cold Auto-inflammatory Syndrome (FCAS), Familial Cold Urticaria (FCU), Muckle-Well Syndrome (MWS), Chronic Infantile Neurological Cutaneous and, Articular (CINCA) Syndrome, a cryopyrinopathy comprising inherited or de novo gain of function mutations in the NLRP3 gene, a hereditary auto-inflammatory disorder, acute pancreatitis, a severe burns, a trauma, an acute respiratory distress syndrome, an immunotherapy, a monoclonal antibody therapy, secondary to drug use, is secondary to inhalation of toxins, a lipopolysaccharide (LPS), a Gram-positive toxins, fungal toxins, glycosylphosphatidylinositol (GPI), or modulation of RIG-1 gene expression.

n=10 per group. A repeated ANOVA with an unstructured covariance structure was used to compare percent of baseline body weights between treatment groups over days 12-16 of the dosing period. In the presence of a statistically significant treatment by time interaction, comparisons between the treatment groups were made at day 16 for the percent of baseline body weights using an ANOVA suitable for the completely randomized design. * is p<0.0001 versus Control+IgG at day 16, t is p<0.0001 versus hGDF15+PF-06946860 at day 16.

Figure 9:
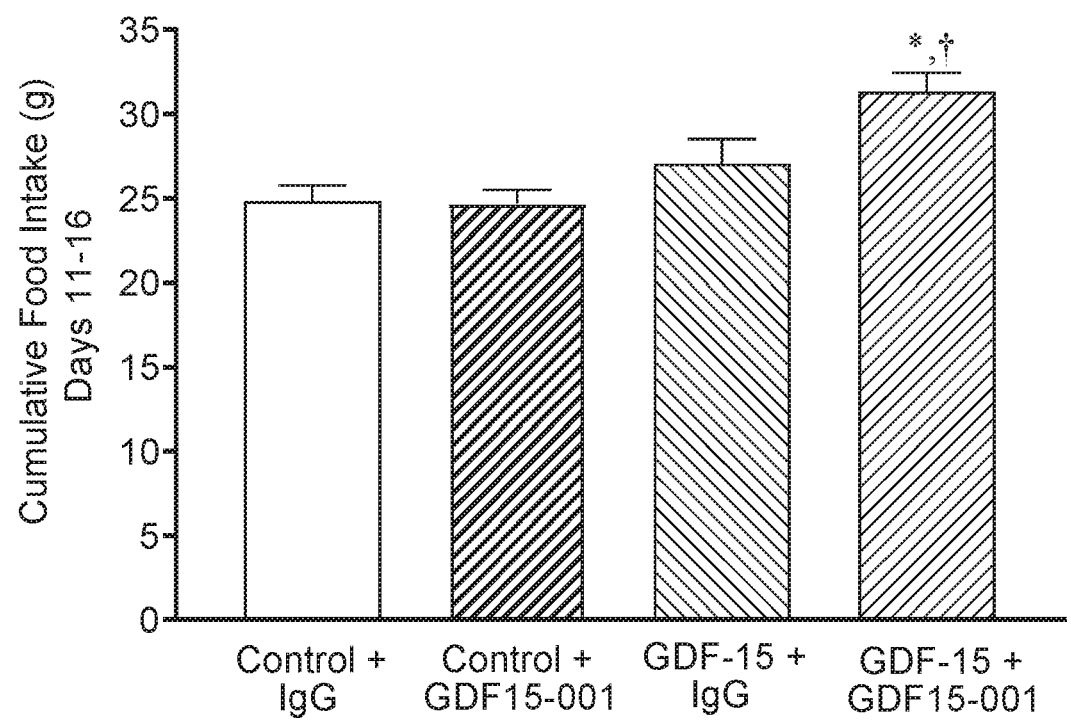

FIG. 9 shows a graph depicting the ability of GDF15_001 to increase food intake following GDF15 treatment in healthy mice. Healthy male C57Bl6N mice were treated with GDF15_001 (30 mg/kg, SC, Q3D) or IgG control. Food intake was measured daily, and a cumulative food intake was calculated. Values are means±SEM. n=8-10 per group. ANOVA was used for treatment group comparisons of cumulative food intake over days 11 through 16 using the Bonferroni multiple comparison adjustment. * is p<0.001 versus Control+IgG, t is p<0.001 versus Control+ GDF15_001, p=0.0505 GDF15+GDF15_001 versus GDF15+IgG.

Figure 10:
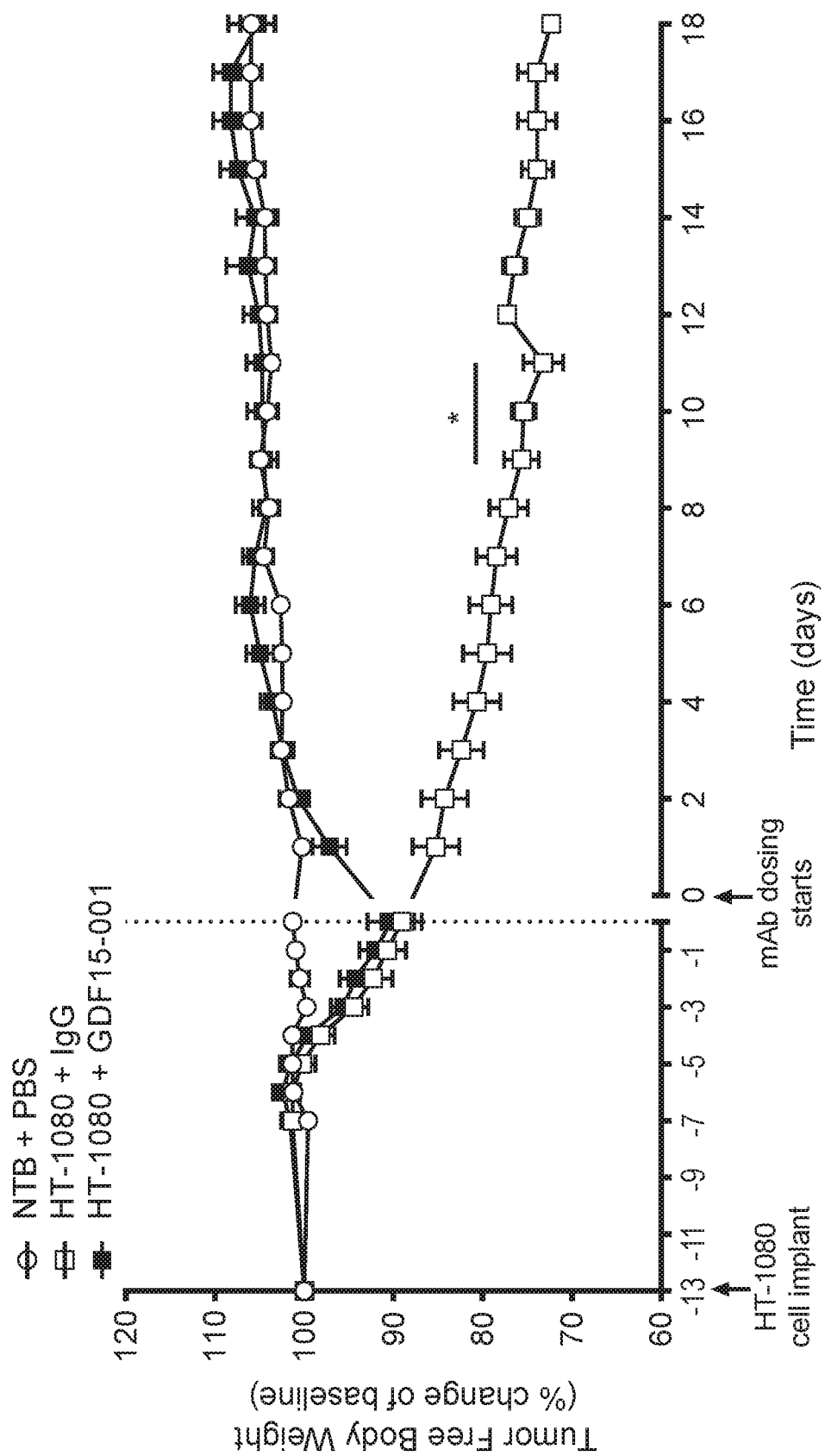

FIG. 10 shows a graph depicting the ability of GDF15_001 to reverse weight loss in HT-1080 (human fibrosarcoma cell line) tumor-bearing mice. Arrows point to the timings of the HT-1080 cell subcutaneous implant (day −13) and the first mAb dose (day 0). Female severe combined immunodeficient mice were treated with GDF15_001 (10 mg/kg, SC, Q3D) or IgG control. Values are means±SEM. n=9-10 per group. Repeated measures ANOVA with an autoregressive (1) covariance structure was used to compare percent change from baseline weights between treatment groups over days 9-11 of the dosing period (where disease had stabilized, and animals had not started dropping out due to weight loss). *=p<0.0001 HT-1080+IgG versus NTB+PBS and HT-1080+GDF15_001 (days 9-11).

Figure 11:
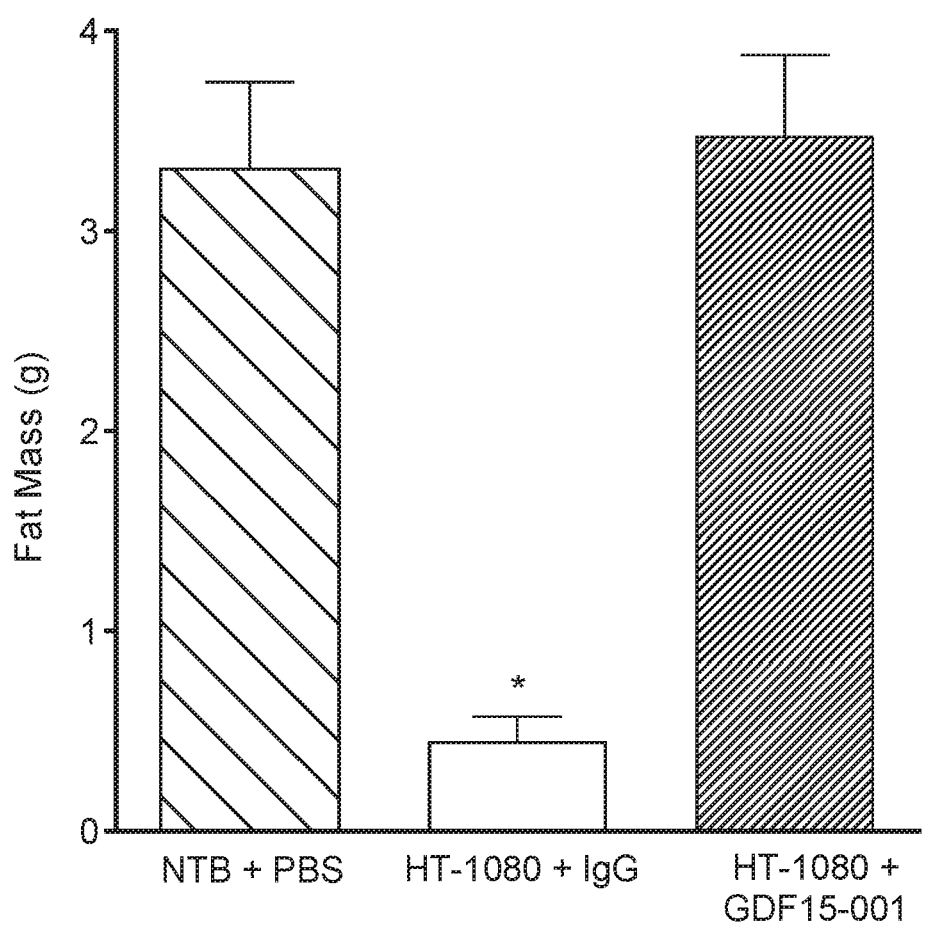

FIG. 11 shows a graph depicting the ability of GDF15_001 to reverse fat mass loss in HT-1080 (human fibrosarcoma cell line) tumor-bearing mice. Female severe combined immunodeficient mice were implanted (subcutaneous) with HT-1080 cells on day −13 followed by the first mAb dose starting on day 0. mAb treatment with GDF15_001 (10 mg/kg, SC, Q3D) or IgG control was continued for 18 days. Body composition was measured at day 18 via echo MRI. Values are means±SEM. n=9-10 per group. Statistical analysis performed with ANOVA. *=p<0.0001 HT-1080+IgG versus NTB+PBS and HT-1080+GDF15_001.

Figure 12:
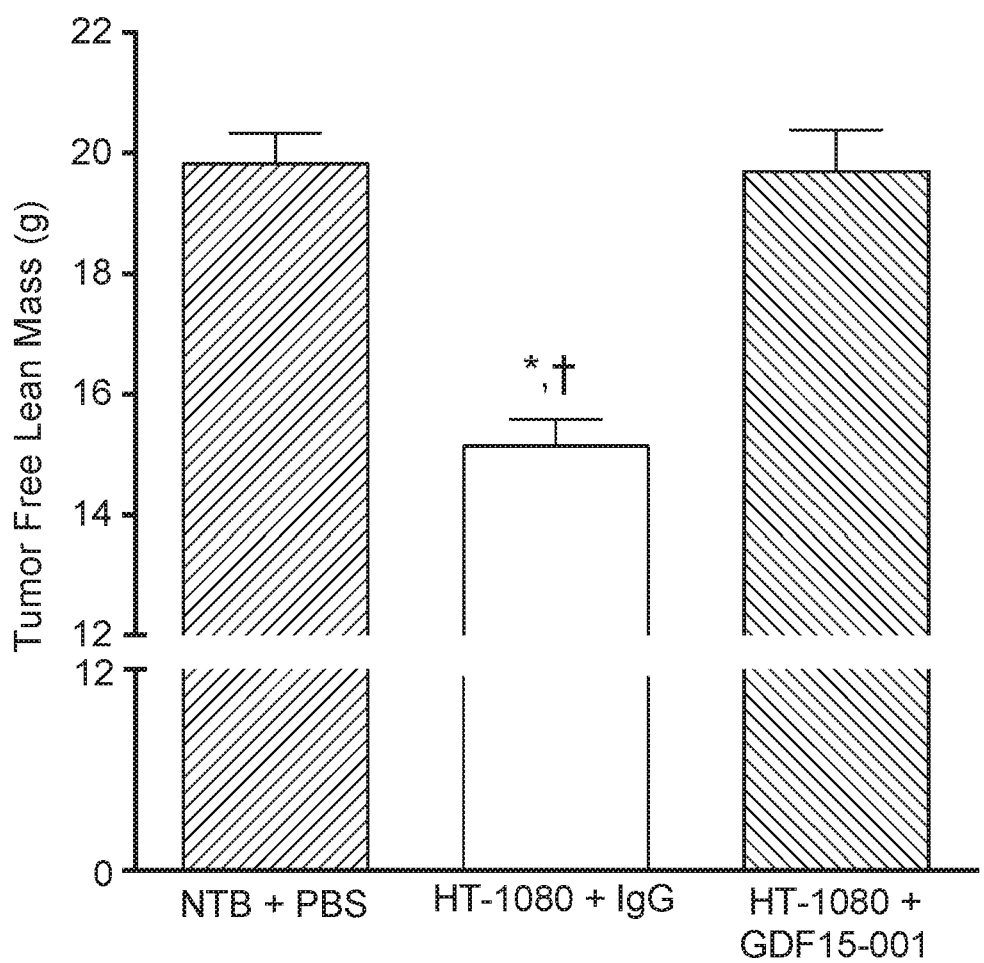

FIG. 12 shows a graph depicting the ability of GDF15_001 to reverse tumor free lean tissue mass loss in HT-1080 (human fibrosarcoma cell line) tumor-bearing mice. Female severe combined immunodeficient mice were implanted (subcutaneous) with HT-1080 cells on day −13 followed by the first mAb dose starting on day 0. mAb treatment with GDF15_001 (10 mg/kg, SC, Q3D) or IgG control was continued for 18 days. Body composition was measured at day 18 via echo MRI. Values are means±SEM. n=9-10 per group. Statistical analysis performed with ANOVA. *=p<0.001 HT-1080+IgG versus NTB+PBS, t=p<0.0001 HT-1080+IgG versus HT-1080+GDF15_001.

Figure 13:
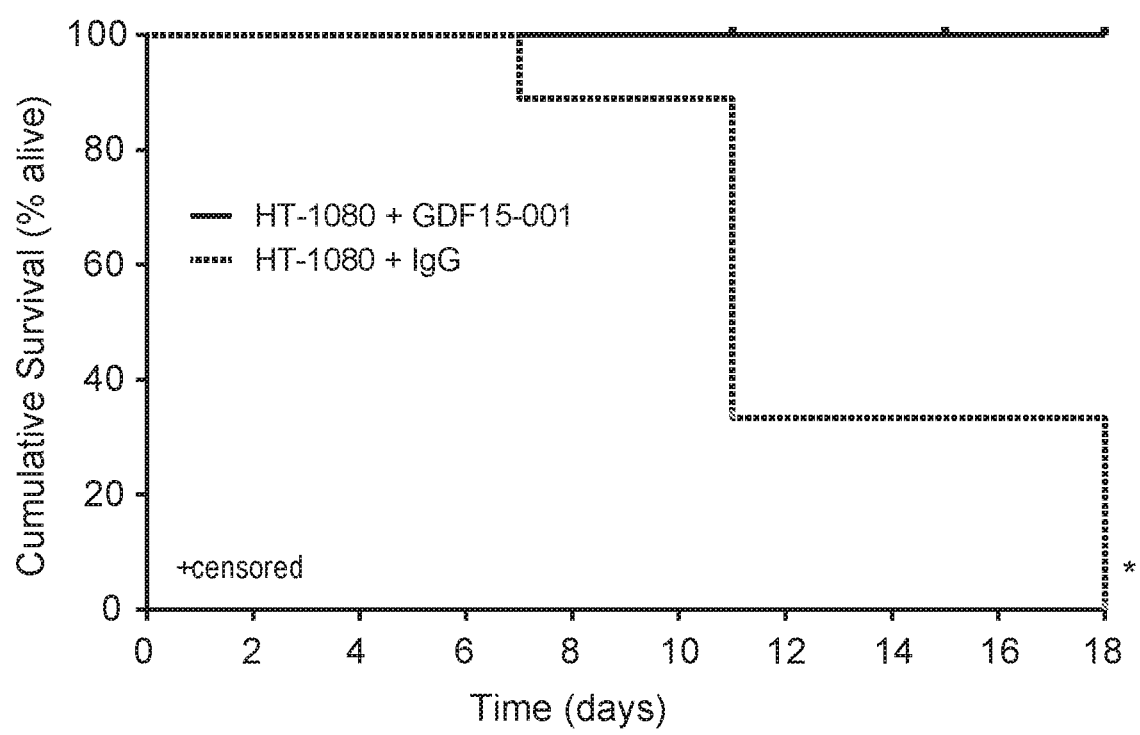

FIG. 13 shows a graph depicting the ability of GDF15_001 to prolong survival in HT-1080 (human fibrosarcoma cell line) tumor-bearing mice. Female severe combined immunodeficient mice were implanted (subcutaneous) with HT-1080 cells on day −13 followed by the first mAb dose starting on day 0. mAb treatment with GDF15_001 (10 mg/kg, SC, Q3D) or IgG control was continued until death or euthanasia (determined by poor health and/or >30% weight loss according to Institutional Animal Care and Use Committee guidelines). n=9-10 per group. Kaplan-Meier survival curves were fit to failure-time data using a log-rank statistic to compare treatment groups. * is p<0.0001 versus HT-1080+GDF15_001 group.

Figure 14:
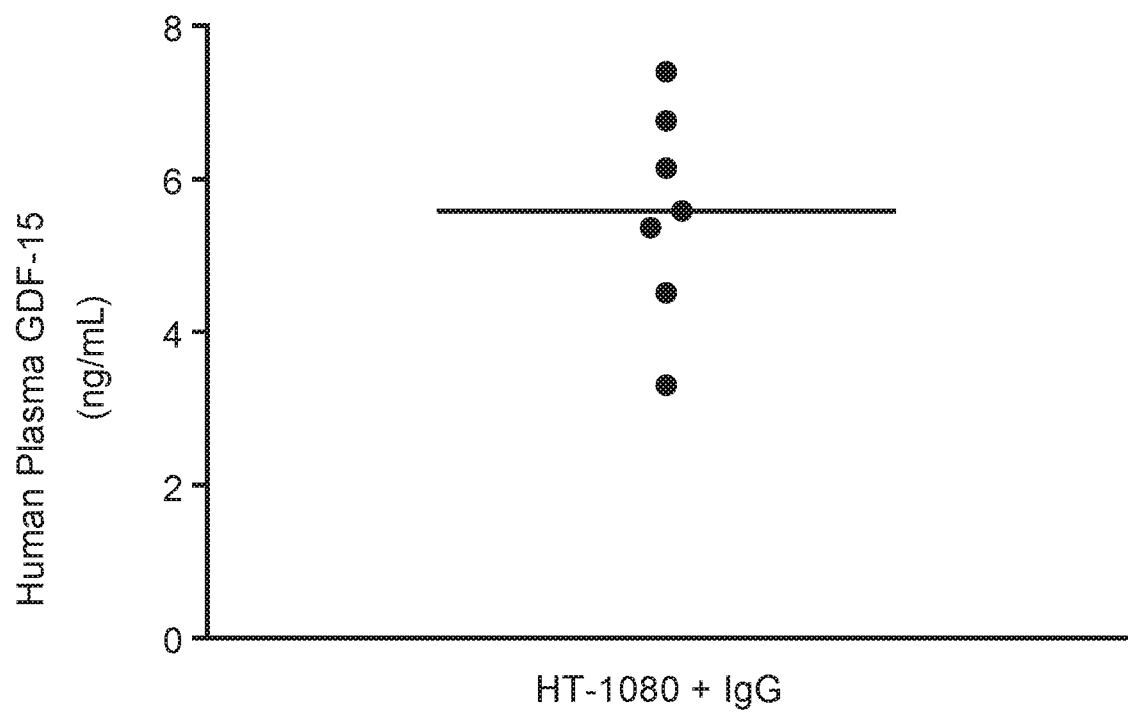

FIG. 14 shows a graph depicting the human plasma GDF15 concentration in HT-1080 (human fibrosarcoma cell line) tumor-bearing mice housed at thermoneutrality (86° F.). Female severe combined immunodeficient mice were implanted (subcutaneous) with HT-1080 cells on day −13 followed by the first mAb (IgG control, 10 mg/kg, SC, Q3D) dose starting on day 0. Plasma GDF15 was measured on day 18 via ELISA (R&D Systems DGD150). Horizontal line represents mean. n=7.

Figure 15:
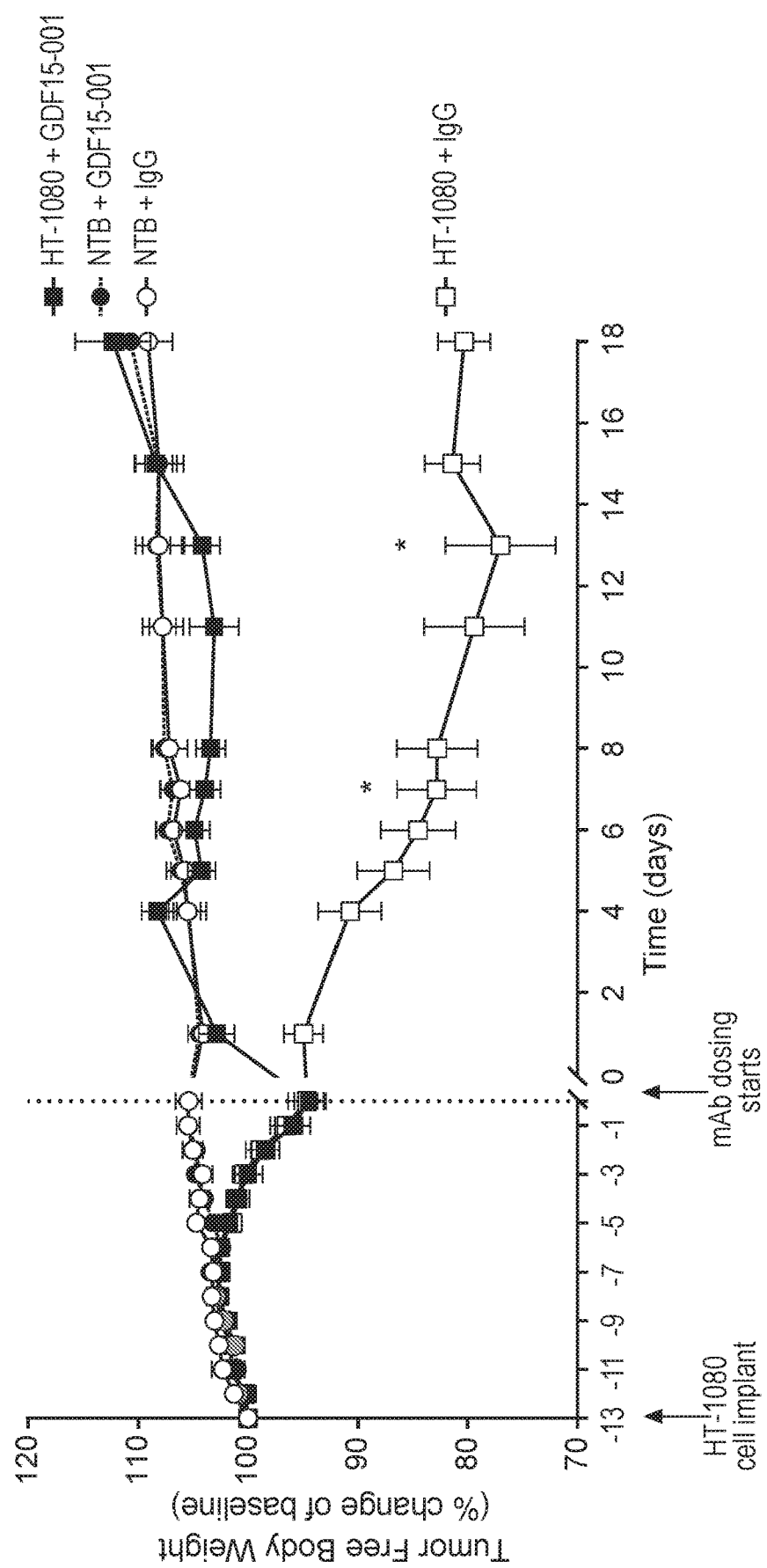

FIG. 15 shows a graph depicting the ability of GDF15_001 to reverse weight loss in HT-1080 (human fibrosarcoma cell line) tumor-bearing mice housed at thermoneutrality (86° F.). Arrows point to the timings of the HT-1080 cell subcutaneous implant (day −13) and the first mAb dose (day 0). Female severe combined immunodeficient mice were treated with GDF15_001 (10 mg/kg, SC, Q3D) or IgG control. Values are means±SEM. n=10 per group. Repeated measures ANOVA with an unstructured covariance structure was used to compare percent of baseline body weights between treatment groups over days 1-13 of the dosing period followed by a comparison between the treatment groups at day 7 and day 13 using an ANOVA. Comparisons of interest between the treatment groups were then tested with t-tests using a pooled estimate of variance from the ANOVA. The Bonferroni multiple comparison adjustment was used to control the experiment-wise error rate for treatment group comparisons. *=p<0.0001 versus NTB+IgG and HT-1080+GDF15_001 (days 7 and 13).

Figure 16:
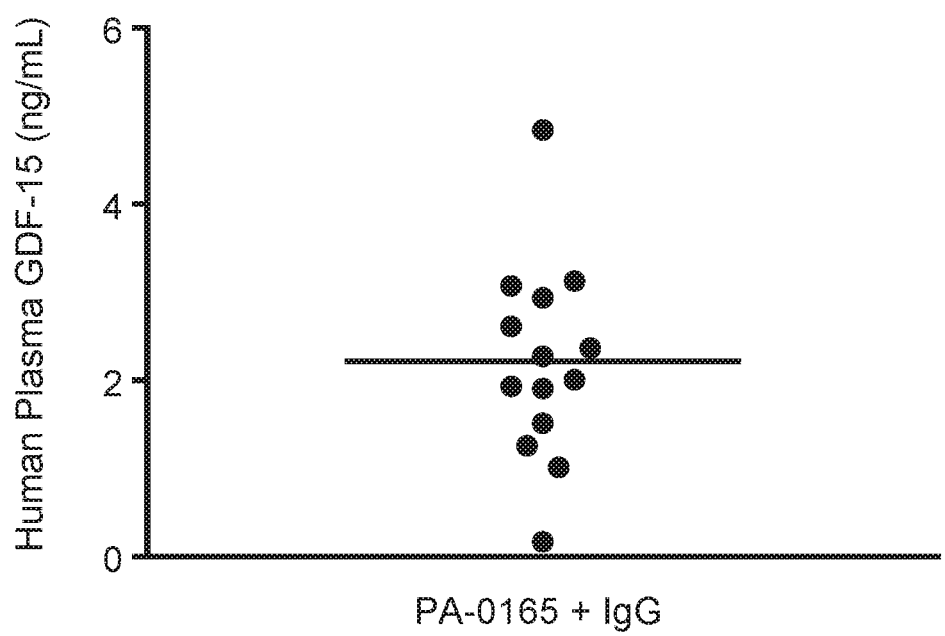

FIG. 16 shows a graph depicting the human plasma GDF15 concentration in PA-1065 (derived from pancreatic tumor liver metastasis) tumor-bearing mice. Female severe combined immunodeficient mice were implanted (subcutaneous) with PA-0165 tumor tissue on day −18 followed by the first mAb (IgG control, 10 mg/kg, SC, Q3D) dose starting on day 0. Plasma GDF15 was measured on day 27 via ELISA (R&D Systems DGD150). Horizontal line represents mean. n=14.

Figure 17:
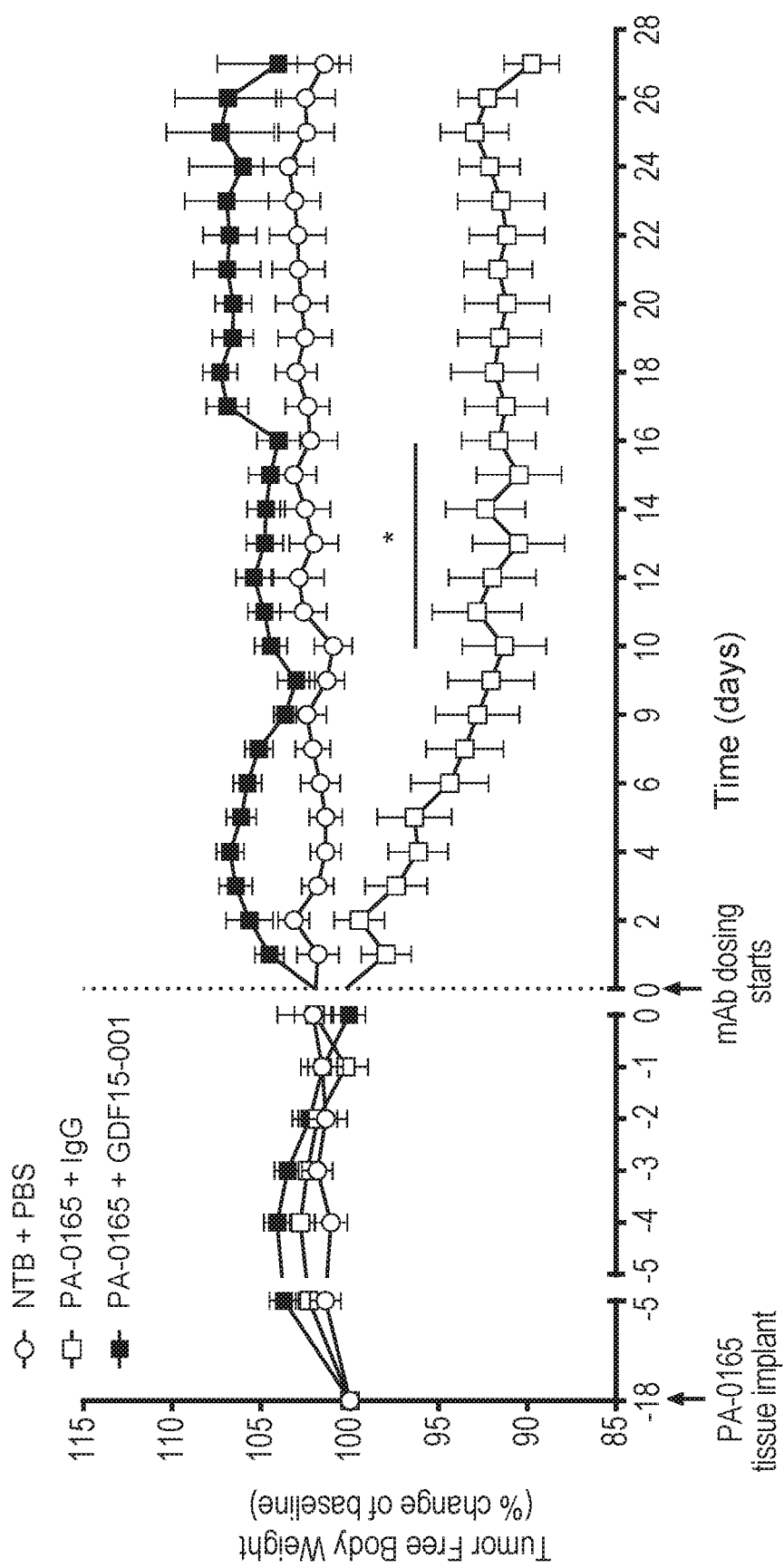

FIG. 17 shows a graph depicting the ability of GDF15_001 to prevent weight loss in PA-0165 (derived from human pancreatic tumor liver metastasis) tumor-bearing mice. Arrows point to the timings of the PA-0165 tumor tissue subcutaneous implant (day −18) and the first mAb dose (day 0). Female severe combined immunodeficient mice were treated with GDF15_001 (10 mg/kg, SC, Q3D) or IgG control. Values are means±SEM. n=10-17 per group. A repeated measures analysis of variance, with an unstructured covariance structure, was used to compare percent of baseline body weights between treatment groups over days 10-16 of the dosing period. In the presence of a statistically significant treatment by time interaction, comparisons between the treatment groups were made at day 16 with t-tests using a pooled estimate of variance from the repeated measures ANOVA. The Bonferroni multiple comparison adjustment was used to control the experiment-wise error rate for treatment group comparisons. *=p<0.0001 versus NTB+PBS and PA-0165+GDF15_001.

Figure 18:
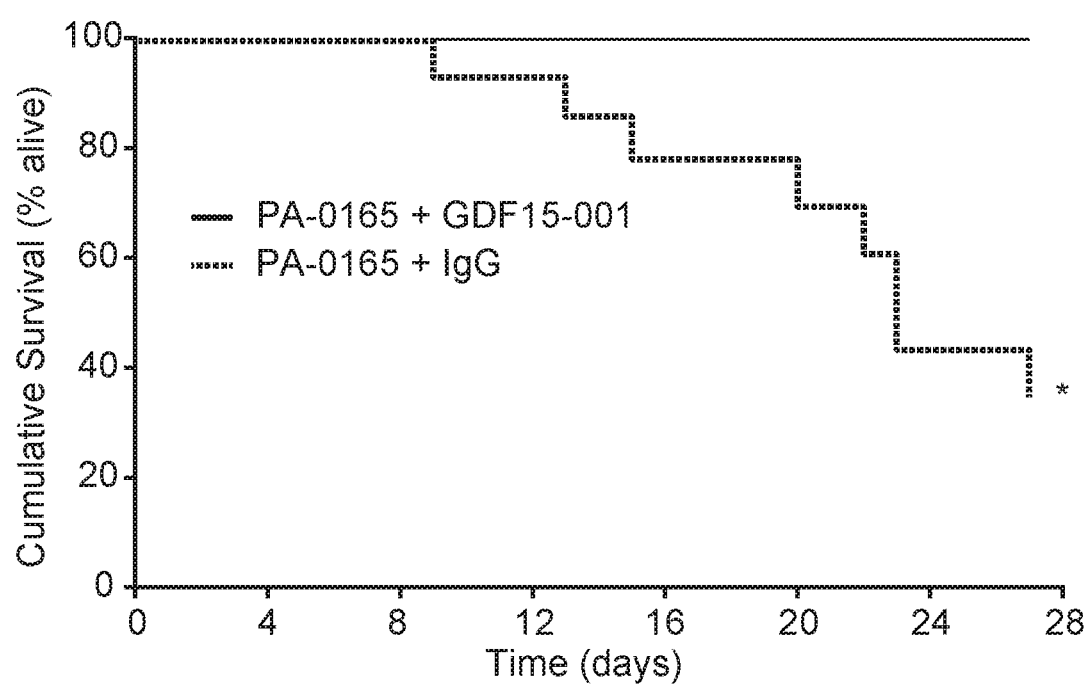

FIG. 18 shows a graph depicting the ability of GDF15_001 to prolong survival in PA-1065 (derived from human pancreatic tumor liver metastasis) tumor-bearing mice. Female severe combined immunodeficient mice were implanted (subcutaneous) with PA-0165 tumor tissue 18 days before the first mAb dose starting on day 0. mAb treatment with GDF15_001 (10 mg/kg, SC, Q3D) or IgG control was continued until death or euthanasia (determined by poor health and/or >30% weight loss according to Institutional Animal Care and Use Committee guidelines). n=17 per group. Kaplan-Meier survival curves were fitted to failure-time data using a log-rank statistic to compare the survival rates between the treatment groups. * is p<0.01 versus PA-0165+GDF15_001.

Figure 19:
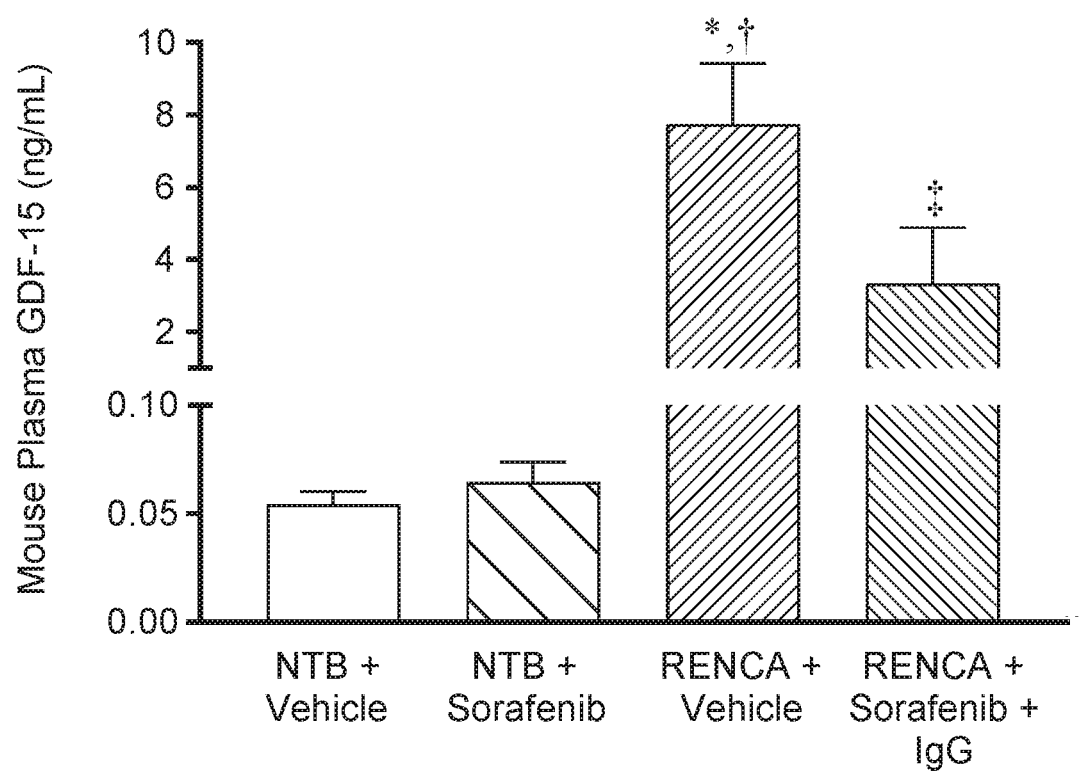

FIG. 19 shows a graph depicting the murine plasma GDF15 concentration in RENCA (murine renal adenocarcinoma cell line) tumor-bearing mice at thermoneutrality (86° F.). Female Balb/c mice were implanted (subcutaneous) with RENCA cells and plasma GDF15 was measured at the end of the study (corresponds to FIG. 17) via ELISA (R&D Systems MGD150). Values are means. n=10-12 per group. ANOVA with the Kenward-Roger adjustment for heterogeneous variances was used for cumulative food intake and natural log transformed plasma GDF15 comparison between treatment groups using the Tukey-Kramer multiple comparison adjustment to control the experiment-wise error rate. Geometric means were produced for natural log transformed GDF15 means and 95% confidence intervals estimates. All response variables were evaluated for meeting the normality assumption with the Shapiro-Wilks Test and Q-Q Plots. * is p<0.0001 different from NTB+Vehicle, j is p<0.0001 different from NTB+Sorafenib, † is p<0.01 versus RENCA+Sorafenib+IgG.

Figure 20:
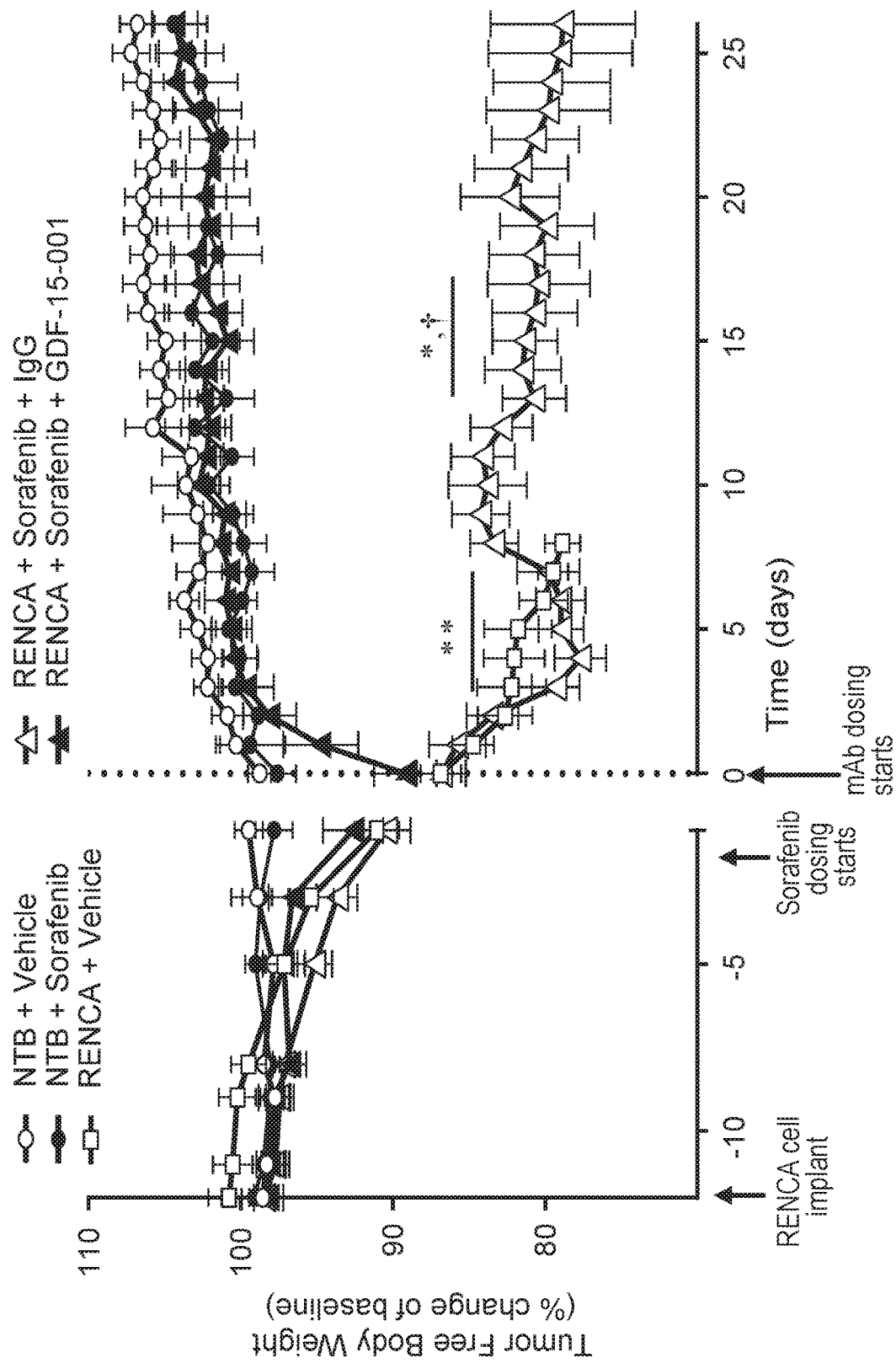

FIG. 20 shows a graph depicting the ability of GDF15_001 to reverse weight loss in RENCA (murine renal adenocarcinoma cell line) tumor-bearing mice treated with anti-cancer agent and housed at thermoneutrality (86° F.). Arrows point to the timings of the RENCA cell subcutaneous implant (day −12), first Sorafenib dose (day −2) and the first mAb dose (day 0). Female Balb/c mice were treated with Sorafenib (15 mg/kg, PO, QD) and GDF15_001 (10 mg/kg, SC, Q3D) or IgG control. Values are means±SEM. n=10-12 per group. Repeated measures ANOVA with a heterogeneous autoregressive (1) covariance structure was used to compare percent change from baseline weights between treatment groups over days 3-7 and 13-17 of the dosing period. The Tukey-Kramer multiple comparison adjustment was used to control the experiment-wise error rate for treatment group comparisons in the repeated measures ANOVA. ** is p<0.0001 different from NTB+Vehicle (days 3-7), * is p<0.0001 different from NTB+Sorafenib (days 13-17), † is p<0.0001 versus RENCA+Sorafenib+GDF15_001 (days 13-17).

Figure 21:
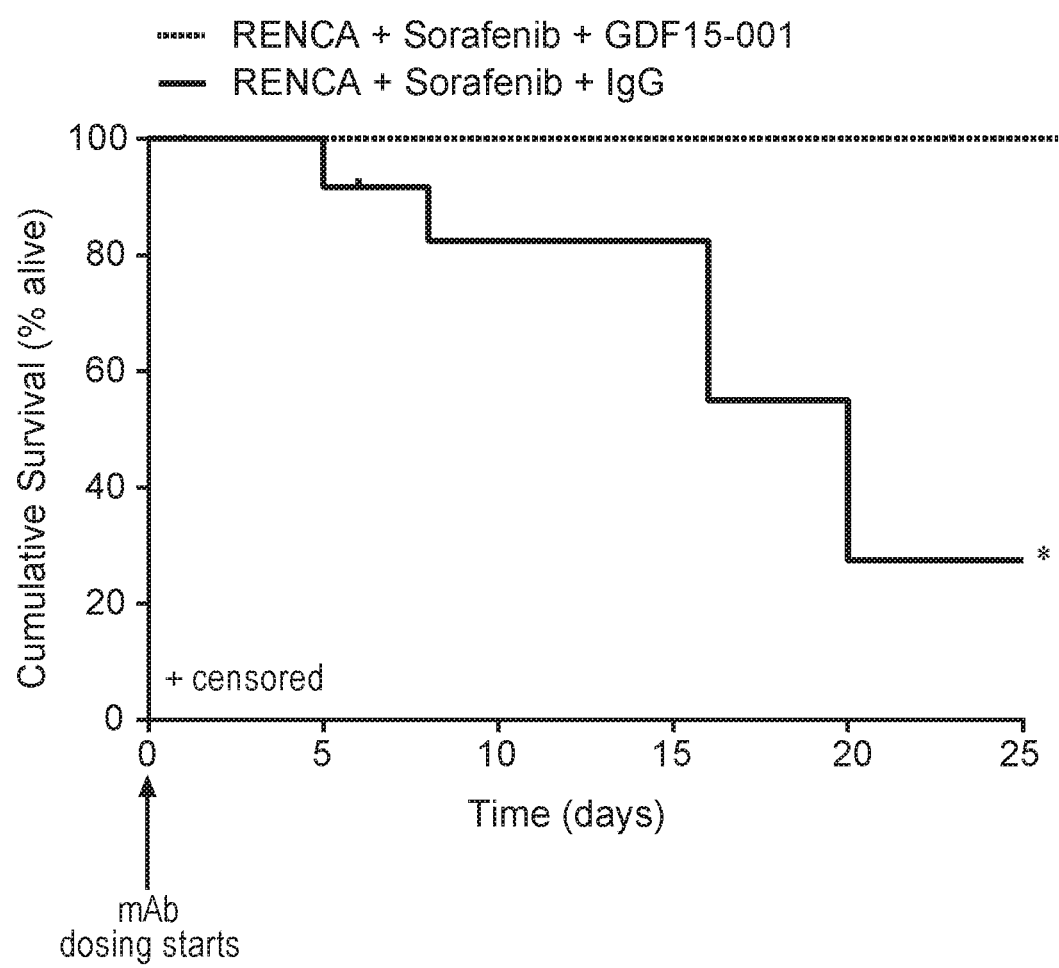

FIG. 21 shows a graph depicting the ability of GDF15_001 to prolong survival in RENCA (murine renal adenocarcinoma cell line) tumor-bearing mice treated with anti-cancer agent and housed at thermoneutrality (86° F.). Female Balb/c mice were implanted (subcutaneous) with RENCA cells 10 days before the first Sorafenib dose followed by the first mAb dose 2 days later (corresponds to day 0). Sorafenib (15 mg/kg, PO, QD) and mAb treatment with GDF15_001 (10 mg/kg, SC, Q3D) or IgG control was continued until death or euthanasia (determined by poor health and/or >30% weight loss according to Institutional Animal Care and Use Committee guidelines). n=10-12 per group. Kaplan-Meier survival curves were fitted to failure-time data using a log-rank statistic to compare the survival rates between the treatment groups. * is p<0.01 versus RENCA+Sorafenib+GDF15_001.

Figure 22:
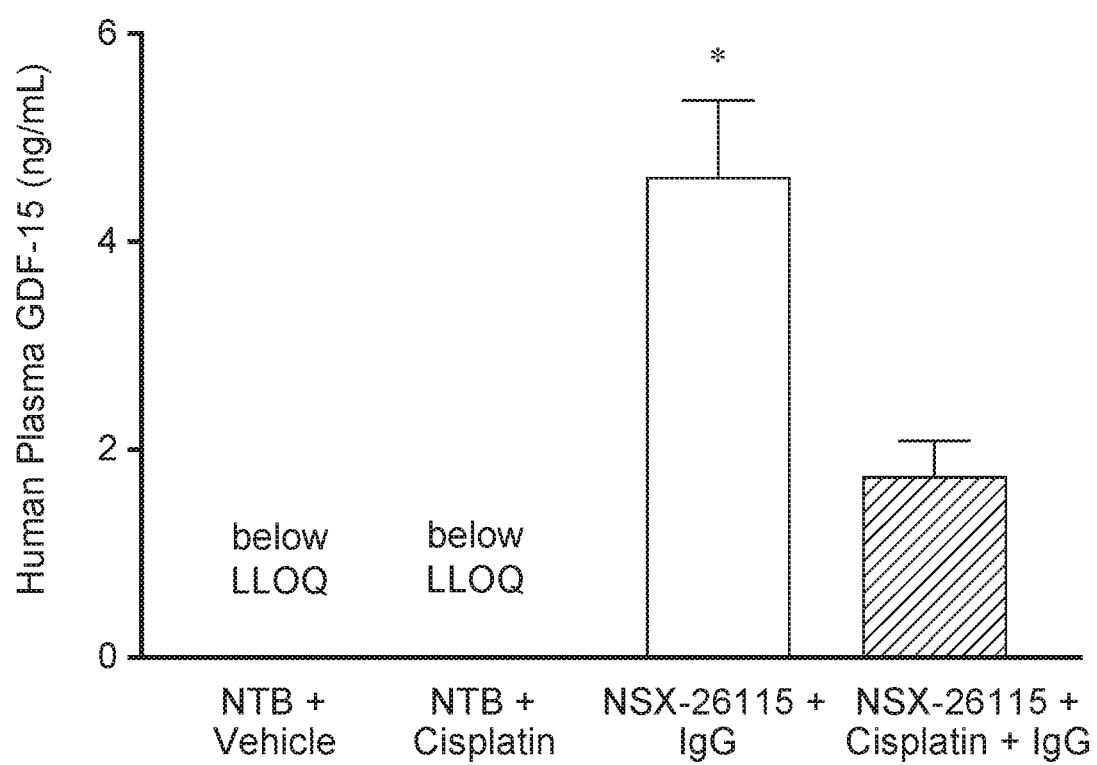

FIG. 22 shows a graph depicting the human plasma GDF15 concentration in NSX-26115 (derived from human non-small cell lung carcinoma adenocarcinoma) tumor-bearing mice. Female severe combined immunodeficient mice were implanted (subcutaneous) with NSX-26115 tumor tissue and plasma GDF15 was measured at the end of the study (corresponds to FIG. 20) via ELISA (R&D Systems DGD150). n=10-12 per group. An ANOVA with the Kenward-Roger adjustment for heterogeneous variances was used to compare GDF15 levels in plasma between the different treatment groups. Normality was assessed using histograms and the Shapiro-Wilk test and homogeneity of variance was assessed using Levene's test. Pairwise comparisons of the treatment group were adjusted for multiple comparisons using the Tukey-Kramer method. * is p<0.01 versus all other groups.

Figure 23:
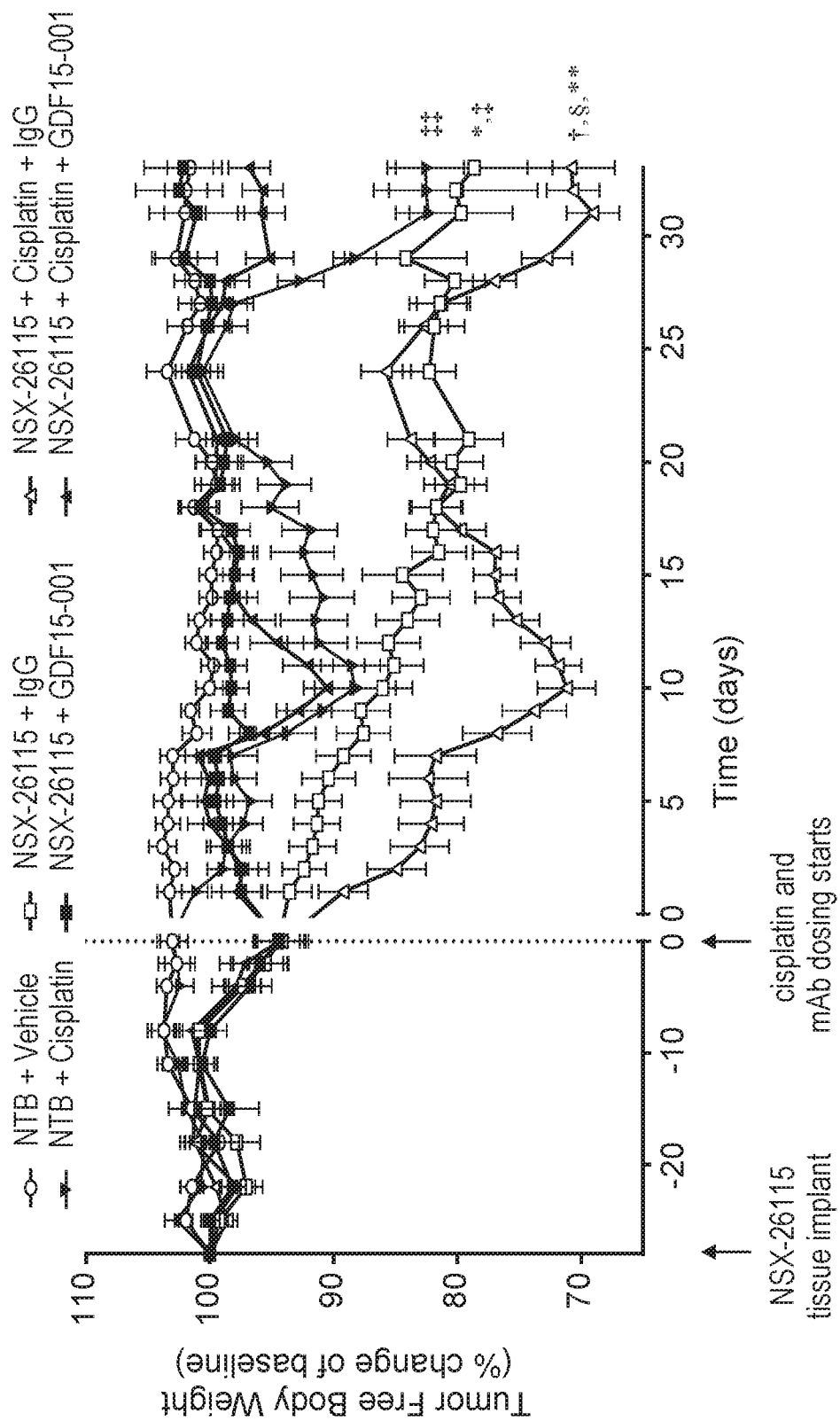

FIG. 23 shows a graph depicting the ability of GDF15_001 to reverse weight loss in NSX-26115 (derived from human non-small cell lung carcinoma adenocarcinoma) tumor-bearing mice treated with or without anti-cancer agent. Arrows point to the timings of the NSX-26115 tumor tissue subcutaneous implant (day −30), first Cisplatin dose (day 0) and the first mAb dose (day 0). Female severe combined immunodeficient mice were treated with Cisplatin (5 mg/kg, IP, Q7D) and/or GDF15_001 (10 mg/kg, SC, Q3D) or IgG control. Values are means±SEM. n=10-12 per group. A repeated ANOVA with a first-order autoregressive covariance structure was used to compare the percent change in body weight over time between treatment groups using data from days 17-19. At this time disease was in a stabilized state with no significant interaction between treatment and day. Multivariate normality was assessed using Mardia's tests for skewness and kurtosis. A one-way ANOVA by treatment was conducted at day 10 to assess differences between treatment groups at the day of maximum cisplatin effect, as informed by the dosing schedule. All pairwise comparisons of treatment groups were adjusted for multiple comparisons using the Tukey-Kramer method. * is p<0.0001 versus NTB+Vehicle (days 17-19), is p<0.0001 versus NSX-26115+GDF15_001 (days 17-19), † is p<0.001 versus NTB+Cisplatin (days 17-19), § is p<0.0001 versus NSX-26115+Cisplatin+GDF15_001 (days 17-19), is p<0.01 versus NTB+Vehicle (day 10), ** is p<0.0001 versus NSX-26115+IgG (day 10).

Figure 24:
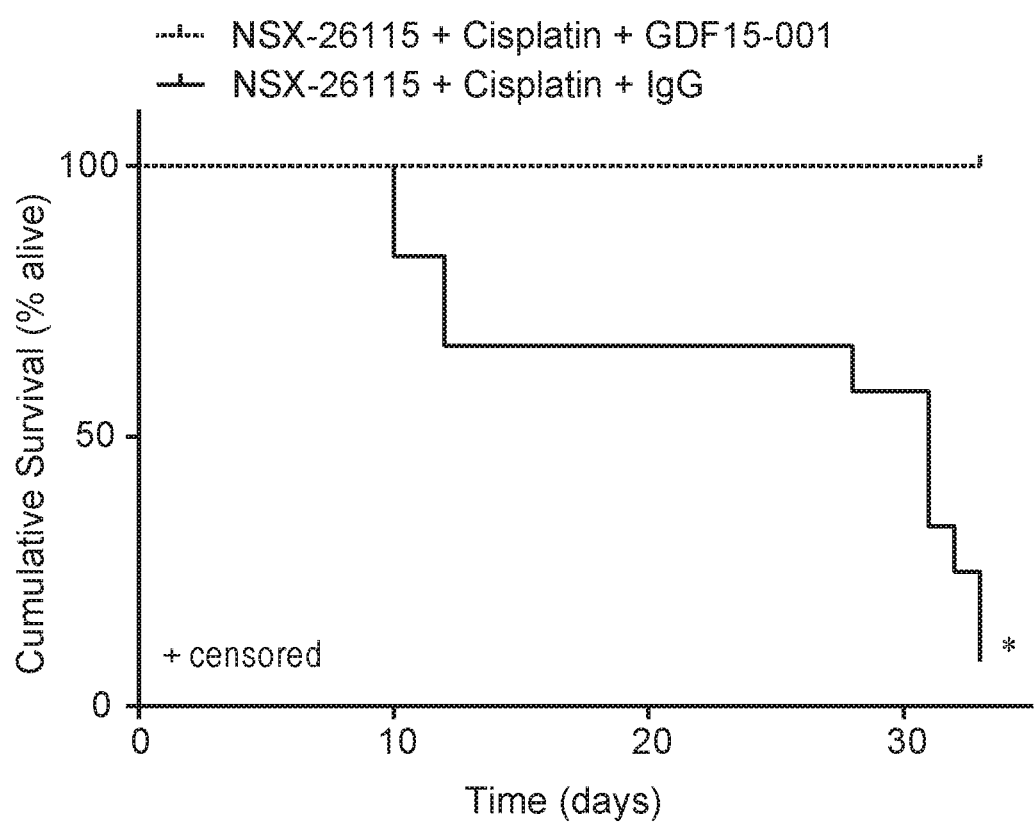

FIG. 24 shows a graph depicting the ability of GDF15_001 to prolong survival in NSX-26115 (derived from human non-small cell lung carcinoma adenocarcinoma) tumor-bearing mice treated with anti-cancer agent. Female severe combined immunodeficient mice were implanted (subcutaneous) with NSX-26115 tumor tissue 30 days before the first Cisplatin and mAb dose (corresponds to day 0). Cisplatin (5 mg/kg, IP, Q7D) and mAb treatment with GDF15_001 (10 mg/kg, SC, Q3D) or IgG control was continued until death or euthanasia (determined by poor health and/or >30% weight loss according to Institutional Animal Care and Use Committee guidelines). n=10-12 per group. Kaplan-Meier survival curves with a log-rank test were used to compare the survival to premature euthanization between groups. * is p<0.0001 versus NSX-26115+Cisplatin+GDF15_001.

Figure 25:
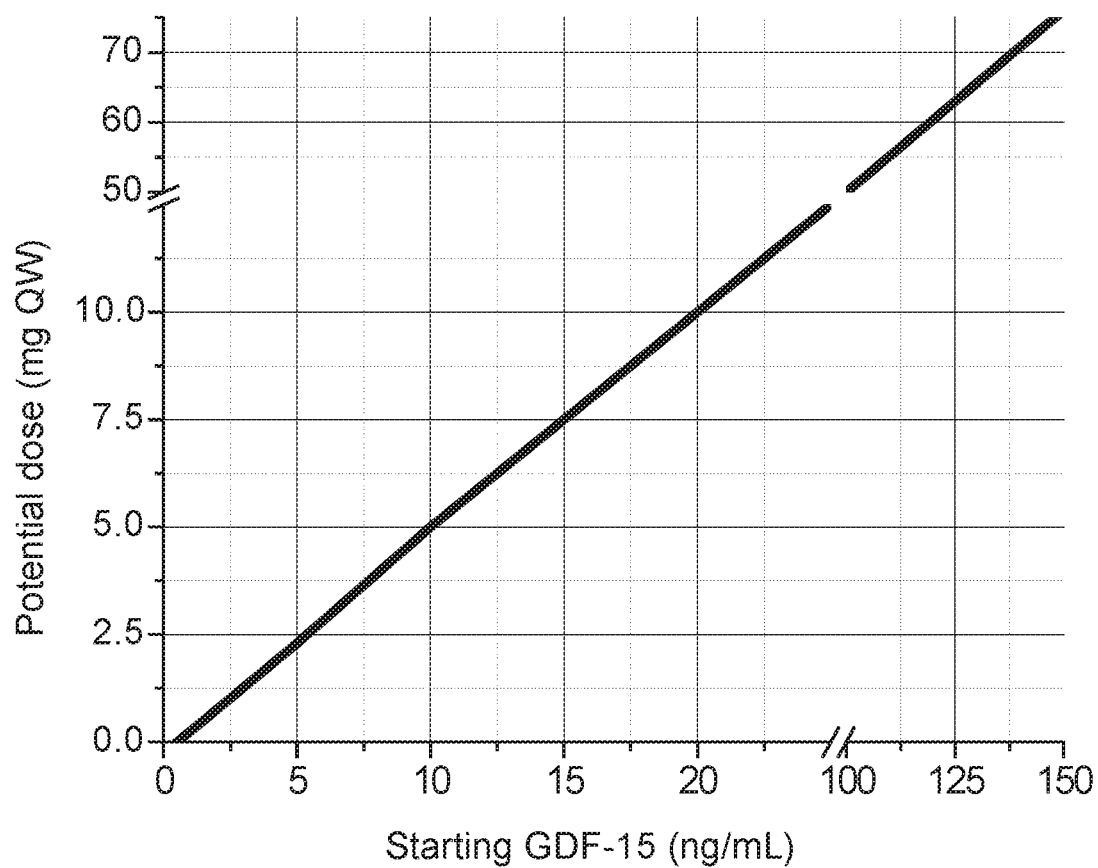

FIG. 25 shows a graph suggesting a weekly subcutaneous dose capable of reducing the free GDF15 level to less than 0.5 ng/mL in a subject, throughout the dosing interval, for GDF15_001, as a function of the starting free GDF15 level in a subject.

Figure 26:
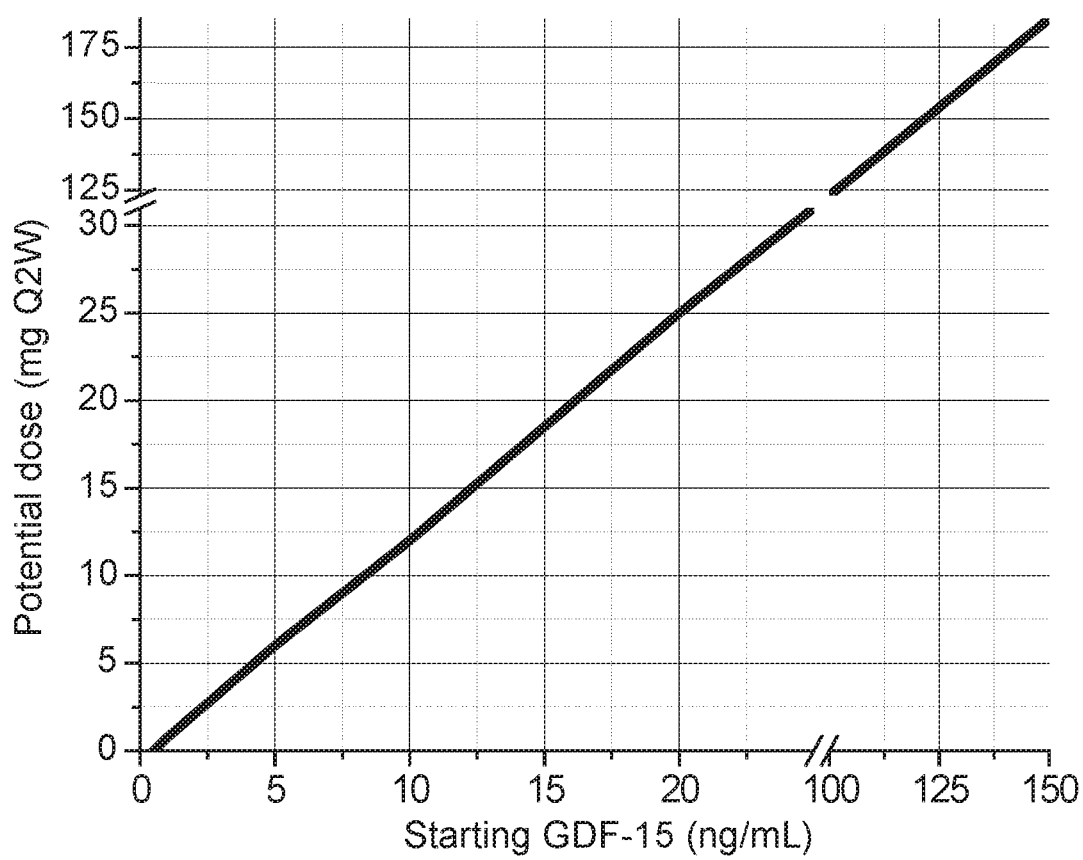

FIG. 26 shows a graph suggesting a weekly subcutaneous dose capable of reducing the free GDF15 level to less than 0.5 ng/mL in a subject, throughout the dosing interval, for GDF15_001, as a function of the starting free GDF15 level in a subject.

Figure 27:
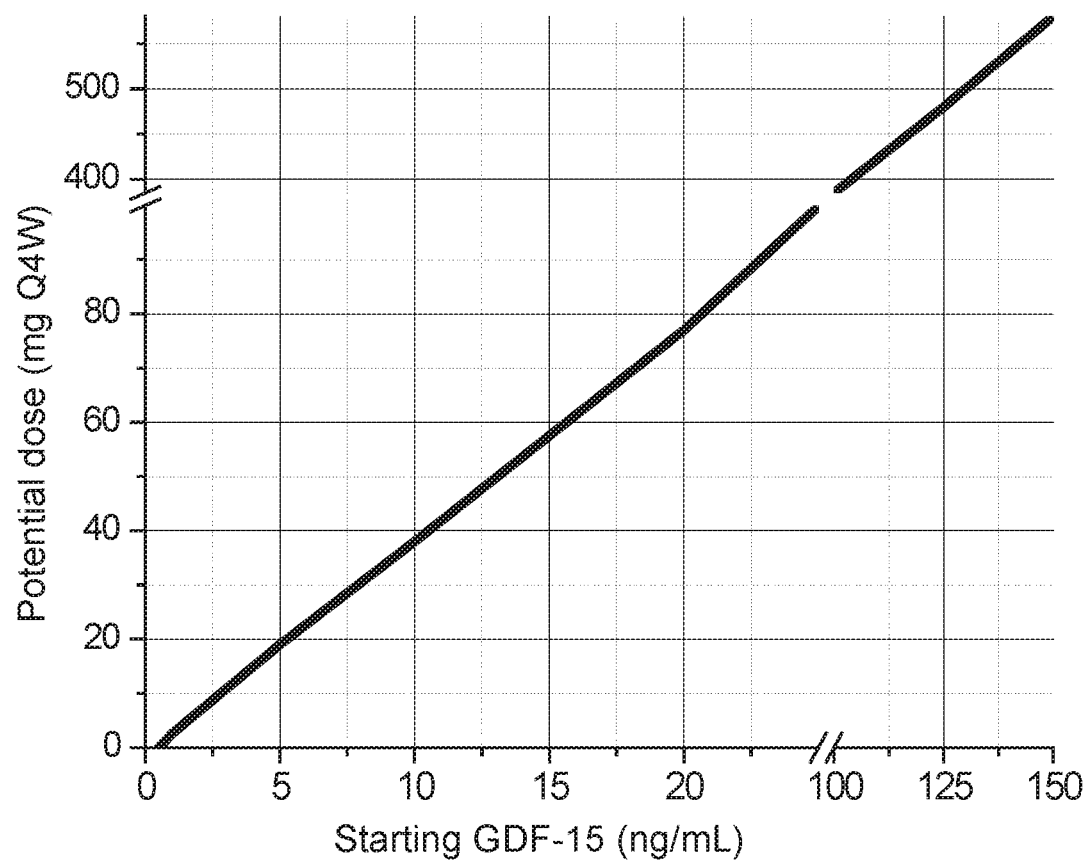

FIG. 27 shows a graph suggesting a weekly subcutaneous dose capable of reducing the free GDF15 level to less than 0.5 ng/mL in a subject, throughout the dosing interval, for GDF15_001, as a function of the starting free GDF15 level in a subject.

FIG. 28 provides a table showing the SEQ ID NOs corresponding to the GDF15 antibodies of the invention.

Figure 29:
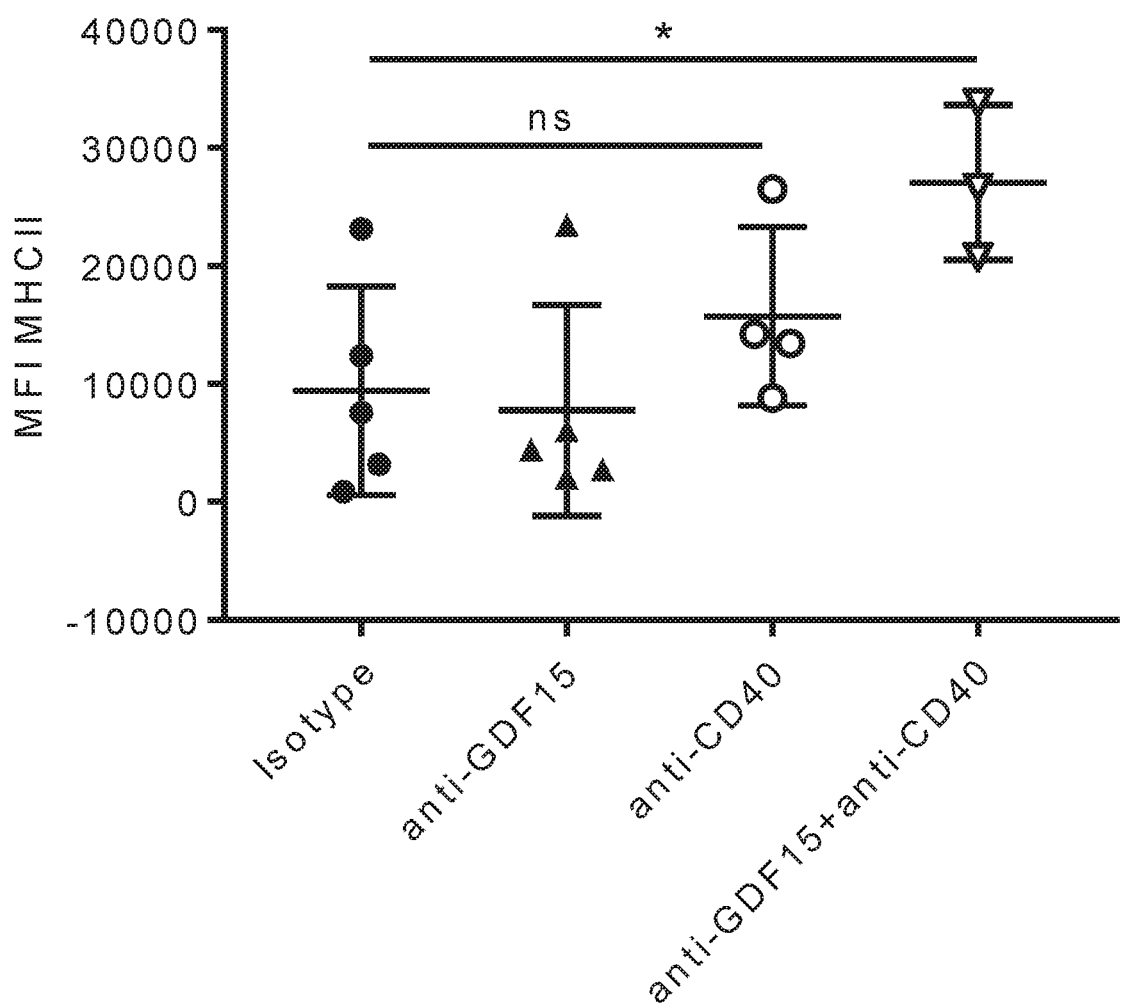

FIG. 29 depicts a graph summarizing results of anti-GDF15 treatment (solid triangles), anti-CD40 antibody treatment (open circles), and combination treatment (upside-down open triangles). MHCII expression levels are presented as mean fluorescent intensity (MFI) in a tumor infiltrating macrophage population.

Figure 30:
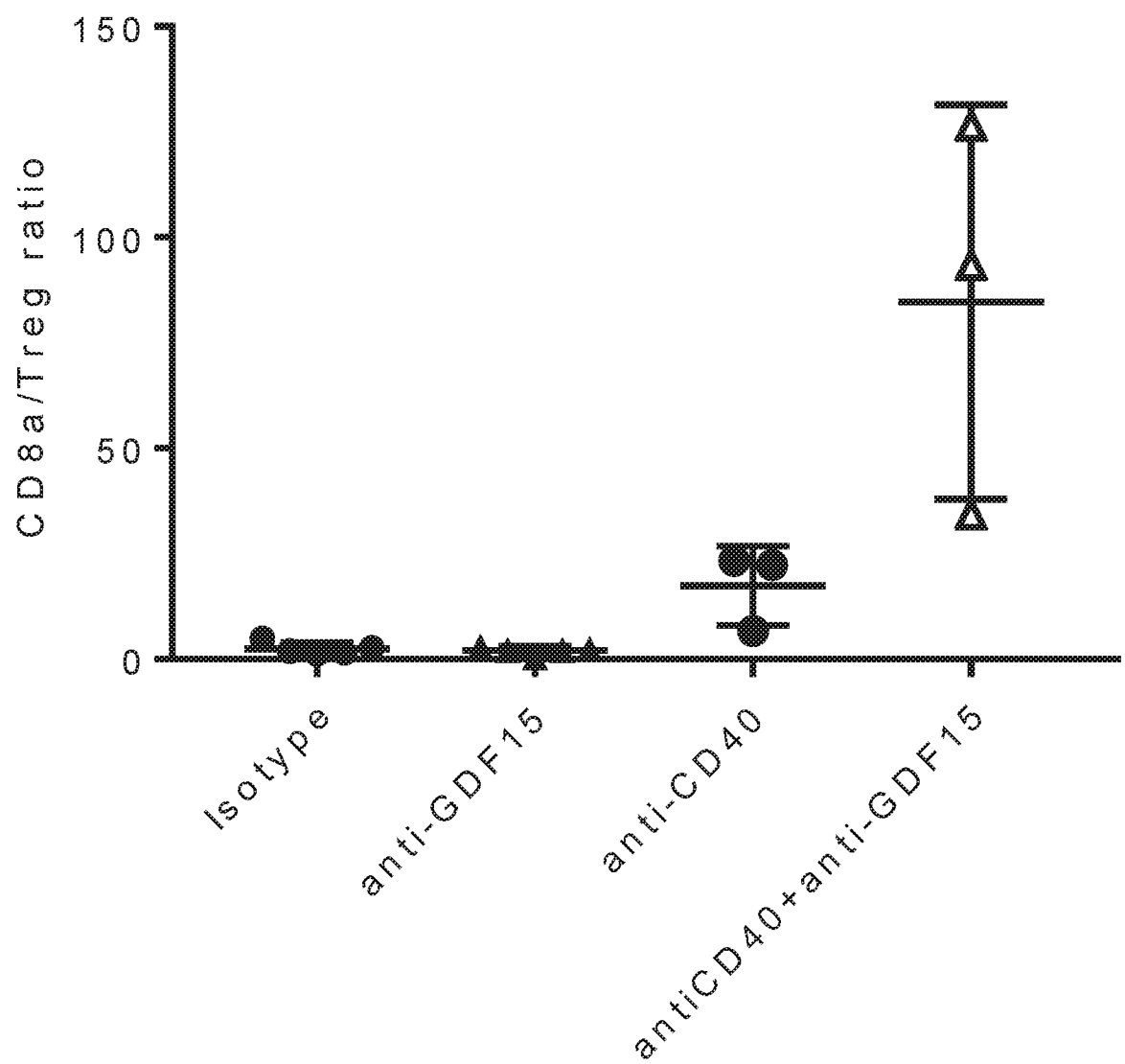

FIG. 30 depicts a graph summarizing results of anti-GDF15 treatment (solid triangles), anti-CD40 antibody treatment (open circles), and combination treatment (open triangles).

Figure 31:
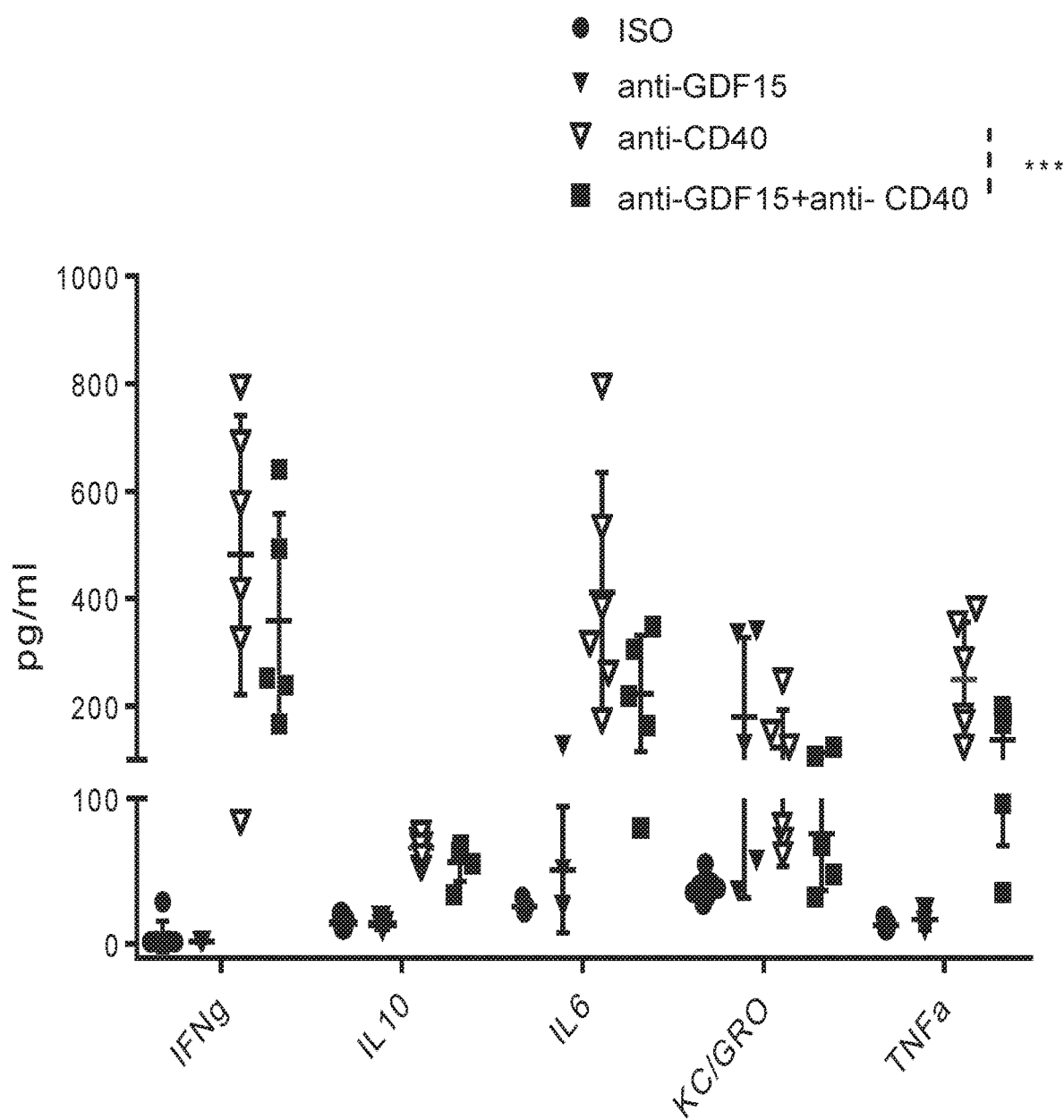

FIG. 31 depicts a graph summarizing results of anti-GDF15 treatment (upside-down solid triangles), anti-CD40 antibody treatment (open triangles), and combination treatment (solid squares).

Figure 32:
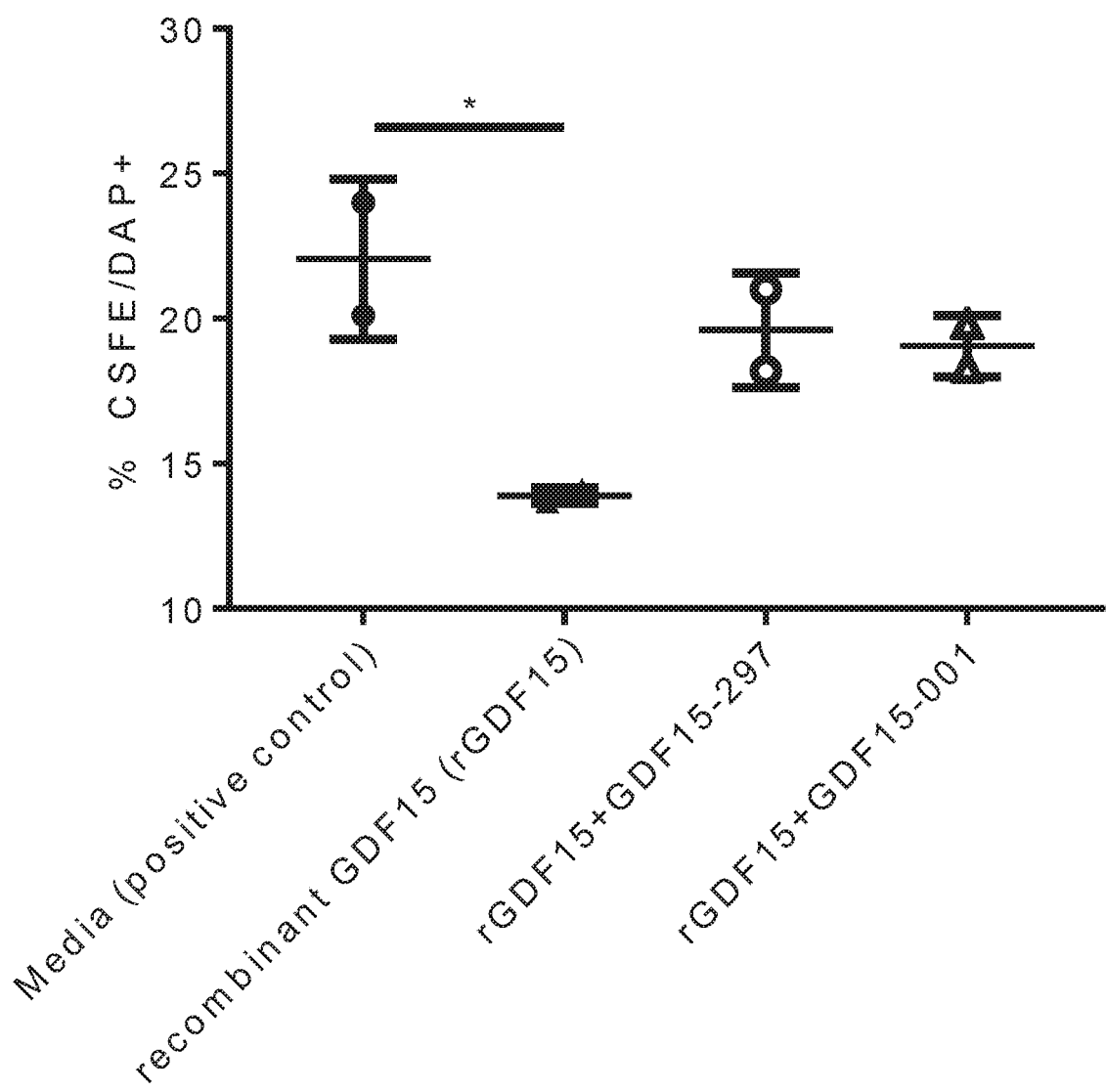

FIG. 32 depicts a graph summarizing results of anti-GD15_297 antibody treatment (open circles) and anti-GD15_001 antibody treatment (open triangles).

DETAILED DESCRIPTION OF THE INVENTION

The present invention provides antibodies, and antigen-binding fragments thereof, that specifically bind to GDF15 and reduce or inhibit GDF15 activity, including but not limited to, the ability of GDF15 to interact with GDNF family receptor α-like protein (GFRAL). The invention also provides processes for making, preparing, or producing the GDF15 antibodies. The antibodies of the invention are useful in the diagnosis, prophylaxis, and/or treatment of disorders or conditions mediated by or associated with GDF15 activity, including, but not limited to, hyperproliferative disorders characterized by GDF15, loss of muscle mass, loss of body weight, loss of fat weight, decreased food intake, and the like. The invention further encompasses expression of the antibodies, and preparation and manufacture of compositions comprising the antibodies of the invention, or antigen-binding fragments thereof, such as medicaments for the use of the antibodies.

Polynucleotides encoding antibodies that bind GDF15, or antigen-binding portions thereof, are provided. Polynucleotides encoding antibody heavy chains or light chains, or both are also provided. Host cells that express anti-GDF15 antibodies are provided. Methods of treatment using antibodies to GDF15 are provided. Such methods include, but are not limited to, methods of treating diseases associated with or mediated by GDF15 expression and/or GDF15 binding to GFRAL, including, but not limited to, inflammatory and immune diseases and hyperproliferative disorders.

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al, Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds); Gene Transfer Vectors for Mammalian Cells (J. M. Miller and M. P. Calos, eds., 1987); PCR: The Polymerase Chain Reaction, (Mullis et al, eds., 1994); Current Protocols in Immunology (J. E. Coligan et al, eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999)); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993); and updated versions thereof.

Antibodies

An "antibody" or "Ab" is an immunoglobulin molecule capable of recognizing and binding to a specific target or antigen (Ag), such as a carbohydrate, polynucleotide, lipid, polypeptide, etc., through at least one antigen recognition site, located in the variable region of the immunoglobulin molecule. As used herein, the term "antibody" can encompass any type of antibody, including but not limited to monoclonal antibodies, polyclonal antibodies, antigen-binding fragments (or portion), of intact antibodies that retain the ability to specifically bind to a given antigen (e.g. GDF15).

The term "antigen" refers to the molecular entity used for immunization of an immunocompetent vertebrate to produce the antibody that recognizes the Ag or to screen an expression library (e.g., phage, yeast or ribosome display library, among others). Herein, Ag is termed more broadly and is generally intended to include target molecules that are specifically recognized by the Ab, thus including fragments or mimics of the molecule used in an immunization process for raising the Ab or in library screening for selecting the Ab. Thus, for antibodies of the invention binding to GDF15, full-length GDF15 from mammalian species (e.g., human, monkey, mouse and rat GDF15), including monomers and multimers, such as dimers, trimers, etc. thereof, as well as truncated and other variants of GDF15, are referred to as an antigen.

An "antigen-binding fragment" of an antibody refers to a fragment of a full-length antibody that retains the ability to specifically bind to an antigen (preferably with substantially the same binding affinity). Examples of an antigen-binding fragment includes (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., 1989 Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al. Science 242:423-426 (1988) and Huston et al., 1988, Proc. Natl. Acad. Sci. USA 85:5879-5883. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger et al, 1993, Proc. Natl. Acad. Sci. USA 90:6444-6448; Poljak et al., 1994, Structure 2:1121-1123).

An antibody "variable domain" refers to the variable region of the antibody light chain (VL) or the variable region of the antibody heavy chain (VH), either alone or in combination. As known in the art, the variable regions of the heavy and light chains each consist of four framework regions (FR) connected by three complementarity determining regions (CDRs) and contribute to the formation of the antigen-binding site of antibodies.

"Complementarity Determining Regions" (CDRs) can be identified according to the definitions of Kabat, Chothia, the accumulation of both Kabat and Chothia, AbM, contact, North, and/or conformational definitions or any method of CDR determination well known in the art. See, e.g., Kabat et al., 1991, Sequences of Proteins of Immunological Interest, 5th ed. (hypervariable regions); Chothia et al., 1989, Nature 342:877-883 (structural loop structures). The identity of the amino acid residues in a particular antibody that make up a CDR can be determined using methods well known in the art. The AbM definition of CDRs is a compromise between Kabat and Chothia and uses Oxford Molecular's AbM antibody modeling software (Accelrys®). The "contact" definition of CDRs is based on observed antigen contacts, set forth in MacCallum et al., 1996, J. Mol. Biol., 262:732-745. The "conformational" definition of CDRs is based on residues that make enthalpic contributions to antigen binding (see, e.g., Makabe et al., 2008, J. Biol. Chem., 283:1156-1166). North has identified canonical CDR conformations using a different preferred set of CDR definitions (North et al., 2011, J. Mol. Biol. 406: 228-256). In another approach, referred to herein as the "conformational definition" of CDRs, the positions of the CDRs may be identified as the residues that make enthalpic contributions to antigen binding (Makabe et al., 2008, J Biol. Chem. 283:1156-1166). Still other CDR boundary definitions may not strictly follow one of the above approaches but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs (or other residue of the antibody) may be defined in accordance with any of Kabat, Chothia, North, extended, AbM, contact, and/or conformational definitions.

"Framework" (FR) residues are antibody variable domain residues other than the CDR residues. A VH or VL domain framework comprises four framework sub-regions, FR1, FR2, FR3 and FR4, interspersed with CDRs in the following structure: FR1-CDR1-FR2-CDR2-FR3-CDR3-FR4.

As known in the art, a "constant region" of an antibody refers to the constant region of the antibody light chain or the constant region of the antibody heavy chain, either alone or in combination.

The terms "Fc region", "Fc domain" and "Fc", as interchangeably used herein refer to the portion of an immunoglobulin (Ig) molecule that correlates to a crystallizable fragment obtained by papain digestion of an Ig molecule. As used herein, the terms relate to the constant region of an antibody excluding the first constant region immunoglobulin domain and further relates to portions of that region. Thus, Fc refers to the last two constant region immunoglobulin domains of IgA, IgD, and IgG, and the last three constant region immunoglobulin domains of IgE and IgM, and the flexible hinge N-terminal to these domains, or portions thereof. For IgA and IgM, Fc may include the J chain.

For IgG, Fc comprises immunoglobulin domains Cγ2 and Cγ3 (C gamma 2 and C gamma 3) and the hinge between Cγ1 (C gamma 1) and Cγ2 (C gamma 2). Although the boundaries of the Fc region may vary, the human IgG heavy chain Fc region is usually defined to comprise residues C226 or P230 to its carboxyl-terminus, wherein the numbering is according to the EU index of Edelman et al., 1969, Proc. Natl. Acad. Sci. USA 63(1):78-85 as described in Kabat et al., 1991. Typically, the Fc domain comprises from about amino acid residue 236 to about 447 of the human IgG1 constant domain. An exemplary human wild type IgG1 Fc domain amino acid sequence is set forth in SEQ ID NO:31. Fc polypeptide may refer to this region in isolation, or this region in the context of an antibody, or an antigen-binding portion thereof, or Fc fusion protein.

The heavy chain constant domain comprises the Fc region and further comprises the CH1 domain and hinge as well as the CH2 and CH3 (and, optionally, CH4 of IgA and IgE) domains of the IgG heavy chain.

In certain embodiments, the antibody, or antigen-binding fragment thereof, described herein comprises an Fc domain. The Fc domain can be derived from IgA (e.g., IgA$_1$ or IgA$_2$), IgD, IgE, IgM, or IgG (e.g., IgG$_1$, IgG$_2$, IgG$_3$, or IgG4).

An "Fc fusion" protein is a protein wherein one or more polypeptides are operably linked to an Fc polypeptide. An Fc fusion combines the Fc region of an immunoglobulin with a fusion partner.

An "epitope" refers to the area or region of an antigen to which an antibody specifically binds, e.g., an area or region comprising residues that interact with the antibody. Epitopes can be linear or conformational.

At its most detailed level, the epitope for the interaction between the Ag and the Ab can be defined by the spatial coordinates defining the atomic contacts present in the Ag-Ab interaction, as well as information about their relative contributions to the binding thermodynamics. At a less detailed level, the epitope can be characterized by the spatial coordinates defining the atomic contacts between the Ag and Ab. At a further less detailed level the epitope can be characterized by the amino acid residues that it comprises as defined by a specific criterion, e.g., by distance between atoms (e.g., heavy, i.e., non-hydrogen atoms) in the Ab and the Ag. At a further less detailed level the epitope can be characterized through function, e.g., by competition binding with other Abs. The epitope can also be defined more generically as comprising amino acid residues for which substitution by another amino acid will alter the characteristics of the interaction between the Ab and Ag (e.g. using alanine scanning).

From the fact that descriptions and definitions of epitopes, dependent on the epitope mapping method used, are obtained at different levels of detail, it follows that comparison of epitopes for different Abs on the same Ag can similarly be conducted at different levels of detail.

Epitopes described at the amino acid level, e.g., determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

Epitopes characterized by competition binding are said to be overlapping if the binding of the corresponding antibodies are mutually exclusive, i.e., binding of one antibody excludes simultaneous or consecutive binding of the other antibody. The epitopes are said to be separate (unique) if the antigen is able to accommodate binding of both corresponding antibodies simultaneously.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a GDF15, PD-1 or PD-L1 epitope is an antibody that binds this epitope with greater affinity, avidity, more readily, and/or with greater duration than it binds to other GDF15, PD-1 or PD-L1 epitopes or non-GDF15, PD-1, PD-L1 epitopes. Generally, but not necessarily, reference to binding means preferential binding. "Specific binding" or "preferential binding" includes a compound, e.g., a protein, a nucleic acid, an antibody, and the like, which recognizes and binds to a specific molecule in a sample, but does not substantially recognize or bind other molecules in the sample. For instance, an antibody or a peptide receptor which recognizes and binds to a cognate ligand or binding partner (e.g., an anti-human tumor antigen antibody that binds a tumor antigen, a PD-1 molecule that binds PD-L1 or PD-L2, etc.) in a sample but does not substantially recognize or bind other molecules in the sample, specifically binds to that cognate ligand or binding partner. Thus, under designated assay conditions, the specified binding moiety (e.g., an antibody or an antigen-binding portion thereof or a receptor or a ligand binding portion thereof) binds preferentially to a particular target molecule and does not bind in a significant amount to other components present in a test sample.

A variety of assay formats may be used to select an antibody or peptide that specifically binds a molecule of interest. For example, solid-phase ELISA immunoassay, immunoprecipitation, BIAcore™ (GE Healthcare, Piscataway, N.J.), fluorescence-activated cell sorting (FACS), Octet™ (ForteDo, Inc., Menlo Park, Calif.) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice background signal or noise and more typically more than 10 times background, even more specifically, an antibody is said to "specifically bind" an antigen when the equilibrium dissociation constant ($K_D$) is 1 pM, preferably 100 nM, more preferably 10 nM, even more preferably, 100 pM, yet more preferably, 10 pM, and even more preferably, 1 pM.

The term "compete", as used herein with regard to an antibody, means that binding of a first antibody, or an antigen-binding portion thereof, to an antigen reduces the subsequent binding of the same antigen by a second antibody or an antigen-binding portion thereof. In general, the binding a first antibody creates steric hindrance, conformational change, or binding to a common epitope (or portion thereof), such that the binding of the second antibody to the same antigen is reduced. Standard competition assays may be used to determine whether two antibodies compete with each other. One suitable assay for antibody competition involves the use of the Biacore technology, which can measure the extent of interactions using surface plasmon resonance (SPR) technology, typically using a biosensor system (such as a BIACORE system). For example, SPR can be used in an in vitro competitive binding inhibition assay to determine the ability of one antibody to inhibit the binding of a second antibody. Another assay for measuring antibody competition uses an ELISA-based approach.

Furthermore, a high throughput process for "binning" antibodies based upon their competition is described in International Patent Application No. WO2003/48731. Competition is present if one antibody (or fragment) reduces the binding of another antibody (or fragment) to GDF15. For example, a sequential binding competition assay may be used, with different antibodies being added sequentially. The first antibody may be added to reach binding that is close to saturation. Then, the second antibody is added. If the binding of second antibody to GDF15 is not detected, or is significantly reduced (e.g., at least about 10%, at least about 20%, at least about 30%, at least about 40%, at least about 50%, at least about 60%, at least about 70%, at least about 80%, or at least about 90% reduction) as compared to a parallel assay in the absence of the first antibody (which value can be set as 100%), the two antibodies are considered as competing with each other.

A variant antibody may comprise 1, 2, 3, 4, 5, up to 10, up to 20, up to 30 or more amino acid substitutions and/or deletions and/or insertions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" shown below, or as further described below in reference to amino acid classes, may be introduced and the products screened.

TABLE 1

Amino Acids and Substitutions

| Original Residue | Conservative Substitutions | Exemplary Substitutions |
| --- | --- | --- |
| alanine Ala (A) | Val | Val; Leu; Ile |
| arginine Arg (R) | Lys | Lys; Gln; Asn |
| asparagine Asn (N) | Gln | Gln; His; Asp, Lys; Arg |
| aspartatic Asp (D) | Glu | Glu; Asn |
| cysteine Cys (C) | Ser | Ser; Ala |
| glutamine Gln (Q) | Asn | Asn; Glu |
| glutamic Glu (E) | Asp | Asp; Gln |
| glycine Gly (G) | Ala | Ala |
| histidine His (H) | Arg | Asn; Gln; Lys; Arg |
| isoleucine Ile (I) | Leu | Leu; Val; Met; Ala; Phe; Norleucine |
| leucine Leu (L) | Ile | Norleucine; Ile; Val; Met; Ala; Phe |
| lysine Lys (K) | Arg | Arg; Gln; Asn |
| methionine Met (M) | Leu | Leu; Phe; Ile |
| phenylalanine Phe (F) | Tyr | Leu; Val; Ile; Ala; Tyr |
| proline Pro (P) | Ala | Ala |
| serine Ser (S) | Thr | Thr |
| threonine Thr (T) | Ser | Ser |
| tryptophan Trp (W) | Tyr | Tyr; Phe |
| tyrosine Tyr (Y) | Phe | Trp; Phe; Thr; Ser |
| valine Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a beta-sheet or helical conformation, (b) the charge or hydrophobicity of the molecule at the target site, or (c) the bulk of the side chain. Naturally occurring residues are divided into groups based on common side-chain properties:

i. Non-polar: Norleucine, Met, Ala, Val, Leu, Ile;
   ii. Polar without charge: Cys, Ser, Thr, Asn, Gln;
   iii. Acidic (negatively charged): Asp, Glu;
   iv. Basic (positively charged): Lys, Arg;
   v. Residues that influence chain orientation: Gly, Pro; and
   vi. Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. As used herein, the term "germline" refers to the nucleotide sequences and amino acid sequences of the antibody genes and gene segments as they are passed from parents to offspring via the germ cells. This germline sequence is distinguished from the nucleotide sequences encoding antibodies in mature B cells which have been altered by recombination and hypermutation events during the course of B cell maturation. An antibody that "utilizes" a particular germline has a nucleotide or amino acid sequence that most closely aligns with that germline nucleotide sequence or with the amino acid sequence that it specifies. Such antibodies frequently are mutated compared with the germline sequence. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., J. Mol. Biol. 227:776-798, 1992; and Cox et al., Eur. J. Immunol. 24:827-836, 1994.)

Binding Affinity

The binding affinity of an antibody can be expressed as $K_D$ value, which refers to the dissociation rate of a particular antigen-antibody interaction. $K_D$ is the ratio of the rate of dissociation, also called the "off-rate $(k_{off})$", to the association rate, or "on-rate $(k_{on})$". Thus, $K_D$ equals $k_{off}/k_{on}$ and is expressed as a molar concentration (M), and the smaller the $K_D$, the stronger the affinity of binding. $K_D$ values for antibodies can be determined using methods well established in the art. One exemplary method for measuring Kd is surface plasmon resonance (SPR), typically using a biosensor system such as a BIACORE® system. BIAcore kinetic analysis comprises analyzing the binding and dissociation of an antigen from chips with immobilized molecules (e.g. molecules comprising epitope binding domains), on their surface. Another method for determining the Kd of an antibody is by using Bio-Layer Interferometry, typically using OCTET technology (Octet QKe system, ForteBio). Alternatively, or in addition, a KinExA (Kinetic Exclusion Assay) assay, available from Sapidyne Instruments (Boise, Id.) can also be used.

Antibodies to GDF15

The invention provides anti-GDF15 antibodies. An anti-GDF15 antibody, preferably, a high affinity antibody, may be effective in the plasma and multiple tissue compartments, where GDF15 is thought to act on its target cells. Antibodies of the invention have the potential to modify a pathway that drives the development and progression of cachexia associated with cancers, heart failure, or COPD, among others.

A neutralizing or "blocking" antibody refers to an antibody whose binding to GDF15 interferes with, limits, or inhibits the interaction between GDF15 or a GDF15 fragment and a GDF15 receptor, such as GFRAL, or GDF15 receptor component; and/or (ii) results in inhibition of at least one biological function of GDF15. Assays to determine the neutralization by an antibody of the invention are described elsewhere herein and are well-known in the art.

As used herein, the term "GDF15" includes variants, isoforms, homologs, orthologs and paralogs of human GDF15. In some aspects of the invention, the antibodies cross-react with GDF15 from species other than human, such as GDF15 of mouse, rat, or non-human primate, as well as different forms of GDF15. In other aspects, the antibodies may be completely specific for human GDF15 and may not exhibit species or other types of cross-reactivity. As used herein the term GDF15 refers to naturally occurring human GDF15 unless contextually dictated otherwise. Therefore, a "GDF15 antibody", "anti-GDF15 antibody" or other similar designation means any antibody (as defined herein) that specifically associates, binds or reacts with the GDF15 type ligand or isoform, or fragment or derivative thereof. The full length, mature form of human GDF15, as represented by UniProtKB/Swiss-Prot accession number Q99988.1 is herein provided as SEQ ID NO:1.

Without wishing to be bound by any particular theory, upon interaction with GDF15, GFRAL interacts with Proto-oncogene tyrosine-protein kinase receptor Ret (RET) and induces cellular signaling through activation of MAPK- and AKT-signaling pathways. RET signaling then induces or mediates phosphorylation of, e.g., ERK, S6, among others. As used herein, the term "GFRAL" includes variants, isoforms, homologs, orthologs and paralogs of human GFRAL. The full length, mature form of human GFRAL, is represented by UniProtKB/Swiss-Prot accession number Q6UXV0. As used herein, the term "RET" includes variants, isoforms, homologs, orthologs and paralogs of human RET. The full length, mature form of human RET, is represented by UniProtKB/Swiss-Prot accession number P07949.

"Biological function" or "biological activity" of GDF15 is meant to include regulating inflammatory and apoptotic pathways in tissues and the stress response program of cells after cellular injury. "Biological function" or "biological activity" of GDF15 includes mediating increasing: cachexia, decreased food intake, decreased appetite, decreased body weight, weight loss, decreased fat mass, decreased lean mass, binding of GFRAL, activation of RET, phosphorylation of ERK, and phosphorylation of S6, among others now known in the art or later identified. The biological function or biological activity of GDF15 can, but need not be, mediated by the interaction between GDF15 and its cognate receptor GFRAL.

The invention includes an antibody, or antigen-binding portion thereof, that can modulate a biological activity of GDF15. That is, the invention includes an isolated antibody, or antigen-binding portion thereof, that specifically binds GDF15 and modulates at least one detectable GDF15 activity such that the antibody: (a) increases food intake; (b) increases appetite; (c) increases body weight; (d) decreases weight loss; (e) increases fat mass; (f) increases lean mass; (g) decreases loss of fat mass, (h) decreases loss of lean muscle mass, (i) decreases GDF15 binding to GFRAL; (j) decreases downstream signaling mediated by RET; (k) decreases or inhibits phosphorylation of ERK; (l) decreases or inhibits phosphorylation of S6; (m) decreases RET activation of the MAPK signaling pathway; (n) decreases RET activation of the AKT-signaling pathway; and/or (o) decreases activation of the PLC-□1 signaling pathway.

The biological activity of GDF15 and GDF15-dependent signaling activity can be assessed in vitro using HEK293 or CHO cells co-expressing GFRAL and RET, among many art recognized assays. Activation of the MAPK pathway following stimulation with GDF15 can be measured using, among others, a luciferase-based gene reporter system (e.g., PathDetect, Agilent Technologies). Phospho-protein assays based on the homogenous time-resolved fluorescence technology (Cisbio Inc.) can also be used as orthogonal approaches to measure activation of MAPK and AKT pathways (e.g., phospho-ERK1/2) in response to GDF15 binding it receptor. The ability of neutralizing antibodies to prevent GDF15-dependent signaling can also be assessed by incubating cells with a fixed concentration of GDF15 in the absence or presence of increasing concentrations of the anti-GDF15 antibody.

In one aspect of the invention, a GDF15 antibody of the invention encompasses an antibody that competes for binding to human GDF15 with, and/or binds the same epitope as, an antibody, or antigen-binding fragment thereof, having the amino acid sequence of a heavy chain variable region set forth as SEQ ID NO:166 and the amino acid sequence of a light chain variable region set forth as SEQ ID NO:163.

In one aspect of the invention, a GDF15 antibody of the invention encompasses an antibody that inhibits or reduces binding of GDF15 with GFRAL.

In one aspect, the invention encompasses an antibody that competes with an antibody, or antigen-binding fragment thereof, having the amino acid sequence of a heavy chain variable region set forth as SEQ ID NO:166 and the amino acid sequence of a light chain variable region set forth as SEQ ID NO:163, in inhibiting the binding of GDF15 with GFRAL.

In some aspects of the invention, the antibody, or antigen-binding fragment thereof, includes an IgG1 heavy chain constant region, for example a GDF15 heavy chain set forth as SEQ ID NO:164. In other aspects, the antibody, or antigen-binding fragment thereof, includes a kappa light chain constant region, for example a GDF15 light chain set forth as SEQ ID NO:162.

Table 2 provides the amino acid (protein) sequences and associated nucleic acid (DNA) sequences of the anti-GDF15 antibodies of the present invention. The CDRs of the anti-GDF15 VHs and anti-GDF15 VLs, as defined by Kabat and by Chothia, are set forth as separate sequences.

In some aspects, the CDRs comprise SEQ ID NOs: 171, 172, 173, 174, 175, and 176. These CDR sequences incorporate the consensus based on favorable sequence analysis and biophysical profile data presented in Examples 1 through 10 below. These CDR sequences possess advantages based on their sequence, binding, thermal stability, stability at low pH and viscosity profiles.

TABLE 2

Sequences of GDF15 peptides and anti-GDF15 antibodies.

| SEQ ID NO | Description | Sequence |
|---|---|---|
| 1 | human GDF15, mature form | ARNGDHCPLG PGRCCRLHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI |
| 2 | Murine dimeric IgG1 Fc-human GDF-15 with FXa cleavage site | GCKPCICTVP EVSSVFIFPP KPKDVLTITL TPKVTCVVVD ISKDDPEVQF SWFVDDVEVH TAQTQPREEQ FNSTFRSVSE LPIMHQDWLN GKEFKCRVNS AAFPAPIEKT ISKTKGRPKA PQVYTIPPPK EQMAKDKVSL TCMITDFFPE DITVEWQWNG QPAENYKNTQ PIMDTDGSYF VYSKLNVQKS NWEAGNTFTC SVLHEGLHNH HTEKSLSHSP GKIEGRMDGG GGSARNGDHC PLGPGRCCRL HTVRASLEDL GWADWVLSPR EVQVTMCIGA CPSQFRAANM HAQIKTSLHR LKPDTVPAPC CVPASYNPMV LIQKTDTGVS LQTYDDLLAK DCHCI |
| 3 | Human CH23 Fc-human GDF15 with TEV cleavage site | GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR EEMTKNQVNL TCLVKGFYPS DIAVEWESNG QPENNYKTTP PVLDSDGSFF LNSTLTVDKS RWQQGNVFSC SVLHEALHSH YTQKSLSLSP KGSENLYFQG ARNGDHCPLG PGRCCRLHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI |
| 4 | Murine dimeric IgG1 Fc-cyno GDF-15 with FXa cleavage site | GCKPCICTVP EVSSVFIFPP KPKDVLTITL TPKVTCVVVD ISKDDPEVQF SWFVDDVEVH TAQTQPREEQ FNSTFRSVSE LPIMHQDWLN GKEFKCRVNS AAFPAPIEKT ISKTKGRPKA PQVYTIPPPK EQMAKDKVSL TCMITDFFPE DITVEWQWNG QPAENYKNTQ PIMDTDGSYF VYSKLNVQKS NWEAGNTFTC SVLHEGLHNH HTEKSLSHSP GKIEGRMDGG GGSARNGDRC PLGPGRCCRL HTVHASLEDL GWADWVLSPR EVQVTMCIGA CPSQFREANM HAQIKMNLHR LKPDTVPAPC CVPASYNPMV LIQKTDTGVS LQTYDDLLAK DCHCV |
| 5 | Murine dimeric IgG1 Fc-murine GDF-15 with FXa cleavage site | GCKPCICTVP EVSSVFIFPP KPKDVLTITL TPKVTCVVVD ISKDDPEVQF SWFVDDVEVH TAQTQPREEQ FNSTFRSVSE LPIMHQDWLN GKEFKCRVNS AAFPAPIEKT ISKTKGRPKA PQVYTIPPPK EQMAKDKVSL TCMITDFFPE DITVEWQWNG QPAENYKNTQ PIMDTDGSYF VYSKLNVQKS NWEAGNTFTC SVLHEGLHNH HTEKSLSHSP GKIEGRMDGG GGSARNGDHC PLGPGRCCRL HTVRASLEDL GWADWVLSPR EVQVTMCIGA CPSQFRAANM HAQIKTSLHR LKPDTVPAPC CVPASYNPMV LIQKTDTGVS LQTYDDLLAK DCHCI |
| 6 | GDF15_200 LC | EIVLTQSPAT LSLSPGERAT LSCRASQSVH SYLAWYQQKP GQAPRLLIYD ASNRATGIPA RFSGSGSGTD FTLTISSLEP EDFAVYYCQQ FWSWPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 7 | GDF15_200 LCDR-1 LCDR-1 | RASQSVHSYL A |
| 8 | GDF15_010 LCDR-2 GDF15_013 LCDR-2 GDF15_014 LCDR-2 GDF15_200 LCDR-2 | DASNRAT |
| 9 | GDF15_001 LCDR-3 GDF15_002 LCDR-3 GDF15_005 LCDR-3 GDF15_007 LCDR-3 GDF15_009 LCDR-3 GDF15_200 LCDR-3 | QQFWSWPWT |
| 10 | LC CL | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 11 | GDF15_200 VL | EIVLTQSPAT LSLSPGERAT LSCRASQSVH SYLAWYQQKP GQAPRLLIYD ASNRATGIPA RFSGSGSGTD FTLTISSLEP EDFAVYYCQQ FWSWPWTFGQ GTKVEIK |
| 12 | IgG1 Light Chain JK | FGQGTKVEIK R |
| 13 | IgG1 Heavy Chain Hinge | EPKSCDKTHT CPPCP |
| 14 | IgG1 Heavy Chain CH2 | APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK |

TABLE 2-continued

Sequences of GDF15 peptides and anti-GDF15 antibodies.

| SEQ ID NO | Description | Sequence |
|---|---|---|
| 15 | Heavy Chain CH3 | GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 16 | GDF15_200 HC | QVQLVQSGAE VKKPGSSVKV SCKASGYTFS SYNISWVRQA PGQGLEWMGG INPINGLAFY NQKFQGRVTI TADESTSTAY MELSSLRSED TAVYYCAREA ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 17 | GDF15_200 HCDR-1 | GYTFSSYNIS |
| 18 | GDF15_200 HCDR-2 | GINPINGLAF YNQKFQG |
| 19 | GDF15_007 HCDR-3 GDF15_010 HCDR-3 GDF15_013 HCDR-3 GDF15_014 HCDR-3 GDF15_017 HCDR-3 GDF15_018 HCDR-3 GDF15_020 HCDR-3 GDF15_100 HCDR-3 GDF15_200 HCDR-3 | EAITTVGAMD Y |
| 20 | Heavy Chain CH1 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKK |
| 21 | GDF15_200 VH | QVQLVQSGAE VKKPGSSVKV SCKASGYTFS SYNISWVRQA PGQGLEWMGG INPINGLAFY NQKFQGRVTI TADESTSTAY MELSSLRSED TAVYYCAREA ITTVGAMDYW GQGTLVTVSS |
| 22 | Framework H1 | QVQLVQSGAE VKKPGSSVKV SCKAS |
| 23 | Framework H2 | WVRQAPGQGL EWMG |
| 24 | Framework H3 | RVTITADEST STAYMELSSL RSEDTAVYYC AR |
| 25 | JH | WGQGTLVTVS S |
| 26 | GDF15_100 LC | EIVLTQSPAT LSLSPGERAT LSCRTSQNVH SYLAWYQQKP GQAPRLLIYD ASTRADGIPA RFSGSGSGTD FTLTISSLEP EDFAVYYCQQ FWSDPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 27 | GDF15_008 LCDR-1 GDF15_009 LCDR-1 GDF15_100 LCDR-1 | RTSQNVHSYL A |
| 28 | GDF15_001 LCDR-2 GDF15_004 LCDR-2 GDF15_012 LCDR-2 GDF15_018 LCDR-2 GDF15_020 LCDR-2 GDF15_100 LCDR-2 | DASTRAD |
| 29 | GDF15_100 LCDR-3 | QQFWSDPWT |
| 30 | GDF15_100 VL | EIVLTQSPAT LSLSPGERAT LSCRTSQNVH SYLAWYQQKP GQAPRLLIYD ASTRADGIPA RFSGSGSGTD FTLTISSLEP EDFAVYYCQQ FWSDPWTFGQ GTKVEIK |
| 31 | GDF15_100 HC | QVQLVQSGAE VKKPGSSVKV SCKASGYTFS SYNIDWVRQA PGQGLEWMGQ INPNNGLAFY NQKFQGRVTI TADESTSTAY MELSSLRSED TAVYYCAREA ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ |

TABLE 2-continued

Sequences of GDF15 peptides and anti-GDF15 antibodies.

| SEQ ID NO | Description | Sequence |
|---|---|---|
|  |  | VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 32 | GDF15_001 HCDR-1<br>GDF15_002 HCDR-1<br>GDF15_004 HCDR-1<br>GDF15_021 HCDR-1<br>GDF15_100 HCDR-1 | GYTFSSYNID |
| 33 | GDF15_003 HCDR-2<br>GDF15_009 HCDR-2<br>GDF15_015 HCDR-2<br>GDF15_017 HCDR-2<br>GDF15_100 HCDR-2 | QINPNNGLAF YNQKFQG |
| 34 | GDF15_100 VH | QVQLVQSGAE VKKPGSSVKV SCKASGYTFS SYNIDWVRQA PGQGLEWMGQ INPNNGLAFY NQKFQGRVTI TADESTSTAY MELSSLRSED TAVYYCAREA ITTVGAMDYW GQGTLVTVSS |
| 35 | GDF15_022 LC | EIVLTQSPAT LSLSPGERAT LSCRTSQSVH SYLAWYQQKP GQAPRLLIYD AKTRADGIPA RFSGSGSGTD FTLTISSLEP EDFAVYYCQQ FSSDPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 36 | GDF15_022 LCDR-1 | RTSQSVHSYL A |
| 37 | GDF15_005 LCDR-2<br>GDF15_022 LCDR-2 | DAKTRAD |
| 38 | GDF15_003 LCDR-3<br>GDF15_012 LCDR-3<br>GDF15_017 LCDR-3<br>GDF15_022 LCDR-3 | QQFSSDPYT |
| 39 | GDF15_022 VL | EIVLTQSPAT LSLSPGERAT LSCRTSQSVH SYLAWYQQKP GQAPRLLIYD AKTRADGIPA RFSGSGSGTD FTLTISSLEP EDFAVYYCQQ FSSDPYTFGQ GTKVEIK |
| 40 | GDF15_022 HC | QVQLVQSGAE VKKPGSSVKV SCKASGYTFS DYNIDWVRQA PGQGLEWMGQ INPNNGLIFF NQKFQGRVTI TADESTSTAY MELSSLRSED TAVYYCAREV ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 41 | GDF15_010 HCDR-1<br>GDF15_022 HCDR-1 | GYTFSDYNID |
| 42 | GDF15_022 HCDR-2 | QINPNNGLIF FNQKFQG |
| 43 | GDF15_012 HCDR-3<br>GDF15_022 HCDR-3 | EVITTVGAMD Y |
| 44 | GDF15_022 VH | QVQLVQSGAE VKKPGSSVKV SCKASGYTFS DYNIDWVRQA PGQGLEWMGQ INPNNGLIFF NQKFQGRVTI TADESTSTAY MELSSLRSED TAVYYCAREV ITTVGAMDYW GQGTLVTVSS |
| 45 | GDF15_021 LC | EIVLTQSPAT LSLSPGERAT LSCRTSENVH SYLAWYQQKP GQAPRLLIYD ASNLADGIPA RFSGSGSGTD FTLTISSLEP EDFAVYYCQQ FWSDPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 46 | GDF15_007 LCDR-1<br>GDF15_021 LCDR-1 | RTSENVHSYL A |
| 47 | GDF15_021 LCDR-2 | DASNLAD |
| 48 | GDF15_004 LCDR-3<br>GDF15_009 LCDR-3 | QQFWSDPYT |

TABLE 2-continued

Sequences of GDF15 peptides and anti-GDF15 antibodies.

| SEQ ID NO | Description | Sequence |
|---|---|---|
| | GDF15_014 LCDR-3 GDF15_020 LCDR-3 GDF15_021 LCDR-3 | |
| 49 | GDF15_021 VL | EIVLTQSPAT LSLSPGERAT LSCRTSENVH SYLAWYQQKP GQAPRLLIYD ASNLADGIPA RFSGSGSGTD FTLTISSLEP EDFAVYYCQQ FWSDPYTFGQ GTKVEIK |
| 50 | GDF15_021 HC | QVQLVQSGAE VKKPGSSVKV SCKASGYTFS SYNIDWVRQA PGQGLEWMGG INPINGLIFF NQKFQGRVTI TADESTSTAY MELSSLRSED TAVYYCAREA ITTVGAMDHW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 51 | GDF15_021 HCDR-2 | GINPINGLIF FNQKFQG |
| 52 | GDF15_001 HCDR-3 GDF15_021 HCDR-3 | EAITTVGAMD H |
| 53 | GDF15_021 VH | QVQLVQSGAE VKKPGSSVKV SCKASGYTFS SYNIDWVRQA PGQGLEWMGG INPINGLIFF NQKFQGRVTI TADESTSTAY MELSSLRSED TAVYYCAREA ITTVGAMDHW GQGTLVTVSS |
| 54 | GDF15_020 LC | EIVLTQSPAT LSLSPGERAT LSCRASQNLH SYLAWYQQKP GQAPRLLIYD ASTRADGIPA RFSGSGSGTD FTLTISSLEP EDFAVYYCQQ FWSDPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 55 | GDF15_020 LCDR-1 | RASQNLHSYL A |
| 56 | GDF15_020 VL | EIVLTQSPAT LSLSPGERAT LSCRASQNLH SYLAWYQQKP GQAPRLLIYD ASTRADGIPA RFSGSGSGTD FTLTISSLEP EDFAVYYCQQ FWSDPYTFGQ GTKVEIK |
| 57 | GDF15_020 HC | QVQLVQSGAE VKKPGSSVKV SCKASGYTFS DYNMDWVRQA PGQGLEWMGQ INPNNGLANY NQKFQGRVTI TADESTSTAY MELSSLRSED TAVYYCAREA ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 58 | GDF15_005 HCDR-1 GDF15_012 HCDR-1 GDF15_013 HCDR-1 GDF15_015 HCDR-1 GDF15_020 HCDR-1 | GYTFSDYNMD |
| 59 | GDF15_020 HCDR-2 | QINPNNGLAN YNQKFQG |
| 60 | GDF15_020 VH | QVQLVQSGAE VKKPGSSVKV SCKASGYTFS DYNMDWVRQA PGQGLEWMGQ INPNNGLANY NQKFQGRVTI TADESTSTAY MELSSLRSED TAVYYCAREA ITTVGAMDYW GQGTLVTVSS |
| 61 | GDF15_018 LC | EIVLTQSPAT LSLSPGERAT LSCRASQNVH SYLAWYQQKP GQAPRLLIYD ASTRADGIPA RFSGSGSGTD FTLTISSLEP EDFAVYYCQQ FWNDPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 62 | GDF15_018 LCDR-1 | RASQNVHSYL A |
| 63 | GDF15_008 LCDR-3 GDF15_018 LCDR-3 | QQFWNDPYT |

TABLE 2-continued

Sequences of GDF15 peptides and anti-GDF15 antibodies.

| SEQ ID NO | Description | Sequence |
|---|---|---|
| 64 | GDF15_018 VL | EIVLTQSPAT LSLSPGERAT LSCRASQNVH SYLAWYQQKP GQAPRLLIYD ASTRADGIPA RFSGSGSGTD FTLTISSLEP EDFAVYYCQQ FWNDPYTFGQ GTKVEIK |
| 65 | GDF15_018 HC | QVQLVQSGAE VKKPGSSVKV SCKASGYTFT DYNIDWVRQA PGQGLEWMGQ INPNNGLIFY NQKFQGRVTI TADESTSTAY MELSSLRSED TAVYYCAREA ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 66 | GDF15_017 HCDR-1 GDF15_018 HCDR-1 | GYTFTDYNID |
| 67 | GDF15_018 HCDR-2 | QINPNNGLIF YNQKFQG |
| 68 | GDF15_018 VH | QVQLVQSGAE VKKPGSSVKV SCKASGYTFT DYNIDWVRQA PGQGLEWMGQ INPNNGLIFY NQKFQGRVTI TADESTSTAY MELSSLRSED TAVYYCAREA ITTVGAMDYW GQGTLVTVSS |
| 69 | GDF15_017 LC | EIVLTQSPAT LSLSPGERAT LSCRTSQSVH SYLAWYQQKP GQAPRLLIYD AKTRATGIPA RFSGSGSGTD FTLTISSLEP EDFAVYYCQQ FSSDPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 70 | GDF15_017 LCDR-2 | DAKTRAT |
| 71 | GDF15_017 VL | EIVLTQSPAT LSLSPGERAT LSCRTSQSVH SYLAWYQQKP GQAPRLLIYD AKTRATGIPA RFSGSGSGTD FTLTISSLEP EDFAVYYCQQ FSSDPYTFGQ GTKVEIK |
| 72 | GDF15_017 HC | QVQLVQSGAE VKKPGSSVKV SCKASGYTFT DYNIDWVRQA PGQGLEWMGQ INPNNGLAFY NQKFQGRVTI TADESTSTAY MELSSLRSED NAVYYCAREA ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 73 | GDF15_017 VH | QVQLVQSGAE VKKPGSSVKV SCKASGYTFT DYNIDWVRQA PGQGLEWMGQ INPNNGLAFY NQKFQGRVTI TADESTSTAY MELSSLRSED NAVYYCAREA ITTVGAMDYW GQGTLVTVSS |
| 74 | GDF15_017 FW_H3 | RVTITADEST STAYMELSSL RSEDNAVYYC AR |
| 75 | GDF15_015 LC | EIVLTQSPAT LSLSPGERAT LSCRTSQNVH SYLAWYQQKP GQAPRLLIYD ASNLADGIPA RFSGSGSGTD FTLTISSLEP EDFAVYYCQQ FSNDPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 76 | GDF15_015 LCDR-3 | QQFSNDPWT |
| 77 | GDF15_015 VL | EIVLTQSPAT LSLSPGERAT LSCRTSQNVH SYLAWYQQKP GQAPRLLIYD ASNLADGIPA RFSGSGSGTD FTLTISSLEP EDFAVYYCQQ FSNDPWTFGQ GTKVEIK |
| 78 | GDF15_015 HC | QVQLVQSGAE VKKPGSSVKV SCKASGYTFS DYNMDWVRQA PGQGLEWMGQ INPNNGLAFY NQKFQGRVTI TADESTSTAY MELSSLRSED TAVYYCAREA ITTVGATDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |

TABLE 2-continued

Sequences of GDF15 peptides and anti-GDF15 antibodies.

| SEQ ID NO | Description | Sequence |
|---|---|---|
| 79 | GDF15_015 HCDR-3 | EAITTVGATD Y |
| 80 | GDF15_015 VH | QVQLVQSGAE VKKPGSSVKV SCKASGYTFS DYNMDWVRQA PGQGLEWMGQ INPNNGLAFY NQKFQGRVTI TADESTSTAY MELSSLRSED TAVYYCAREA ITTVGATDYW GQGTLVTVSS |
| 81 | GDF15_014 LC | EIVLTQSPAT LSLSPGERAT LSCRTSQNVH NYLAWYQQKP GQAPRLLIYD ASNRATGIPA RFSGSGSGTD FTLTISSLEP EDFAVYYCQQ FWSDPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 82 | GDF15_014 LCDR-1 | RTSQNVHNYL A |
| 83 | GDF15_014 VL | EIVLTQSPAT LSLSPGERAT LSCRTSQNVH NYLAWYQQKP GQAPRLLIYD ASNRATGIPA RFSGSGSGTD FTLTISSLEP EDFAVYYCQQ FWSDPYTFGQ GTKVEIK |
| 84 | GDF15_014 HC | QVQLVQSGAE VKKPGSSVKV SCKASGYTFS SYNIDWVRQA PGQGLEWMGQ INPINGLAFY NQKFQGRVTI TADESTSTAY MELSSLRSED TAVYYCAREA ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 85 | GDF15_014 HCDR-2 | QINPINGLAF YNQKFQG |
| 86 | GDF15_014 VH | QVQLVQSGAE VKKPGSSVKV SCKASGYTFS SYNIDWVRQA PGQGLEWMGQ INPINGLAFY NQKFQGRVTI TADESTSTAY MELSSLRSED TAVYYCAREA ITTVGAMDYW GQGTLVTVSS |
| 87 | GDF15_013 LC | EIVLTQSPAT LSLSPGERAT LSCRTSESVH SYLAWYQQKP GQAPRLLIYD ASNRATGIPA RFSGSGSGTD FTLTISSLEP EDFAVYYCQQ FWNWPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 88 | GDF15_004 LCDR-1 GDF15_013 LCDR-1 | RTSESVHSYL A |
| 89 | GDF15_013 LCDR-3 | QQFWNWPWT |
| 90 | GDF15_013 VL | EIVLTQSPAT LSLSPGERAT LSCRTSESVH SYLAWYQQKP GQAPRLLIYD ASNRATGIPA RFSGSGSGTD FTLTISSLEP EDFAVYYCQQ FWNWPWTFGQ GTKVEIK |
| 91 | GDF15_013 HC | QVQLVQSGAE VKKPGSSVKV SCKASGYTFS DYNMDWVRQA PGQGLEWMGG INPNNGLAFY NQKFQGRVTI TADESTSTAY MELSSLRSED TAVYYCAREA ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 92 | GDF15_013 HCDR-2 | GINPNNGLAF YNQKFQG |
| 93 | GDF15_013 VH | QVQLVQSGAE VKKPGSSVKV SCKASGYTFS DYNMDWVRQA PGQGLEWMGG INPNNGLAFY NQKFQGRVTI TADESTSTAY MELSSLRSED TAVYYCAREA ITTVGAMDYW GQGTLVTVSS |
| 94 | GDF15_012 LC | EIVLTQSPAT LSLSPGERAT LSCRTSQSVH NYLAWYQQKP GQAPRLLIYD ASTRADGIPA RFSGSGSGTD FTLTISSLEP EDFAVYYCQQ FSSDPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 95 | GDF15_001 LCDR-1 GDF15_012 LCDR-1 | RTSQSVHNYL A |

TABLE 2-continued

Sequences of GDF15 peptides and anti-GDF15 antibodies.

| SEQ ID NO | Description | Sequence |
|---|---|---|
| 96 | GDF15_012 VL | EIVLTQSPAT LSLSPGERAT LSCRTSQSVH NYLAWYQQKP GQAPRLLIYD ASTRADGIPA RFSGSGSGTD FTLTISSLEP EDFAVYYCQQ FSSDPYTFGQ GTKVEIK |
| 97 | GDF15_012 HC | QVQLVQSGAE VKKPGSSVKV SCKASGYTFS DYNMDWVRQA PGQGLEWMGQ INPIFGLAFY AQKFQGRVTI TADESTSTAY MELSSLRSED TAVYYCAREV ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 98 | GDF15_012 HCDR-2 | QINPIFGLAF YAQKFQG |
| 99 | GDF15_012 VH | QVQLVQSGAE VKKPGSSVKV SCKASGYTFS DYNMDWVRQA PGQGLEWMGQ INPIFGLAFY AQKFQGRVTI TADESTSTAY MELSSLRSED TAVYYCAREV ITTVGAMDYW GQGTLVTVSS |
| 100 | GDF15_010 LC | EIVLTQSPAT LSLSPGERAT LSCRTSQSLH SYLAWYQQKP GQAPRLLIYD ASNRATGIPA RFSGSGSGTD FTLTISSLEP EDFAVYYCQQ FWNDPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 101 | GDF15_010 LCDR-1 | RTSQSLHSYL A |
| 102 | GDF15_006 LCDR-3 GDF15_010 LCDR-3 | QQFWNDPWT |
| 103 | GDF15_010 VL | EIVLTQSPAT LSLSPGERAT LSCRTSQSLH SYLAWYQQKP GQAPRLLIYD ASNRATGIPA RFSGSGSGTD FTLTISSLEP EDFAVYYCQQ FWNDPWTFGQ GTKVEIK |
| 104 | GDF15_010 HC | QVQLVQSGAE VKKPGSSVKV SCKASGYTFS DYNIDWVRQA PGQGLEWMGG INPNNGLAFF NQKFQGRVTI TADESTSTAY MELSSLRSED TAVYYCAREA ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 105 | GDF15_010 HCDR-2 | GINPNNGLAF FNQKFQG |
| 106 | GDF15_010 VH | QVQLVQSGAE VKKPGSSVKV SCKASGYTFS DYNIDWVRQA PGQGLEWMGG INPNNGLAFF NQKFQGRVTI TADESTSTAY MELSSLRSED TAVYYCAREA ITTVGAMDYW GQGTLVTVSS |
| 107 | GDF15_009 LC | EIVLTQSPAT LSLSPGERAT LSCRTSQNVH SYLAWYQQKP GQAPRLLIYD AKNRADGIPA RFSGSGSGTD FTLTISSLEP EDFAVYYCQQ FWSDPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 108 | GDF15_003 LCDR-2 GDF15_009 LCDR-2 | DAKNRAD |
| 109 | GDF15_009 VL | EIVLTQSPAT LSLSPGERAT LSCRTSQNVH SYLAWYQQKP GQAPRLLIYD AKNRADGIPA RFSGSGSGTD FTLTISSLEP EDFAVYYCQQ FWSDPYTFGQ GTKVEIK |
| 110 | GDF15_009 HC | QVQLVQSGAE VKKPGSSVKV SCKASGYTFS SYNISWVRQA PGQGLEWMGQ INPNNGLAFY NQKFQGRVTI TADESTSTAY MELSSLRSED TAVYYCAREA ITTVGAMEYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |

TABLE 2-continued

Sequences of GDF15 peptides and anti-GDF15 antibodies.

| SEQ ID NO | Description | Sequence |
|---|---|---|
| 111 | GDF15_009 HCDR-3 | EAITTVGAME Y |
| 112 | GDF15_009 VH | QVQLVQSGAE VKKPGSSVKV SCKASGYTFS SYNISWVRQA PGQGLEWMGQ INPNNGLAFY NQKFQGRVTI TADESTSTAY MELSSLRSED TAVYYCAREA ITTVGAMEYW GQGTLVTVSS |
| 113 | GDF15_008 LC | EIVLTQSPAT LSLSPGERAT LSCRTSQNVH SYLAWYQQKP GQAPRLLIYD ASNRADGIPA RFSGSGSGTD FTLTISSLEP EDFAVYYCQQ FWNDPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 114 | GDF15_002 LCDR-2 GDF15_008 LCDR-2 | DASNRAD |
| 115 | GDF15_008 VL | EIVLTQSPAT LSLSPGERAT LSCRTSQNVH SYLAWYQQKP GQAPRLLIYD ASNRADGIPA RFSGSGSGTD FTLTISSLEP EDFAVYYCQQ FWNDPYTFGQ GTKVEIK |
| 116 | GDF15_008 HC | QVQLVQSGAE VKKPGSSVKV SCKASGYTFT SYNISWVRQA PGQGLEWMGQ INPNNGLIFF AQKFQGRVTI TADESTSTAY MELSSLRSED TAVYYCAREA ITTVGAMDQW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 117 | GDF15_008 HCDR-1 | GYTFTSYNIS |
| 118 | GDF15_008 HCDR-2 | QINPNNGLIF FAQKFQG |
| 119 | GDF15_005 HCDR-3 GDF15_008 HCDR-3 | EAITTVGAMD Q |
| 120 | GDF15_008 VH | QVQLVQSGAE VKKPGSSVKV SCKASGYTFT SYNISWVRQA PGQGLEWMGQ INPNNGLIFF AQKFQGRVTI TADESTSTAY MELSSLRSED TAVYYCAREA ITTVGAMDQW GQGTLVTVSS |
| 121 | GDF15_007 LC | EIVLTQSPAT LSLSPGERAT LSCRTSENVH SYLAWYQQKP GQAPRLLIYD ASTLATGIPA RFSGSGSGTD FTLTISSLEP EDFAVYYCQQ FWSWPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 122 | GDF15_007 LCDR-2 | DASTLAT |
| 123 | GDF15_007 VL | EIVLTQSPAT LSLSPGERAT LSCRTSENVH SYLAWYQQKP GQAPRLLIYD ASTLATGIPA RFSGSGSGTD FTLTISSLEP EDFAVYYCQQ FWSWPWTFGQ GTKVEIK |
| 124 | GDF15_007 HC | QVQLVQSGAE VKKPGSSVKV SCKASGYTFS DYNISWVRQA PGQGLEWMGG INPIFGLAFY NQKFQGRVTI TADESTSTAY MELSSLRSED TAVYYCAREA ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 125 | GDF15_007 HCDR-1 | GYTFSDYNIS |
| 126 | GDF15_002 HCDR-2 GDF15_007 HCDR-2 | GINPIFGLAF YNQKFQG |
| 127 | GDF15_007 VH | QVQLVQSGAE VKKPGSSVKV SCKASGYTFS DYNISWVRQA PGQGLEWMGG INPIFGLAFY NQKFQGRVTI TADESTSTAY MELSSLRSED TAVYYCAREA ITTVGAMDYW GQGTLVTVSS |
| 128 | GDF15_006 LC | EIVLTQSPAT LSLSPGERAT LSCRTSQSVS NYLAWYQQKP GQAPRLLIYD AKNRATGIPA RFSGSGSGTD FTLTISSLEP EDFAVYYCQQ FWNDPWTFGQ GTKVEIKRTV AAPSVFIFPP SDEQLKSGTA SVVCLLNNFY PREAKVQWKV |

TABLE 2-continued

Sequences of GDF15 peptides and anti-GDF15 antibodies.

| SEQ ID NO | Description | Sequence |
|---|---|---|
| | | DNALQSGNSQ ESVTEQDSKD STYSLSSTLT LSKADYEKHK VYACEVTHQG LSSPVTKSFN RGEC |
| 129 | GDF15_006 LCDR-1 | RTSQSVSNYL A |
| 130 | GDF15_006 LCDR-2 | DAKNRAT |
| 131 | GDF15_006 VL | EIVLTQSPAT LSLSPGERAT LSCRTSQSVS NYLAWYQQKP GQAPRLLIYD AKNRATGIPA RFSGSGSGTD FTLTISSLEP EDFAVYYCQQ FWNDPWTFGQ GTKVEIK |
| 132 | GDF15_006 HC | QVQLVQSGAE VKKPGSSVKV SCKASGYTFT DYNISWVRQA PGQGLEWMGQ INPNNGLAFY AQKFQGRVTI TADESTSTAY MELSSLRSED TAVYYCAREF ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 133 | GDF15_006 HCDR-1 | GYTFTDYNIS |
| 134 | GDF15_006 HCDR-2 | QINPNNGLAF YAQKFQG |
| 135 | GDF15_006 HCDR-3 | EFITTVGAMD Y |
| 136 | GDF15_006 VH | QVQLVQSGAE VKKPGSSVKV SCKASGYTFT DYNISWVRQA PGQGLEWMGQ INPNNGLAFY AQKFQGRVTI TADESTSTAY MELSSLRSED TAVYYCAREF ITTVGAMDYW GQGTLVTVSS |
| 137 | GDF15_005 LC | EIVLTQSPAT LSLSPGERAT LSCRTSESVS SYLAWYQQKP GQAPRLLIYD AKTRADGIPA RFSGSGSGTD FTLTISSLEP EDFAVYYCQQ FWSWPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 138 | GDF15_005 LCDR-1 | RTSESVSSYL A |
| 139 | GDF15_005 VL | EIVLTQSPAT LSLSPGERAT LSCRTSESVS SYLAWYQQKP GQAPRLLIYD AKTRADGIPA RFSGSGSGTD FTLTISSLEP EDFAVYYCQQ FWSWPWTFGQ GTKVEIK |
| 140 | GDF15_005 HC | QVQLVQSGAE VKKPGSSVKV SCKASGYTFS DYNMDWVRQA PGQGLEWMGG INPNNGTAFY AQKFQGRVTI TADESTSTAY MELSSLRSED TAVYYCAREA ITTVGAMDQW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 141 | GDF15_005 HCDR-2 | GINPNNGTAF YAQKFQG |
| 142 | GDF15_005 VH | QVQLVQSGAE VKKPGSSVKV SCKASGYTFS DYNMDWVRQA PGQGLEWMGG INPNNGTAFY AQKFQGRVTI TADESTSTAY MELSSLRSED TAVYYCAREA ITTVGAMDQW GQGTLVTVSS |
| 143 | GDF15_004 LC | EIVLTQSPAT LSLSPGERAT LSCRTSESVH SYLAWYQQKP GQAPRLLIYD ASTRADGIPA RFSGSGSGTD FTLTISSLEP EDFAVYYCQQ FWSDPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 144 | GDF15_004 VL | EIVLTQSPAT LSLSPGERAT LSCRTSESVH SYLAWYQQKP GQAPRLLIYD ASTRADGIPA RFSGSGSGTD FTLTISSLEP EDFAVYYCQQ FWSDPYTFGQ GTKVEIK |
| 145 | GDF15_004 HC | QVQLVQSGAE VKKPGSSVKV SCKASGYTFS SYNIDWVRQA PGQGLEWMGQ INPNNGLANY AQKFQGRVTI TADESTSTAY MELSSLRSED TAVYYCAREA ITTIGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP |

TABLE 2-continued

Sequences of GDF15 peptides and anti-GDF15 antibodies.

| SEQ ID NO | Description | Sequence |
|---|---|---|
|  |  | KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 146 | GDF15_004 HCDR-2 | QINPNNGLAN YAQKFQG |
| 147 | GDF15_004 HCDR-3 | EAITTIGAMD Y |
| 148 | GDF15_004 VH | QVQLVQSGAE VKKPGSSVKV SCKASGYTFS SYNIDWVRQA PGQGLEWMGQ INPNNGLANY AQKFQGRVTI TADESTSTAY MELSSLRSED TAVYYCAREA ITTIGAMDYW GQGTLVTVSS |
| 149 | GDF15_003 LC | EIVLTQSPAT LSLSPGERAT LSCRASQSLS SYLAWYQQKP GQAPRLLIYD AKNRADGIPA RFSGSGSGTD FTLTISSLEP EDFAVYYCQQ FSSDPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 150 | GDF15_003 LCDR-1 | RASQSLSSYL A |
| 151 | GDF15_003 VL | EIVLTQSPAT LSLSPGERAT LSCRASQSLS SYLAWYQQKP GQAPRLLIYD AKNRADGIPA RFSGSGSGTD FTLTISSLEP EDFAVYYCQQ FSSDPYTFGQ GTKVEIK |
| 152 | GDF15_003 HC | QVQLVQSGAE VKKPGSSVKV SCKASGYTFT SYNIDWVRQA PGQGLEWMGQ INPNNGLAFY NQKFQGRVTI TADESTSTAY MELSSLRSED TAVYYCAREQ ITTVGAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 153 | GDF15_003 HCDR-1 | GYTFTSYNID |
| 154 | GDF15_003 HCDR-3 | EQITTVGAMD Y |
| 155 | GDF15_003 VH | QVQLVQSGAE VKKPGSSVKV SCKASGYTFT SYNIDWVRQA PGQGLEWMGQ INPNNGLAFY NQKFQGRVTI TADESTSTAY MELSSLRSED TAVYYCAREQ ITTVGAMDYW GQGTLVTVSS |
| 156 | GDF15_002 LC | EIVLTQSPAT LSLSPGERAT LSCRASQNVH NYLAWYQQKP GQAPRLLIYD ASNRADGIPA RFSGSGSGTD FTLTISSLEP EDFAVYYCQQ FWSWPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 157 | GDF15_002 LCDR-1 | RASQNVHNYL A |
| 158 | GDF15_002 VL | EIVLTQSPAT LSLSPGERAT LSCRASQNVH NYLAWYQQKP GQAPRLLIYD ASNRADGIPA RFSGSGSGTD FTLTISSLEP EDFAVYYCQQ FWSWPWTFGQ GTKVEIK |
| 159 | GDF15_002 HC | QVQLVQSGAE VKKPGSSVKV SCKASGYTFS SYNIDWVRQA PGQGLEWMGG INPIFGLAFY NQKFQGRVTI TADESTSTAY MELSSLRSED TAVYYCAREA ITTVGAMDPW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 160 | GDF15_002 HCDR-3 | EAITTVGAMD P |
| 161 | GDF15_002 VH | QVQLVQSGAE VKKPGSSVKV SCKASGYTFS SYNIDWVRQA PGQGLEWMGG INPIFGLAFY NQKFQGRVTI TADESTSTAY MELSSLRSED TAVYYCAREA ITTVGAMDPW GQGTLVTVSS |
| 162 | GDF15_001 LC | EIVLTQSPAT LSLSPGERAT LSCRTSQSVH NYLAWYQQKP GQAPRLLIYD ASTRADGIPA RFSGSGSGTD FTLTISSLEP EDFAVYYCQQ FWSWPWTFGQ GTKVEIKRTV AAPSVFIFPP SDEQLKSGTA SVVCLLNNFY PREAKVQWKV |

TABLE 2-continued

Sequences of GDF15 peptides and anti-GDF15 antibodies.

| SEQ ID NO | Description | Sequence |
|---|---|---|
| | | DNALQSGNSQ ESVTEQDSKD STYSLSSTLT LSKADYEKHK VYACEVTHQG LSSPVTKSFN RGEC |
| 163 | GDF15_001 VL | EIVLTQSPAT LSLSPGERAT LSCRTSQSVH NYLAWYQQKP GQAPRLLIYD ASTRADGIPA RFSGSGSGTD FTLTISSLEP EDFAVYYCQQ FWSWPWTFGQ GTKVEIK |
| 95 | GDF15_001 LCDR-1 | RTSQSVHNYL A |
| 28 | GDF15_001 LCDR-2 | DASTRAD |
| 9 | GDF15_001 LCDR-3 | QQFWSWPWT |
| 164 | GDF15_001 HC | QVQLVQSGAE VKKPGSSVKV SCKASGYTFS SYNIDWVRQA PGQGLEWMGG INPIFGTAFY NQKFQGRVTI TADESTSTAY MELSSLRSED TAVYYCAREA ITTVGAMDHW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 32 | GDF15_001 HCDR-1 | GYTFSSYNID |
| 165 | GDF15_001 HCDR-2 | GINPIFGTAF YNQKFQG |
| 52 | GDF15_001 HCDR-3 | EAITTVGAMD H |
| 166 | GDF15_001 VH | QVQLVQSGAE VKKPGSSVKV SCKASGYTFS SYNIDWVRQA PGQGLEWMGG INPIFGTAFY NQKFQGRVTI TADESTSTAY MELSSLRSED TAVYYCAREA ITTVGAMDHW GQGTLVTVSS |
| 167 | GDF15_001 VL DNA | GAAATTGTGC TGACCCAGAG CCCGGCGACC CTGAGCCTGA GCCCGGGCGA ACGCGCGACC CTGAGCTGCC GCACCAGCCA GAGCGTTCAT AACTATCTGG CGTGGTATCA GCAGAAACCG GGCCAGGCGC CGCGCCTGCT GATTTATGAT GCGAGCACCC GTGCGGATGG CATTCCGGCA CGCTTTAGCG GCAGCGGCAG CGGCACCGAT TTTACCCTGA CCATTAGCAG CCTGGAACCG GAAGATTTTG CGGTGTATTA TTGCCAGCAG TTTTGGAGCT GGCCGTGGAC CTTTGGCCAG GGCACCAAAG TGGAAATTAAA |
| 168 | GDF15_001 VH DNA | CAGGTGCAGC TGGTGCAGAG CGGCGCGGAA GTGAAAAAAC CGGGCAGCAG CGTGAAAGTG AGCTGCAAAG CGAGCGGCTA CCTTTAGC AGCTATAACA TTGATTGGGT GCGCCAGGCG CCGGGCCAGG GCCTGGAATG GATGGGCGGT ATTAACCCGA TTTTTGGCAC CGCATTTTAT AACCAGAAAT TCAGGGCCG CGTGACCATT ACCGCGGATG AAAGCACCAG CACCGCGTAT ATGGAACTGA GCAGCCTGCG CAGCGAAGAT ACCGCGGTGT ATTATTGCGC ACGCGAAGCG ATTACCACCG TGGGCGCGAT GGATCATTGG GGCCAGGGCA CCCTGGTGAC CGTGAGCAGC |
| 169 | GDF15_001 LC DNA | GAAATTGTGC TGACCCAGAG CCCGGCGACC CTGAGCCTGA GCCCGGGCGA ACGCGCGACC CTGAGCTGCC GCACCAGCCA GAGCGTTCAT AACTATCTGG CGTGGTATCA GCAGAAACCG GGCCAGGCGC CGCGCCTGCT GATTTATGAT GCGAGCACCC GTGCGGATGG CATTCCGGCA CGCTTTAGCG GCAGCGGCAG CGGCACCGAT TTTACCCTGA CCATTAGCAG CCTGGAACCG GAAGATTTTG CGGTGTATTA TTGCCAGCAG TTTTGGAGCT GGCCGTGGAC CTTTGGCCAG GGCACCAAAG TGGAAATTAA ACGTACGGTG GCTGCACCAT CTGTCTTCAT CTTCCCGCCA TCTGATGAGC AGTTGAAATC TGGAACTGCC TCTGTTGTGT GCCTGCTGAA TAACTTCTAT CCCAGAGAGG CCAAAGTACA GTGGAAGGTG GATAACGCCC TCCAATCGGG TAACTCCCAG GAGAGTGTCA CAGAGCAGGA CAGCAAGGAC AGCACCTACA GCCTCAGCAG CACCCTGACG CTGAGCAAAG CAGACTACGA GAAACACAAA GTCTACGCCT GCGAAGTCAC CCATCAGGGC CTGAGCTCGC CCGTCACAAA GAGCTTCAAC AGGGGAGAGT GT |
| 170 | GDF15_001 HC DNA | CAGGTGCAGC TGGTGCAGAG CGGCGCGGAA GTGAAAAAAC CGGGCAGCAG CGTGAAAGTG AGCTGCAAAG CGAGCGGCTA CCTTTAGC AGCTATAACA TTGATTGGGT GCGCCAGGCG CCGGGCCAGG GCCTGGAATG GATGGGCGGT ATTAACCCGA TTTTTGGCAC CGCATTTTAT AACCAGAAAT TCAGGGCCG CGTGACCATT ACCGCGGATG AAAGCACCAG CACCGCGTAT ATGGAACTGA GCAGCCTGCG CAGCGAAGAT ACCGCGGTGT ATTATTGCGC ACGCGAAGCG ATTACCACCG TGGGCGCGAT GGATCATTGG GGCCAGGGCA CCCTGGTGAC CGTGAGCAGC GCGTCGACCA AGGGCCCATC GGTCTTCCCC CTGGCACCCT CCTCCAAGAG CACCTCTGGG GGCACAGCGG CCCTGGGCTG CCTGGTCAAG GACTACTTCC CCGAACCGGT GACGGTGTCG TGGAACTCAG GCGCCCTGAC |

TABLE 2-continued

Sequences of GDF15 peptides and anti-GDF15 antibodies.

| SEQ ID NO | Description | Sequence |
|---|---|---|
| | | CAGCGGCGTG CACACCTTCC CGGCTGTCCT ACAGTCCTCA GGACTCTACT CCCTCAGCAG CGTGGTGACC GTGCCCTCCA GCAGCTTGGG CACCCAGACC TACATCTGCA ACGTGAATCA CAAGCCCAGC AACACCAAGG TGGACAAGAA AGTTGAGCCC AAATCTTGTG ACAAAACTCA CACATGCCCA CCGTGCCCAG CACCTGAAGC CGCTGGGGCA CCGTCAGTCT TCCTCTTCCC CCCAAAACCC AAGGACACCC TCATGATCTC CCGGACCCCT GAGGTCACAT GCGTGGTGGT GGACGTGAGC CACGAAGACC CTGAGGTCAA GTTCAACTGG TACGTGGACG GCGTGGAGGT GCATAATGCC AAGACAAAGC CGCGGGAGGA GCAGTACAAC AGCACGTACC GTGTGGTCAG CGTCCTCACC GTCCTGCACC AGGACTGGCT GAATGGCAAG GAGTACAAGT GCAAGGTCTC CAACAAAGCC CTCCCAGCCC CCATCGAGAA AACCATCTCC AAAGCCAAAG GGCAGCCCCG AGAACCACAG GTGTACACCC TGCCCCCATC CCGGGAGGAG ATGACCAAGA ACCAGGTCAG CCTGACCTGC CTGGTCAAAG GCTTCTATCC CAGCGACATC GCCGTGGAGT GGGAGAGCAA TGGGCAGCCG GAGAACAACT ACAAGACCAC GCCTCCCGTG CTGGACTCCG ACGGCTCCTT CTTCCTCTAT AGCAAGCTCA CCGTGGACAA GAGCAGGTGG CAGCAGGGGA ACGTCTTCTC ATGCTCCGTG ATGCATGAGG CTCTGCACAA CCACTACACG CAGAAGAGCC TCTCCCTGTC CCCCGGA |
| 171 | GDF15 HCDR-1 Consensus Sequence | GYTFX$_1$X$_2$YNID wherein X$_1$ is S or T and X$_2$ is S or D |
| 172 | GDF15 HCDR-2 Consensus Sequence | X$_3$INPX$_4$X$_5$GX$_6$AX$_7$X$_8$X$_9$QKFW, wherein X$_3$ is G or Q; X$_4$ is I or N; X$_5$ is F or N; X$_6$ is T or L; X$_7$ is F or N; X$_8$ is Y or F and X$_9$ is N or A |
| 173 | GDF15 HCDR-3 Consensus Sequence | EX$_{10}$ITTK$_{11}$GAMDX$_{12}$, wherein X$_{10}$ is A or Q; X$_{11}$ is V or I; and X$_{12}$ is H or Y |
| 174 | GDF15 LCDR-1 Consensus Sequence | RX$_1$SQX$_2$X$_3$X$_4$X$_5$YLA, wherein X$_1$ is T or A, X$_2$ is S or N, X$_3$ is V or L, X$_4$ is H or S, and X$_5$ is N or S |
| 175 | GDF15 LCDR-2 Consensus Sequence | DAX$_6$X$_7$RAX$_8$, wherein X$_6$ is S or K; X$_7$ is T or N; and X$_8$ is D or T |
| 176 | GDF15 LCDR-3 consensus Sequence | QQFX$_9$X$_{10}$X$_{11}$PX$_{12}$T, wherein X$_9$ is W or S; X$_{10}$ is S or N; X$_{11}$ is W or D; and $_{X12}$ is W or Y |
| 177 | hu01G06 VH | QVQLVQSGAE VKKPGASVKV SCKASGYTFT DYNMDWVRQA PGQSLEWMGQ INPNNGLIFF NQKFQGRVTL TTDTSTSTAY MELRSLRSDD TAVYYCAREA ITTVGAMDYW GQGTLVTVSS |
| 178 | hu01G06 VL | DIQMTQSPSS LSASVGDRVT ITCRTSENLH NYLAWYQQKP GKSPKLLIYD AKTLADGVPS RFSGSGSGTD YTLTISSLQP EDFATYYCQH FWSDPYTFGQ GTKLEIK |
| 179 | GDF15_0297 HCDR-1 GDF15_0301 HCDR-1 GDF15_0470 HCDR-1 | GYPFEGWYIH |
| 180 | GDF15_0297 HCDR-2 GDF15_0301 HCDR-2 GDF15_0470 HCDR-2 | WNNPRTGLTNHAQKFQG |
| 181 | GDF15_0297 HCDR-3 GDF15_0301 HCDR-3 GDF15_0470 HCDR-3 | GVGADAAFDI |
| 182 | GDF15_0297 VH | QVQLQQPGAE LVKPGASVKM SCKASGYPFE GWYIHWVKQR PGQGLEWMGW NNPRTGLTNH AQKFQGKVTM TRDTSSSTAY MQLSSLTSED SAVYYCARGV GADAAFDIWG QGTTLTVSS |
| 183 | GDF15_0297 HC | QVQLQQPGAE LVKPGASVKM SCKASGYPFE GWYIHWVKQR PGQGLEWMGW NNPRTGLTNH AQKFQGKVTM TRDTSSSTAY MQLSSLTSED SAVYYCARGV GADAAFDIWG QGTTLTVSSA KTTPPSVYPL APGSAAQTNS MVTLGCLVKG YFPEPVTVTW NSGSLSSGVH TFPAVLQSDL YTLSSSVTVP SSTWPSETVT CNVAHPASST KVDKKIVPRD CGCKPCICTV PEVSSVFIFP PKPKDVLTIT LTPKVTCVVV AISKDDPEVQ FSWFVDDVEV HTAQTQPREE QFNSTFRSVS ELPIMHQDWL NGKEFKCRVN SAAFPAPIEK TISKTKGRPK APQVYTIPPP KEQMAKDKVS LTCMITDFFP EDITVEWQWN GQPAENYKNT QPIMDTDGSY FIYSKLNVQK SNWEAGNTFT CSVLHEGLHN HHTEKSLSHS PGK |

TABLE 2-continued

Sequences of GDF15 peptides and anti-GDF15 antibodies.

| SEQ ID NO | Description | Sequence |
|---|---|---|
| 184 | GDF15_0297 LCDR-1<br>GDF15_0301 LCDR-1<br>GDF15_0470 LCDR-1 | RSSQSLLWKHGYNYLD |
| 185 | GDF15_0297 LCDR-2<br>GDF15_0301 LCDR-2<br>GDF15_0470 LCDR-2 | LDRNRAH |
| 186 | GDF15_0297 LCDR-3<br>GDF15_0301 LCDR-3<br>GDF15_0470 LCDR-3 | MQSFETPIT |
| 187 | GDF15_0297 VL | DIVMTQSPSS LSVSAGEKVT MSCRSSQSLL WKHGYNYLDW YQQKPGQPPK LLIYLDRNRA HGVPDRFTGS GSGTDFTLTI SSVQAEDLAV YYCMQSFETP ITFGGGTKLE IK |
| 188 | GDF15_0297 LC | DIVMTQSPSS LSVSAGEKVT MSCRSSQSLL WKHGYNYLDW YQQKPGQPPK LLIYLDRNRA HGVPDRFTGS GSGTDFTLTI SSVQAEDLAV YYCMQSFETP ITFGGGTKLE IKRADAAPTV SIFPPSSEQL TSGGASVVCF LNNFYPKDIN VKWKIDGSER QNGVLNSWTD QDSKDSTYSM SSTLTLTKDE YERHNSYTCE ATHKTSTSPI VKSFNRNEC |
| 189 | GDF15 0301 VH | QVQLQQPGAE LVKPGASVKM SCKASGYPFE GWYIHWVKQR PGQGLEWMGW NNPRTGLTNH AQKFQGKATL TVDTSSTAY MQLSSLTSED SAVYYCARGV GADAAFDIWG QGTTLTVSS |
| 190 | GDF15 0301 HC | QVQLQQPGAE LVKPGASVKM SCKASGYPFE GWYIHWVKQR PGQGLEWMGW NNPRTGLTNH AQKFQGKATL TVDTSSTAY MQLSSLTSED SAVYYCARGV GADAAFDIWG QGTTLTVSSA KTTPPSVYPL APGSAAQTNS MVTLGCLVKG YFPEPVTVTW NSGSLSSGVH TFPAVLQSDL YTLSSSVTVP SSTWPSETVT CNVAHPASST KVDKKIVPRD CGCKPCICTV PEVSSVFIFP PKPKDVLTIT LTPKVTCVVV AISKDDPEVQ FSWFVDDVEV HTAQTQPREE QFNSTFRSVS ELPIMHQDWL NGKEFKCRVN SAAFPAPIEK TISKTKGRPK APQVYTIPPP KEQMAKDKVS LTCMITDFFP EDITVEWQWN GQPAENYKNT QPIMDTDGSY FIYSKLNVQK SNWEAGNTFT CSVLHEGLHN HHTEKSLSHS PGK |
| 191 | GDF15 0301 VL | DIVLTQSPSS LSVSAGEKVT MSCRSSQSLL WKHGYNYLDW YQQKPGQPPK LLIYLDRNRA HGVPDRFTGS GSGTDFTLTI SSVQAEDLAV YYCMQSFETP ITFGGGTKLE IK |
| 192 | GDF15 0301 LC | DIVLTQSPSS LSVSAGEKVT MSCRSSQSLL WKHGYNYLDW YQQKPGQPPK LLIYLDRNRA HGVPDRFTGS GSGTDFTLTI SSVQAEDLAV YYCMQSFETP ITFGGGTKLE IKRADAAPTV SIFPPSSEQL TSGGASVVCF LNNFYPKDIN VKWKIDGSER QNGVLNSWTD QDSKDSTYSM SSTLTLTKDE YERHNSYTCE ATHKTSTSPI VKSFNRNEC |
| 193 | GDF15 0470 VH | QVQLVQSGAE VKKPGASVKV SCKASGYPFE GWYIHWVRQA PGQGLEWMGW NNPRTGLTNH AQKFQGRVTM TRDTSISTAY MELSRLRSDD TAVYYCARGV GADAAFDIWG QGTMVTVSS |
| 194 | GDF15 0470 HC | QVQLVQSGAE VKKPGASVKV SCKASGYPFE GWYIHWVRQA PGQGLEWMGW NNPRTGLTNH AQKFQGRVTM TRDTSISTAY MELSRLRSDD TAVYYCARGV GADAAFDIWG QGTMVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSREEM TKNQVSLTCL VKGFYPSDIA VEWESNGQPE NNYKTTPPVL DSDGSFFLYS KLTVDKSRWQ QGNVFSCSVM HEALHNHYTQ KSLSLSPG |
| 195 | GDF15 0470 VL | EIVLTQSPA TLSLSPGER ATLSCRSSQ SLLWKHGYN YLDWYQQKP GQAPRLLIY LDRNRAHGI PARFSGSGS GTDFTLTIS SLEPEDFAV YYCMQSFET PITFGQGTK VEIK |
| 196 | GDF15 0470 LC | EIVLTQSPA TLSLSPGER ATLSCRSSQ SLLWKHGYN YLDWYQQKP GQAPRLLIY LDRNRAHGI PARFSGSGS GTDFTLTIS SLEPEDFAV YYCMQSFET PITFGQGTK VEIKRTVAA PSVFIFPPS DEQLKSGTA SVVCLLNNF YPREAKVQW KVDNALQSG NSQESVTEQ DSKDSTYSL SSTLTLSKA DYEKHKVYA CEVTHQGLS SPVTKSFNR GEC |

In certain embodiments, the substitution is human germline substitution in which a (donor) CDR residue is replaced with the corresponding human germline (acceptor) residue, to increase the human amino acid content and potentially reduce immunogenicity of the antibody as described in, e.g., US Patent Application Publication No. 2017/0073395 and Townsend et al., 2015, Proc. Nat. Acad. Sci. USA 112(50): 15354-15359). For example, if human germline IGHV1-69*01 framework is used and the exemplary antibody, GDF15_001 VH (SEQ ID NO:166) is compared, then the alignment of the HCDR-1 of GDF15_001 antibody (SEQ ID NO:32) and human germline IGHV1-69*01 is as follows:

|  | Position | | | | | | | | | |
| --- | --- | --- | --- | --- | --- | --- | --- | --- | --- | --- |
|  | 26 | 27 | 28 | 29 | 30 | 31 | 32 | 33 | 34 | 35 |
| Human Germline IGHV1-69*01 | G | G | T | F | S | S | Y | A | / | S |
| GDF15_001 VH (SEQ ID NO: 166) | G | Y | T | F | S | S | Y | N | / | D |

For amino acid position numbers 26, 28, 29, 30, 31, 32 and 34 (italics), the human germline residue (acceptor) and the corresponding GDF15_001 residues (donor) are the same, and a germline substitution is not possible. For positions 27, 33 and 35 (bold and underlined), the human germline (acceptor) residue and the corresponding GDF15_001 (donor) residue are different. Residues of GDF15_001 at these positions may be replaced with the corresponding human germline IGHV1-69*01 residue to further increase the human residue content. The same process can be followed for each heavy and light chain CDR to increase the content of human amino acid residues while conserving the binding characteristics, e.g., epitope binding, affinity, and the like, while minimizing the content of mouse residues thereby decreasing any potential immunogenicity, e.g., human anti mouse antibody (HAMA) immune response, to the antibody in a human.

Methods and libraries for introducing human germline residues in antibody CDRs are described in detail in US Patent Application Publication No. 2017/0073395, and Townsend et al., 2015, Proc. Natl. Acad. Sci. USA. 112(50): 15354-15359, and both are herein incorporated by reference in their entirety.

The anti-GDF15 antibodies, or antigen-binding fragments thereof, may comprise a VH framework comprising a human germline VH framework sequence. In some aspects, VH frameworks from the following germlines may be used: IGHV1-2*02, IGHV1-3*01, IGHV1-46*01, IGHV1-69*01, IGHV1-69*02, IGHV1-8*01, IGHV3-13*01, IGHV3-23*01, IGHV3-23*04, IGHV3-30*01, IGHV3-30*18, IGHV5-10-1*01, IGHV5-10-1*04, or IGHV5-51*01 (germline names are based on IMGT germline definition). In some aspects, VL frameworks from the following germlines may be used: IGKV1-12*01, IGKV1-13*02, IGKV1-33*01, IGKV1-39*01, IGKV1-5*01, IGKV3-11*01, IGKV3-15*01, IGKV3-20*01, IGKV3D-20*02, and IGKV4-1*01 (germline names are based on IMGT germline definition. Sequences of human germline frameworks are available from various public databases, such as V-base, IMGT, NCBI, or Abysis.

The anti-GDF15 antibodies, or antigen-binding fragments thereof, may comprise a VL framework comprising a human germline VL framework sequence. The VL framework may comprise one or more amino acid substitutions, additions, or deletions, while still retaining functional and structural similarity with the germline from which it was derived. In some aspects, the VL framework is at least 53%, 58%, 60%, 63%, 71%, 72%, 90%, 91%, 92%, 93%, 94%, 95%, 96%, 97%, 98%, or 99% identical to the human germline sequence from which it was derived. In some aspects, the antibody, or antigen binding fragment thereof, comprises a VL framework comprising 1, 2, 3, 4, 5, 6, 7, 8, 9, 10 amino acid substitutions, additions or deletions relative to the human germline VL framework sequence. In some aspects, the 1, 2, 3, 4, 5, 6, 7, 8, 9, or 10 amino acid substitutions, additions or deletions are only in the framework regions. In some aspects, the percent (%) identity is based on similarity with VL excluding those portions herein defined as CDRs.

The anti-GDF15 antibodies, or antigen-binding fragments thereof, may comprise a VH framework comprising a human germline VH framework sequence. The VH framework may comprise one or more amino acid substitutions, additions, or deletions, while still retaining functional and structural similarity with the germline from which it was derived. In some aspects, the VH framework is at least 72%, 74%, 75%, 77%, 90%, 91%, 92%, 93%, 94%, 95%, 96%, 97%, 98%, or 99% identical to the human germline sequence from which it was derived. In some aspects, the antibody, or antigen binding fragment thereof, comprises a VH framework comprising 1, 2, 3, 4, 5, 6, 7, 8, 9, 10 amino acid substitutions, additions or deletions relative to the human germline VH framework sequence. In some aspects, the 1, 2, 3, 4, 5, 6, 7, 8, 9, or 10 amino acid substitutions, additions or deletions are only in the framework regions. In some aspects, the % identity is based on similarity with VH excluding those portions herein defined as CDRs.

The anti-GDF15 antibodies, or antigen-binding fragments thereof, may comprise a VH comprising an amino acid sequence at least 90% identical to the amino acid sequence of SEQ ID NO:6. The VH may comprise an amino acid sequence at least 91%, 92%, 93%, 94%, 95%, 96%, 97%, 98%, or 99%, identical to the amino acid sequence of SEQ ID NOs: 21, 34, 44, 53, 60, 68, 73, 80, 86, 93, 99, 106, 112, 120, 127, 136, 142, 148, 155, 161 and 166. The VH may comprise the amino acid sequence of SEQ ID NOs: 21, 34, 44, 53, 60, 68, 73, 80, 86, 93, 99, 106, 112, 120, 127, 136, 142, 148, 155, 161 and 166.

The antibody or antigen-binding fragment may comprise a VL comprising an amino acid sequence at least 90% identical to the amino acid sequence of SEQ ID NO:1. The VL may comprise an amino acid sequence at least 91%, 92%, 93%, 94%, 95%, 96%, 97%, 98%, or 99%, identical to the amino acid sequence SEQ ID NOs: 11, 30, 39, 49, 56, 64, 71, 77, 83, 90, 96, 103, 109, 115, 123, 131, 139, 144, 151, 158 and 163. The VL may comprise the amino acid sequence of SEQ ID NOs: 11, 30, 39, 49, 56, 64, 71, 77, 83, 90, 96, 103, 109, 115, 123, 131, 139, 144, 151, 158 and 163.

In some aspects, the antibody, or antigen-binding portion thereof, comprises a LCDR-1, a LCDR-2, and a LCDR-3 as set forth in the amino acid sequence of at least one of SEQ ID NOs: 11, 30, 39, 49, 56, 64, 71, 77, 83, 90, 96, 103, 109, 115, 123, 131, 139, 144, 151, 158, and 163.

In some aspects, the antibody, or antigen-binding portion thereof, further comprises a HCDR-1, a HCDR-2, and a HCDR-3 as set forth in the amino acid sequence of at least one of SEQ ID NOs: 21, 34, 44, 53, 60, 68, 73, 80, 86, 93, 99, 106, 112, 120, 127, 136, 142, 148, 155, 161, and 166.

In some aspects, the antibody, or antigen binding portion thereof, comprises a LCDR-1, a LCDR-2, a LCDR-3 as set forth in the amino acid sequence of SEQ ID NO:163, and a HCDR-1, a HCDR-2, and a HCDR-3 as set forth in the amino acid sequence of SEQ ID NO:166.

The antibody, or antigen-binding portion thereof, may comprise a VL comprising an amino acid sequence at least 90% identical to the amino acid sequence of SEQ ID NO:163. The VL may comprise an amino acid sequence at least 91%, 92%, 93%, 94%, 95%, 96%, 97%, 98%, or 99%, identical to the amino acid sequence of SEQ ID NO:163. The VL may comprise the amino acid sequence of SEQ ID NO:163.

The antibody, or antigen-binding portion thereof, may comprise a VH comprising an amino acid sequence at least 90% identical to the amino acid sequence of SEQ ID NO:166. The VH may comprise an amino acid sequence at least 91%, 92%, 93%, 94%, 95%, 96%, 97%, 98%, or 99%, identical to the amino acid sequence of SEQ ID NO:166. The VH may comprise the amino acid sequence of SEQ ID NO:166.

The antibody or antigen-binding fragment may comprise a HC comprising an amino acid sequence at least 90%, 91%, 92%, 93%, 94%, 95%, 96%, 97%, 98%, or 99%, identical to the amino acid sequence of SEQ ID NO:164. The HC may comprise the amino acid sequence of SEQ ID NO:164.

The antibody or antigen-binding fragment may comprise a LC comprising an amino acid sequence at least 90%, 91%, 92%, 93%, 94%, 95%, 96%, 97%, 98%, or 99%, identical to SEQ ID NO:162. The LC may comprise the amino acid sequence of SEQ ID NO:162.

PD-1 Axis Binding Antagonists

The term "PD-1 axis binding antagonist" as used herein refers to a molecule that inhibits the interaction of a PD-1 axis binding partner with either one or more of its binding partners, so as to remove T-cell dysfunction resulting from signaling on the PD-1 signaling axis (also referred to as the "PD-1/PD-L pathway" or "PD-1/PD-L signaling pathway"), with a result being to restore or enhance T-cell function. As used herein, a PD-1 axis binding antagonist includes a PD-1 binding antagonist, a PD-L1 binding antagonist and a PD-L2 binding antagonist. In some embodiments, the PD-1 axis binding antagonist is an anti PD-1 antibody. In some embodiments, the PD-1 axis binding antagonist is an anti PD-L1 antibody. In some embodiments, the PD-1 axis binding antagonist is an anti-PD-L2 antibody.

In some aspects, a PD-1 axis antagonist, a PD-1 axis binding antagonist, a PD-1 binding antagonist, and an anti-PD-L1 antibody does not include avelumab. That is, optionally, avelumab is excluded from the agent that inhibits the PD-1 axis signaling axis.

Exemplary PD-1 axis binding antagonists for use in the treatment method, medicaments and uses of the present invention, include, without limitation, nivolumab, pembrolizumab, AMP-224 with or without the signal sequence as described in International Patent Publication No. WO2010/027827 and WO2011/066342, mAb7 and mAb15 as disclosed in International Patent Publication No. WO2016/092419, and avelumab as described in WO2013/079174. The disclosures of WO2010/027827, WO2011/066342, WO2016/092419 and WO2013/079174 are hereby incorporated by reference in their entireties. Table 3 lists the various sequences of the some of the exemplified PD-1 axis binding antagonists.

TABLE 3

| SEQ ID NO | Description | Sequence |
|---|---|---|
| 197 | mAb7 (RN888) or mAb15 full-length heavy chain (HC) with CDRs underlined, including terminal lysine (K). | QVQLVQSGAE VKKPGASVKV SCKASGYTFT SYWINWVRQA PGQGLEWMGN IYPGSSLTNY NEKFKNRVTM TRDTSTSTVY MELSSLRSED TAVYYCARLS TGTFAYWGQG TLVTVSSAST KGPSVFPLAP CSRSTSESTA ALGCLVKDYF PEPVTVSWNS GALTSGVHTF RPNLQSSGLY SLSSVVTVPS SSLGTKTYTC NVDHKPSNTK VDKRVESKYG PPCPPCPAPE FLGGPSVFLF PPKPKDTLMI SRTPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLGK (SEQ ID NO: 1 IN US 62/750579) (SEQ ID NO: 29 in WO 16/092419) |
| 198 | mAb7 (RN888) or mAb15 full-length heavy chain without the C-terminal lysine, with CDRs underlined. | QVQLVQSGAE VKKPGASVKV SCKASGYTFT SYWINWVRQA PGQGLEWMGN IYPGSSLTNY NEKFKNRVTM TRDTSTSTVY MELSSLRSED TAVYYCARLS TGTFAYWGQG TLVTVSSAST KGPSVFPLAP CSRSTSESTA ALGCLVKDYF PEPVTVSWNS GALTSGVHTF PAVLQSSGLY SLSSVVTVPS SSLGTKTYTC NVDHKPSNTK VDKRVESKYG PPCPPCPAPE FLGGPSVFLF PPKPKDTLMI SRTPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLG (SEQ ID NO: 2 IN US 62/750579) (SEQ ID NO: 38 in WO 16/092419) |
| 199 | mAb7 (RN888) full-length light chain, with CDRs underlined. | DIVMTQSPDS LAVSLGERAT INCKSSQSLW DSGNQKNFLT WYQQKPGQPP KLLIYWTSYR ESGVPDRFSG SGSGTDFTLT ISSLQAEDVA VYYCQNDYFY PHTFGGGTKV EIKRGTVAAP SVFIFPPSDE QLKSGTASVV CLLNNFYPRE AKVQWKVDNA LQSGNSQESV TEQDSKDSTY SLSSTLTLSK ADYEKHKVYA CEVTHQGLSS PVTKSFNRGE C (SEQ ID NO: 3 IN US 62/750579) (SEQ ID NO: 39 in WO 16/092419) |

TABLE 3-continued

| SEQ ID NO | Description | Sequence |
|---|---|---|
| 200 | mAb7 (RN888) light chain variable region, with CDRs underlined. | QVQLVQSGAE VKKPGASVKV SCKASGYTFT <u>SYWINWVRQA PGQGLEWMGN IYPGSSLTNY NEKFKN</u>RVTM TRDTSTSTVY MELSSLRSED TAVYYCARL<u>S TGTFAY</u>WGQG TLVTVSS (SEQ ID NO: 4 IN US 62/750579) (SEQ ID NO: 8 in WO 16/092419) |
| 201 | mAb7 (RN888) and mAb15 heavy chain variable region, with CDRs underlined. | QVQLVQSGAE VKKPGASVKV SCKASGYTFT <u>SYWINWVRQA PGQGLEWMGN IWPGSSLTNY NEKFKN</u>RVTM TRDTSTSTVY MELSSLRSED TAVYYCARL<u>L TGTFAY</u>WGQG TLVTVSS (SEQ ID NO: 5 IN US 62/750579) (SEQ ID NO: 4 in WO 16/092419) |
| 202 | mAb15 light chain variable region, with CDRs underlined. | DIVMTQSPDS LAVSLGERAT IN<u>CKSSQSLWD SGNQKNFLT</u> WYQQKPGQPP KLLIY<u>WTSYR ES</u>GVPDRFSG SGSGTDFTLTI SSLQAEDVA VYYCQ<u>NDYFY PHT</u>FGGGTKV EIK (SEQ ID NO: 6 IN US 62/750579) |
| 203 | nivolumab, MDX1106, full length heavy chain From WO2006/121168 | QVQLVESGGG WQPGRSLRLD CKASGITFSN SGMHWVRQAP GKGLEWVAVR WYDGSKRYYA DSVKGRFTIS RDNSKNTLFL QMNSLRAEDT AVYYCATNDD YWGQGTLVTV SSASTKGPSV FPLAPCSRST SESTAALGCL VDYFPEPVTV SWNSGALTSG VHTFPAVLQS SGLYSLSSVV TVPSSSLGTT YTCNVDHKPS NTKVDRVESY GPPCPPCPAP EFLGGPSVFL FPPKPKDTLM ISRTPEVTCW VDVSQEDPEV QFNWYYDGVE VHNATKPREE QFNSTYRVVS VLTVLHQDWL NGKEYKCKVS NKGLPSSIEK TISKAGQPRE PQVYTLPPSQ EEMTKNQVSL TCLVKGFYPS DIAVEWESNG QPENYKTTP PVLDSDGSFF LYSRLTVDKS RWQEGNVFSC SVMHEALHNH YTQKSLSLSL GK |
| 204 | nivolumab, MDX1106, full length light chain From WO2006/121168 | EIVLTQSPAT LSLSPGERAT LSCRASQSVS SYLAWYQQPG QAPRLLIYDA SNRATGIPAR FSGSGSGTDF TLTISSLEPE DFAVYYCQQS SNWPRTFGQG TKVEIRTVAA PSVFIFPPSD EQLSGTASVV CLLNNFYPRE AVQWKVDNAL QSGNSQESVT EQDSDSTYSL SSTLTLSKAD YEKHKVYACE VTHQGLSSPV TSFNRGEC |
| 205 | pembrolizumab, MK3475, full length heavy chain From WO2009/114335 | QVQLVQSGVE VKKPGASVK VSCKASGYTF TNYYMYWVRQA PGQGLEWMGG INPSNGGTNF NEKFKNRVT LTTDSSTTTA YMELKSLQFDD TAVYYCARRD YRFDMGFDYW GQGTTVTVS SASTKGPSVF PLAPCSRSTS EGSTAALGCLVK DYFPEPVTVS WNSGALTSG VHTFPAVLQS SGLYSLSSVVT VPSSSLGTKT YTCNVDHKPS NTKVDKRVE SKYGPPCPPC PAPEFLGGPSV FLFPPKPKDT LMISRTPEVT CVVVDVSQE DPEVQFNWYV DGVEVHNAKTK PREEQFNSTY RVVSVLTVLH QDWLNGKEY KCKVSNKGLP SSIEKTISKAK GQPREPQVYT LPPSQEEMTK NQVSLTCLV KGFYPSDIAV EWESNGQPENN YKTTPPVLDS DGSFFLYSRL TVDKSRWQE GNVFSCSVMH EALHNYTQKS LSLSLGK |
| 206 | pembrolizumab, MK3475, full length light chain From WO2009/114335 | EIVLTQSPAT LSLSPGERA TLSCRASKGV STSGYSYLHW YQQKPGQAPRL LIYLASYLES GVPARFSGS GSGTDFTLTI SSLEPEDFAVY YCQHSRDLPL TFGGGTKVEI KRTVAAPSV FIFPPSDEQL KSGTASVVCLL NNFYPREAKV QWKVDNALQS GNSQESVTE QDSKDSTYSL SSTLTLSKADY EKHKVYACEV THQGLSSPVT KSFNRGEC |
| 207 | AMP-224, without signal sequence From WO2010/027827 and WO2011/066342 | LFTVTVPKEL YIIEHGSNVT LECNFDTGSH VNLGAITASL QKVENDTSPH RERATLLEEQ LPLGKASFHI PQVQVRDEGQ YQCIIIYGVA WDYKYLTLKV KASYRKINTH ILKVPETDEV ELTCQATGYP LAEVSWPNVS VPANTSHSRT PEGLYQVTSV LRLKPPPGRN FSCVFWNTHV RELTLASIDL QSQMEPRTHP TWEPKSCDKT HTCPPCPAPE LLGGPSVFLF PPKPKDTLMI SRTPEVTCVV DVSHEDPEVK FNWYVDGVEV HNAKTKPREE QYNSTYRWSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 208 | YW243.55.S70, MPDL3280A) heavy chain variable region From WO2010/077634 | EVQLVESGGG LVQPGGSLRL SCAASGFTFS DSWIHWVRQA PGKGLEWVAW ISPYGGSTYY ADSVKGRFTI SADTSKNTAY LQMNSLRAED TAVYYCARRH WPGGFDYWGQ GTLVTVSA |

TABLE 3-continued

| SEQ ID NO | Description | Sequence |
|---|---|---|
| 209 | YW243.55.S70 MPDL3280A, light chain variable region From WO2010/077634 | DIQMTQSPSS LSASVGDRVT ITCRASQDVS TAVAWYQQKP GKAPKLLIYS ASFLYSGVPS RFSGSGSGTD FTLTISSLQP EDFATYYCQQ YLYHPATFGQ GTKVEIKR |

The term "PD-1 binding antagonist" as used herein refers to a molecule that specifically binds PD-1 and decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist specifically binds PD-1 and thereby inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist specifically binds PD-1 and thereby reduces the negative co-stimulatory signal mediated by or through cell surface proteins expressed on T lymphocytes mediated via signaling through PD-1 so as render a dysfunctional T-cell less non-dysfunctional. In some embodiments, the PD-1 binding antagonist is an anti-PD-1 antibody including, but not limited to, nivolumab, pembrolizumab, spartalizumab, tislelizumab, pidilizumab, AMP-224, AMP-554, cemiplimab, and PF-06801591.

PF-06801951 is also referred to as sasanlimab (CAS Registry No. 2206792-50-7), RN888, and is disclosed in International Patent Publication No. WO 2016/092419, which is incorporated by reference as if set forth in its entirety herein. Sasanlimab is a humanized, hinge region-stabilized IgG4-kappa (κ) monoclonal antibody. The amino acid sequences of sasanlimab (PF-06801951; RN888) are set forth in Table 4 below.

In a specific aspect, a PD-1 binding antagonist is nivolumab. In another specific aspect, a PD-1 binding antagonist is pembrolizumab. In another specific aspect, a PD-1 binding antagonist is pidilizumab.

The term "PD-L1 binding antagonist" as used herein refers to a molecule that specifically binds PD-L1 and decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In some aspects, the PD-L1 binding antagonist does not include avelumab. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated by signaling through PD-L1 so as render a dysfunctional T-cell less non-dysfunctional. In some embodiments, a PD-L1 binding antagonist is an anti-PD-L1 antibody. In a specific aspect, an anti-PD-L1 antibody is avelumab (disclosed as A09-246-2, in International Patent Publication No. WO2013/079174). In some aspects, avelumab is not included as a PD-1 axis antagonist.

In another specific aspect, an anti-PD-L1 antibody is atezolizumab. In another specific aspect, an anti-PD-L1 antibody is durvalumab. In another specific aspect, an anti-PD-L1 antibody is BMS-936559 (MDX-1105).

As used herein, an anti-human PD-L1 antibody refers to an antibody that specifically binds to mature human PD-L1, or portion thereof, wherein the mature human PD-L1 molecule consists of amino acids 19-290 of the following sequence:

(SEQ ID NO: 221)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET.

TABLE 4

ANTI-HUMAN PD-L1 MONOCLONAL ANTIBODY SASANLIMAB (PF-06801951, RN888, mAb7) SEQUENCES

| SEQ ID NO | Description | Amino Acid Sequence |
|---|---|---|
| 210 | HCDR-1 (Chothia) (SEQ ID NO: 14 IN WO 2016/092419) | GYTFTSY |

TABLE 4-continued

ANTI-HUMAN PD-L1 MONOCLONAL ANTIBODY SASANLIMAB (PF-06801951, RN888, mAb7) SEQUENCES

| SEQ ID NO | Description | Amino Acid Sequence |
|---|---|---|
| 211 | HCDR-1 (extended) (SEQ ID NO: 13 IN WO 2016/092419) | GYTFTSYWIN |
| 212 | HCDR-1 (Kabat) (SEQ ID NO: 15 IN WO 2016/092419) | SYWIN |
| 213 | HCDR-2 (Chothia) (SEQ ID NO: 16 IN WO 2016/092419) | NIYPGSSL |
| 214 | HCDR-2 (extended) (SEQ ID NO: 17 IN WO 2016/092419) | NIYPGSSLTNYNEKFK |
| 215 | HCDR-3 (SEQ ID NO: 23 IN WO 2016/092419) | LSTGTFAY |
| 216 | LCDR-1 SEQ ID NO: 10 IN WO 2016/092419) | KSSQSLWDSGNQKNFLT |
| 217 | LCDR-2 (SEQ ID NO: 20 IN WO 2016/092419) | WTSYRES |
| 218 | LCDR-3 (SEQ ID NO: 21 IN WO 2016/092419) | QNDYFYPHT |
| 219 | VH (SEQ ID NO: 4 IN WO 2016/092419) Chothia (bold), Kabat (underlined), and extended (both), CDRs are indicated; | QVQLVQSGAE VKKPGASVKV SCKASGYTFT SYWINWVRQA PGQGLEWMGN IYPGSSLTNY NEKFKNRVTM TRDTSTSTVY MELSSLRSED TAVYYCARLS TGTFAYWGQG TLVTVSS |
| 220 | VL (SEQ ID NO: 8 IN WO 2016/092419) CDRs are indicated in bold and underlined lettering | DIVMTQSPDS LAVSLGERAT INCKSSQSLW DSGNQKNFLT WYQQKPGQPP KLLIYWTSYR ESGVPDRFSG SGSGTDFTLT ISSLQAEDVA VYYCQNDYFY PHTFGGGTKV EIK |
| 197 | Heavy chain (HC) (SEQ ID NO: 29 IN WO 16/092419) Terminal lysine (K) is optional; Chothia CDRs are indicated in bold lettering; Kabat CDRs are underlined; extended CDRs (both) | QVQLVQSGAEVKKPGASVKVSCKASGYTFTSYWINWVRQA PGQGLEWMGNIYPGSSLTNYNEKFKNRVTMTRDTSTSTVY MELSSLRSEDTAVYYCARLSTGTFAYWGQGTLVTVSSAST KGPSVFPLAPCSRSTSESTAALGCLVKDYFPEPVTVSWNS GALTSGVHTFPAVLQSSGLYSLSSVVTVPSSSLGTKTYTC NVDHKPSNTKVDKRVESKYGPPCPPCPAPEFLGGPSVFLF PPKPKDTLMISRTPEVTCVVVDVSQEDPEVQFNWYVDGVE VHNAKTKPREEQFNSTYRVVSVLTVLHQDWLNGKEYKCKV SNKGLPSSIEKTISKAKGQPREPQVYTLPPSQEEMTKNQV SLTCLVKGFYPSDIAVEWESNGQPENNYKTTPPVLDSDGS FFLYSRLTVDKSRWQEGNVFSCSVMHEALHNHYTQKSLSL SLG(K) |
| 199 | Light chain (LC) (SEQ ID NO: 39 IN WO 2016/092419) CDRs are indicated in bold and underlined lettering | DIVMTQSPDSLAVSLGERATINCKSSQSLWDSGNQKNFLT WYQQKPGQPPKLLIYWTSYRESGVPDRFSGSGSGTDFTLT ISSLQAEDVAVYYCQNDYFYPHTFGGGTKVEIKRGTVAAP SVFIFPPSDEQLKSGTASVVCLLNNFYPREAKVQWKVDNA LQSGNSQESVTEQDSKDSTYSLSSTLTLSKADYEKHKVYA CEVTHQGLSSPVTKSFNRGEC |
| 221 | human PD-L1 protein; Mature human PD-L1 consists of amino acid residues 29-290; the residues not included in the mature protein are underlined | <u>MRIFAVFIFM TYWHLLNAFT VTVPKDLYVV</u> EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH |

TABLE 4-continued

ANTI-HUMAN PD-L1 MONOCLONAL ANTIBODY SASANLIMAB (PF-06801951, RN888, mAb7) SEQUENCES

| SEQ ID NO | Description | Amino Acid Sequence |
|---|---|---|
| | | LVILGAILLC LGVALTFIFR LRKGRMMDVK KCGIQDTNSK KQSDTHLEET |

The term "PD-L2 binding antagonists" as used herein refers to a molecule that specifically binds PD-L2 and decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that specifically bind PD-L2 and decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated via signaling through PD-L2 so as render a dysfunctional T-cell less non-dysfunctional. In some embodiments, a PD-L2 binding antagonist is a PD-L2 immunoadhesin.

Nucleic Acids

The invention also provides polynucleotides encoding any of the antibodies of the invention, including antibody portions and modified antibodies described herein. The invention also provides a method of making any of the polynucleotides described herein. Polynucleotides can be made and expressed by procedures known in the art.

The sequence of a desired antibody, or antigen-binding fragment thereof, and nucleic acid encoding such antibody, or antigen-binding fragment thereof, can be determined using standard sequencing techniques. A nucleic acid sequence encoding a desired antibody, or antigen-binding fragment thereof, may be inserted into various vectors (such as cloning and expression vectors) for recombinant production and characterization. A nucleic acid encoding the heavy chain, or an antigen-binding fragment of the heavy chain, and a nucleic acid encoding the light chain, or an antigen-binding fragment of the light chain, can be cloned into the same vector, or different vectors.

In one aspect, the invention provides polynucleotides encoding the amino acid sequences of any of the following GDF15 antibodies and antigen-binding portions thereof: GDF15_001, GDF15_002, GDF15_003, GDF15_004, GDF15_005, GDF15_006, GDF15_007, GDF15_008, GDF15_009, GDF15_010, GDF15_011, GDF15_012, GDF15_013, GDF15_014, GDF15_015, GDF15_017, GDF15_018, GDF15_020, GDF15_021, GDF15_022, GDF15_100, GDF15_200, GDF15_297, GDF15_301, GDF15-470.

The invention provides polynucleotides encoding one or more proteins comprising the amino acid sequence selected from the group consisting of: (i) SEQ ID NOs:21, 34, 44, 53, 60, 68, 73, 80, 86, 93, 99, 106, 112, 120, 127, 136, 142, 148, 155, 161, 166, 11, 30, 39, 49, 56, 64, 71, 77, 83, 90, 96, 103, 109, 115, 123, 131, 139, 144, 151, 158, 163, 166, 183, 187, 189, 191, 193, and 195.

The invention provides polynucleotides comprising the nucleic acid sequence as set forth as one or more of SEQ ID NOs: 167, 168, 169, and 170. The invention provides a polynucleotide comprising the nucleic acid sequence as set forth as SEQ ID NO: 167. The invention provides a polynucleotide comprising the nucleic acid sequence as set forth as SEQ ID NO:168. The invention provides a polynucleotide comprising the nucleic acid sequence as set forth as SEQ ID NO:169. The invention provides a polynucleotide comprising the nucleic acid sequence as set forth as SEQ ID NO:170. Due to the degeneracy of the genetic code, the invention further provides a nucleic acid sequence wherein the nucleotide at position number 1344 of SEQ ID NO:170 can be A, C, G, T, and/or the nucleotide at position number 1347 can be A,C,G,T. The last two codons provided in SEQ ID NO:170 still encode proline and glycine, respectively.

The invention provides a polynucleotide comprising the nucleic acid sequence of the insert of the plasmid deposited with the ATCC and having Accession No. PTA-125038 encoding the VH domain of GDF15_001. The invention also provides a polynucleotide comprising the nucleic acid sequence of the insert of the plasmid deposited with the ATCC and having Accession No. PTA-125039 encoding the VL domain of GDF15_001. In addition, the invention provides a polypeptide comprising the amino acid sequence encoded by the DNA insert of the plasmid deposited with the ATCC and having Accession No. PTA-125038, encoding the VH domain of GDF15_001. The invention further provides a polypeptide comprising the amino acid sequence encoded by the insert of the plasmid deposited with the ATCC and having Accession No. PTA-125039 encoding the VL domain of GDF15_001.

The invention also provides a polynucleotide comprising the nucleic acid sequence of the insert of the plasmid deposited with the ATCC and having Accession No. PTA-125038, encoding the VH domain of GDF15_001 and the nucleic acid sequence of the insert of the plasmid deposited with the ATCC and having Accession No. PTA-125039, encoding the VL domain of GDF15_001.

In another aspect, the invention provides polynucleotides and variants thereof encoding an anti-GDF15 antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% nucleic acid sequence identity to any of the nucleic acid sequences disclosed or referred to herein. These amounts are not meant to be limiting and increments between the recited percentages are specifically envisioned as part of the disclosure.

The invention provides polypeptides encoded by the nucleic acid molecules described herein.

In one embodiment, the VH and VL domains, or antigen-binding portion thereof, or full-length HC or LC, are encoded by separate polynucleotides. Alternatively, both VH and VL, or antigen-binding portion thereof, or HC and LC, are encoded by a single polynucleotide.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a nucleic acid sequence that encodes an antibody or a portion thereof or may comprise a variant of such a sequence. Polynucleotide variants contain one or more substitutions, additions, deletions and/or insertions such that the binding characteristics of the encoded polypeptide is not diminished relative to a native antibody molecule. The effect on the binding characteristics of the polypeptide encoded by the variant nucleic acid sequence may generally be assessed as described herein. In some embodiments, polynucleotide variants exhibit at least about 70% identity, in some embodiments, at least about 80% identity, in some embodiments, at least about 90% identity, and in some embodiments, at least about 95% identity to a polynucleotide sequence that encodes the original (parent) antibody not comprising any substitution, addition, deletion and/or insertion, or a portion thereof. These percent identities are not meant to be limiting and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

In some embodiments, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Polynucleotide variants may also, or alternatively, be substantially homologous to a gene, or a portion or complement thereof. Such polynucleotide variants are capable of hybridizing under moderately stringent conditions to a naturally occurring DNA sequence encoding an antibody (or a complementary sequence).

Suitable "moderately stringent conditions" include prewashing in a solution of 5×SSC, 0.5% SDS, 1.0 mM EDTA (pH 8.0); hybridizing at about 50° C. to 65° C., 5×SSC (0.75 M NaCl, 0.075 M sodium citrate), overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC, 50 mM sodium phosphate (pH 6.8), 0.1% sodium pyrophosphate, 5×Denhardt's solution, sonicated salmon sperm DNA (50 pg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, for example.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

Suitable cloning and expression vectors can include a variety of components, such as promoter, enhancer, and other transcriptional regulatory sequences. The vector may also be constructed to allow for subsequent cloning of an antibody variable domain into different vectors. Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen. Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into a host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Thus, a "host cell" includes an individual cell or cell culture that can be or has been a recipient for polynucleotides and/or vector(s) comprising polynucleotides for incorporation of the polynucleotides and/or vectors. Host cells include progeny of a single host cell, and the progeny may not necessarily be completely identical (in morphology or in genomic DNA complement) to the original parent cell due to natural, accidental, or deliberate mutation. A host cell includes cells transfected and/or transformed in vivo with a polynucleotide of this invention.

The antibody, or antigen-binding fragment thereof, may be made recombinantly using a suitable host cell. A nucleic acid encoding the antibody or antigen-binding fragment thereof can be cloned into an expression vector, which can then be introduced into a host cell, such as *E. coli* cell, a yeast cell, an insect cell, a simian COS cell, a Chinese hamster ovary (CHO) cell, or a myeloma cell where the cell does not otherwise produce an immunoglobulin protein, to obtain the synthesis of an antibody in the recombinant host cell. Preferred host cells include a CHO cell, a Human embryonic kidney (HEK) 293 cell, a NS0 cell, or a Sp2.0 cell, among many cells well-known in the art. An antibody fragment can be produced by proteolytic or other degradation of a full-length antibody, by recombinant methods, or by chemical synthesis. A polypeptide fragment of an antibody, especially shorter polypeptides up to about 50 amino acids, can be conveniently made by chemical synthesis. Methods of chemical synthesis for proteins and peptides are known in the art and are commercially available.

The antibody, or antigen-binding fragment thereof, of the invention may be affinity matured. For example, an affinity matured antibody can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and WO2004/058184).

Immunogenicity

Immunogenicity is a major barrier to the development and utilization of protein therapeutics, including antibodies and Fc fusion proteins. Several factors can contribute to protein immunogenicity, including but not limited to the protein sequence, the route and frequency of administration, and the patient population. Although immune responses are typically most severe for non-human proteins, such as murine antibodies, even therapeutics with mostly or entirely human sequence content may be immunogenic. Immunogenicity is a complex series of responses to a substance that is perceived as foreign and may include production of neutralizing and non-neutralizing antibodies, formation of immune complexes, complement activation, mast cell activation, inflammation, and anaphylaxis. Unwanted immune responses may reduce the efficacy of antibody and Fc fusion protein therapeutics by directly interfering with antigen recognition, altering interactions with effector molecules, or perturbing the serum half-life or tissue distribution of the therapeutic.

Protein therapeutics can be analyzed to predict the presence of potential immunogenic epitopes using commercially available services such as provided by Epivax, Inc. of Providence, R.I. In some embodiments, in silico algorithms can predict epitopes that bind to Class II MHC molecules. Analysis of a data set of the polypeptide with such algorithms provides predicted epitopes. The predicted epitopes are used to make peptides prepared by standard methods of automated peptide synthesis or recombinant DNA techniques. The scoring information provided from Epivax can provide an indication of how widespread a predicted epitope recognized in the population.

As described in Example 10 below, the antibodies of the present invention were screened for the presence of epitopes recognized by T cells, also referred to herein as T cell epitopes, "T-regitopes" or "tReg", using the EpiMatrix algorithm developed by EpiVax. Antibody sequences are parsed into overlapping 9-mer frames where each frame overlaps the last by 8 amino acids. Each of the resulting frames is then scored for predicted binding affinity with respect to a panel of eight common MHC Class II HLA alleles (DRB1*0101, DRB1*0301, DRB1*0401, DRB1*0701, DRB1*0801, DRB1*1101, DRB1*1301, and DRB1*1501). Raw scores are normalized against the scores of a large sample of randomly generated peptides, and a resulting "Z" score is reported.

An overall sequence score, a tReg Adjusted Score, can be calculated, using the EpiMatrix Z-score, to predict the immunogenicity of an antibody. As described in Example 10, the tReg Adjusted Score is calculated by summing the EpiMatrix Z-scores of the 9-mer frames (the running total) and noting the number of HLA type observations. All individual combinations of 9-mer and HLA type ("observations") are examined, regardless of whether the 9-mer is an epitope. If a particular observation indicates the peptide is in the top 5% of binders for a given HLA type, the EpiMatrix Z-score for this observation is added to a running total associated with the entire protein sequence. The total number of observations examined is also recorded. The only exception is that all observations on 9-mers identified by the ISPRI software package developed by EpiVax as "T-regitopes" are assumed to have EpiMatrix scores of zero. As used herein, "T-regitopes" are amino acid sequences within the monoclonal antibody framework region that can potentially activate natural regulatory T cells and reduce unwanted immune responses. The tReg Adjusted Score is computed as follows: tReg Adjusted Score=(Running total)*1000/(Number of observations). In the running total, a baseline score of 0.05*2.2248 is subtracted from each observation (including T-regitopes). A lower tReg-Adjusted score predicts a lower potential for immunogenicity risk.

Uses

Methods for Treating Cachexia

In some aspects, the invention provides for therapeutic methods for reducing or inhibiting GDF15 activity using an anti-GDF15 antibody or antigen-binding fragment thereof, wherein the therapeutic methods comprise administering a therapeutically effective amount of a pharmaceutical composition comprising an antibody or antigen-binding fragment thereof. The disorder treated is any disease or condition which is improved, ameliorated, inhibited or prevented by removal, inhibition or reduction of GDF15 activity or signaling.

The invention encompasses a method of reducing the level of free GDF15 in a subject in need thereof. The method comprises determining the level of free GDF15 in a subject, administering a therapeutic amount of the antibody of the invention, or antigen-binding fragment thereof, and comparing the level of GDF15 before administration to the level of free GDF15 after administration of the antibody, or antigen-binding fragment thereof, thereby reducing the level of free GDF15 in the subject.

In one embodiment, reduction of the level of free GDF15 reduces an undesirable, deleterious or unwanted biological activity of GDF15. Such activity of GDF15 includes, but is not limited to, (a) decreasing food intake; (b) decreasing appetite; (c) decreasing body weight; (d) increasing weight loss; (e) decreasing fat mass; (f) decreasing lean mass; (g) increasing loss of fat mass, (h) increasing loss of lean muscle mass, (i) binding to GFRAL; (j) increasing downstream signaling mediated by RET; (k) increasing phosphorylation of ERK; (l) increasing phosphorylation of S6; (m) increasing RET-mediated activation of the MAPK signaling pathway; (n) increasing RET activation of the AKT-signaling pathway; and (o) increasing activation of the PLC-γ1 signaling pathway.

In one embodiment, the invention includes a method of reducing a biological activity of GDF15 in a subject in need thereof. The method comprises administering a therapeutic amount of the antibody of the invention, or antigen-binding fragment thereof, thereby reducing a biological activity of GDF15.

In one aspect, the biological activity of GDF15 includes, but is not limited to, (a) decreasing food intake; (b) decreasing appetite; (c) decreasing body weight; (d) increasing weight loss; (e) decreasing fat mass; (f) decreasing lean mass; (g) increasing loss of fat mass, (h) increasing loss of lean muscle mass, (i) binding to GFRAL; (j) increasing downstream signaling mediated by RET; (k) increasing phosphorylation of ERK; (l) increasing phosphorylation of S6; (m) increasing RET-mediated activation of the MAPK signaling pathway; (n) increasing RET activation of the AKT-signaling pathway; and (o) increasing activation of the PLC-γ1 signaling pathway.

The terms "treatment" or "treated" include prophylactic and/or therapeutic treatments. If it is administered prior to clinical manifestation of a condition, the treatment is considered prophylactic. Therapeutic treatment includes, e.g., ameliorating or reducing the severity of a disease, or shortening the length of the disease.

As used herein, the term "cachexia" includes a metabolic disorder and comorbidity that occurs with several chronic diseases including cancer, chemotherapy, chemotherapy in combination with immuno-oncology therapy, chronic heart failure, congestive heart failure, sarcopenia, chronic obstructive pulmonary disease (COPD), sarcopenia, and chronic kidney disease (CKD).

The invention encompasses methods of treating a disease, disorder or condition mediated by or associated with GDF-15. In one aspect, the disorder is cachexia. In other aspects, the disorder is cachexia associated with cancer, chemotherapy, chemotherapy in combination with an immuno-oncology therapy, chronic obstructive pulmonary disease, chronic kidney disease, chronic heart failure, congestive heart failure, or sarcopenia. In some aspects, the cancer is a solid tumor cancer, pancreatic cancer, lung cancer, non-small cell lung cancer, colorectal cancer, prostate cancer, ovarian cancer, cervical cancer, or testicular cancer. In some aspects, the chemotherapy is platin-based chemotherapy. The disease or disorder or symptom may be alleviated, or reduced in severity, duration or frequency of occurrence.

The invention further encompasses an antibody, or antigen binding fragment thereof, or pharmaceutical composition, as defined herein for use in the defined methods of treatment. In embodiments that refer to a method of treatment as described herein, such embodiments are also further embodiments concerning an antibody, or antigen binding fragment thereof, or pharmaceutical composition, for use in that treatment, or alternatively for the manufacture of a medicament for use in that treatment.

The antibodies and antibody fragments thereof may be administered in combination with one or more additional therapeutically active compounds. The additional therapeutically active compounds include agents used for the treatment of chronic disorders associated with cachexia, anti-cancer agents (e.g., immune therapy and chemotherapy), anti-cancer agents that induce cellular stress (e.g. platinum-based chemotherapy agents such as cisplatin), muscle anabolic agents (e.g. selective androgen receptor modulators (SARMs), myostatin inhibitors, and Activin A receptor inhibitor), anti-inflammatory agents (e.g. JAK inhibitors, IL-6 inhibitors, IL-8 inhibitors), appetite stimulants (e.g. ghrelin mimetics, melanocortin 4 receptor inhibitors), and agents that improve metabolism (e.g. metformin). The prophylactic or therapeutic agents of the combination therapies, including the antibodies, or antigen-binding fragments thereof, can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

A "chemotherapeutic agent" is a chemical compound useful in the treatment of cancer. Examples of chemotherapeutic agents include alkylating agents such as thiotepa and cyclophosphamide (CYTOXAN); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL); beta-lapachone; lapachol;

colchicines; betulinic acid; a camptothecin (including the synthetic analogue topotecan (HYCAMTIN), CPT-11 (irinotecan, CAMPTOSAR), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g. calicheamicin, especially calicheamicin gamma I and calicheamicin omegaI (see, e.g., Nicolaou et al, Angew. Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN, morpholino-doxorubicin, cyanomorpholino-doxorubicin, 2-pyrrolino-doxorubicin, doxorubicin HCl liposome injection (DOXIL) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR), tegafur (UFTORAL), capecitabine (XELODA), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-it inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDIS1NE, FILDESIN); dacarbazine; mannomustine; mitobronitol; mitolactol; pipobroman; gacytosine; arabinoside ("Ara-C"); thiotepa; taxoids, e.g., paclitaxel (TAXOL), albumin-engineered nanoparticle formulation of paclitaxel (ABRAXANE), and doxetaxel (TAXOTERE); chlorambucil; 6-thioguanine; mercaptopurine; methotrexate; platinum analogs such as cisplatin and carboplatin; vinblastine (VELBAN); platinum; etoposide (VP-16); ifosfamide; mitoxantrone; vincristine (ONCOVIN); oxaliplatin; leucovorin; vinorelbine (NAVELBINE); novantrone; edatrexate; daunomycin; aminopterin; ibandronate; topoisomerase inhibitor RFS 2000; difluorometlhylomithine (DMFO); retinoids such as retinoic acid; inotuzumab ozogamicin (BESPONSA), bosutinib (BOSULIF), palbociclib (IBRANCE), axitinib (INLYTA), sunitinib malate (SUTENT), crizotinib (XALKORI), enzalutamide (XTANDI); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX tamoxifen), raloxifene (EVISTA), droloxifene, 4-hydroxytamoxifen, trioxifene, keoxifene, LY 11 7018, onapristone, and toremifene (FARESTON®); anti-progesterones; estrogen receptor down-regulators (ERDs); estrogen receptor antagonists such as fulvestrant (FASLODEX); agents that function to suppress or shut down the ovaries, for example, leutinizing hormone-releasing hormone (LHRFI) agonists such as leuprolide acetate (LUPRON and ELIGARD), goserelin acetate, buserelin acetate and tripterelin; anti-androgens such as fiutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE), exemestane (AROMASIN), formestanie, fadrozole, vorozole (RJVISOR), letrozole (FEMARA), and anastrozole (ARIMIDEX). In addition, such definition of chemotherapeutic agents includes bisphosphonates such as clodronate (for example, BONEFOS or OSTAC), etidronate (DIDROCAL), NE-58095, zoledronic acid/zoledronate (ZOMETA), alendronate (FOSAMAX), pamidronate (AREDIA), tiludronate (SKELID), or risedronate (ACTONEL); as well as troxacitabine (a 1,3-dioxolane nucleoside cytosine analog); anti-sense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE vaccine and gene therapy vaccines, for example, ALLOVECTIN vaccine, LEUVECTIN vaccine, and VAXID vaccine; topoisomerase 1 inhibitor (e.g., LURTOTECAN); an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH (e.g., ABARELIX); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

A "chemotherapy" as used herein, refers to a chemotherapeutic agent, as defined above, or a combination of two, three or four chemotherapeutic agents, for the treatment of cancer. When a chemotherapy consists of more than one chemotherapeutic agents, the chemotherapeutic agents can be administered to the patient on the same day or on different days in the same treatment cycle.

A "platinum-based chemotherapy" as used herein, refers to a chemotherapy wherein at least one chemotherapeutic agent is a coordination complex of platinum. Exemplary platinum-based chemotherapy includes, without limitation, cisplatin, carboplatin, oxaliplatin, nedaplatin, gemcitabine in combination with cisplatin, carboplatin in combination with pemetremed.

A "platinum-based doublet" as used herein, refers to a chemotherapy comprising two and no more than two chemotherapeutic agents and wherein at least one chemotherapeutic agent is a coordination complex of platinum. Exemplary platinum-based doublet includes, without limitation, gemcitabine in combination with cisplatin, carboplatin in combination with pemetrexed.

As used herein, the term "systemic anti-cancer therapy" refers to the systemic administration of pharmaceutical agent(s) approved by the regulatory agencies of any countries in the world, or in human clinical trials conducted under the regulatory agencies of any countries in the world, with the general intent to change the outcome of cancer. Systemic anti-cancer therapy includes, but is not limited to, chemotherapy, hormonal therapy, targeted anti-cancer therapy, cancer vaccines, oncolytic vaccines and adoptive T cell therapy.

Method of Treating Cancer

The invention encompasses a method of treating cancer comprising administering to a patient in need thereof an effective amount of GDF15 antibody. In some embodiments, the cancer is selected from the group consisting of gastric cancer, sarcoma, lymphoma, leukemia, head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, renal cell carcinoma, bladder cancer, cervical cancer, choriocarcinoma, colon cancer, oral cancer, skin cancer, and melanoma. In some embodiments, the subject is a previously treated adult patient with locally advanced or metastatic melanoma, squamous cell head and neck cancer (SCHNC), ovarian carcinoma, sarcoma, or relapsed or refractory classic Hodgkin's Lymphoma (cHL). In some embodiments, the cancer can be a platinum resistant and/or platinum refractory cancer, such as, for example, platinum resistant and/or refractory ovarian cancer, platinum resistant and/or/refractory breast cancer, or platinum resistant and/or refractory lung cancer.

In another aspect, the invention provides a method of inhibiting tumor growth or progression in a subject who has a tumor, comprising administering to the subject an effective amount of the pharmaceutical composition as described herein.

In another aspect, the invention provides a method of inhibiting or preventing metastasis of cancer cells in a subject, comprising administering to the subject in need thereof an effective amount of the pharmaceutical composition as described herein.

In another aspect, the invention provides a method of inducing tumor regression in a subject who has a tumor, comprising administering to the subject an effective amount of the pharmaceutical composition as described herein.

In some embodiments, the method can further comprise administering an effective amount of a second therapeutic agent. In some embodiments, the second therapeutic agent is, for example, an immune modulator. The term "immune modulator" refers to a substance capable of altering (e.g., inhibiting, decreasing, increasing, enhancing, or stimulating) the immune response (as defined herein) or the working of any component of the innate, humoral or cellular immune system of a host mammal. Thus, the term "immune modulator" encompasses the "immune-effector-cell enhancer" as defined herein and the "immune-suppressive-cell inhibitor" as defined herein, as well as substance that affects other components of the immune system of a mammal. In some embodiments, the immune modulator may be an anti-CD40 agonist antibody.

The invention further encompasses an antibody, or antigen binding fragment thereof, or pharmaceutical composition, as defined herein for use in the defined methods of treatment. In embodiments that refer to a method of treatment as described herein, such embodiments are also further embodiments concerning an antibody, or antigen binding fragment thereof, or pharmaceutical composition, for use in that treatment, or alternatively for the manufacture of a medicament for use in that treatment.

Thus, also provided is an anti-GDF15 antibody, or antigen binding fragment thereof, or pharmaceutical composition, provided herein for use in the treatment of cancer or for inhibiting tumor growth or progression in a subject in need thereof.

Also provided is the use of any of the anti-GDF15 antibodies provided herein in the manufacture of a medicament for the treatment of cancer or for inhibiting tumor growth or progression in a subject in need thereof.

The antibodies and antibody fragments thereof may be administered in combination with one or more additional therapeutically active compounds. The additional therapeutically active compounds include agents used for the treatment of chronic disorders associated with cachexia, anti-cancer agents (e.g., immune therapy and chemotherapy), anti-cancer agents that induce cellular stress (e.g. platinum-based chemotherapy agents such as cisplatin), muscle anabolic agents (e.g. selective androgen receptor modulators (SARMs), myostatin inhibitors, and Activin A receptor inhibitor), anti-inflammatory agents (e.g. JAK inhibitors, IL-6 inhibitors, IL-8 inhibitors), appetite stimulants (e.g. ghrelin mimetics, melanocortin 4 receptor inhibitors), and agents that improve metabolism (e.g. metformin).

The prophylactic or therapeutic agents of the combination therapies, including the antibodies, or antigen-binding fragments thereof, can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

The term "immune response" refers to any detectable response to a particular substance (such as an antigen or immunogen) by the immune system of a host mammal, such as innate immune responses (e.g., activation of Toll receptor signaling cascade), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids).

The term "immunogenic" refers to the ability of a substance to cause, elicit, stimulate, or induce an immune response, or to improve, enhance, increase or prolong a pre-existing immune response, against a particular antigen, whether alone or when linked to a carrier, in the presence or absence of an adjuvant.

The compositions and methods for treating cancer provided herein can further comprise one or more other immune modulators In some embodiments, the immune modulator may be an anti-CD40 agonist antibody. The antibody can be, for example, a human, humanized or part-human chimeric anti-CD40 antibody. Examples of specific anti-CD40 monoclonal antibodies include the G28-5, mAb89, EA-5 or S2C6 monoclonal antibody, CP870893, or APX005M. In a particular embodiment, the anti-CD40 agonist antibody is CP870893 or dacetuzumab (SGN-40).

CP-870,893 is a fully human agonistic anti-CD40 monoclonal antibody that has been investigated clinically as an anti-tumor therapy. The structure and preparation of CP870,893 is disclosed in WO2003040170, in which antibody CP870,893 is identified as antibody "21.4.1". The amino acid sequences of the heavy chain and light chain of CP-870,893 are set forth in SEQ ID NO: 46 and SEQ ID NO: 48, respectively, as well as in Table 7, in WO2003040170. In clinical trials, CP870,893 was administered by intravenous infusion at doses generally in the ranges of 0.05-0.25 mg/kg per infusion. In the methods for treating cancer provided herein, CP-870,893 may be administered intradermally, subcutaneously, or topically.

Dacetuzumab (also known as SGN-40 or huS2C6; CAS number 88-486-59-9) is another exemplary anti-CD40 agonist antibody that has been investigated in clinical trials for indolent lymphomas, diffuse large B cell lymphomas and multiple myeloma. In the methods for treating cancer provided herein, dacetuzumab may be administered intradermally, subcutaneously, or topically.

Cytokine Release Syndrome (CRS)

The invention encompasses a method for treating CRS comprising administering to a patient in need thereof an effective amount of GDF15 antibody. CRS is a systemic inflammatory response sometimes seen following the administration of monoclonal antibodies and T cell immunotherapeutic agents. (Shimabukuro-Vornhagen et al., Journal for ImmunoTherapy of Cancer 6, 56(2018). Little is known about the pathophysiology of CRS and the initiating events which trigger the massive release of a variety of cytokines that perpetuate the systemic inflammatory response of CRS.

In some embodiments, the invention provides a method of treating CRS in a subject in need thereof, comprising administering to the subject an effective amount of the pharmaceutical composition as described herein.

In other embodiments, the method can further comprise administering an effective amount of a second therapeutic agent. The second therapeutically agents include anti-inflammatory agents, for example, IL-6 inhibitors, tumor necrosis factor alpha (TNF-α) inhibitors, interferon gamma (IFN-γ) inhibitors, corticosteroids, antihistamines), antipyretics, and/or antibiotics. In some embodiments, the second therapeutic agent is an antibody, for example, tocilizumab and/or siltuximab.

The invention also provides a GDF15 antibody, or antigen binding fragment thereof, or a pharmaceutical composition, as defined herein for use in a method for treating CRS. The invention also provides the use of a GDF15 antibody, or antigen binding fragment thereof, or a pharmaceutical composition, as defined herein, in the manufacture of a medicament for treating CRS. In embodiments that refer to a method of treatment as described herein, such embodiments are also further embodiments concerning an antibody, or antigen binding fragment thereof, or pharmaceutical composition, for use in that treatment, or alternatively for the manufacture of a medicament for use in that treatment.

Combination Therapy of GDF15 Antibody and PD-1 Axis Binding Antagonist

The invention encompasses a method for treating cancer comprising administering to a patient in need thereof a GDF15 antibody in combination with a PD-1 axis binding antagonist, which combination is effective in treating cancer. That is, the data disclosed herein demonstrate that combination of an anti-GDF15 antibody and a PD-1 axis antagonist provides a therapeutic effect in treatment of cancer. The data further demonstrate that the combination of the anti-GDF-15 and the PD-1 axis antagonist provides a synergistic therapeutic effect that is a therapeutic effect that is greater than the predicted additive effect of each therapy administered alone.

The invention encompasses a method for treating cancer comprising administering to a patient in need thereof an amount of a GDF15 inhibitor in combination with an amount of a PD-1 axis binding antagonist that is effective in treating cancer. The invention also encompasses a method for treating cancer comprising administering to a patient in need thereof an amount of a GDF15 inhibitor and an amount of a PD-1 axis binding antagonist, wherein the amounts together are effective in treating cancer. In another embodiment, the invention is related to a method for treating cancer comprising administering to a patient in need thereof an amount of a GDF15 inhibitor and an amount of a PD-1 axis binding antagonist, wherein the amounts together achieve synergistic effects in the treatment of cancer, that is, the combination is "synergistic." In one aspect, the GDF15 inhibitor is anti GDF15 antibody GDF15_001 and the PD-1 axis binding antagonist is selected from the group consisting of avelumab, PF-06801591 (sasanlimab, RN-888), nivolumab, pembrolizumab, atezolizumab and durvalumab. The invention encompasses a pharmaceutical composition comprising a GDF15 inhibitor and a PD-1 axis binding antagonist, and a pharmaceutically acceptable carrier for use in the treatment of cancer. The invention encompasses a pharmaceutical composition comprising a synergistically effective amount of a GDF15 inhibitor, a synergistic therapeutically effective amount of a PD-1 axis binding antagonist, and a pharmaceutically acceptable carrier for use in the treatment of cancer. The composition can further comprise an additional therapeutic agent, such as, but not limited to at least one chemotherapeutic agent.

One skilled in the art would understand, based on the disclosure provided therein, that the method of treating cancer of the invention encompasses administering a synergistic therapeutically effective amount of an anti-GDF15 antibody and a synergistic therapeutically effective amount of a PD-1 axis binding antagonist (e.g., an anti-PD-1 antibody, an anti-PD-L1 antibody, etc.) to a patient either previously treated with, or currently receiving, at least one additional therapeutic agent to treat the cancer. Such additional therapeutic agent encompasses an agent that is standard of care to treat the cancer. That is, the combination therapy of the invention may be added to the therapeutic regimen of a cancer patient already receiving a different therapy including, but not limited to, surgery, radiation, chemotherapy, and any other therapy known in the art.

Those skilled in the art will be able to determine, according to known methods, the appropriate amount, dose or dosage of each compound, as used in the combination of the present invention, to administer to a patient, taking into account factors such as age, weight, general health, the compound administered, the route of administration, the nature and advancement of the cancer requiring treatment, and the presence of other medications.

In an embodiment, the GDF15 inhibitor is an anti GDF15 antibody, or an antigen binding portion thereof, and is administered intravenously (IV) or subcutaneously (SC) in an initial dose of about 0.025 mg/kg to about 20 mg/kg. The initial dose may be followed by one or more subsequent doses. In some embodiments, one or more subsequent dose may be administered at least any of weekly, every other week, every three weeks, every four weeks, every five weeks, every six weeks, every seven weeks, every eight weeks, every nine weeks, every ten weeks, every eleven weeks, or every twelve weeks.

In some embodiments, the GDF15 inhibitor is an anti GDF15 antibody and is administered intravenously (IV) or subcutaneously (SC) as a fixed dose of about 0.25 mg to about 2000 mg. In some embodiments, the antibody, is administered weekly, every other week, every three weeks, every four weeks, every five weeks, every six weeks, every seven weeks, every eight weeks, every nine weeks, every ten weeks, every eleven weeks, or every twelve weeks.

In some embodiments, the GDF15 inhibitor is an anti GDF15 antibody, wherein the anti GDF15 antibody is administered intravenously (IV) or subcutaneously (SC) as a fixed dose of about 0.1 to about 60 mg every week. In some embodiments, the anti GDF15 antibody is administered as a fixed dose of about 2 mg, about 5 mg, about 7 mg, about 10 mg, about 12 mg, about 15 mg, about 25 mg, about 40 mg, and about 50 mg weekly.

In some embodiments, the GDF15 inhibitor is an anti GDF15 antibody, wherein the anti GDF15 antibody is administered intravenously (IV) or subcutaneously (SC) as a fixed dose of about 0.1 to about 130 mg every other week. In some embodiments, the anti GDF15 antibody is administered as a fixed dose of about 5 mg, about 10 mg, about 12 mg, about 15 mg, about 20 mg, about 25 mg, about 30 mg, about 35 mg, about 40 mg, about 50 mg, about 60 mg, about 70 mg, about 75 mg, about 80 mg, about 90 mg, about 100 mg, about 110 mg, about 120 mg and about 125 mg bi-weekly.

In some embodiments, the GDF15 inhibitor is an anti GDF15 antibody, wherein the anti GDF15 antibody is administered intravenously (IV) or subcutaneously (SC) as a fixed dose of about 0.1 to about 400 mg every 21 days (±2 days). In some embodiments, the anti GDF15 antibody is administered as a fixed dose in about 15 mg, about 25 mg, about 30 mg, about 40 mg, about 50 mg, about 60 mg, about 75 mg, about 100 mg, about 115 mg, about 125 mg, about 150 mg, about 175 mg, about 200 mg, about 225 mg, about 250 mg, about 275 mg, about 300 mg, about 325 mg, about 350 mg, about 375 mg and about 385 mg administered every 21 days (±2 days).

In some embodiments, the GDF15 inhibitor is an anti GDF15 antibody, wherein the anti GDF15 antibody is administered intravenously (IV) or subcutaneously (SC) as a fixed dose of about 0.1 to about 400 mg every 28 days (±2 days). In some embodiments, the anti GDF15 antibody is administered as a fixed dose in about 15 mg, about 25 mg, about 30 mg, about 40 mg, about 50 mg, about 60 mg, about 75 mg, about 100 mg, about 115 mg, about 125 mg, about 150 mg, about 175 mg, about 200 mg, about 225 mg, about 250 mg, about 275 mg, about 300 mg, about 325 mg, about 350 mg, about 375 mg and about 385 mg administered every 28 days (±2 days).

The practice of the method of this invention may be accomplished through various administration or dosing regimens. The compounds of the combination of the present invention can be administered intermittently, concurrently or sequentially. In an embodiment, the compounds of the combination of the present invention can be administered in a concurrent dosing regimen.

Repetition of the administration or dosing regimens may be conducted as necessary to achieve the desired reduction or diminution of cancer cells. A "continuous dosing schedule", as used herein, is an administration or dosing regimen without dose interruptions, e.g., without days off treatment. Repetition of 21 or 28-day treatment cycles without dose interruptions between the treatment cycles is an example of a continuous dosing schedule. In an embodiment, the compounds of the combination of the present invention can be administered in a continuous dosing schedule. In an embodiment, the compounds of the combination of the present invention can be administered concurrently in a continuous dosing schedule.

In an embodiment, the GDF15 inhibitor is an anti GDF15 antibody. In some embodiments, the anti GDF15 antibody is GDF-001.

In some embodiments, the PD-1 axis binding antagonist is a PD-L1 binding antagonist. In some embodiments the PD-L1 binding antagonist is an anti-PD-L1 antibody such as, but not limited to, MED14736, MPDL3280A (YW243.55.s70), BMS-936559 (MDX-1105), avelumab, atezolizumab, and durvalumab. In some embodiments, the anti-PD-L1 antibody is avelumab and may be administered intravenously at a dose of about 1, 2, 3, 4, 5, 6, 7, 8, 9, 10, 11, 12, 13, 14, 15, 16, 17, 18, 19 or 20 mg/kg at intervals of about 14 days (±2 days) or about 21 days (±2 days) or about 30 days (±2 days) throughout the course of treatment. In some embodiment, avelumab is administered as a flat dose of about 80, 150, 160, 200, 240, 250, 300, 320, 350, 400, 450, 480, 500, 550, 560, 600, 640, 650, 700, 720, 750, 800, 850, 880, 900, 950, 960, 1000, 1040, 1050, 1100, 1120, 1150, 1200, 1250, 1280, 1300, 1350, 1360, 1400, 1440, 1500, 1520, 1550 or 1600 mg, preferably 800 mg, 1200 mg or 1600 mg at intervals of about 14 days (±2 days) or about 21 days (±2 days) or about 30 days (±2 days) throughout the course of treatment. In certain embodiments, a subject will be administered an intravenous (IV) infusion of a medicament comprising any of the PD-1 axis binding antagonists described herein. In certain embodiment, the subject will be administered a subcutaneous (SC) infusion of a medicament comprising any of the PD-1 axis binding antagonist described herein.

In some embodiments, the PD-1 axis antagonist is a PD-1 axis binding antagonist. In some embodiments, the PD-1 axis binding antagonist is an anti-PD-1 antibody, e.g., PF-06801591 (sasanlimab, RN888), nivolumab, pembrolizumab, pidilizumab, tislelizumab, AMP-224, AMP-514, cemiplimab, and anti-GDF15 antibody will be administered intravenously or subcutaneously, but preferably subcutaneously, at a dose of about 1, 2, 3, 4, 5, 6, 7 or 8 mg/kg at intervals of about 14 days (±2 days) or about 21 days (±2 days) or about 30 days (±2 days) throughout the course of treatment. In some embodiments, PF-06801591 (sasanlimab, RN-888) as disclosed in US 2016/159905, is administered as a flat dose of about 80, 150, 160, 200, 240, 250, 300, 320, 350, 400, 450, 500, 550 or 600 mg, preferably 300 mg, at intervals of about 14 days (±2 days) or about 21 days (±2 days) or about 30 days (±2 days) or about 35 days (±2 days), or about 42 days (±2 days). In some embodiments, PF-06801591 (sasanlimab, RN888) is administered subcutaneously in an amount of 300 mg Q4W. In some embodiments, PF-06801591 (sasanlimab, RN888, mAb7) is administered subcutaneously in an amount of 600 mg Q6W.

Further, the invention is related to a method for treating cancer comprising administering to a patient in need thereof an amount of a GDF15 antibody and an amount of a PD-1 axis binding antagonist, wherein the amounts together achieve synergistic effects in the treatment of cancer that are greater that the therapeutic effect of the anti-GDF15 antibody and the therapeutic effect of the PD-1 axis binding inhibitor where the separate effects are added together. The method or use of the invention is related to a synergistic combination of targeted therapeutic agents, specifically a GDF15 antibody and a PD-1 axis binding antagonist. In one aspect of the embodiments, the GDF15 inhibitor is an anti GDF15 antibody and the PD-1 axis binding antagonist is selected from the group consisting of nivolumab, pembrolizumab, tislelizumab, pidilizumab, AMP-224, AMP-514, cemiplimab, PF-06801591 (sasanlimab, RN888, mAb7), avelumab, atezolizumab and durvalumab. In one aspect of the embodiments, the GDF15 inhibitor is an anti GDF15 antibody and the PD-1 axis binding antagonist is selected from the group consisting of nivolumab, pembrolizumab, tislelizumab, pidilizumab, AMP-224, AMP-514, cemiplimab, PF-06801591 (sasanlimab, RN888, mAb7), atezolizumab, durvalumab, and it is not avelumab.

In accordance with the present invention, an amount of a first compound or component, for example, a GDF15 inhibitor, is administered with an amount of a second compound or component, for example, a PD-1 axis binding antagonist (which not include avelumab), and the amounts together are effective in the treatment of cancer. The amounts, which together are effective, will relieve to some extent one or more of the symptoms of the disorder being treated. In reference to the treatment of cancer, an effective amount refers to that amount which has the effect of (1) reducing the size of the tumor, (2) inhibiting (that is, slowing to some extent, preferably stopping) tumor metastasis emergence, (3) inhibiting to some extent (that is, slowing to some extent, preferably stopping) tumor growth or tumor invasiveness, and/or (4) relieving to some extent (or, preferably, eliminating) one or more signs or symptoms associated with the cancer. Therapeutic or pharmacological effectiveness of the doses and administration regimens may also be characterized as the ability to induce, enhance, maintain or prolong disease control and/or overall survival in patients with these specific tumors, which may be measured as prolongation of the time before disease progression.

The invention provides methods for the administration of an anti-GDF15 antibody, or antigen-binding portions thereof, of the disclosure alone or in combination with other therapies to a subject in need thereof. The combination therapies (e.g., anti-GDF15 and PD-1 axis antagonists) of the present disclosure can be administered concomitantly or sequentially to a subject. The anti-GDF15 and PD-1 axis antagonist combination therapy of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The invention further encompasses an anti-GDF15 antibody, or antigen binding fragment thereof, or pharmaceutical composition, as defined herein for use in the defined methods of treatment in which the antibody, or antigen binding fragment thereof, or pharmaceutical composition, is administered in combination with a PD-1 axis binding antagonist as defined herein. In embodiments that refer to a method of treatment as described herein, such embodiments are also further embodiments concerning an antibody, or antigen binding fragment thereof, or pharmaceutical composition, for use in that treatment, or alternatively for the manufacture of a medicament for use in that treatment.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising a GDF15 antibody, or antigen-binding portion thereof, of the disclosure is administered to a subject in a sequence and within a time interval such that the antibody can act together with the other therapy(ies) (e.g., a PD-1 axis antagonist which may not include avelumab) to provide an increased benefit greater than if they were administered otherwise, more preferably, the combination therapy provides a "synergistic therapeutic effect" in that the therapeutic effect is greater than the additive effect of the two therapies administered separately. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. The anti-GDF15 antibody, or antigen binding fragment thereof, can be any antibody of the invention, preferably, GDF-15_001. The PD-1 axis antagonist, includes, but is not limited to, a PD-1 binding antagonist, a PD-L1 binding antagonist and a PD-L2 binding antagonist. In other aspects, the PD-1 binding antagonist is an anti-PD-1 antibody, or antigen binding fragment thereof. In further aspects, the anti-PD-1 antibody includes, but is not limited to, nivolumab, pembrolizumab, spartalizumab, tislelizumab, pidilizumab, AMP-224, AMP-514, cemiplimab, and PF-06801591 (sasanlimab, RN888). In other aspects, the PD-L1 binding antagonist is an anti-PD-L1 antibody, or antigen binding fragment thereof. In other aspects, the anti-PD-L1 antibody is BMS-936559 (MDX-1105), avelumab, atezolizumab, durvalumab. In other aspects, the PD-L1 binding antagonist is an anti-PD-L1 antibody, or antigen binding fragment thereof, but it is not avelumab.

In various embodiments, the anti-GDF15 antibody, or antigen-binding fragment thereof, is administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart from administration of a PD-1 axis antagonist (e.g., an anti-PD-1 antibody, an anti-PD-L1 antibody, which may not include avelumab, or an anti-PD-L2 antibody, among others). In other embodiments, two or more therapies (e.g., an anti-GDF15 antibody, an anti-PD-L1 antibody, which may not include avelumab, and a chemotherapeutic agent) are administered to a patient within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Diagnostic Methods

The anti-GDF15 antibodies, antibody compositions, and methods of the present invention have in vitro and in vivo utilities including immunoassays and use for the diagnosis and assessment of treatment of GDF15 mediated disorders. The methods are particularly suitable for diagnosing, assessing, and treating human patients having a disorder associated with the existence of GDF15 and, more preferably, with an increased level of GDF15, where increased level of GDF15 encompasses an increased level above the plasma concentrations of free GDF-15 in human healthy volunteers. This disorder associated with the existence of GDF15 includes, but is not limited to, cachexia associated with cancer, chemotherapy, chemotherapy in combination with an immuno-oncology therapy, chronic obstructive pulmonary disease, chronic kidney disease, chronic heart failure, congestive heart failure, or sarcopenia.

The invention provides a method for detecting the presence of GDF15 in a sample, the method comprising contacting a sample suspected of comprising GDF15 with an antibody specific for GDF15 and detecting the presence of GDF15 bound with the antibody thereby detecting GDF15 in the sample. Methods for detecting GDF15 bound with the antibody are well-known in the art including, but not limited to, an assay where GDF15 is bound to a solid support and a sample is added thereto allowing the antibody to bind GDF15 in the sample. A second GDF15 antibody that is either the same or different from the antibody bound to the solid support is added and can be detected by either direct labeling (i.e., the second antibody is conjugated to a detectable label) or by adding a third antibody, e.g., from another species which reacts with the constant domain of the second antibody and which comprises a detectable label. Thus, the assay can be used to detect the presence or absence of GDF15 in a sample.

In another embodiment, the invention includes a kit for detecting the presence of GDF15 in a sample, the kit comprising an antibody specific for GDF15, an applicator, and an instructional material for the use thereof.

The invention also provides a method for determining the concentration of GDF15 in a sample, said method comprising providing a labeled competitor comprising GDF15 coupled to a detectable label; providing an antibody, or antigen binding fragment thereof, that specifically binds GDF15; combining the sample, the antibody, and the labeled competitor, wherein the GDF15 in the sample competes with the labeled competitor for binding to the antibody; and determining the concentration of GDF15 in said sample by measuring the amount of labeled competitor not bound to antibody by detection of the label. The amount of labeled competitor bound to the antibody in the absence of the sample is compared with the amount of labeled competitor bound to the antibody when the sample is added. The amount of decrease of bound labeled-competitor in the presence of the sample is an indicator of the amount of non-labeled GDF15 present in the sample such that the assay can be used to assess the presence and level of GDF15 in a sample.

In one embodiment, the invention provides a method for assessing the effectiveness of a treatment for a disease or disorder associated with an increased level of GDF15 in a subject, the method comprising administering a treatment to the subject and comparing the level of GDF15 in a sample obtained from the subject prior to the treatment with the level of GDF15 in an otherwise identical sample obtained from the subject after the treatment, wherein the level of GDF15 in a sample is assessed using a GDF15 specific antibody, and further wherein a lower, level of GDF15 in the sample collected from the subject after the treatment compared with the level of GDF15 in a sample collected from the subject prior to treatment is an indication of the effectiveness of the course of treatment.

The term "labeled," with regard to the GDF15 specific antibody or labeled competitor, includes direct labeling by coupling (i.e., physically linking) a detectable substance to the antibody or labeled competitor, as well as indirect labeling of the antibody or labeled competitor by coupling it with another reagent that is directly labeled. An example of indirect labeling includes detection of a primary antibody using a fluorescent-labeled secondary antibody. In vitro techniques for detection of a polypeptides of the invention include enzyme linked immunosorbent assays (ELISAs), Western blots, immunoprecipitation, and immunofluorescence.

The term "biological sample" is intended to include tissues, cells, and biological fluids isolated from a subject, as well as tissues, cells, and fluids present within a subject.

The antibodies, labeled competitors, and potential therapeutic compounds described herein are also suitable for use with any of a number of other homogeneous and heterogeneous immunoassays with a range of detection systems.

Compositions

The GDF15 antibodies of the invention can be formulated as a pharmaceutical composition. The pharmaceutical composition may further comprise a pharmaceutically acceptable carrier, excipient, and/or stabilizer (Remington: The Science and practice of Pharmacy 21st Ed., 2005, Lippincott Williams and Wilkins, Ed. K. E. Hoover), in the form of lyophilized formulation or aqueous solution. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

The pharmaceutical composition of the disclosure may further comprise a PD-1 axis antagonist as described herein and a GDF15 inhibitor, as described herein. In one embodiment, the GDF15 inhibitor is an anti GDF15 antibody GDF15_001 or GDF15_297 and the PD-1 axis antagonist is selected from the group consisting, optionally, of avelumab, PF-06801591 (also referred to as "sasanlimab", and "RN-888" and mAb7, all as disclosed in WO 2016/092419), nivolumab, pembrolizumab, atezolizumab and durvalumab. In one embodiment, the PD-1 axis antagonist does not include avelumab.

The pharmaceutical compounds of the disclosure may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A pharmaceutical composition of the present disclosure may be prepared, packaged, or sold in a formulation suitable for ophthalmic administration. Such formulations may, for example, be in the form of eye drops including, for example, a 0.1%-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Remington's Pharmaceutical Sciences, Genaro, ed., Mack Publishing Co., Easton, Pa. (1985), which is incorporated herein by reference.

In one embodiment, the GDF15 antibody, or antigen-binding portion thereof, is administered in an intravenous formulation as a sterile aqueous solution containing 5 mg/mL, or in some embodiments, about 10 mg/mL, or in some embodiments, about 15 mg/mL, or in some embodiments, about 20 mg/mL of antibody, or in some embodiments, about 25 mg/mL, or in some embodiments, about 50 mg/mL, with sodium acetate, polysorbate 80, and sodium chloride at a pH ranging from about 5 to 6. In some embodiments, the intravenous formulation is a sterile aqueous solution containing 5 or 10 mg/mL of antibody, with 20 mM sodium acetate, 0.2 mg/mL polysorbate 80, and 140 mM sodium chloride at pH 5.5. Further, a solution comprising an antibody, or antigen-binding portion thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 50 mg/mL GDF15 antibody or antigen-binding portion of the present disclosure, 20 mM histidine, 8.5% sucrose, and 0.02% polysorbate 80, 0.005% EDTA at pH 5.8; in another embodiment a pharmaceutical composition of the present invention comprises the following components: 100 mg/mL GDF15 antibody or antigen-binding portion of the present disclosure, 10 mM histidine, 5% sucrose, and 0.01% polysorbate 80 at pH 5.8. This composition may be provided as a liquid formulation or as a lyophilized powder. When the powder is reconstituted at full volume, the composition retains the same formulation. Alternatively, the powder may be reconstituted at half volume, in which case the composition comprises 100 mg GDF15 antibody or antigen-binding portion thereof of the present disclosure, 20 mM histidine, 10% sucrose, and 0.02% polysorbate 80 at pH 5.8.

In one embodiment, part of the dose is administered by an intravenous bolus and the rest by infusion of the antibody formulation. For example, a 0.01 mg/kg intravenous injection of the GDF15 antibody, or antigen-binding portion thereof, may be given as a bolus, and the rest of the antibody dose may be administered by intravenous injection. A predetermined dose of the GDF15 antibody, or antigen-binding portion thereof, may be administered, for example, over a period of an hour and a half to two hours to five hours.

With regard to a therapeutic agent, where the agent is, e.g., a small molecule, it can be present in a pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment the compositions of the disclosure are pyrogen-free formulations which are substantially free of pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food and Drug Administration ("FDA") has set an upper limit of 5 endotoxin units (EU) per dose per kilogram body weight in a single one-hour period for intravenous drug applications (The United States Pharmacopeial Convention, Pharmacopeial Forum 26 (1):223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In another embodiment, endotoxin and pyrogen levels in the composition are less than about 10 EU/mg, or less than about 5 EU/mg, or less than about 1 EU/mg, or less than about 0.1 EU/mg, or less than about 0.01 EU/mg, or less than about 0.001 EU/mg.

In one embodiment, the disclosure comprises administering a composition wherein said administration is oral, parenteral, intramuscular, intranasal, vaginal, rectal, lingual, sublingual, buccal, intrabuccal, intravenous, cutaneous, subcutaneous or transdermal.

In another embodiment the disclosure further comprises administering a composition in combination with other therapies, such as surgery, chemotherapy, hormonal therapy, biological therapy, immunotherapy or radiation therapy.

Dosage

To prepare pharmaceutical or sterile compositions including a GDF15 antibody, or antigen-binding portion thereof of the disclosure, the antibody is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.), 1993, Monoclonal Antibodies and Peptide Therapy in Autoimmune Diseases, Marcel Dekker, New York, N.Y.; Baert, et al., 2003, New Engl. J. Med. 348:601-608; Milgrom, et al., 1999, New Engl. J. Med. 341:1966-1973; Slamon, et al., 2001, New Engl. J. Med. 344:783-792; Beniaminovitz, et al., 2000, New Engl. J. Med. 342:613-619; Ghosh, et al., 2003, New Engl. J. Med. 348:24-32; Lipsky, et al., 2000, New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects.

"Reducing the level of GDF15" or "lowering the level of GDF15," as the terms are used herein, means to lower the level of free GDF15 compared to the level of free GDF15 before any therapeutic intervention. As used herein, "free GDF15," means GDF15 that is not bound or otherwise in a complex with another molecule (e.g., an antibody or binding molecules present in, e.g., the plasma).

The level of GDF15 includes the level of free GDF15 in a subject where the level is assessed using the methods disclosed herein or any other method for assessing the level of free GDF15 known in the art.

In one embodiment, the level of free GDF15 is reduced compared to the level of GDF15 in the subject before administration of an antibody of the invention. In one embodiment, the level of free GDF15 is reduced compared to a standard level of free GDF15 that is associated with or indicates that the subject is not afflicted with a disease, disorder or condition associated with or mediated by an increased level of free GDF15. In one embodiment, the standard, or reference, level of free GDF15 is from about 0.05 ng/mL to about 3 ng/mL in plasma. In another embodiment, the standard, or reference, level of free GDF15 is within a range whose lower value is selected from the group consisting of 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 ng/mL and whose upper value is selected from the group consisting of 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, and 3.0 ng/mL. In a further embodiment, the standard, or reference, level of free GDF15 is less than 1 ng/mL, preferably, less than 0.9 ng/mL, even more preferably, less than 0.8 ng/mL, yet more preferably, less than 0.7 ng/mL, even more preferably, less than 0.6 ng/mL, yet more preferably, less than 0.5 ng/mL, and even more preferably, less than 0.4 ng/ml. In one embodiment, the level of free GDF15 is the level in plasma.

The invention is not limited to the free GDF15 level being less than 0.5 ng/mL; instead, it would be understood by one skilled in the art, that a therapeutic level can be lower or higher than 0.5 ng/mL for a particular subject. Therefore, the invention encompasses reducing the level of free GDF15 to a level where there is a decrease, or complete lack of, detectable deleterious effect(s) mediated by or associated with an increased level of free GDF15. Such effects include, but are not limited to, cachexia, decreased food intake, decreased appetite, decreased body weight, weight loss, decreased fat mass, decreased lean mass, and the like.

As used herein, an "effective dosage", "effective dose", "effective amount", or "therapeutically effective amount" of a drug, compound, or pharmaceutical composition is an amount sufficient to effect any one or more beneficial or desired results. For prophylactic use, beneficial or desired results include eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include detectable clinical results such as reducing, or decreasing the rate of, weight loss or reducing one or more symptoms resulting from high expression of active GDF15 (e.g., decreased food intake, decreased appetite, decreased body weight, weight loss, decreased fat mass, and decreased lean mass) decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

In some embodiments, the effective dosage of the antibody, or antigen binding fragment thereof, of the invention is based on the plasma concentration of free GDF-15 in human healthy volunteers and in affected patients. The overall efficacious dose depends on the initial plasma concentration of free GDF-15 in the affected patient. In one embodiment, an effective dosage may be a dosage with the ability to lower or reduce free GDF15 levels in a subject to the same or lower average level measured in human healthy volunteers for an entire dosing interval at steady-state. In another embodiment, an effective dosage may be a dosage with the ability to lower or reduce free GDF15 levels in a patient to less than 0.5 ng/mL for an entire dosing interval at steady-state. In yet another embodiment, an effective dosage may be the dosage given to a 70 kg subject that can lower or reduce the free GDF15 level in the subject to less than 0.5 ng/mL throughout the dosing interval at steady state.

An "individual", "patient", or a "subject" is a mammal, more preferably, a human. Mammals also include, but are not limited to, farm animals, sport animals, pets, primates, horses, dogs, cats, mice and rats. In some embodiments, the individual is considered to be at risk for a disease, disorder or condition mediated by or associated with GDF15 binding to its receptor and signaling mediated thereby. In certain embodiments, the subject has cachexia associated with cancer, chemotherapy, chemotherapy in combination with immuno-oncology therapy, chronic heart failure, congestive heart failure, sarcopenia, chronic obstructive pulmonary disease (COPD), sarcopenia, and chronic kidney disease (CKD).

In some embodiments, the method or use comprises administering an initial dose of about 0.025 mg/kg to about 20 mg/kg of an antibody, or antigen binding fragment thereof, or a pharmaceutical composition of the invention. The initial dose may be followed by one or more subsequent doses. In some embodiments, one or more subsequent dose may be administered at least any of weekly, every other week, every three weeks, every four weeks, every five weeks, every six weeks, every seven weeks, every eight weeks, every nine weeks, every ten weeks, every eleven weeks, or every twelve weeks.

In some embodiments, the method or use comprises administering a fixed dose of about 0.25 mg to about 2000 mg of an antibody, or antigen binding fragment thereof, of the invention. In some embodiments, the antibody, or antigen binding fragment thereof, is administered weekly, every other week, every three weeks, every four weeks, every five weeks, every six weeks, every seven weeks, every eight weeks, every nine weeks, every ten weeks, every eleven weeks, or every twelve weeks.

In other embodiments, the method or use comprises administering a fixed dose of about 0.1 to about 60 mg of an antibody, or antigen binding fragment thereof, of the invention every week. In some embodiments, the fixed dose of an antibody, or antigen binding fragment thereof, of the invention is about 2 mg, about 5 mg, about 7 mg, about 10 mg, about 12 mg, about 15 mg, about 25 mg, about 40 mg, and about 50 mg administered weekly.

In some embodiments, the method or use comprises administering a fixed dose of about 0.1 to about 130 mg of an antibody, or antigen binding fragment thereof, of the invention every other week. In some embodiments, the fixed dose of an antibody, or antigen binding fragment thereof, of the invention is about 5 mg, about 12 mg, about 20 mg, about 25 mg, about 30 mg, about 40 mg, about 60 mg, about 90 mg, and about 125 mg administered bi-weekly.

In some embodiments, the method or use comprises administering a fixed dose of about 0.1 to about 400 mg of an antibody, or antigen binding fragment thereof, of the invention every four weeks. In some embodiments, the fixed dose of an antibody, or antigen binding fragment thereof, of the invention is about 15 mg, about 40 mg, about 60 mg, about 75 mg, about 100 mg, about 115 mg, about 200 mg, about 300 mg, and about 385 mg administered every four weeks.

Kits

The invention also provides kits or an article of manufacture comprising an antibody, or antigen binding fragment thereof, of the invention, and instructions for use. Accordingly, in some embodiments, provided is a kit or an article of manufacture, comprising a container, a composition within the container comprising an anti-GDF15 antibody, and a package insert containing instructions to administer a therapeutically effective amount of the anti-GDF15 antibody for treatment of a patient in need thereof.

In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In one embodiment, the invention provides a kit for determining the concentration of GDF15 in a sample, the kit comprising a labeled competitor comprising GDF15 coupled to a detectable label; an antibody, or antigen binding fragment thereof, that specifically binds GDF15; an applicator; and an instructional material for the use thereof.

The invention further provides, a competitive immunoassay kit for determining the amount of GDF15 in a test sample, the competitive immunoassay comprising an antibody, or an antigen binding fragment thereof, that specifically binds GDF15; a labeled competitor comprising GDF15 conjugated to a detectable label; wherein the labeled competitor competes with the GDF15 in the test sample for binding with the antibody, and further wherein the label provides a signal indicative of the amount of GDF15 in the test sample. In an exemplary embodiment, the decrease in label bound by the antibody in the test sample compared with the label bound by the antibody in an otherwise identical sample that does not contain GDF15 is an indication of the amount of GDF15 in the test sample.

In one embodiment, the invention provides a kit for determining the concentration of GDF15 in a sample, the kit comprising a labeled competitor comprising GDF15 coupled to a detectable label; an antibody, or antigen binding fragment thereof, that specifically binds GDF15; an applicator; and an instructional material for the use thereof.

In an alternative embodiment, the invention provides a kit for identifying a human patient at risk for cachexia comprising a GDF15 specific antibody, or antigen binding fragment thereof, an applicator, and an instructional material for the use thereof.

In some embodiments, provided is a kit or an article of manufacture, comprising a first container, a composition within the container comprising an anti-GDF15 antibody, a second container, a composition within the second container comprising a PD-1 axis binding antagonist, and a package insert containing instructions to administer a therapeutically effective amount of the anti-GDF15 antibody and the PD-1 axis binding antagonist for treatment of a patient in need thereof.

The invention encompasses a kit or an article of manufacture, comprising a first container, a composition within the container comprising a synergistic therapeutically effective amount of an anti-GDF15 antibody, a second container, a composition within the second container comprising a therapeutically effective therapeutic amount of a PD-1 axis binding antagonist, and a package insert containing instructions to administer a synergistic therapeutically effective amount of the anti-GDF15 antibody and the PD-1 axis binding antagonist for combination treatment of a patient in need thereof.

In some aspects, the PD-1 axis binding antagonist is selected from the group consisting of a PD-1 antibody, or an antigen binding fragment thereof, a PD-L1 antibody, or an antigen binding fragment thereof, and a PD-L2 antibody, or an antigen binding fragment thereof. In some aspects, the PD-1 antibody is selected from the group consisting of nivolumab, pembrolizumab, spartalizumab, tislelizumab, pidilizumab, AMP-224, AMP-514, cemiplimab, and PF-06801591 (sasanlimab, RN888). In other aspects, the PD-L1 antibody is selected from the group consisting of, optionally, avelumab, atezolizumab, durvalumab. In other aspects, the PD-L1 antibody is not avelumab.

In other embodiments, provided is a kit or an article of manufacture, comprising a first container, a composition within the container comprising an anti-GDF15 antibody, a second container, a composition within the second container comprising an anti-cancer therapeutic agent, and a package insert containing instructions to administer a therapeutically effective amount of the anti-GDF15 antibody and the anti-cancer therapeutic agent for treatment of a patient in need thereof. In some aspects, the anti-cancer therapeutic agent is an anti-CD40 antibody.

The invention encompasses a kit or an article of manufacture, comprising a first container, a composition within the container comprising a synergistic therapeutically effective amount of an anti-GDF15 antibody, a second container, a composition within the second container comprising a therapeutically effective therapeutic amount of an anti-cancer therapeutic agent, and a package insert containing instructions to administer a synergistic therapeutically effective amount of the anti-GDF15 antibody and the anti-cancer therapeutic agent for combination treatment of a patient in need thereof. In some embodiments, the anti-cancer therapeutic agent is an anti-CD40 antibody.

The instructions relating to the use of an antibody, or an antigen binding fragment thereof, of the invention generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). The container may further comprise a second pharmaceutically active agent.

Kits may optionally provide additional components such as buffers and interpretive information. Normally, the kit comprises a container and a label or package insert(s) on or associated with the container.

Definitions

"About" or "approximately," unless otherwise defined herein, when used in connection with a measurable numerical variable, refers to the indicated value of the variable and to all values of the variable that are within the experimental error of the indicated value (e.g. within the 95% confidence interval for the mean) or within 10 percent of the indicated value, whichever is greater. Numeric ranges are inclusive of the numbers defining the range.

The term "identity," as known in the art, refers to a relationship between the sequences of two or more polypeptide molecules or two or more nucleic acid molecules, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model of computer programs (i. e. "algorithms").

The term "similarity" is a related concept, but in contrast to "identity", refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10 out of 20 identical amino acids, and the remainder are all nonconservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

The use of the term "or" in the claims is used to mean "and/or" unless explicitly indicated to refer to alternatives only or the alternatives are mutually exclusive, although the disclosure supports a definition that refers to only alternatives and "and/or." As used herein the specification, "a" or "an" may mean one or more, unless clearly indicated otherwise. As used herein in the claim(s), when used in conjunction with the word "comprising", the words "a" or "an" may mean one or more than one. As used herein "another" may mean at least a second or more. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The words "comprises/comprising" and the words "having/including" when used herein with reference to the present invention are used to specify the presence of stated features, integers, steps or components but does not preclude the presence or addition of one or more other features, integers, steps, components or groups thereof.

As used herein, as describing the amount of carboplatin administered to the patient, the term "calculated AUC 3 dose", "calculated AUC 4 dose", "calculated AUC 5 dose", "calculated AUC 6 dose", etc., refers to the amount of carboplatin calculated according to the Calvert Equation based on the targeted area under the curve (AUC) being 3, 4, 5, and 6 mg·min/mL respectively and the patient's glomerular filtration rate (GFR, mL/min): carboplatin dose (mg) =target AUC (mg·min/mL)×(GFR+25), as described in the National Comprehensive Cancer Network® (NCCN) Chemotherapy Order Templates Appendix B as updated February 2018.

As used herein, the term "cytokine" refers generically to proteins released by one cell population that act on another cell as intercellular mediators or have an autocrine effect on the cells producing the proteins. Examples of such cytokines include lymphokines, monokines; interleukins ("ILs") such as IL-1, IL-1a, IL-2, IL-3, IL-4, IL-5, IL-6, IL-7, IL-8, IL-9, IL10, IL-11, IL-12, IL-13, IL-15, IL-17A-F, IL-18 to IL-29 (such as IL-23), IL-31, including PROLEUKIN® rIL-2; a tumor-necrosis factor such as TNF-α or TNF-β, TGF-I-3; and other polypeptide factors including leukemia inhibitory factor ("LIF"), ciliary neurotrophic factor ("CNTF"), CNTF-like cytokine ("CLC"), cardiotrophin ("CT"), and kit ligand ("L").

As used herein, the term "chemokine" refers to soluble factors (e.g., cytokines) that have the ability to selectively induce chemotaxis and activation of leukocytes. They also trigger processes of angiogenesis, inflammation, wound healing, and tumorigenesis. Example chemokines include IL-8, a human homolog of murine keratinocyte chemoattractant (KC).

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, Hodgkin's lymphoma, non-Hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Another particular example of cancer includes renal cell carcinoma.

The term "treating", as used herein, unless otherwise indicated, means reversing, alleviating, inhibiting the progress of, or preventing the disorder or condition to which such term applies, or one or more symptoms of such disorder or condition.

A "patient" to be treated according to this invention includes any warm-blooded animal, such as, but not limited to human, monkey or other lower-order primate, horse, dog, rabbit, guinea pig, or mouse. For example, the patient is human. Those skilled in the medical art are readily able to identify individual patients who are afflicted with non-small cell lung cancer and who are in need of treatment.

The terms "treatment regimen", "dosing protocol" and dosing regimen are used interchangeably to refer to the dose and timing of administration of each therapeutic agent in a combination of the invention.

"Ameliorating" means a lessening or improvement of one or more symptoms as compared to not administering a treatment. "Ameliorating" also includes shortening or reduction in duration of a symptom.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Individual response" or "response" can be assessed using any endpoint indicating a benefit to the individual, including, without limitation, (1) inhibition, to some extent, of disease progression (e.g., cancer progression), including slowing down or complete arrest; (2) a reduction in tumor size; (3) inhibition (i.e., reduction, slowing down, or complete stopping) of cancer cell infiltration into adjacent peripheral organs and/or tissues; (4) inhibition (i.e. reduction, slowing down, or complete stopping) of metastasis; (5) relief, to some extent, of one or more symptoms associated with the disease or disorder (e.g., cancer); (6) increase or extension in the length of survival, including overall survival and progression free survival; and/or (7) decreased mortality at a given point of time following treatment.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and/or progression-free survival); resulting in an objective response (including a complete response or a partial response); or improving signs or symptoms of cancer.

An "objective response" refers to a measurable response, including complete response (CR) or partial response (PR). In some embodiments, the "objective response rate (ORR)" refers to the sum of complete response (CR) rate and partial response (PR) rate.

"Complete response" or "CR" as used herein means the disappearance of all signs of cancer (e.g., disappearance of all target lesions) in response to treatment. This does not always mean the cancer has been cured.

As used herein, "partial response" or "PR" refers to a decrease in the size of one or more tumors or lesions, or in the extent of cancer in the body, in response to treatment. For example, in some embodiments, PR refers to at least a 30% decrease in the sum of the longest diameters (SLD) of target lesions, taking as reference the baseline SLD.

"Sustained response" refers to the sustained effect on reducing tumor growth after cessation of a treatment. For example, the tumor size may be the same size or smaller as compared to the size at the beginning of the medicament administration phase. In some embodiments, the sustained response has a duration of at least the same as the treatment duration, at least 1.5×, 2×, 2.5×, or 3× length of the treatment duration, or longer.

As used herein, "progression-free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

In some embodiments, the anti-cancer effect of the method of treating cancer, including "objective response", "complete response", "partial response", "progressive disease", "stable disease", "progression free survival", "duration of response", as used herein, are as defined and assessed by the investigators using RECIST v1.1 (Eisenhauer et al, Eur J of Cancer 2009; 45(2):228-47) in patients with locally advanced or metastatic solid tumors other than metastatic CRPC, and RECIST v1.1 and PCWG3 (Scher et al, J Clin Oncol 2016 Apr. 20; 34(12):1402-18) in patients with metastatic CRPC. The disclosures of Eisenhauer et al, Eur J of Cancer 2009; 45(2):228-47 and Scher et al, J Clin Oncol 2016 Apr. 20; 34(12):1402-18 are herein incorporated by references in their entireties.

In some embodiments, the anti-cancer effect of the treatment, including "immune-related objective response" (irOR), "immune-related complete response" (irCR), "immune-related partial response" (irCR), "immune-related progressive disease" (irPD), "immune-related stable disease" (irSD), "immune-related progression free survival" (irPFS), "immune-related duration of response" (irDR), as used herein, are as defined and assessed by Immune-related response criteria (irRECIST, Nishino et. al. J Immunother Cancer 2014; 2:17) for patients with locally advanced or metastatic solid tumors other than patients with metastatic CRPC. The disclosure of Nishino et. al. J Immunother Cancer 2014; 2:17 is herein incorporated by reference in its entirety.

As used herein, "overall survival" (OS) refers to the percentage of individuals in a group who are likely to be alive after a particular duration of time.

By "extending survival" is meant increasing overall or progression-free survival in a treated patient relative to an untreated patient (i.e. relative to a patient not treated with the medicament).

As used herein, "drug related toxicity", "infusion related reactions" and "immune related adverse events" ("irAE"), and the severity or grades thereof are as exemplified and defined in the National Cancer Institute's Common Terminology Criteria for Adverse Events v 4.0 (NCI CTCAE v 4.0).

As used herein, "in combination with" or "in conjunction with" refers to administration of one treatment modality in addition to another treatment modality. As such, "in combination with" or "in conjunction with" refers to administration of one treatment modality before, during, or after administration of the other treatment modality to the individual.

A "low-dose amount", as used herein, refers to an amount or dose of a substance, agent, compound, or composition, that is lower than the amount or dose typically used in a clinical setting.

The term "advanced", as used herein, as it relates to solid tumors, includes locally advanced (non-metastatic) disease and metastatic disease. Locally advanced solid tumors, which may or may not be treated with curative intent, and metastatic disease, which cannot be treated with curative intent are included within the scope of "advanced solid tumors, as used in the present invention. Those skilled in the art will be able to recognize and diagnose advanced solid tumors in a patient.

"Duration of Response" for purposes of the present invention means the time from documentation of tumor model growth inhibition due to drug treatment to the time of acquisition of a restored growth rate similar to pretreatment growth rate.

The term "additive" is used to mean that the result of the combination of two compounds, components or targeted agents is no greater than the sum of each compound, component or targeted agent individually. The term "additive" means that there is no improvement in the disease condition or disorder being treated over the use of each compound, component or targeted agent individually.

The terms "synergy" or "synergistic" are used to mean that the effect of the combination of two compounds, components or targeted agents is greater than the sum of the effect each agent provides alone. The terms "synergy" or "synergistic" means that there is an improvement in the disease condition or disorder being treated, over the separate use of each compound, component or targeted agent individually. This improvement in the disease condition or disorder being treated is a "synergistic effect" or "synergistic therapeutic effect." A "synergistic amount," "synergistic effective amount" or "synergistic therapeutically effective amount" is an amount of a compound, component or targeted agent when administered in combination that results in a synergistic effect, as "synergistic" is defined herein. Determining a synergistic interaction between two or more components, the optimum range for the effect and absolute dose ranges of each component for the effect may be definitively measured by administration of the components over different w/w (weight per weight) ratio ranges and doses to patients in need of treatment. However, the observation of synergy in in vitro models or in vivo models can be predictive of the effect in humans and other species and in vitro models or in vivo models exist, as described herein, to measure a synergistic effect and the results of such studies can also be used to predict effective dose and plasma concentration ratio ranges and the absolute doses and plasma concentrations required in humans and other species by the application of pharmacokinetic/pharmacodynamic methods.

Equivalents

The foregoing description and following Examples detail certain specific embodiments of the disclosure and describes the best mode contemplated by the inventors. It will be appreciated, however, that no matter how detailed the foregoing may appear in text, the disclosure may be practiced in many ways and the disclosure should be construed in accordance with the appended claims and any equivalents thereof.

Although the disclosed teachings have been described with reference to various applications, methods, kits, and compositions, it will be appreciated that various changes and modifications can be made without departing from the teachings herein and the claimed disclosure below. The following examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

General Techniques

It is to be understood that this invention is not limited to specific synthetic methods of making that may of course vary. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Sambrook and Russell, Molecular Cloning: A Laboratory Manual, 3rd. ed., Cold Spring Harbor Laboratory Press, Cold Spring Harbor, N.Y. (2001); Ausubel et al., Current Protocols in Molecular Biology, John Wiley & Sons, N Y (2002); Harlow and Lane Using Antibodies: A Laboratory Manual, Cold Spring Harbor Laboratory Press, Cold Spring Harbor, N.Y. (1998); Coligan et al., Short Protocols in Protein Science, John Wiley & Sons, N Y (2003); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Biological Deposits

Representative materials of the present invention were deposited in the American Type Culture Collection, 10801 University Boulevard, Manassas, Va. 20110-2209, USA, on Apr. 4, 2018. Vector GDF15_001-VH having ATCC Accession No. PTA-125038 comprises a plasmid comprising a DNA insert encoding the heavy chain variable region of antibody GDF15_001, and vector GDF15_001-VL having ATCC Accession No. PTA-125039 comprises a plasmid comprising a DNA insert encoding the light chain variable region of antibody GDF15_001. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

Example 1: Anti-GDF15 Antibodies

A panel of antibodies (See Tables 2 and 5 and FIG. 29) were generated and compared across a range of binding and biophysical assays.

The anti-GDF15 antibodies of the present invention were analyzed based on their amino acid sequences and the presence of "hot spots" in the CDR regions (e.g. potential glycosylation, oxidation, and chemical degradation sites). The hot spot sequence analysis of the anti-GDF15 antibodies is represented in Table 5 below. GDF15_005, GDF15_006, GDF15_007, GDF15_008, GDF15_009, and GDF15_200 demonstrated the presence of N-linked glycosylation sites in the CDR region and were not selected for further study.

TABLE 5

Sequence Analysis of anti-GDF15 Antibodies

| Antibody | HCDR1 | HCDR2 | HCDR3 | LCDR1 | LCDR2 | LCDR3 |
|---|---|---|---|---|---|---|
| GDF15_001 | GYTFSSYNID (SEQ ID NO: 32) | GINPIFGTAFYNQKFQG (SEQ ID NO: 165) | EAITTVGAMDH (SEQ ID NO: 52) | RTSQSVHNYLA (SEQ ID NO: 95) | DASTRAD (SEQ ID NO: 28) | QQFWSWPWT (SEQ ID NO: 9) |
| GDF15-002 | GYTFSSYNID (SEQ ID NO: 32) | GINPIFGLAFYNQKFQG (SEQ ID NO: 126) | EAITTVGAMDP (SEQ ID NO: 160) | RASQNVHNYLA (SEQ ID NO: 157) | DASNRAD (SEQ ID NO: 114) | QQFWSWPWT (SEQ ID NO: 9) |
| GDF15-003 | GYTFTSYNID (SEQ ID NO: 153) | QINPNNGLAFYNQKFQG (SEQ ID NO: 33) | EQITTVGAMDY (SEQ ID NO: 154) | RASQSLSSYLA (SEQ ID NO: 150) | DAKNRAD (SEQ ID NO: 108) | QQFSSDPYT (SEQ ID NO: 38) |
| GDF15-004 | GYTFSSYNID (SEQ ID NO: 32) | QINPNNGLANYAQKFQG (SEQ ID NO: 146) | EAITTIGAMDY (SEQ ID NO: 147) | RTSESVHSYLA (SEQ ID NO: 88) | DASTRAD (SEQ ID NO: 28) | QQFWSDPYT (SEQ ID NO: 48) |
| GDF15-005 | GYTFSDYNMD (SEQ ID NO: 58) | GINPNNGTAFYAQKFQG (SEQ ID NO: 141) | EAITTVGAMDQ (SEQ ID NO: 119) | RTSESVSSYLA (SEQ ID NO: 138) | DAKTRAD (SEQ ID NO: 37) | QQFWSWPWT (SEQ ID NO: 9) |
| GDF15-006 | GYTFTDYNIS (SEQ ID NO: 133) | QINPNNGLAFYAQKFQG (SEQ ID NO: 134) | EFITTVGAMDY (SEQ ID NO: 135) | RTSQSVSNYLA (SEQ ID NO: 129) | DAKNRAT (SEQ ID NO: 130) | QQFWNDPWT (SEQ ID NO: 102) |
| GDF15-007 | GYTFSDYNIS (SEQ ID NO: 125) | GINPIFGLAFYNQKFQG (SEQ ID NO: 126) | EAITTVGAMDY (SEQ ID NO: 19) | RTSENVHSYLA (SEQ ID NO: 46) | DASTLAT (SEQ ID NO: 122) | QQFWSWPWT (SEQ ID NO: 9) |
| GDF15-008 | GYTFTSYNIS (SEQ ID NO: 117) | QINPNNGLIFFAQKFQG (SEQ ID NO: 118) | EAITTVGAMDQ (SEQ ID NO: 119) | RTSQNVHSYLA (SEQ ID NO: 27) | DASNRAD (SEQ ID NO: 114) | QQFWNDPYT (SEQ ID NO: 63) |
| GDF15-009 | GYTFSSYNIS (SEQ ID NO: 17) | QINPNNGLAFYNQKFQG (SEQ ID NO: 33) | EAITTVGAMEY (SEQ ID NO: 111) | RTSQNVHSYLA (SEQ ID NO: 27) | DAKNRAD (SEQ ID NO: 108) | QQFWSDPYT (SEQ ID NO: 48) |
| GDF15-010 | GYTFSDYNID (SEQ ID NO: 41) | GINPNNGLAFFNQKFQG (SEQ ID NO: 105) | EAITTVGAMDY (SEQ ID NO: 19) | RTSQSLHSYLA (SEQ ID NO: 101) | DASNRAT (SEQ ID NO: 8) | QQFWNDPWT (SEQ ID NO: 102) |
| GDF15-012 | GYTFSDYNMD (SEQ ID NO: 58) | QINPIFGLAFYAQKFQG (SEQ ID NO: 98) | EVITTVGAMDY (SEQ ID NO: 43) | RTSQSVHNYLA (SEQ ID NO: 95) | DASTRAD (SEQ ID NO: 28) | QQFSSDPYT (SEQ ID NO: 38) |
| GDF15-013 | GYTFSDYNMD (SEQ ID NO: 58) | GINPNNGLAFYNQKFQG (SEQ ID NO: 92) | EAITTVGAMDY (SEQ ID NO: 19) | RTSESVHSYLA (SEQ ID NO: 88) | DASNRAT (SEQ ID NO: 8) | QQFWNWPWT (SEQ ID NO: 89) |
| GDF15-014 | GYTFSSYNID (SEQ ID NO: 32) | QINPINGLAFYNQKFQG (SEQ ID NO: 85) | EAITTVGAMDY (SEQ ID NO: 19) | RTSQNVHNYLA (SEQ ID NO: 82) | DASNRAT (SEQ ID NO: 8) | QQFWSDPYT (SEQ ID NO: 48) |
| GDF15-015 | GYTFSDYNMD (SEQ ID NO: 58) | QINPNNGLAFYNQKFQG (SEQ ID NO: 33) | EAITTVGATDY (SEQ ID NO: 79) | RTSQNVHSYLA (SEQ ID NO: 27) | DASNLAD (SEQ ID NO: 47) | QQFSNDPWT (SEQ ID NO: 76) |
| GDF15-017 | GYTFTDYNID (NO: 66) | QINPNNGLAFYNQKFQG (SEQ ID NO: 33) | EAITTVGAMDY (SEQ ID NO: 19) | RTSQSVHSYLA (NO: 36) | DAKTRAT (SEQ ID NO: 70) | QQFSSDPYT (SEQ ID NO: 38) |

TABLE 5-continued

Sequence Analysis of anti-GDF15 Antibodies

| Antibody | HCDR1 | HCDR2 | HCDR3 | LCDR1 | LCDR2 | LCDR3 |
|---|---|---|---|---|---|---|
| GDF15-018 | GYTFTDYNID (SEQ ID NO: 66) | QINPNNGLIFYNQKFQG (SEQ ID NO: 67) | EAITTVGAMDY (SEQ ID NO: 19) | RASQNVHSYLA (SEQ ID NO: 62) | DASTRAD (SEQ ID NO: 28) | QQFWNDPYT (SEQ ID NO: 63) |
| GDF15-020 | GYTESDYNMD (SEQ ID NO: 58) | QINPNNGLANYNQKFQG (SEQ ID NO: 59) | EAITTVGAMDY (SEQ ID NO: 19) | RASQNLHSYLA (SEQ ID NO: 55) | DASTRAD (SEQ ID NO: 28) | QQFWSDPYT (SEQ ID NO: 48) |
| GDF15-021 | GYTFSSYNID (SEQ ID NO: 32) | GINPINGLIFFNQKFQG (SEQ ID NO: 51) | EAITTVGAMDH (SEQ ID NO: 52) | RTSENVHSYLA (SEQ ID NO: 46) | DASNLAD (SEQ ID NO: 47) | QQFWSDPYT (SEQ ID NO: 48) |
| GDF15-022 | GYTFSDYNID (SEQ ID NO: 41) | QINPNNGLIFFNQKFQG (SEQ ID NO: 42) | EVITTVGAMDY (SEQ ID NO: 43) | RTSQSVHSYLA (SEQ ID NO: 36) | DAKTRAD (SEQ ID NO: 37) | QQFSSDPYT (SEQ ID NO: 38) |
| GDF15-100 | GYTFSSYNID (SEQ ID NO: 32) | QINPNNGLAFYNQKFQG (SEQ ID NO: 33) | EAITTVGAMDY (SEQ ID NO: 19) | RTSQNVHSYLA (SEQ ID NO: 27) | DASTRAD (SEQ ID NO: 28) | QQFWSDPWT (SEQ ID NO: 29) |
| GDF15-200 | GYTFSSYNIS (SEQ ID NO: 17) | GINPINGLAFYNQKFQG (SEQ ID NO: 18) | EAITTVGAMDY (SEQ ID NO: 19) | RASQSVHSYLA (SEQ ID NO: 7) | DASNRAT (SEQ ID NO: 8) | QQFWSWPWT (SEQ ID NO: 9) |

Potential sequence liability sites (e.g. deamidation: NG, isomerization: DG, cleavage: DP) are underlined as well.

Example 2: Binding Properties of the Anti-GDF15 Antibodies: Binding Activity to Human, Cynomolgus Monkey, and Murine GDF15 by SPR The binding affinity of antibody GDF15_001 (comprising a VH comprising the amino acid sequence of SEQ ID NO:166 and a VL comprising the amino acid sequence of SEQ ID NO:163) to human, cyno and murine GDF15 was determined using a BIAcore T200 instrument (GE Healthcare) at 37° C. with a collection rate of 10 Hz. Mouse Fc-human GDF15 (Mu IgG1Fc_Fxa_Hu GDF15; SEQ ID NO:2), Mouse Fc-mouse GDF15 (Mu IgG1Fc_Fxa_Mu GDF15; SEQ ID NO:5) and Mouse Fc-cynomolgus monkey GDF15 (Mu IgG1Fc_Fxa_Cyno GDF15; SEQ ID NO:4) were captured onto three different flow cells of a CM4 sensorchip (catalogue number BR100534, GE Healthcare) surface using the Mouse Antibody Capture Kit (BR100838, GE Healthcare) according to the manufacturer's protocol. The running and sample buffer was 10 mM HEPES pH 7.4, 0.15M NaCl, 3 mM EDTA, 0.05% P-20 (HBS-EP+). The final capture levels of Mu IgG1Fc_Fxa_Hu GDF15, Mu IgG1Fc_Fxa_Mu GDF15 and Mu IgG1Fc_Fxa_Cyno GDF15 were 40 resonance units (RU), 32 RU and 25 RU respectively. Flow cell 1 was used as a reference flow cell. A two-fold dilution series of GDF15_001 with concentrations ranging from 10 nM to 0.625 nM was injected over the sensor surface for 120 seconds. The dissociation was monitored for 2.8 hours and the surface was regenerated with 10 mM Glycine pH 1.7. Binding affinities and rate constants were determined for murine and cynomolgus monkey GDF15 by fitting the resulting sensorgram data to a 1:1 Langmuir model in BIAcore T200 Evaluation software version 2.0 (GE Healthcare). Affinity values were determined as shown in Table 6 below.

The binding affinities of several clones of GDF15 binding antibodies to Mouse Fc-human GDF15 were also determined using the methodology described here in Example 2 and are shown in Table 6 below. All clones tested in bivalent format demonstrated apparent KD value below 150 pM, suggesting that they are strong binders for human GDF15. Additionally, the binding of clone GDF15_001 to cynomolgus monkey and mouse GDF15 was measured using above mentioned BIAcore assay (Table 7). Clone GDF15_001 exhibits strong binding to cynomolgus monkey GDF-15 (apparent KD 8.28 pM) and maintains binding to mouse GDF15 (apparent KD 142.3 pM), making clone GDF15_001 suitable for preclinical studies in both species.

TABLE 6

BIAcore Kinetic Data of Antibody Clones Binding to Human GDF15

| Ligand | Analyte | Ka (1/Ms) | Kd (1/s) | T½ min | Rmax (RU) | % Chi2/Rmax | Apparent KD (pM) |
|---|---|---|---|---|---|---|---|
| Mu IgG1Fc_Fxa_Hu GDF15 | GDF15_001 | 1.69E+06 | 9.22E−06 | 1252.8 | 23.2 | 1.2 | <10 |
| | GDF15_001 | 2.03E+06 | 6.25E−06 | 1848 | 70.6 | 1 | <10 |
| | GDF15_001 | 2.18E+06 | 4.78E−06 | 2417.3 | 64.8 | 0.05 | <10 |
| | Avg | 1.97E+06 | 6.75E−06 | | | | <10 |

TABLE 6-continued

BIAcore Kinetic Data of Antibody Clones Binding to Human GDF15

| Ligand | Analyte | Ka (1/Ms) | Kd (1/s) | T½ min | Rmax (RU) | % Chi2/Rmax | Apparent KD (pM) |
|---|---|---|---|---|---|---|---|
| Mu | GDF15_003 | 2.64E+06 | 7.22E−05 | 160.04 | 23.91 | 0.133 | 27.4 |
| IgG1Fc_Fxa_Hu GDF15 | GDF15_003 | 3.43E+06 | 9.19E−05 | 125.73 | 17.73 | 2.51 | 26.8 |
|  | Avg | 3.03E+06 | 8.20E−05 |  |  |  | 27.1 ± 0.3 |
| Mu | GDF15_004 | 2.22E+06 | 7.14E−05 | 161.86 | 45.77 | 0.291 | 32.2 |
| IgG1Fc_Fxa_Hu GDF15 |  | 1.96E+06 | 8.20E−05 | 140.85 | 37.03 | 0.51 | 41.9 |
|  | Avg | 2.09E+06 | 7.67E−05 |  |  |  | 37 ± 4.8 |
| Mu | GDF15_010 | 1.31E+06 | 1.47E−05 | 783.58 | 34.1 | 1.302 | 11.3 |
| IgG1Fc_Fxa_Hu GDF15 | GDF15_010 | 8.85E+05 | 1.78E−05 | 649.24 | 33.33 | 1.287 | 20.1 |
|  | Avg | 1.10E+06 | 1.63E−05 |  |  |  | 15.7 ± 4.4 |
| Mu | GDF15_013 | 2.42E+06 | 6.66E−05 | 173.35 | 33.56 | 1.54 | 27.5 |
| IgG1Fc_Fxa_Hu GDF15 | GDF15_013 | 7.30E+06 | 7.51E−05 | 153.88 | 25.04 | 0.57 | 10.3 |
|  | Avg | 4.86E+06 | 7.08E−05 |  |  |  | 18.0 ± 8.6 |
| Mu | GDF15_014 | 1.88E+06 | 1.79E−05 | 644.89 | 29.2 | 0.13 | <10 |
| IgG1Fc_Fxa_Hu GDF15 | GDF15_014 | 1.90E+06 | 1.48E−05 | 779.88 | 23.53 | 0.13 | <10 |
|  | Avg | 1.89E+06 | 1.64E−05 |  |  |  | <10 |
| Mu | GDF15_015 | 1.67E+06 | 9.93E−05 | 116.28 | 23.28 | 0.42 | 59.4 |
| IgG1Fc_Fxa_Hu GDF15 | GDF15_015 | 1.81E+06 | 1.04E−04 | 111.59 | 17.68 | 0.49 | 57.3 |
|  | Avg | 1.74E+06 | 1.01E−04 |  |  |  | 58.4 ± 1.1 |
| Mu | GDF15_017 | 3.24E+06 | 8.66E−05 | 133.39 | 26.35 | 0.12 | 26.7 |
| IgG1Fc_Fxa_Hu GDF15 | GDF15_017 | 1.90E+06 | 8.18E−015 | 141.22 | 23.1 | 0.16 | 43 |
|  | Avg | 2.57E+06 | 8.42E−05 |  |  |  | 34.9 ± 8.2 |
| Mu | GDF15_020 | 9.72E+05 | 9.46E−05 | 122.08 | 22.23 | 0.1 | 97.4 |
| IgG1Fc_Fxa_Hu GDF15 | GDF15_020 | 6.86E+05 | 1.13E−04 | 102.3 | 21.57 | 0.17 | 165 |
|  | Avg | 8.29E+05 | 1.04E−04 |  |  |  | 131.2 ± 33.8 |
| Mu | GDF15_021 | 2.05E+06 | 2.91E−04 | 39.64 | 28.58 | 0.36 | 142 |
| IgG1Fc_Fxa_Hu GDF15 | GDF15_021 | 2.14E+06 | 3.52E−04 | 32.84 | 22.75 | 0.27 | 165 |
|  | Avg | 2.09E+06 | 3.22E−04 |  |  |  | 153.5 ± 11.5 |
| Mu | GDF15_022 | 1.34E+06 | 1.77E−05 | 654.39 | 30.58 | 0.26 | 13.2 |
| IgG1Fc_Fxa_Hu GDF15 | GDF15_022 | 8.13E+05 | 1.45E−05 | 795.45 | 38.96 | 0.33 | 17.9 |
|  | Avg | 1.08E+06 | 1.61E−05 |  |  |  | 15.6 ± 2.4 |
| Mu | GDF15_0297 | 5.54E+06 | 1.09E−05 | 1060.61 | 52.25 | 0.36 | <10 |
| IgG1Fc_Fxa_Hu GDF15 | GDF15_0297 | 5.50E+06 | 1.29E−05 | 894.66 | 53.67 | 0.39 | <10 |
|  | Avg | 5.52E+06 | 1.19E−05 |  |  |  | <10 |
| Mu IgG1Fc_Fxa_Hu GDF15 | GDF15_0301 | 3.36E+06 | 1.04E−06 | 11105.77 | 58.42 | 1.16 | <10 |
|  | GDF15_0301 | 5.58E+06 | 7.08E−06 | 1632.05 | 46.84 | 0.29 | <10 |
|  | GDF15_0301 | 5.22E+06 | 1.28E−05 | 903.76 | 46.75 | 0.30 | <10 |
|  | Avg | 4.72E+06 | 6.97E−06 |  |  |  | <10 |
| Mu IgG1Fc_Fxa_Hu GDF15 | GDF15_0470 | 1.20E+07 | 5.21E−05 | 221.86 | 43.46 | 0.17 | <10 |
|  | GDF15_0470 | 1.30E+07 | 4.30E−05 | 268.36 | 39.94 | 0.22 | <10 |
|  | Avg | 1.25E+07 | 4.76E−05 |  |  |  | <10 |

TABLE 7

BIAcore Kinetic Data of GDF15_001 to Human, Murine and Cyno GDF15

| Ligand | Analyte | Ka (1/Ms) | Kd (1/s) | T½ min | Rmax (RU) | % Chi2/Rmax | Apparent KD (pM) |
|---|---|---|---|---|---|---|---|
| Mu | GDF15_001 | 1.69E+06 | 9.22E−06 | 1252.8 | 23.2 | 1.2 | <10 |
| IgG1Fc_Fxa_Hu | GDF15_001 | 2.03E+06 | 6.25E−06 | 1848 | 70.6 | 1 | <10 |
| GDF15 | GDF15_001 | 2.18E+06 | 4.78E−06 | 2417.3 | 64.8 | 0.05 | <10 |
|  | Avg | 1.97E+06 | 6.75E−06 |  |  |  | <10 |
| Mu | GDF15_001 | 2.55E+06 | 2.92E−04 | 39.6 | 86.7 | 1.5 | 114.0 |
| IgG1Fc_Fxa_Mu | GDF15_001 | 2.46E+06 | 4.31E−04 | 26.8 | 58.9 | 1.1 | 175.0 |
| GDF15 | GDF15_001 | 2.51E+06 | 3.47E−04 | 33.3 | 54.0 | 1.5 | 138.0 |
|  | Avg | 2.51E+06 | 3.56E−04 |  |  |  | 142.3 ± 30.7 |
| Mu | GDF15_001 | 1.47E+06 | 1.30E−05 | 886.4 | 96.0 | 0.89 | 8.86 |
| IgG1Fc_Fxa_Cyno | GDF15_001 | 1.85E+06 | 1.24E−05 | 928.5 | 49.6 | 0.28 | 6.71 |
| GDF15 | GDF15_001 | 1.12E+06 | 1.03E−05 | 1119.2 | 76.50 | 0.07 | 9.26 |
|  | Avg | 1.48E+06 | 1.19E−05 |  |  |  | 8.28 ± 1.37 |

Example 3: Binding Properties of the Anti-GDF15 Antibodies: Binding Activity of Monomeric Anti-GDF15 Antibody to Human, Cynomolgus Monkey, and Murine GDF15 by SPR To understand the KD value, without the avidity effect, of GDF15_001 binding to GDF15, monomeric Fc-Fab was produced and tested in the same assay used in Example 2. The binding affinity of monomeric GDF15_001 to human, cyno and murine GDF15 was determined using a BIAcore T200 instrument (GE Healthcare) at 37° C. with a collection rate of 10 Hz. Mu IgG1Fc_Fxa_Hu GDF15, Mu IgG1Fc_Fxa_Mu GDF15 and Mu IgG1Fc_Fxa_Cyno GDF15 were captured onto three different flow cells of a CM4 sensorchip (catalogue number BR100534, GE Healthcare) surface using the Mouse Antibody Capture Kit (BR100838, GE Healthcare) according to the manufacturer's protocol. The running and sample buffer was 10 mM HEPES pH 7.4, 0.15M NaCl, 3 mM EDTA, 0.05% P-20 (HBS-EP+). The final capture levels of Mu IgG1Fc_Fxa_Hu GDF15, Mu IgG1Fc_Fxa_Mu GDF15 and Mu IgG1Fc_Fxa_Cyno GDF15 were 19 resonance units (RU), 22 RU and 19 RU respectively. Flow cell 1 was used as a reference flow cell. A two-fold dilution series of monomeric GDF15_001 with concentrations ranging from 10 nM to 1.25 nM was injected over the sensor surface for 120 seconds. The dissociation was monitored for 1200 seconds and the surface was regenerated with 10 mM Glycine pH 1.7. Binding affinities and rate constants were determined by fitting the resulting sensorgram data to a 1:1 Langmuir model in BIAcore T200 Evaluation software version 2.0 (GE Healthcare). Monomeric clone GDF15_001 demonstrated strong binding to human (KD 21.3 pM) and cynomolgus monkey GDF15 (KD 62.0 pM) with weaker binding to murine GDF15 (KD 1965.0 pM), as shown in Table 8 below.

TABLE 8

BIAcore Kinetic Data of Monomeric GDF15_001 to Human, Murine and Cyno GDF15

| Ligand | Analyte | Ka (1/Ms) | Kd (1/s) | T½ min | Rmax (RU) | % Chi2/ Rmax | Apparent KD (pM) |
|---|---|---|---|---|---|---|---|
| Mu IgG1Fc_Fxa_Hu GDF15 | CH23LS-GDF15_001 | 1.52E+06 | 2.25E−05 | 512.65 | 29.94 | 0.655 | 14.9 |
|  | CH23LS-GDF15_001 | 1.66E+06 | 4.58E−05 | 252.24 | 24.61 | 1.601 | 27.6 |
|  | Avg | 1.59E+06 | 3.42E−05 |  |  |  | 21.3 ± 6.4 |
| Mu IgG1Fc_Fxa_Mu GDF15 | CH23LS-GDF15_001 | 1.62E+06 | 3.41E−03 | 3.39 | 32.44 | 0.364 | 2110 |
|  | CH23LS-GDF15_001 | 1.70E+06 | 3.10E−03 | 3.73 | 26.86 | 0.521 | 1820 |
|  | Avg | 1.66E+06 | 3.26E−03 |  |  |  | 1965.0 ± 145.0 |
| Mu IgG1Fc_Fxa_Cyno GDF15 | GDF15_001 | 1.63E+06 | 7.48E−05 | 154.33 | 29.65 | 0.661 | 45.8 |
|  | GDF15_001 | 1.20E+06 | 9.39E−05 | 123.07 | 30.11 | 0.661 | 78.2 |
|  | Avg | 1.42E+06 | 8.43E−05 |  |  |  | 62.0 ± 16.2 |

Example 4: Binding Properties of the Anti-GDF15 Antibodies: Binding Specificity of GDF15_001 to Human GDF15

To assess the binding specificity of GDF15_001 to human GDF15, GDF15_001 binding to additional TGFβ family members was tested. Analysis was carried out on an Octet Red instrument.

An OctetRED 384 (ForteBio, Menlo Park, Calif.) was used to evaluate off-target binding of monomeric GDF15_001 (CH23LS-GBT-GDF15_001) to ten TGFβ family members including human GDNF (R&D, 212-GD/CF), human Inhibin A (R&D, 8506-AB/CF), human Activin B (R&D, 659-AB/CF) human TGFβ-1 (R&D, 240-B/CF) human BMP2 (R&D, 355-BM/CF), human BMP3b (R&D, 1543-BP/CF), human BMP6 (R&D, 507-BP/CF), human BMP9 (R&D, 3209-BP/CF), human BMP11 (R&D, 1958-CD/CF), human GDF8 (Pfizer, 41075-201) and control human GDF15 (Mu IgG1Fc_Fxa_Hu GDF15). The TGFβ family members were diluted to 10 ug/ml in 10 mM Sodium Acetate pH 4.5 and amine coupled onto AR2G biosensors (catalogue #18-5092, ForteBio) according to the manufacturer's instructions. Monomeric GDF15_001 was diluted to 200 nM in kinetics buffer (catalogue #18-5032 ForteBio). Octet assays were conducted at room temperature with an association time of 300 seconds and a dissociation time of 180 seconds. The data was double referenced (Myszka, D., J. Mol. Recognit 1999; 279-284) and analyzed with Octet Data Analysis software version 8.1 (ForteBio).

GDF15_001 bound to human GDF15 as expected. No binding to other TGFβ family members (GDF-11, BMP-9, GDF-8, BMP-2, BMP-6, TGFß-1, activin-B, inhibin-A) was detected at 200 nM of monomeric clone GDF15_001, demonstrating the high specificity of GDF15_001, which does not bind to these other related family members. The high specificity of GDF15_001 minimizes the risk of off-target binding and indicates that GDF15_001 is a potential novel, useful, human therapeutic.

Example 5: Anti-GDF15 Antibodies Prevent GDF15 Binding to GFRAL

The ability of GDF15_001 to prevent human GDF15 binding to the extracellular domain of GFRAL was assessed by in a competition assay. Analysis was carried out using a BIAcore T200 instrument (GE Healthcare, Chicago, Ill.).

GDF15_001 was titrated into 10 nM human GDF-15 at concentrations ranging from 10 nM to 2.5 nM. The mixtures GDF-15, GDF15_001, and controls were injected over the extracellular domain of human GFRAL which was directly immobilized on a CM4 sensor chip. Concentration dependent inhibition of human GDF15 binding to GFRAL was observed. Binding of human GDF15 to human GFRAL ECD was completely blocked by 7.5 nM GDF15_001.

These data demonstrate that GDF15_001 blocks the interaction between human GDF15 and its cognate receptor, GFRAL, and can thereby interfere with GFRAL signaling. This further demonstrates that GDF15_001 may be novel potentially useful therapeutic to decrease an activity mediated by GDF15 binding to GFRAL.

Example 6: Biophysical Properties of the Anti-GDF15 Antibodies: Thermal Stability Thermal stability of the anti-GDF15 antibodies was assessed by Differential Scanning calorimetry (DSC). Proteins were diluted in a phosphate-buffered saline (PBS) solution to 0.3 mg/ml in a volume of 400 µl. PBS was used as a buffer blank in the reference cell. PBS contained 137 mM NaCl, 2.7 mM KCl, 8.1 mM $Na_2HPO_4$, and 1.47 mM $KH_2PO_4$, pH 7.2. Samples were dispensed into the sample tray of a MicroCal VP-Capillary DSC with Autosampler (Malvern Instruments Ltd, Malvern, UK). Samples were equilibrated for 5 minutes at 10° C. and then scanned up to 110° C. at a rate of 100° C. per hour. A filtering period of 16 seconds was selected. Raw data was baseline corrected and the protein concentration was normalized. Origin Software 7.0 (OriginLab Corporation, Northampton, Mass.) was used to fit the data to an MN2-State Model with an appropriate number of transitions.

Figure 1A:
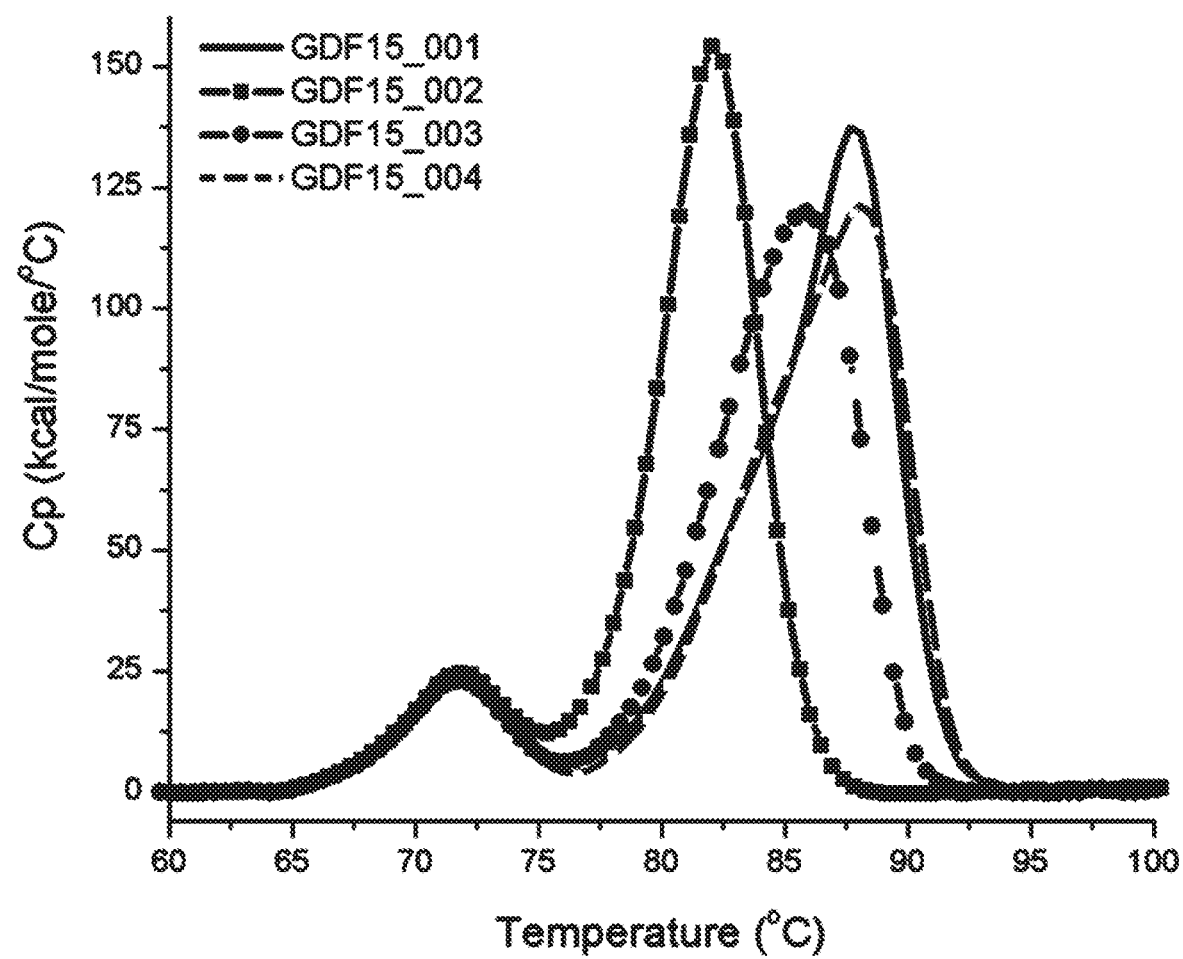
FIG. 1A shows a graph depicting the transition temperatures ($T_m1$) for the anti-GDF15 antibodies of the invention, as determined by Differential Scanning calorimetry (DSC). The $T_m1$ represents the temperature at which the $C_H2$ of the antibody is 50% unfolded.
Figure 1B:
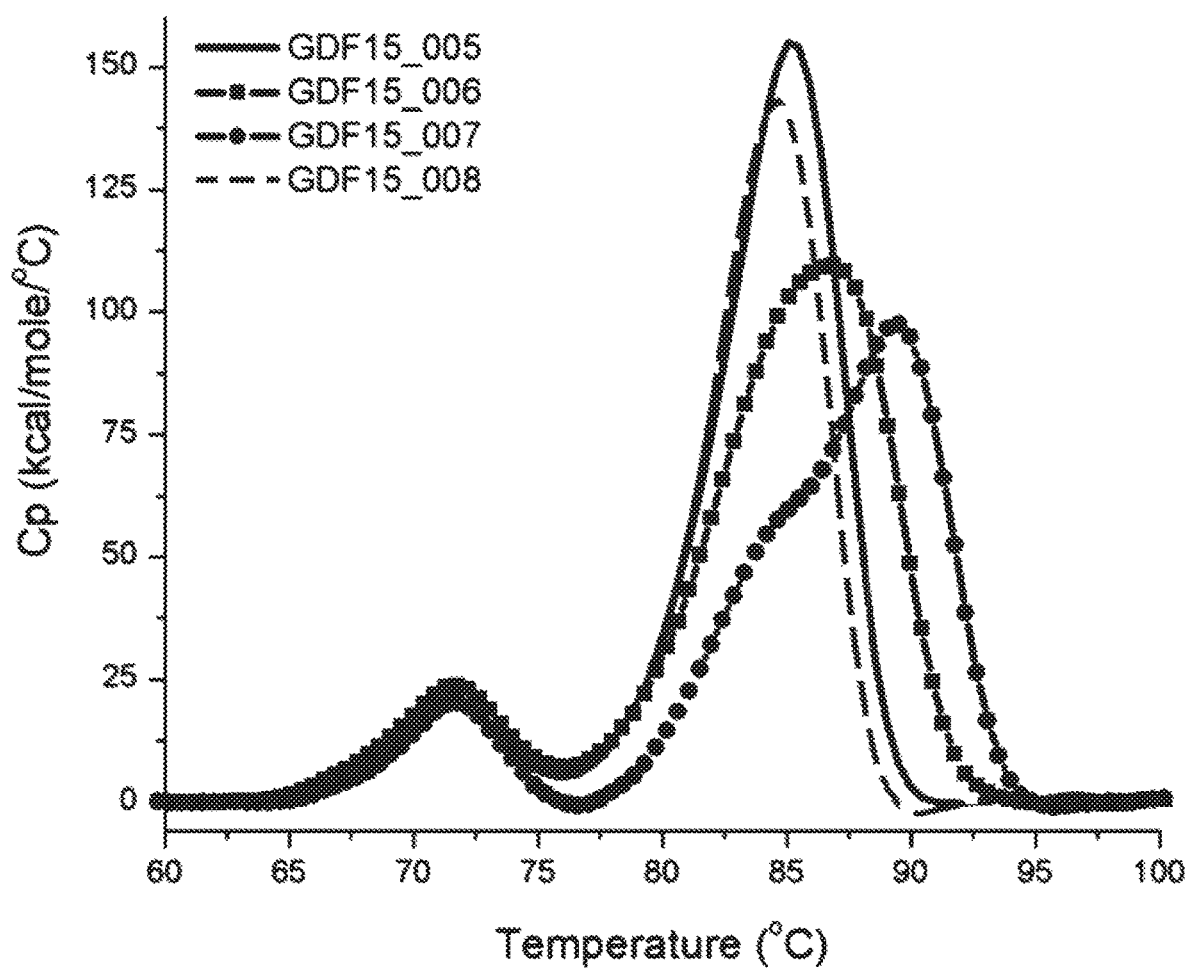
FIG. 1B shows a graph depicting the transition temperatures ($T_m2$) for the anti-GDF15 antibodies of the invention, as determined by Differential Scanning calorimetry (DSC). The $T_m2$ represents the temperature at which the Fab of the antibody is 50% unfolded.
Figure 1C:
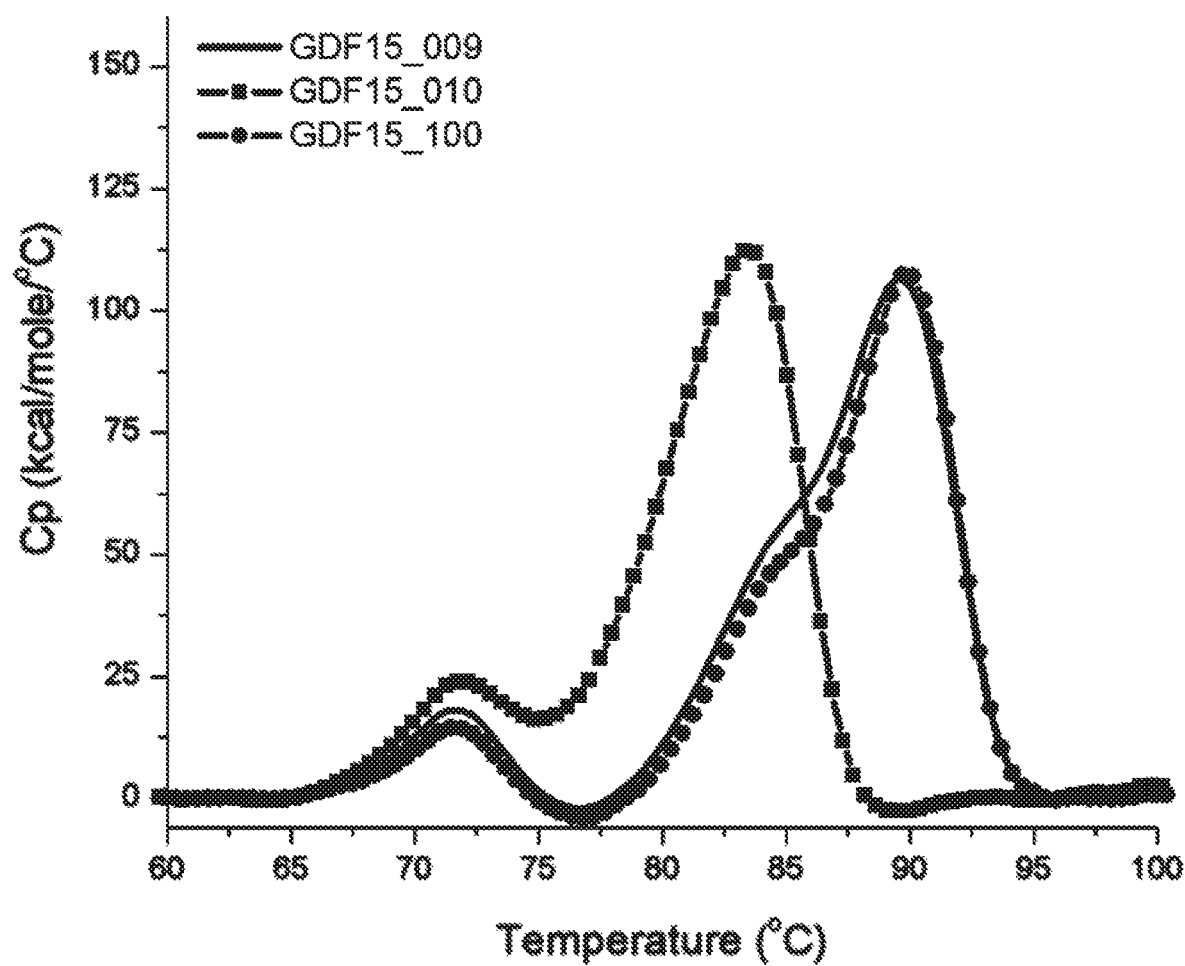
FIG. 1C shows a graph depicting the transition temperatures ($T_m3$) for the anti-GDF15 antibodies of the invention, as determined by Differential Scanning calorimetry (DSC). The $T_m3$ represents the temperature at which the $C_H3$ of the antibody is 50% unfolded.

The transition temperatures are shown in FIGS. 1A, 1B, and 1C and are listed in Table 9. The $T_m1$ represents the temperature at which the $C_H2$ of the antibody is 50% unfolded. The $T_m2$ represents the temperature at which the Fab of the antibody is 50% unfolded. The $T_m3$ represents the temperature at which the $C_H3$ of the antibody is 50% unfolded. All clones with a melting temperature ($T_m1$) over 65° C. are designed as stable clones, which will be stable during manufacturing and storage.

TABLE 9

Transition temperatures of anti-GDF15 antibodies.

| Clone | $T_m1$ (° C.) | $T_m2$ (° C.) | $T_m3$ (° C.) |
|---|---|---|---|
| GDF15_001 | 71.67 ± 0.08 | 84.30 ± 0.25 | 88.00 ± 0.04 |
| GDF15_002 | 71.81 ± 0.06 | 80.51 ± 1.10 | 82.51 ± 0.21 |
| GDF15_003 | 71.67 ± 0.10 | 83.69 ± 0.37 | 86.66 ± 0.12 |
| GDF15_004 | 71.57 ± 0.11 | 84.94 ± 0.29 | 88.50 ± 0.07 |
| GDF15_005 | 71.37 ± 0.14 | 83.30 ± 0.67 | 85.79 ± 0.18 |
| GDF15_006 | 71.40 ± 0.09 | 84.45 ± 0.26 | 87.92 ± 0.11 |
| GDF15_007 | 71.41 ± 0.11 | 85.14 ± 0.23 | 89.72 ± 0.07 |
| GDF15_008 | 71.70 ± 0.14 | 83.05 ± 0.76 | 85.33 ± 0.24 |
| GDF15_009 | 71.35 ± 0.15 | 85.42 ± 0.31 | 89.88 ± 0.09 |
| GDF15_010 | 72.14 ± 0.20 | 81.18 ± 0.64 | 84.13 ± 0.19 |
| GDF15_100 | 71.33 ± 0.17 | 85.45 ± 0.28 | 90.02 ± 0.07 |
| GDF15_0297 | 73.01 ± 0.20 | 74.45 ± 0.07 | 80.80 ± 0.07 |
| GDF15_0301 | 76.14 ± 0.06 | 77.20 ± 0.04 | 78.82 ± 0.05 |

Example 7: Biophysical Properties of the Anti-GDF15 Antibodies: Size Exclusion Chromatography Antibody clones were analyzed by analytical size exclusion chromatography (aSEC). Proteins were diluted in a phosphate-buffered saline (PBS) solution to 1.0 mg/ml and analyzed by aSEC on an YMC-Pack Diol-200, 300×8 mm column with isocratic running buffer containing 20 mM sodium phosphate pH 7.2, 400 mM NaCl. Native SEC was used to determine the relative amounts of high molecular mass (aggregate) and monomeric intact antibody. The percent aggregate was calculated as the peak area of the high molecular mass divided by the total (aggregate and monomer) peak area multiplied by 100. The retention time in minutes was recorded and compared with an assay control. Antibody clones with normal retention time and peak shape from aSEC analysis may suggest minimal interactions with stationary phase resin and optimal hydrophobicity, these are useful characteristics and indicate that the antibody may be a potential useful therapeutic.

The retention time for each antibody clone tested is shown in Table 10. GDF15_002 showed delayed retention time and broad peak shape and was therefore not studied further.

TABLE 10 aSEC retention time for anti-GDF15 antibodies

| Antibody | aSEC Retention time (min) |
|---|---|
| control mAb | 10.40 |
| GDF15_001 | 10.79 |
| GDF15_002 | 11.69 |
| GDF15_003 | 10.22 |
| GDF15_004 | 10.24 |
| GDF15_005 | 9.74 |
| GDF15_100 | 10.30 |
| GDF15_0297 | 9.96 |
| GDF15_0301 | 9.91 |

Example 8: Biophysical Properties of the Anti-GDF15 Antibodies: Stability at Low pH Since antibodies are purified by Protein A capture and elution is at low pH conditions, the anti-GDF15 antibody clones were tested for low pH hold stability. Antibody at 1.0 mg/ml in PBS, pH 7.2 was acidified with glycine pH 3.4, and incubated at 25° C. for 5 hours, then neutralized with Tris Base and run on aSEC to determine the amount of high molecular mass species (HMMS) and low molecular mass species (LMMS), Table 11. All clones tested show acceptable amount of increases of HMMS (<5%) post low pH challenge. This indicates that the anti-GDF15 antibodies will remain stable during purification processes and may be potentially useful therapeutics.

TABLE 11

Amount of HMMS and LMMS following low pH challenge.

| GDF15 | % HMMS neutral control | % increase HMMS acidified then neutralized | % LMMS neutral control | % increase LMMS acidified then neutralized | % decrease monomer peak area acidified then neutralized |
|---|---|---|---|---|---|
| GDF15_001 | 2.9 | −1.5 | 0 | 0 | −0.4 |
| GDF15_002 | 3.0 | −0.7 | 0 | 0 | −0.6 |

TABLE 11-continued

Amount of HMMS and LMMS following low pH challenge.

| GDF15 | % HMMS neutral control | % increase HMMS acidified then neutralized | % LMMS neutral control | % increase LMMS acidified then neutralized | % decrease monomer peak area acidified then neutralized |
|---|---|---|---|---|---|
| GDF15_003 | 2.0 | −0.3 | 0 | 0 | 1.5 |
| GDF15_004 | 1.9 | −0.3 | 0 | 0 | 1.4 |
| GDF15_005 | 6.4 | −0.6 | 0 | 0 | 1.3 |
| GDF15_100 | 5.5 | −0.3 | 0 | 0 | 3.0 |

Example 9: Biophysical Properties of the Anti-GDF15 Antibodies: Viscosity

The viscosity of the GDF15_001 was analyzed by Anton Paar instrument. GDF15_001 was concentrated to 215 mg/mL using 30 kDa molecular weight cut-off Amicon centrifugal filter units (EMD Millipore, Billerica, Mass.). A series of dilutions ranging from 46-178 mg/mL was prepared with 20 mM Histidine, 85 g/L sucrose, 0.05 mg/ml EDTA pH 5.8 buffer as diluent. Protein concentrations were determined by 280 nm analysis on the SoloVPE Variable Pathlength System (C Technologies, Inc, Bridgewater, N.J.). Viscosity measurements were performed using the CP25-1 cone and plate on the MCR-302 rheometer (Anton Paar USA Inc., Ashland, Va.) at a constant rotational speed of 150 rpm at 25° C. A total of 10 measurements of 10 seconds each were collected per sample and the data was analyzed using the Rheoplus (Anton Paar USA Inc.) V 3.62 software. The viscosity is reported in centipoise (cP) units.

Figure 2:
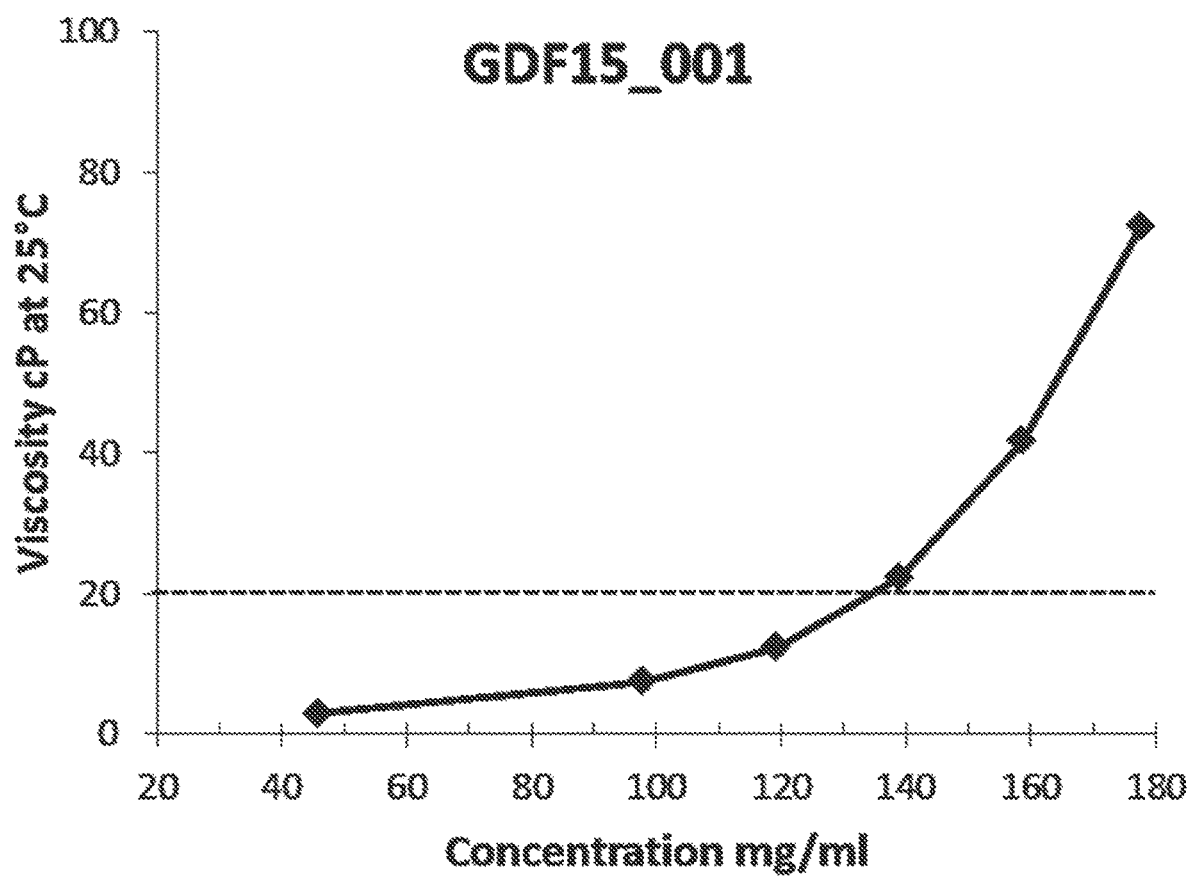
FIG. 2 shows the viscosity of GDF15_001 as analyzed by an Anton Parr instrument. The acceptable viscosity limit (20 cP) is reached at about 140 mg/ml.

The viscosity of GDF15_001 is shown in FIG. 2. The data shows that the acceptable viscosity limit (20 cP) is reached at about 140 mg/ml, making subcutaneous injection of GDF15_001 feasible, further indicating that this antibody is a useful potential therapeutic.

Example 10: Immunogenicity of Anti-GDF15 Antibodies

Based on the detection of non-germline T-cell epitopes, and a calculated tReg-Adjusted score, the immunogenicity of the anti-GDF15 antibodies of the present invention and another anti-GDF15 antibody known in the art as hu01G06 (the VH and VL sequences of hu01G06 are provided herein as SEQ ID NO:177 and SEQ ID NO:178, respectively (VH, SEQ ID NO:248 of WO2014/100689 and VL, SEQ ID NO:254 of WO2014/100689)), was predicted. A lower tReg-Adjusted score predicts a low potential for immunogenicity risk.

Sequences were analyzed using two protocols (Protocols 1 and 2 below) to identify the epitopes. Any sequence identified by the rules described herein for either protocol was considered an epitope. Sequences were examined at the level of amino acid 9-mers.

Protocol 1—ISPRI/EpiMatrix:

Sequences were submitted for EpiMatrix analysis in the ISPRI software package (ISPRI v 1.8.0, EpiVax Inc., Providence, R.I. (2017); Schafer et al. Vaccine 16(19), 1880-84 (1998)). The raw results provide rankings of the likelihood of binding of each 9-mer amino acid fragment against 8 different HLA types. Thus, there are 8 predictions ("observations") for each 9-mer. The 9-mers are generated starting at each individual linear numbering position of the sequence. It is possible for the same 9-mer to occur more than once in the same sequence. If any 4 observations indicate that the 9-mer is in the top 5% of binders, meaning it is predicted to be in the top 5% of binders for at least 4 HLA types, the 9-mer is considered a predicted epitope. Alternatively, if any 1 of the 8 predictions indicate that the 9-mer is in the top 1% of binders, the 9-mer is also considered a predicted epitope.

Protocol 2—IEDB Consensus Method:

Sequences were submitted for analysis using the MHC-II binding Consensus Method (Wang et al. BMC Bioinformatics 11, 568 (2010); Wang et al. PLoS Comput Biol. 4(4), e1000048 (2008)) in the immune epitope database (IEDB) (IEDB MHC-II Binding Predictions, http://www.iedb.org; Vita et al., Nucleic Acids Res. January 28 (43), D405-12 (2015). The output of the software arranges results by 15-mer. A consensus score and percentile ranking are provided for each combination of 15-mer and HLA type. However, the individual scores from which each 15-mer's consensus is derived are rankings of certain 9-mers found in the 15-mer: each method used for the consensus reports a percentile rank for a 9-mer within the 15-mer, and the consensus taken as the value for the overall 15-mer is the prediction for the 9-mer having the median score. A 9-mer is classified as an epitope if (a) it is chosen as the consensus representative for the 15-mer and (b) has a percentile ranking in the top 10% of binders for the HLA type being considered, and if criteria (a) and (b) occur for three or more distinct HLA types for the same 9-mer (i.e., three observations). The HLA types considered were DRB1*01, 1*03, 1*04, 1*07, 1*08, 1*11, 1*13, and 1*15, which are the same HLA types in a standard ISPRI/EpiMatrix report. For ease of comparison with Protocol 1, the data is reinterpreted to obtain a list of predicted 9-mer epitopes, although the primary output of the Consensus Method is a ranking of 15-mers.

Each epitope is classified as a germline or non-germline epitope. For antibodies, each epitope is further classified based on its location within the antibody (e.g. CDR or non-CDR). Sequences of human V domains obtained from IMGT (www.imgt.org) are filtered to remove germlines annotated as pseudogenes or open reading frames. Any predicted 9-mer epitope found in the remaining sequences is considered a germline epitope. Epitopes found in the J or C regions (including IgG1, IgG2, IgG3, and IgG4) or the junctions between these regions were also classified as germline epitopes. Otherwise, an epitope was classified as a non-germline epitope.

CDR definitions were based on the method of Kabat, where the CDRs are defined to include the following residues: HCDR-1 (H26-H35 including insertions such as H35A, up to but not including H36), HCDR-2 (H50-H65 inclusive), HCDR-3 (H95-H102 inclusive) LCDR-1 (L24-L34 inclusive), LCDR-2 (L54-L56 inclusive), LCDR-3

(L89-L97, inclusive). A predicted 9-mer epitope is defined as a CDR epitope if any one of its amino acids is part of a CDR region. Overall Sequence Score (tReq Adjusted Score): For an individual chain, or for a pairing of an antibody VH and VL domain, an overall score can be calculated by summing over each of the constituent 9-mers as described below.

All individual combinations of 9-mer and HLA type ("observations") are examined, regardless of whether the 9-mer is an epitope. If a particular observation indicates the peptide is in the top 5% of binders for a given HLA type, the EpiMatrix Z-score for this observation is added to a running total associated with the entire protein sequence. The total number of observations examined is also recorded. The only exception is that all observations on 9-mers identified by ISPRI as "T-regitopes" (amino acid sequences within the monoclonal antibody framework region that can potentially activate natural regulatory T cells and reduce unwanted immune responses), are assumed to have EpiMatrix scores of zero.

In the running total, a baseline score of 0.05*2.2248 is subtracted from each observation (including T-regitopes). The final score is computed as follows: tReg Adjusted Score=(Running total)*1000/(Number of observations)

The calculated scores are listed in Table 12. As stated above, a lower score indicates lower predicted immunogenic potential. The anti-GDF15 antibodies of the present invention had lower scores that hu01G06. Clones GDF15_001, GDF15_004, GDF15_005 and GDF15_013 had the lowest scores, therefore had the lowest potential predicted risk of eliciting immunogenic responses. This further indicates that the antibodies of the invention are potential useful therapeutics.

TABLE 12

Immunogenicity Risk Prediction for GDF15 mAbs, tReg Adjusted Score

| Clone # | Score (tReg-Adjusted) |
| --- | --- |
| GDF15_001 | −41.58 |
| GDF15_002 | −39.34 |
| GDF15_003 | −26.99 |
| GDF15_004 | −42.06 |
| GDF15_005 | −50.36 |
| GDF15_006 | −34.21 |
| GDF15_007 | −39.6 |
| GDF15_008 | −24.95 |
| GDF15_009 | −29.30 |
| GDF15_010 | −34.08 |
| GDF15_012 | −38.79 |
| GDF15_013 | −42.09 |
| GDF15_014 | −34.36 |
| GDF15_015 | −34.18 |
| GDF15_017 | −38.82 |
| GDF15_018 | −33.79 |
| GDF15_020 | −33.64 |
| GDF15_021 | −31.56 |
| GDF15_022 | −33.16 |
| GDF15_100 | −36.41 |
| GDF15_200 | −26.01 |
| hu01G06 | −20.36 |

The predicted T-cell epitopes of GDF15_001 and hu01G06 were also compared, based on the in silico methods described above. As shown in Table 13 below, hu01G06 has two predicted T-cell epitopes in the heavy chain and one predicted T-cell epitope in the light chain, while GDF15_001 does not have any predicted T-cell epitopes. This indicates that GDF15_001 also has a lower potential risk of eliciting immunogenic responses when compared to hu01G06. This further indicates that GDF15_001 is a potential useful novel therapeutic with improved characteristics.

TABLE 13

Predicted T-cell epitopes of GDF15_001 and hu01G06

| Name | Heavy Chain | Light Chain |
| --- | --- | --- |
| Hu01G06 | 2 | 1 |
| GDF15_001 | 0 | 0 |

Example 11: Inhibition of Human and Murine GDF15 in Healthy Mice

Figure 3:
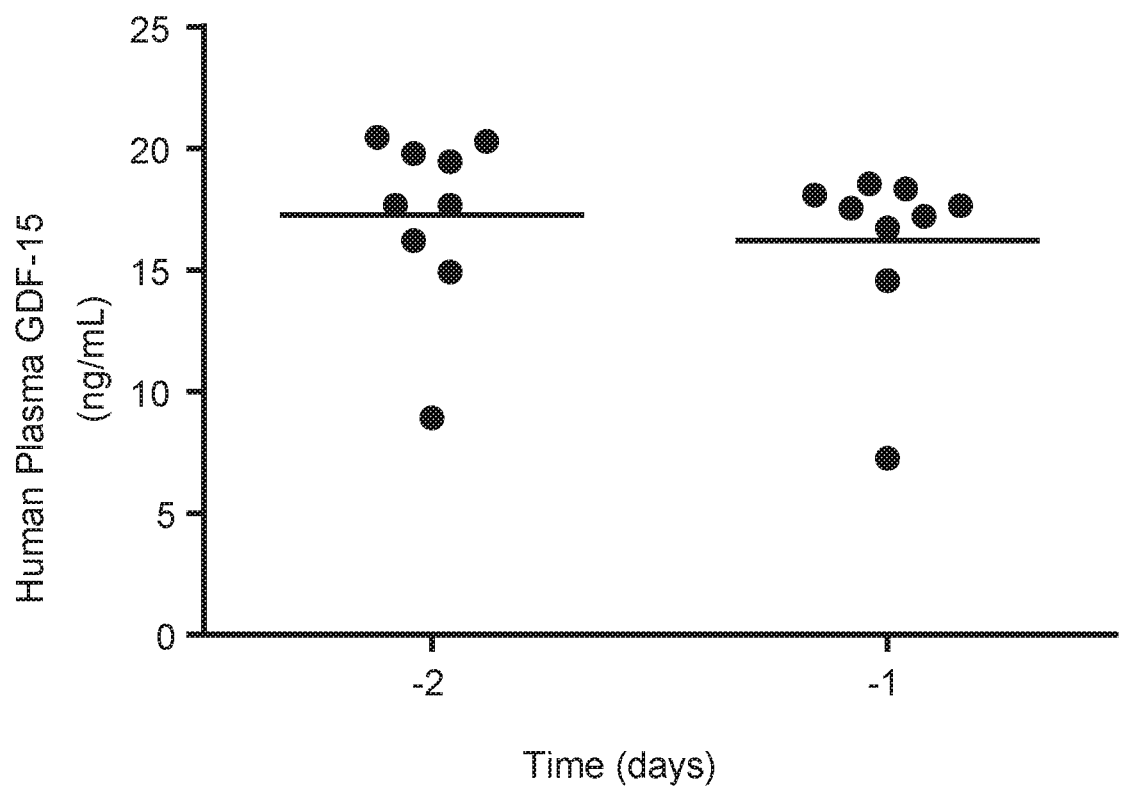
FIG. 3 shows the human plasma GDF15 concentration following adeno-associated virus (AAV)-human GDF15 injection in healthy male C57Bl6N mice. Plasma GDF15 was measured at 13 and 14 days following AAV injection (corresponds to days −2 and −1 on FIG. 3) via ELISA (R&D Systems DGD150). Horizontal lines represent means. n=9 per group.
Figure 4:
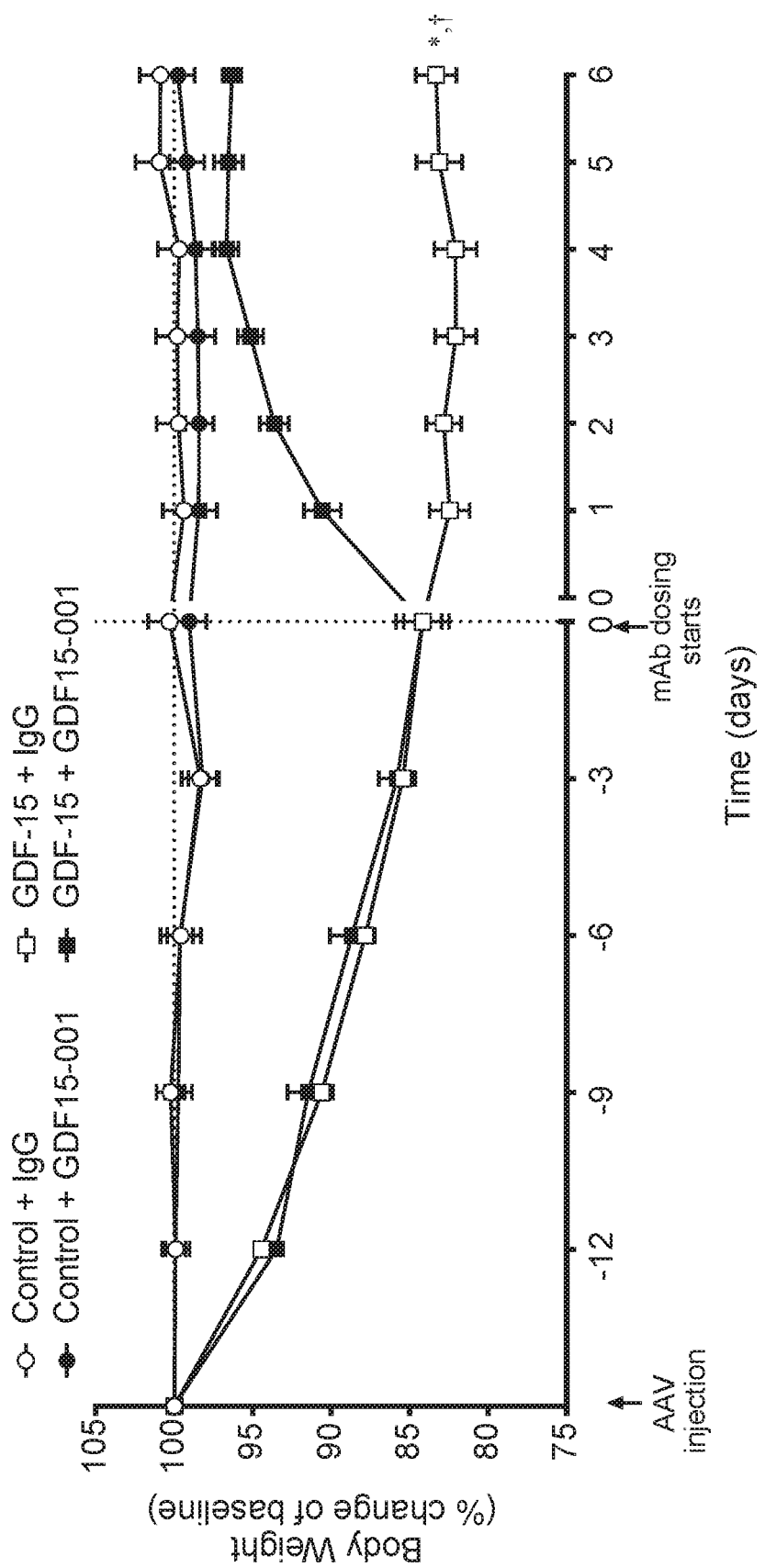
FIG. 4 depicts a graph showing the ability of GDF15_001 to reverse GDF15-induced weight loss in healthy mice. Arrows point to the timings of the AAV-human GDF15 injection (day −15) and the first monoclonal antibody (mAb) dose (day 0). Healthy male C57Bl6N mice were treated with GDF15_001 (30 mg/kg, subcutaneously (SC) every third day (Q3D)) or immunoglobulin G (IgG) control. Values are means±SEM. n=8 per group. Repeated measures ANOVA with an autoregressive (1) covariance structure was used to compare percent change from baseline body weights between treatment groups over days 4-6 of the dosing period. The Tukey-Kramer multiple comparison adjustment was used to control the experiment-wise error rate for treatment group comparisons in the repeated measures analysis of variance (ANOVA). * is $p<0.0001$ versus Control+IgG (days 4-6); † is $p<0.0001$ versus GDF15+GDF15_001 (days 4-6).
Figure 5:
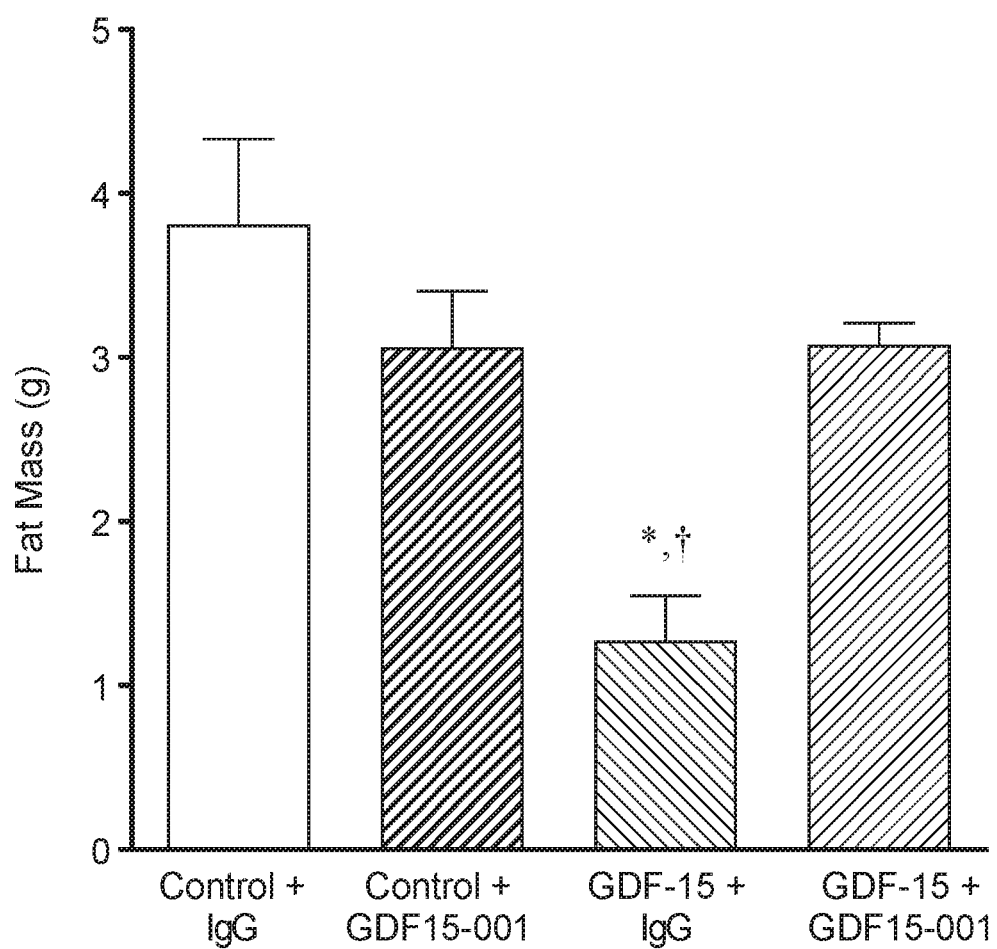
FIG. 5 depicts a graph showing the ability of GDF15_001 to reverse GDF15-induced fat tissue mass loss. Healthy male C57Bl6N mice were injected with AAV-human GDF15 on day −15 followed by the first mAb dose starting on day 0. mAb treatment with GDF15_001 (30 mg/kg, SC, Q3D) or IgG control was continued for 6 days. Body composition was measured at day 6 via magnetic resonance imaging (MRI). Values are means±SEM. n=8 per group. Statistical analysis performed with ANOVA. * is $p<0.0001$ versus Control+IgG, † is $p<0.01$ versus GDF15+GDF15_001.
Figure 6:
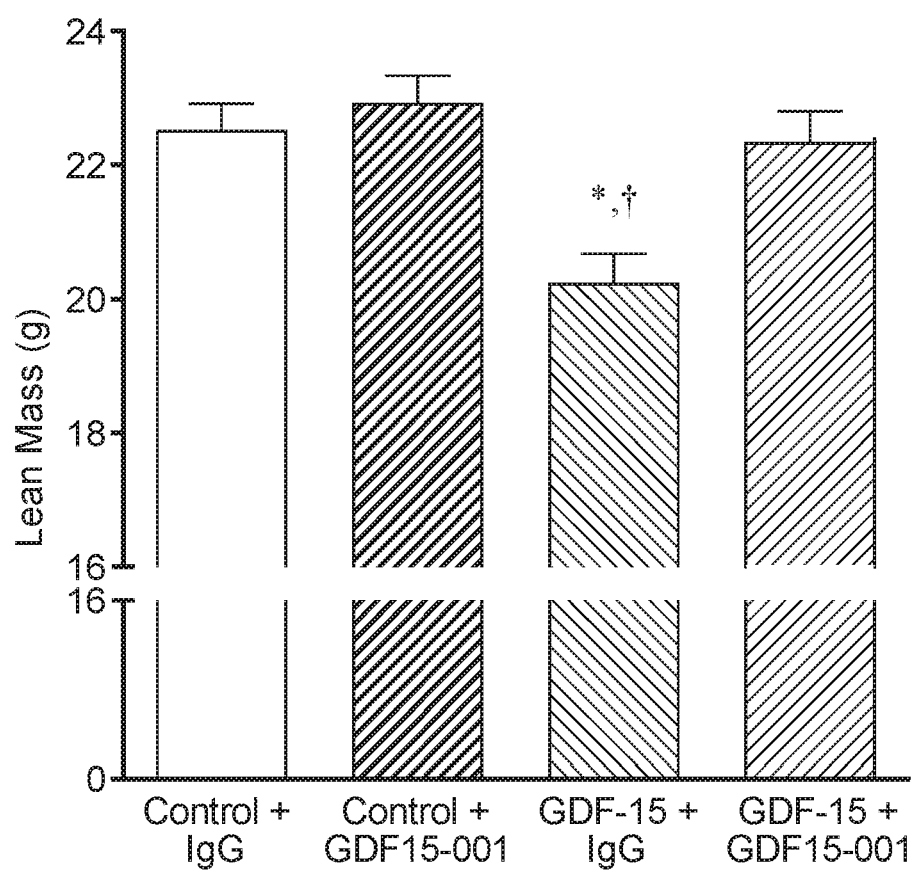
FIG. 6 depicts a graph showing the ability of GDF15_001 to reverse GDF15-induced lean tissue mass loss. Healthy male C57BL6N mice were injected with AAV-human GDF15 on day −15 followed by the first mAb dose starting on day 0. mAb treatment with GDF15_001 (30 mg/kg, subcutaneously ever third day) or IgG control was continued for 6 days. Body composition was measured at day 6 via MRI. Values are means±SEM. n=8 per group. Statistical analysis performed with ANOVA. * is $p<0.01$ versus Control+IgG; † is $p<0.01$ versus GDF15+GDF15_001.

The ability of GDF15_001 to inhibit human GDF15 activity was assessed in healthy C57Bl6N mice treated with adeno-associated virus (AAV)-human GDF15. Two weeks after AAV-human GDF15 treatment, circulating human GDF15 levels increased to approximately 17 ng/mL (FIG. 3), and body weight decreased by 15% (FIG. 4). Administration of GDF15_001 rapidly reversed body weight, (FIG. 4), fat (FIG. 5), and lean mass loss (FIG. 6) in AAV-human GDF15-treated mice versus IgG control. GDF15_001 had no effect in AAV control vector treated mice.

Figure 7:
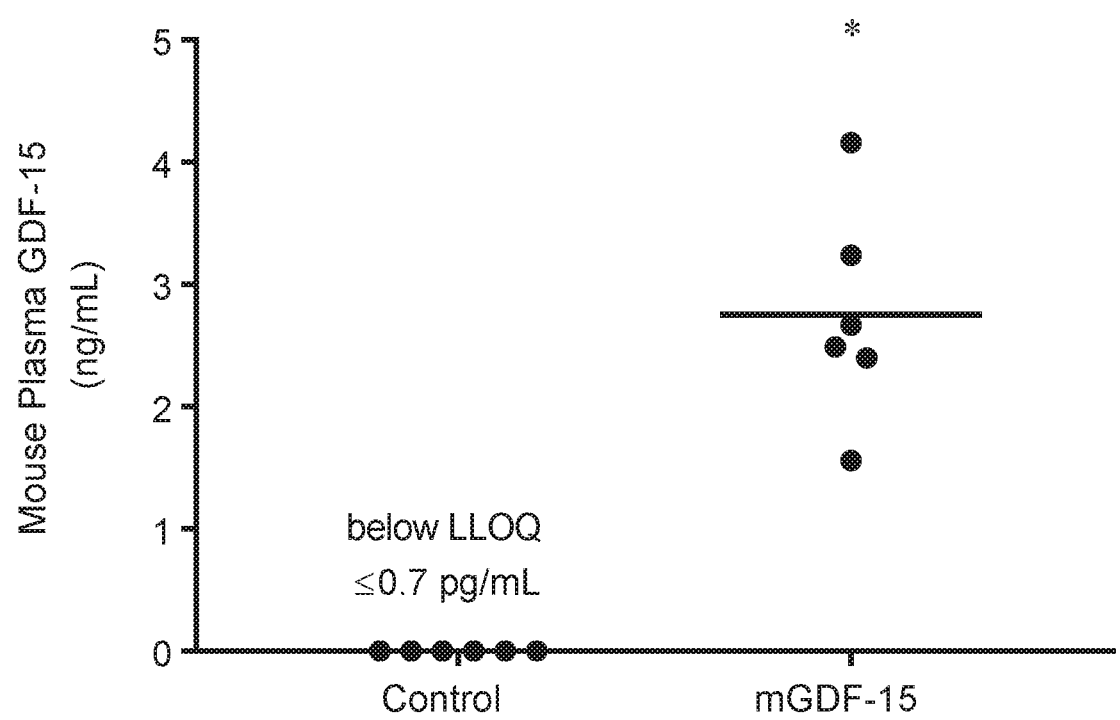
FIG. 7 depicts a graph showing the murine plasma GDF15 concentration following AAV-murine GDF15 injection in healthy male C57Bl6N mice. Plasma GDF15 was measured at 9 days following AAV injection (corresponds to day 9 on FIG. 5) via ELISA (R&D Systems MGD150). Horizontal lines represent means. n=6 per group. Mean plasma GDF15 levels were compared between treatments with a t-test using the Satterthwaite adjustment for unequal variances. * is $p<0.001$ versus Control.
Figure 8:
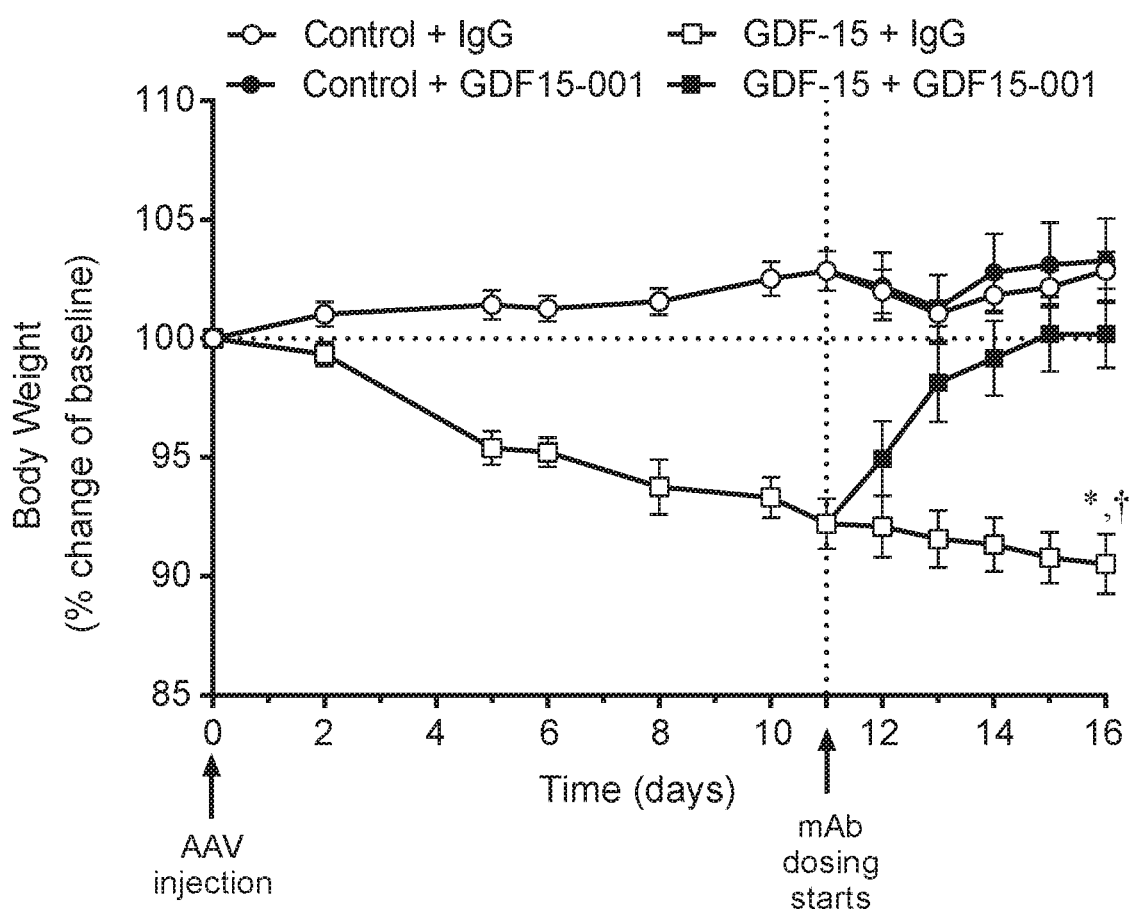
FIG. 8 shows a graph depicting the ability of GDF15_001 to reverse GDF15-induced weight loss in healthy mice. Arrows point to the timings of the AAV-murine GDF15 injection (day 0) and the first mAb dose (day 11). Healthy male C57Bl6N mice were treated with GDF15_001 (30 mg/kg, SC, Q3D) or IgG control. Values are means±SEM.

The ability of GDF15_001 to inhibit murine GDF15 activity was also assessed in healthy C57Bl6N mice treated with AAV-murine GDF15. Eleven days after AAV-murine GDF15 administration, circulating murine GDF15 levels increased to approximately 3 ng/mL (FIG. 7) and body weight decreased by approximately 10% (FIG. 8). Administration of GDF15_001 rapidly reversed weight loss (FIG. 8) and increased food intake (FIG. 9) in AAV-human GDF15-treated mice versus IgG control. GDF15_001 had no effect in AAV control vector treated mice.

These data demonstrate that GDF15_001 reverses weight loss, due to both lean and fat mass loss, and increases food intake in healthy mice even in the presence of increased levels of GDF15.

Example 12: Inhibition of Human GDF15 in Fibrosarcoma Tumor (HT-1080) Bearing Mice To determine if GDF15_001 could reverse cachexia and increase lifespan in tumor bearing mice, severe immuno-compromised (SCID) mice were implanted subcutaneously with HT-1080 human fibrosarcoma cells. Two weeks after tumor implantation, body weight decreased by approximately 10% (FIG. 10). Administration of GDF15_001 rapidly reversed body weight mass loss (FIG. 10), fat mass loss (FIG. 11), and lean mass loss (FIG. 12) versus IgG control. In addition to the body composition improvement, GDF15_001 increased survival (FIG. 13) compared to IgG control.

To confirm the metabolic benefit of GDF15_001 in HT-1080 tumor bearing mice under thermoneutral conditions, where cold-stress elevation of the basal metabolic rate is eliminated, the study was repeated when mice were housed at 86° F. Circulating human GDF15 was elevated to ~5 ng/mL (FIG. 14). Administration of GDF15_001 maintained rapid reversal of weight loss (FIG. 15) versus IgG control. GDF15_001 had no effect on any of these parameters in otherwise identical non-tumor bearing mice.

These data demonstrate that GDF15_001 increases survival and reverses cachexia in tumor bearing mice. Thus, these results further indicate that GDF15_001 is a potential novel human therapeutic.

Example 13: Inhibition of Human GDF15 in Pancreatic Tumor Bearing Mice

To further evaluate whether GDF15_001 could reverse cachexia and increase lifespan in tumor bearing mice, SCID mice were implanted subcutaneously with PA-0165, derived from pancreatic tumor liver metastasis, tumor tissue fragments. Circulating human GDF15 was elevated to ~2 ng/mL (FIG. 16). Four weeks after tumor implantation, body weight decreased by approximately 10% (FIG. 17). Administration of GDF15_001 completely prevented weight loss (FIG. 17) versus IgG control. In addition to the body weight improvement, GDF15_001 increased survival (FIG. 18) compared to IgG control.

These data also demonstrate that GDF15_001 increases survival and reverses cachexia in tumor bearing mice. Thus, these results further indicate that GDF15_001 is a potential novel human therapeutic.

Example 14: Inhibition of Human GDF15 in Tumor Bearing Mice Treated with Anti-Cancer Agents To determine if GDF15_001 could reverse cachexia and increase survival in tumor bearing mice treated with anti-cancer agents, BALB/c mice were implanted subcutaneously with RENCA (murine renal adenocarcinoma) cells. Circulating murine GDF15 was elevated to ~8 ng/mL (FIG. 19). When tumor size reached 100 mg, treatment with the anti-cancer agent sorafenib was started followed by the addition of GDF15_001 or IgG control when 10% weight loss was achieved (FIG. 20). Administration of GDF15_001 to the sorafenib treated mice completely reversed weight loss (FIG. 20). Along with the body weight improvement, the combination of sorafenib+GDF15_001 increased survival compared to sorafenib+IgG control (FIG. 21).

The ability of GDF15_001 to improve body weight was also examined in tumor bearing mice treated with the anti-cancer agent cisplatin. SCID mice were implanted subcutaneously with NSX-26115 (derived from human non-small cell lung carcinoma adenocarcinoma) tumor tissue fragments. Circulating human GDF15 was elevated to ~4.5 ng/mL (FIG. 22). When tumor size reached 100 mg, 10% weight loss was achieved and treatment with the anti-cancer agent cisplatin was started along with GDF15_001 or IgG control (FIG. 23). GDF15_001 or IgG control were also given without cisplatin. Administration of GDF15_001 reversed weight loss when given with or without cisplatin versus IgG control (FIG. 23). Along with the body weight improvement, the combination of cisplatin+GDF15_001 increased survival (FIG. 24) compared to cisplatin+IgG control.

These data also demonstrate that GDF15_001 increases survival and reverses cachexia in tumor bearing mice treated with anti-cancer agents. Thus, these results further indicate that GDF15_001 is a novel potential human therapeutic.

Example 15: Dosing of Anti-GDF15 Antibodies

There are challenges associated with identifying the efficacious doses and dosing regimens for anti-GDF15 antibodies for the treatment of cachexia. The overall efficacious dose depends on the, initial circulating GDF15 concentration in a patient, which is known to be variable. In addition, the free GDF15 levels in cachexia patients are reduced at different rates in response to therapy. Thus, the efficacious dose may be defined for a given dosing interval as the amount given to a 70 kg patient that reduces the free GDF15 level to less than 0.5 ng/mL throughout the dosing interval at steady state (i.e., after a number of doses such that the maximum concentration following a dose is substantially the same as the maximum concentration following the previous dose). This free GDF15 level is selected based on data reported for healthy subjects (Wollert et al, 2017, J Appl Lab Med 1(5):510-521). Thus, the efficacious dosages disclosed herein are described as a function of the starting free GDF15 level in an affected subject and the reduction of that level to less than 0.5 ng/mL. The free GDF level of in a sample can be measured, for example, using an electrochemiluminescence immunoassay, such as the ELECSYS GDF15 assay (Roche Diagnostics). The ELECSYS GDF15 assay, uses biotin-streptavidin technology and is based on the sandwich immunoassay principle (see Wollert et al, 2017). Other assays that can measure the amount of free GDF15 in a sample, that are known in the art, can also be used to determine the free GDF15 level in a patient.

In order to overcome the challenges to predict efficacious doses and dose regimens for the antibodies disclosed herein, a two-compartment pharmacokinetic model was developed. Subcutaneous dosing of an anti-GDF15 antibody was simulated by dosing a specified amount into a depot, which is then absorbed into the central compartment with specified rate $k_a$. The antibody distributes into a peripheral compartment and is then cleared from the central compartment. As used herein, the term "depot" refers to the site at which a drug is deposited (e.g., the subcutaneous space), the term "central compartment" refers to the vascular space and highly perfused organs (e.g., liver, kidney and lungs), and the term "peripheral compartment" refers to less perfused tissue (e.g. fat and muscle).

Parameters for GDF15_001 were determined by scaling from parameters in a pharmacokinetic study of GDF15_001 in human FcRn-expressing mouse. Briefly, 6 mice were dosed with 1 mg/kg of GDF15_001 intravenously and were monitored for 1000 hours; the resulting antibody pharmacokinetics were fit to the two-compartmental pharmacokinetic model. Parameters for other antibodies disclosed herein could be determined in a similar fashion. GDF15_001 is produced in the central compartment, distributes to the peripheral compartment, and is cleared from both spaces. The volumes and distribution rate were assumed to be the same as determined for GDF15_001 in the pharmacokinetic study described above. The turnover was selected to give a 16.6-hour half-life for GDF15_001, based on an experiment quantifying stable isotope labeled amino acid incorporation into circulating GDF15 in two healthy volunteers (experimental methodology essentially as provided in Lassman et al., 2014, Clin Chem 60(9):1217-1224). The GDF15 synthesis rate was selected to give a specified circulating level of GDF15. This circulating level might represent the highest level reported for a given disease (to treat all patients with a corresponding condition), a lower threshold but still above the values for a specified fraction of subjects (to control maximum dose while allowing treatment of most patients), or the specific level determined for a specific subject to permit a more precise, individualized dose. For the ranges of GDF15 levels associated with human disease, see, for example, Mutlu et al, 2015, Inflammation 38(5):1805-1813; Montero et al, 2016, PLoS One 11(2):e0148709; Kempf and Wollert, 2009, Heart Fail Clin 5(4):537-547; and Lerner et al, 2016, Oncol Lett 12(5): 4219-4223.

In both the central and peripheral compartments, GDF15 can reversibly bind to the anti-GDF15 antibody, based on the association and dissociation rate constants for the antibody. For GDF15_001, these parameters were determined to be $1.59 \times 10^6$ M$^{-1}$ s$^{-1}$ ($k_a$) and $3.42 \times 10^{-5}$ s$^{-1}$ ($k_d$), respectively (equating to an equilibrium dissociation constant of 21.3 pM), based on Biacore measurements (see Table 8 above). Similar assays can be performed for the other antibodies disclosed herein, or the parameters can be used as input parameters to explore the effect of changing affinity on dose. Without wishing to be bound by any particular theory, the antibody/GDF15 complex distributes between the two compartments and is cleared from the central compartment using the same pharmacokinetic parameters as determined for the antibody itself. The parameters for the two-compartment dosing model are shown in Table 14.

TABLE 14

GDF15_001 two compartment dosing model parameters

| Parameter | Value | Units | Source |
|---|---|---|---|
| V1 | 49 | mL/kg | Scaled from pharmacokinetic parameters determined in hFcRn expressing mice using present best practice methodology |
| V2 | 46 | mL/kg | |
| Q | 0.42 | mL/hr/kg | |
| CL | 0.24 | mL/hr/kg | |
| Body weight | 70 | kg | Typical human |
| $t_{1/2, GDF15}$ | 16.6 | hr | Determined from stable isotope incorporation in human GDF15 in healthy subjects |
| $k_{deg}$ | 0.0418 | | Turnover, $\ln(2)/t_{1, 2, GDF15}$ |
| $k_{on}$ | $1.59 \times 10^6$ | M$^{-1}$ s$^{-1}$ | Measured by SPR |
| $k_{off}$ | $3.42 \times 10^{-5}$ | s$^{-1}$ | Measured by SPR |
| $K_D$ | 21.3 | pM | $k_{off}/k_{on}$ |
| [GDF15]$_{baseline}$ | 0.5 | ng/mL | ELECSYS GDF15 assay insert (Roche Diagnostics) |
| Dose | Varies | mg | Input specification OR determined to give target level of free GDF15 reduction |
| $k_a$ | 0.0108 | hr$^{-1}$ | Typical |
| MW$_{GDF15}$ | 25 | kDa | Derived from gene entry at Uniprot http://www.uniprot.org/uniprot/Q99988 |
| Antibody MW | 150 | kDa | Typical |
| Bioavailability | 0.5 | dimensionless | Assumed |

The predicted therapeutically effective subcutaneous doses for GDF15_001 as a function of the starting free GDF15 level in a subject are shown in Tables 15, 16, and 17 and FIGS. 25, 26, and 27. The predicted therapeutically effective doses for weekly, bi-weekly and approximately monthly dosing are shown.

The dosing data provided herein suggests that GDF15_001 can be administered in such amounts and dosing intervals that it can achieve a potentially therapeutic level turnoff reduction of the level of free GDF15. These results demonstrate that dosing of GDF15_001 can be achieved and maintained at a dosing regimen that is both feasible and will assure patient compliance.

TABLE 15

Potential weekly dosing for subcutaneous administration of GDF15_001 for decreasing GDF15 level

| Starting Free GDF15 (ng/mL) | Weekly Subcutaneous Dose (mg) |
|---|---|
| 5 | 2 |
| 10 | 5 |
| 15 | 7 |
| 20 | 10 |
| 25 | 12 |
| 30 | 15 |
| 50 | 25 |
| 75 | 40 |
| 100 | 50 |

TABLE 16

Potential dosing for bi-weekly subcutaneous administration of GDF15_001 for decreasing GDF15 level

| Starting Free GDF15 (ng/mL) | Bi-Weekly Subcutaneous Dose (mg) |
|---|---|
| 5 | 5 |
| 10 | 12 |
| 15 | 20 |
| 20 | 25 |
| 25 | 30 |
| 30 | 40 |

TABLE 16-continued

Potential dosing for bi-weekly subcutaneous administration of GDF15_001 for decreasing GDF15 level

| Starting Free GDF15 (ng/mL) | Bi-Weekly Subcutaneous Dose (mg) |
|---|---|
| 50 | 60 |
| 75 | 90 |
| 100 | 125 |

TABLE 17

Potential dosing for approximately monthly subcutaneous administration of GDF15_001 for decreasing GDF15 level

| Starting Free GDF15 (ng/mL) | Every Four Weeks Subcutaneous Dose (mg) |
|---|---|
| 5 | 15 |
| 10 | 40 |
| 15 | 60 |
| 20 | 75 |
| 25 | 100 |
| 30 | 115 |
| 50 | 200 |
| 75 | 300 |
| 100 | 385 |

Example 16: Combination Treatment with Anti-PD-1 (F2) Antibody and Anti-GDF15 (GDF15-297) in Subcutaneous Model of RCC The data disclosed herein demonstrates the synergistic therapeutic effect of anti GDF15 antibody and anti-PD1 antibody combination therapy in murine RENCA metastatic renal cell carcinoma (RCC) model.

The tumor-bearing animals were generated as follows: Six (6)- to 8-week old female BALB/c mice were purchased from the Jackson Laboratories. All animals were housed in a pathogen free vivarium facility at CID and experiments were conducted according to the protocols in accordance with the Institutional Animal Care and Use Committee (IACUC) guidelines. The RENCA cell line was purchased from American Type Culture Collection (ATCC). Cells were cultured in Dulbecco's Modified Eagle's Medium (DMEM) supplemented with 10% fetal bovine serum (FBS), 2 mM L-glutamine at 37° C. in 5% carbon dioxide ($CO_2$), and IMPACT-tested for pathogens at Research Animal Diagnostic Laboratory (RADIL) (Columbia, Mo.). Pathogen-free cells growing in an exponential growth phase were harvested and used for tumor inoculation. BALB/c mice were inoculated subcutaneously at the right flank with $0.2 \times 10^6$ RENCA in 0.1 mL of serum free DMEM.

Tumor volume analysis was performed as follows: when tumors reached target size, mice were randomized into treatment groups. Treatment was started on the same day as randomization, i.e., day 0. Tumor size was measured twice weekly in 2 dimensions using a caliper, and the volume was expressed in cubic millimeters using the formula: $V=0.5 \, L \times W^2$ where L is the longest diameter of the tumor and W is the diameter perpendicular to L. Body weight was recorded twice weekly.

The therapeutic antibodies used in this study were: mouse anti-mouse PD1 F2 (mouse immunoglobulin G1 [mIgG1]), and mouse anti-mouse GDF15_0297 comprising a mouse IgG1 effector function null D265A, i.e., aspartic (Asp, D) to alanine (Ala, A) at amino acid residue number 265), mutation in the Fc. Antibody GDF15_0297 is essentially a mouse surrogate antibody of GDF15_001 which binds similarly to that antibody. Likewise, F2 is a mouse surrogate antibody that binds similarly to sasanlimab (RN888). The anti-PD1 antibody and anti-GDF15 antibody were each diluted to a concentration of 2 mg/mL in phosphate buffered saline (PBS) (Life Technologies) and dosed at 10 mg/kg of per mouse intraperitoneally (ip) on "day of treatment 0" (d0). One-way or 2-way ANOVA was applied to compare the statistical differences among multiple groups relative to the isotype control (negative control mouse IgG1) or other treatment groups. Unpaired t test was applied to compare the statistical difference between two groups. P<0.05 was considered as significant difference.

The RENCA model was used to evaluate the therapeutic efficacy of anti-GDF15 in combination with anti-PD1 in rRCC model, the average starting tumor size 25 to 38 $mm^3$ (n=10 animals per group). The animals were monitored for two weeks following initiation of the treatment. The treatment, i.e., i.p. administration of anti-GDF15 and anti-PD1, was initiated 11 days after transplantation. Anti-GDF15 antibody and Anti-PD1 antibody combinatorial treatment significantly inhibited progression of RENCA rRCC subcutaneous tumor when compared to the control isotype treated group. Anti-GDF15 monotherapy and anti-PD1 monotherapy were not effective in inhibiting tumor progression in this setting (Table 18 and Table 19).

TABLE 18

Tumor Measurements (Mean ± SEM) of Subcutaneous RENCA Renal Carcinoma over Time

| Day of treatment | Mean Tumor Size ($mm^3$) | SEM | N |
|---|---|---|---|
| Group 1. Isotype control | | | |
| 0 | 24.8179 | 18.48923 | 10 |
| 3 | 41.10472 | 16.01365 | 10 |
| 7 | 118.3017 | 38.05085 | 10 |
| 11 | 316.4947 | 87.86244 | 10 |
| 14 | 458.5579 | 180.3841 | 10 |

| Days Post-Tumor Inoculation | Mean Tumor Size ($mm^3$) | SEM | N |
|---|---|---|---|
| Group 2. Anti-GDF15 antibody (10 mg/kg) | | | |
| 0 | 38.6903 | 23.46297 | 10 |
| 3 | 74.46177 | 55.75148 | 10 |
| 7 | 118.0962 | 76.10373 | 10 |
| 11 | 242.452 | 131.6799 | 10 |
| 14 | 421.239 | 250.0879 | 10 |
| Group 3. Anti-PD1 antibody (10 mg/kg) | | | |
| 0 | 30.47708 | 19.57651 | 10 |
| 3 | 46.06364 | 33.32501 | 10 |
| 7 | 81.07916 | 48.32548 | 10 |
| 11 | 188.6607 | 104.1654 | 10 |
| 14 | 279.6987 | 159.2461 | 10 |
| Group 4. Anti-PD1 and Anti-GDF15 antibody (10 mg/kg each) | | | |
| 0 | 31.10019 | 20.06108 | 10 |
| 3 | 58.65684 | 27.55265 | 10 |
| 7 | 100.9666 | 49.4239 | 10 |
| 11 | 179.1596 | 73.56688 | 10 |
| 14 | 367.1608 | 165.8177 | 10 |

Tumor volume is expressed in $mm^3$.
N = number of animals within each group; SEM = Standard error of the mean.

TABLE 19

Statistical comparison between tumor measurements of subcutaneous RENCA Renal Carcinoma over time compared to Isotype Control

| Day | Anti-GDF15 (10 mg/kg) | Anti-PD1 (10 mg/kg) | Anti-GDF15 (10 mg/kg) + Anti-PD1 (10 mg/kg) |
|---|---|---|---|
| 0 | 0.9995 | >0.9999 | >0.9999 |
| 3 | 0.9721 | 0.9986 | >0.9999 |
| 7 | >0.9999 | 0.9987 | 0.9554 |
| 11 | 0.5250 | 0.0205 | 0.0394 |
| 14 | 0.9549 | 0.2835 | 0.0007 |

The statistical analysis results shown in Table 19 demonstrate that treatment with anti-GDF15 antibody in combination with anti-PD1 has a synergistic effect in early stages of tumor progression in RCC cancer model.

Example 17: Treatment of Pancreatic Cancer with Combination of Anti-PD1 Antibody and Anti-GDF15 Antibody This example illustrates the synergistic therapeutic effect of anti-GDF15 antibody and anti-PD1 antibody combination therapy in a murine metastatic pancreatic adenocarcinoma model, i.e., Pan02 model. To facilitate identification of tumor growth in the orthotopic model, Pan02 (NHI/NCI) cells were infected with firefly luciferase construct generating Pan02-luciferase cells.

Six 8-week old female B6(Cg)-Tyrc-2J/J (B6 albino) mice were purchased from the Jackson Laboratories. All animals were housed in a pathogen free vivarium facility at CID and experiments were conducted according to the protocols in accordance with the Institutional Animal Care and Use Committee (IACUC) guidelines.

The Pan02 cell line was obtained from NHI/NCI. Cells were cultured in Dulbecco's Modified Eagle's Medium (DMEM) supplemented with 10% fetal bovine serum (FBS), 2 mM L glutamine at 37° C. in 5% carbon dioxide ($CO^2$), and IMPACT-tested for pathogens at Research Animal Diagnostic Laboratory (RADIL) (Columbia, Mo.). Pathogen-free cells growing in an exponential growth phase were harvested and used for tumor transplantation. Albino B6 mice were injected in the pancreas with 20 µL of tumor cells: matrigel mixture containing $0.2 \times 10^6$ mL Pan02-luciferase serum free DMEM and matrigel (Corning, ref 356237). Four days after the transplantation, the tumor burden was assessed by the level of luminescence. The animals were stratified into the groups and the trial was initiated. To detect luciferase emission animals were injected with 0.1 mL of 30 mg/mL D-luciferin monosodium salt in saline (Pierce, #88292). The levels of luminescence were detected on IVIS Spectrum CT (Caliper Life Science) following 1-15 sec exposure at medium binning, 1 F/stop. The images were analyzed by LivingImage 4.5.1 Software. The tumor burden was calculated as photon/second in ROI (region of interest) after subtracting background values. In one example the average emission at the time of enrollment was $4.8 \times 10^8$ photon/second. In another example the average emission at the time of enrollment was $1.8 \times 10^8$ photon/second.

Mouse anti-mouse PD1 F2 antibody (mouse immunoglobulin G1 [mIgG1]) and mouse anti-mouse GDF15_0297 antibody were as described in Example 16. Anti-PD1 antibody and anti-GDF15 antibody were each diluted to a concentration of 2 mg/mL in phosphate buffered saline (PBS) (Life Technologies) and dosed at 10 mg/kg of per mouse intraperitoneally (ip). In another example, anti-PD1 antibody was diluted to a concentration of 1 mg/mL and dosed at 5 mg/kg of per mouse. In each case, the PD-1 antibody and the GDF15 antibody were administered on the same day (day of treatment 0).

Tumor progression was monitored weekly based on the level of luminescent in the treated animals. The levels of luminescent were determined as described above. Body weight was recorded weekly.

At day 35 post transplantation, changes in tumor burden between in animals from isotype antibody, anti-GDF15 antibody, anti-PD1 antibody and anti-GDF15 antibody+anti-PD1 combination were determined following the formula: changes in tumor burden=(photon flux at d35−photon flux at d4)/photon flux at day 4. Anti-GDF15 antibody+anti-PD1 antibody treatment significantly reduced tumor burden of animals transplanted with Pan02 tumors resulting in 8 out of 12 animals showing signs of tumor regression, compared to anti-PD1, anti-GDF15 and isotype groups (4/12; 1/12 and 0/12, respectively). Results are summarized below in Table 20. In Table 20, the individual results from each of twelve animals per groups are set forth.

TABLE 20

Changes in tumor burden in Pan02 transplanted animals 35 days after the transplantation.

| Isotype (10 mg/kg) (n = 12) | Anti-GDF15 (10 mg/kg) (n = 12) | Anti-PD1 (10 mg/kg) (n = 12) | Anti-GDF15 (10 mg/kg) + anti-PD1 (10 mg/kg) (n = 12) |
|---|---|---|---|
| 388650.8 | 238089.09 | 51810.29 | 121462.31 |
| 202783.4 | 42471.88 | 5095.89 | 729.61 |
| 146446 | 40946.73 | 1997.97 | 509.41 |
| 20687.27 | 35690.5 | 1435.5 | 117.08 |
| 19259.32 | 17367.64 | 390.93 | −35.58 |
| 11767.25 | 12343.34 | 192.99 | −53.22 |
| 11056.08 | 4468.03 | 145.6 | −79.94 |
| 4223.002 | 1331.72 | 48.91 | −82.36 |
| 1969.562 | 127.73 | −5.73 | −98.16 |
| 1357.696 | 70.79 | −81.18 | −99.36 |
| 561.6385 | 38.24 | −94.2 | −99.63 |
| 477.8538 | −64.21 | −99.55 | −99.67 |

These changes in tumor burden corresponded to increased survival of anti-GDF15 antibody+anti-PD1 antibody treated animals with mean survival increasing to 90 days compared to survival for 66 days (anti-PD1), 52.5 days (anti-GDF15) and 45 days (Isotype control). When compared to control isotype group p value at the end of experiment (day 145), the p values were p<0.0001 (anti-GDF15+anti-PD1), p=0.0010 (anti-PD1) and not statistically significant (ns) (anti-GDF15). At day 79, there was a statistically significant difference between survival of animals treated with anti-GDF15+anti-PD1 in combination and anti-PD1 monotherapy reflected in p=0.05 established by Matel-Cox test, and p=0.042 by Gehan-Breslow-Wilcoxon test.

In another example, in the Pan02 pancreatic model with the average tumor burden estimated by luminescent emission at the time of enrollment $1.8 \times 10^8$ photon/second. (n=13 animals per group), the therapeutic efficacy of 10 mg/kg of anti-GDF15 antibody in combination with 5 mg/kg of anti-PD1 antibody was evaluated. The treatment was initiated four days after transplantation. At day 39, the anti-GDF15+anti-PD1-treated group tumor volume dropped below the limit of detection in 38% of animals. PD1-monotherapy resulted in tumor reduction in only 15% of the animals, while both isotype control and anti-GDF15-monotherapy exhibited no therapeutic benefit in this setting.

These results demonstrate that treatment with anti-GDF15 antibody in combination with anti-PD1 provides a synergistic anti-tumor effect greater than the additive effects of each treatment provided separately on progression in an orthotopic pancreatic cancer model.

Thus, these data demonstrate that combination therapy of anti-GDF15 and a PD-1 axis antagonist would be a novel useful synergistic therapy for treatment of cancer.

Example 18. Selection of Mouse Syngeneic Models for Testing Efficacy in Cancer Immunotherapy For selection of appropriate model to determine the therapeutic efficacy of anti-GDF15 therapy, the following mouse syngeneic cell lines were tested: MC38 (kindly provided by Dr. Antoni Ribas at University of California, Los Angeles, Calif.), Pan02 (NHI/NCI), 4T1 (ATCC), RENCA (ATCC), CT26 (ATCC), ID8 (University of Kansas and the University of Kansas Medical Center), LL2 (ATCC), Bl6F10 (ATCC) and GL261 (NHI/NCI). GDF15 levels in conditioned medium were analyzed by mouse GDF15 ELISA kit (R&D Systems, MGD 150). Cells were plated in triplicate $0.3 \times 10^6$ cells/well in 6 well cell culture dish (353224, Corning), and cultured for forty-eight hours.

Supernatants were collected, centrifuged for 5-10 min at 2.000 rpm, transferred into fresh tubes and stored at +4° C. The amount of live/dead cells was estimated by trypan blue exclusion methods by BioRad TC 20 cell counter. Volume and cell number for each sample was recorded. Results are presented in Table 21.

TABLE 21

| Cell line | pg/ml | SD | Replicate |
| --- | --- | --- | --- |
| 4T1 | 0 | 0.33 | 3 |
| B16-F10 | 12.8 | 0.71 | 3 |
| CT26 | 0 | 0.25 | 3 |
| GL261 | 14.72744 | 2.38 | 3 |
| ID8 | 6.375451 | 0.47 | 3 |
| LL2 | 4.20784 | 1.35 | 3 |
| MC38 | 55.65824 | 3.56 | 3 |
| PAN02 | 38.44435 | 16.32 | 3 |
| RENCA | 342.397 | 8.08 | 3 |

For selection of an appropriate in vivo model, blood from tumor-bearing animals was collected by retro-orbital method and transferred to microtainer blood collection tubes (365967, BD). Tumor volume was recorded and adjusted to 200 mm$^3$ when applicable. Serum from animals bearing Pan02 orthotopic tumors was collected from end stage animals (35-40 days after transplantation). Serum for tumor-free genetic-background-matched animals was collected as a control. Mouse GDF15 levels were determined by mouse GDF15 ELISA kit and presented in Table 22.

TABLE 22

| Strain/Model | pg/ml | SD | Replicate |
| --- | --- | --- | --- |
| BalbC | 31.10779804 | 6.632974 | 3 |
| C57Bl6 | 74.55406 | 2.443727 | 2 |
| FVB/N | 38.96494373 | 13.71892286 | 3 |
| RENCA | 3460.438 | 1398.909 | 3 |
| 4T1 | 32.45177948 | 8.056048 | 3 |
| Pan02 | 1880.244884 | 1095.055333 | 3 |
| MC-38 | 44.13618956 | 21.41318 | 3 |
| PyMT | 146.4433483 | 27.91198329 | 3 |
| B16_F10 | 136.8055 | 193.4721 | 3 |

The metastatic renal RCC mouse model (RENCA) and pancreatic cancer model (Pan02) were identified as the highest producers of GDF15 in vivo and were further used in in vivo studies to determine therapeutic potential of anti-GDF15 therapies in combination with immuno-oncology based therapies.

Example 19. Combination Treatment with Anti-CD40 Antibody and Anti-GDF15 Antibody This example illustrates the therapeutic activity of anti-GDF15 antibody and anti-CD40 antibody combination therapy in a murine RENCA metastatic RCC model.

Six (6)- to 8-week old female BalbC mice were purchased from the Jackson Laboratories. All animals were housed in a pathogen free vivarium facility at CID and experiments were conducted according to the protocols in accordance with the Institutional Animal Care and Use Committee (IACUC) guidelines.

The RENCA cell line was purchased from American Type Culture Collection (ATCC). Cells were cultured in Dulbecco's Modified Eagle's Medium (DMEM) supplemented with 10% fetal bovine serum (FBS), 2 mM L-glutamine at 37° C. in 5% carbon dioxide ($CO_2$), and IMPACT-tested for pathogens at Research Animal Diagnostic Laboratory (RADIL) (Columbia, Mo.). Pathogen-free cells growing in an exponential growth phase were harvested and used for tumor inoculation. BalbC mice were inoculated subcutaneously at the right flank with 0.2×10$^6$ RENCA in 0.1 mL of serum free DMEM.

Anti-mouse CD40 antibody FGK45 (mouse IgG1) and anti-mouse GDF15 antibody GDF_0297 (comprising a mouse effector function null IgG1 Fc comprising a substitution at amino acid residue number 265 from aspartic acid to alanine (D265A)) were diluted to concentrations of 2 mg/mL in phosphate buffered saline (PBS) (Life Technologies), and dosed at 10 mg/kg of per mouse intraperitoneally (ip). In another example, anti-CD40 were diluted to concentration of 1 mg/mL and dosed at 5 mg/kg of per mouse.

When tumors reached target size, mice were randomized into treatment groups. Treatment was started on the same day as randomization. Tumor size was measured twice weekly in two dimensions using a caliper, and the volume was expressed in cubic millimeters using the formula: $V=0.5 L \times W^2$ where L is the longest diameter of the tumor and W is the diameter perpendicular to L. Body weight was recorded twice weekly.

To analyze the outcome of combinatorial treatment on the status of tumor infiltrating and splenic leukocytes the following analysis was performed. Tumors were disseminated into single cell suspension using gentle MACS™ and Miltenyi Mouse Dissociation Kit (Miltenyi Biotec) according to manufacturer's protocol with modification. Ammonium-Chloride-Potassium (ACK) Lysing Buffer (Life Technologies) was used to remove red blood cells. Cells were washed twice with FACS staining buffer (PBS supplemented with 10% FBS) and finally re-suspended in FACS staining buffer. For splenic leukocyte, the excised spleens were perfused with 3 mL of Digestion Solution containing 0.2 mg/mL of Liberase TL (5401020001, Roche) and 20 u/mL DNase I Roche 4716728001, Roche). Spleens were incubated for 15 min at 37° C. with gentle rocking. At the end of incubation, enzymatic activity was quenched by adding 1 mL of FBS, spleens were sliced into small pieces and strained to a 50 mL conical tube, the cells were washed in PBS, centrifuge at 1500 fpm for 5 minutes and the resulting pellet was re-suspended in cold MACS buffer. ACK Lysing Buffer was used to remove red blood cells.

An aliquot of cells was pre-incubated with 0.5 pg/10$^6$ cells of mouse BD Fc Block (Biolegend, 101310) in 10% rat serum in PBS for 10 minutes before phenotyping mAbs were added to specifically stain immune cells. Cell surface antigens were labeled by incubating cells at 4° C. for 30 minutes. After removing unbound mAbs, cells were washed twice with FACS staining buffer, fixed in fixative buffer (PBS+1% paraformaldehyde), and stored at 4° C. in the dark until analyzed by flow cytometry. Intracellular staining was carried out using Foxp3/Transcription Factor Staining Buffer set (eBioscience) according to the manufacturer's protocol. Flow cytometry data were acquired using Fortessa™ SORP (BD Biosciences) and analyzed using FlowJo™ (TreeStar Inc.).

Antibodies used for cell surface or intracellular staining were purchased from BD Biosciences, eBioscience, Invitrogen, or Biolegend. They were rat anti-mouse CD45-PerCP-Cy5.5 (clone 30-F11, BD Biosciences), rat anti-mouse CD11b Texas Red (M1/70, BD Biosciences), rat anti-mouse CD25-BUV395 (PC61, BD Biosciences), rat anti-mouse Ly6G-FITC (1A8, BD Biosciences), rat anti-mouse CD90.2-BV786 (53-2.1, BD Biosciences), rat anti-mouse CD8-BV650 (53-6.7, BD Biosciences), rat anti-mouse Ly6C-BV421 (AL-21, BD Biosciences), rat anti-mouse F4/80-PECy7 (BM8, Invitrogen™), rat anti-mouse CD86-BV605 (GL1, BD Biosciences), Armenian-hamster anti-mouse CD49a-APC (HMA1, BioLegend) rat anti-mouse MHCII (IA-IE)-Alexa Fluor 700 (M5/114.15.2, BioLegend), rat anti-mouse CD4-V450 (RM4-5, BD Biosciences), rat anti-mouse Foxp3-PE (FJK-16s, eBioscience). To avoid staining artefacts, the samples were kept in Brilliant Stain Buffer (BD Biosciences). Live cells were separated from dead cells using LIVE/DEAD Fixable eFluor™ 780 Dead Cell Stain Kit (Invitrogen).

Results were expressed as mean±SEM. Statistical analyses were performed using GraphPad Prism 6.0. One-way or 2-way ANOVA was applied to compare the statistical differences among multiple groups relative to the isotype control or other treatment groups. Unpaired t test was applied to compare the statistical difference between two groups. $P<0.05$ was considered as significant difference.

The RENCA model was used to evaluate the therapeutic efficacy of anti-GDF15 in combination with anti-CD40 in rRCC model, the average starting tumor size 25 to 38 mm$^3$ (n=10 animals per group). The animals were sacrificed when tumor volume reached 2000 mm$^3$ or 20% bodyweight loss. The median survival of animal with the tumors for isotype, anti-GDF15 antibody alone, and anti-CD40 antibody alone and anti-GDF15 antibody+anti-CD40 antibody combination was 26, 25.5, 32.5 and 34 days, respectively. The anti-CD40 antibody+anti-GDF15 antibody group also resulted in 30% complete responders when compared to 0% in isotype, anti-GDF15 antibody alone and anti-CD40 antibody alone groups.

In a separate study the therapeutic efficacy of anti-GDF15 antibody in combination with two different dosages of anti-CD40 antibody (10 mg/kg and 5 mg/kg) was evaluated in the RENCA recurrent renal cell carcinoma (rRCC) model, with the average starting tumor size of 47 to 54 mm$^3$ (n=10 animals per group). The results are summarized in Table 23 and Table 24.

TABLE 23

Tumor Measurements (Mean ± SEM) of Subcutaneous Renca Renal Carcinoma over Time

Group 1. Isotype control

| Days Post-Tumor Inoculation | Mean Tumor Size (mm$^3$) | SEM | N |
|---|---|---|---|
| 10 | 53.90874 | 14.3443 | 10 |
| 13 | 130.8436 | 28.27738 | 10 |
| 17 | 353.1065 | 85.68442 | 10 |
| 20 | 552.0961 | 137.3508 | 10 |
| 25 | 858.6344 | 162.7132 | 10 |
| 27 | 1195.16 | 292.976 | 10 |

TABLE 23-continued

Tumor Measurements (Mean ± SEM) of Subcutaneous Renca Renal Carcinoma over Time

Group 2. Anti-GDF15 antibody (10 mg/kg)

| | | | |
|---|---|---|---|
| 10 | 53.24435 | 13.3418 | 10 |
| 13 | 118.301 | 31.60418 | 10 |
| 17 | 347.7124 | 117.5708 | 10 |
| 20 | 602.2936 | 247.2447 | 10 |
| 25 | 1207.494 | 545.9653 | 9 |
| 27 | 1455.983 | 309.5726 | 8 |

Group 3. Anti-CD40 antibody (10 mg/kg)

| | | | |
|---|---|---|---|
| 10 | 53.44178 | 13.94953 | 10 |
| 13 | 110.619 | 34.34105 | 10 |
| 17 | 224.5232 | 70.38568 | 10 |
| 20 | 338.2354 | 74.07587 | 10 |
| 25 | 532.1088 | 155.9947 | 10 |
| 27 | 715.2596 | 193.4371 | 10 |

Group 4. Anti-CD40 antibody (5 mg/kg)

| | | | |
|---|---|---|---|
| 10 | 53.09616 | 13.09756 | 10 |
| 13 | 96.98625 | 33.47341 | 10 |
| 17 | 254.366 | 86.80886 | 10 |
| 20 | 376.4508 | 110.6125 | 10 |
| 25 | 648.832 | 170.2004 | 10 |
| 27 | 795.9384 | 357.4954 | 10 |

Group 5. Anti-GDF15 antibody + Anti-CD40 antibody (10 mg/kg)

| Days Post-Tumor Inoculation | | | |
|---|---|---|---|
| 10 | 46.99903 | 11.86423 | 10 |
| 13 | 106.4694 | 43.02584 | 10 |
| 17 | 186.6874 | 88.81804 | 10 |
| 20 | 233.0179 | 132.9253 | 10 |
| 25 | 349.6296 | 234.2788 | 10 |
| 27 | 458.9107 | 371.8595 | 10 |

Group 5. Anti-GDF15 antibody + Anti-CD40 antibody (5 mg/kg)

| Days Post-Tumor Inoculation | Mean Tumor Size (mm$^3$) | SEM | N |
|---|---|---|---|
| 10 | 53.78749 | 14.79445 | 10 |
| 13 | 97.36322 | 37.22007 | 10 |
| 17 | 232.1165 | 95.47443 | 10 |
| 20 | 315.4536 | 157.8604 | 10 |
| 25 | 565.9923 | 322.4584 | 9 |
| 27 | 584.3638 | 417.7759 | 9 |

Tumor volume is expressed in mm$^3$.
N = number of animals within each group; SEM = Standard error of the mean.

TABLE 24

Statistical comparison between tumor measurements of subcutaneous RENCA Renal Carcinoma over time compared to Isotype Control

| Day | Anti-CD40 antibody (10 mg) | Anti-CD40 antibody (5 mg) | Anti-GDF15 antibody | Anti-GDF15 antibody + anti-CD40 antibody (10 mg) | Anti-GDF15 antibody + anti-CD40 antibody (10 mg) |
|---|---|---|---|---|---|
| 10 | >0.9999 | >0.9999 | >0.9999 | >0.9999 | >0.9999 |
| 13 | 0.9997 | 0.9983 | 0.9999 | 0.9997 | 0.9983 |
| 17 | 0.6932 | 0.8611 | >0.9999 | 0.4581 | 0.7398 |
| 20 | 0.2271 | 0.4057 | 0.9911 | 0.0256 | 0.152 |
| 25 | 0.0213 | 0.243 | 0.0152 | <0.0001 | 0.0571 |
| 27 | 0.0002 | 0.0028 | 0.1278 | <0.0001 | <0.0001 |

The median survival of animal with the tumors for isotype, anti-GDF15 antibody alone, anti-CD40 antibody (5 mg/kg), anti-CD40 antibody (10 mg/kg), and anti-GDF15 antibody (10 mg/kg)+anti-CD40 antibody (5 mg/kg) combination and anti-GDF15 antibody (10 mg/kg)+anti-CD40 antibody (10 mg/kg) combination was 29.5, 29.5, 36, 36, 38 and 44.5 days respectively.

To determine the contribution of tumor-infiltrating lymphocytes (TILs) in anti-GDF15-mediated anti-tumor response, TILs were isolated from RENCA tumors twenty-four hours after the last treatment and analyzed for markers associated with anti-tumor immune response. Results are summarized in FIG. 29 (p value determine by unpaired t test; p=0.0026).

The combination treatment [anti-GDF15 antibody (10 mg/kg)+anti-CD40 antibody (10 mg/kg)] increased the activation status (MHCII MFI) of macrophages gated as CD11b+; F4/80+; Ly6C− cells in tumors on average by 187% in comparison to the isotype treated group (FIG. 29). In contrast, anti-CD40 monotherapy increased MHCII MFI by 67% (FIG. 29). Anti-GDF15 monotherapy did not increase activation status of macrophages (FIG. 29).

The ratio of CD8+ T cells/regulatory T cell (Treg) in the isotype and anti-GDF15 groups was 2.4 and 2.1, respectively (FIG. 30, solid circles and solid triangles). The CD8+ T cells/Treg ratio increased to 17 in the anti-CD40 antibody treatment alone (FIG. 30, open circles). In contrast, combination treatment with anti-GDF15 antibody plus anti-CD40 antibody resulted in a CD8+ T cells/Treg ratio of 84 (FIG. 30, open triangles).

These results demonstrate that anti-CDF15-based therapy is effective in enhancing anti-tumor efficacy of anti-CD40-therapy.

In addition to enhancing anti-tumor efficacy of anti-CD40-therapy in RRC model, anti-GDF15-based therapy mitigated anti-CD40-induced toxicity manifested in body weight loss of treated animals. While anti-CD40 based therapy resulted in 4.43% body weight loss in treated animals, the anti-GDF15 antibody+anti-CD40 antibody combination group demonstrated 1.5% of body weight gain, compared to 1.2% body weight gain in isotype control treated group (n=20 animals in each group, anti-CD40 antibody vs anti-CD40 antibody+anti-GDF15 antibody, p=0.0006 by unpaired t test). The restoration of body weight in the anti-CD40 antibody+anti-GDF15 antibody group was accompanied by reduction of cytokine expression generally associated with cytokine-mediated toxicity in serum of treated animals.

Serum samples were collected from treated animals as described in Example 1. The cytokine levels were analyzed by V-PLEX® Proinflammatory Panel 1 (mouse) Kit from Meso Scale Discover® (Mescoscale® K15048D). Each sample was diluted 1 to 4 with Diluent 41 (Mescoscale® R50AH-1) and assayed in triplicate according to manufacturer's protocol. Results were analyzed by Meso Scale Discovery® Quickplex® SQ 120 machine and Discovery workbench software. Expression of the following cytokines was analyzed: IFNγ, IL10, IL12p70, IL1 beta, 1L2, 1L4, 1L5, 1L6, KC/GRO, TNFα. As shown in FIG. 31, expression levels of a number of pro-inflammatory cytokines (IFNγ (IFNg), TNFα (TNFα), 1L6, IL10, KC/GRO) were significantly reduced in anti-CD40-treated group following exposure to anti-GDF15 treatment (n=5, anti-CD40 vs anti-CD40+anti-GDF15, p=0.0044 by two-way ANOVA test).

These results demonstrate that treatment with anti-GDF15 antibody in combination with anti-CD40 has a synergistic anti-tumor effect accompanied by the increased levels of activation of CD11b+; F4/80+ cells and increased CD8+ T cell/regulatory T cell (Treg) ratio at the tumor site. Moreover, anti-GDF15 therapy mitigates clinical signs of anti-CD40-therapy toxicities associated with increased cytokine production.

Example 20. Treatment of Pancreatic Cancer with Anti-CD40 Antibody and Anti-GDF15 Antibody This example illustrates the therapeutic activity of anti-GDF15 antibody and anti-CD40 antibody combination therapy in a murine pancreatic adenocarcinoma model (Pan02). The tumor-bearing animals were generated as described in Example 19. The tumor burden was calculated as photon/second in ROI (region of interest) after subtracting background values. The average emission at the time of enrollment was $4.8*10^8$ photon/second.

For this study, the antibodies used were: mouse anti-mouse CD40 antibody FGK45 (mouse immunoglobulin G1 [mIgG1]) (10 mg/kg) and mouse anti-mouse GDF15_0297 (mouse IgG1 effector function null D265A mutation) (10 mg/kg).

Median survival of anti-GDF15 antibody+anti-CD40 antibody treated animals was 126.5 days, compared to 106 days in the anti-CD40 antibody alone treated group, 52.5 days in anti-GDF15 antibody alone treated group, and 45 days in the isotype control group.

These results demonstrate that treatment with anti-GDF15 antibody in combination with anti-CD40 has a synergistic anti-tumor effect on progression of pancreatic cancer.

Example 21. GDF15 Neutralizing Antibodies Reverse GDF15-Mediated Inhibition of Macrophage-Mediated Tumor Killing This example illustrates GDF15 function in modulating tumor killing activity of macrophage.

Peritoneal macrophages were isolated from C57Bl6 mice five days following ip injection with 1 mL 3% Brewer Thioglycollate medium (B2551, Sigma). Macrophages were plated at $0.35 \times 10^6$ cells/well in 24 well cell culture plate concentration in complete macrophage medium (RPMI 1640 supplemented with 10% heat-inactivated FBS, 2 mM L-glutamine, 100 u/ml penicillin, 0.1 mg/ml streptomycin, 10 pM sodium pyruvate, 100 pM nonessential amino acids, 25 mM HEPES [pH 7.4], 50 pM β-mercaptoethanol) alone or at the presence of tested cytokines and antibodies. The following cytokines and antibodies were used in the study: recombinant mouse GDF15 (E. coli purified, RD systems 8944-GD), anti-mouse GDF15_0297 antibody "297", and anti-GDF15_001. Following three hours of incubation with recombinant mouse GDF15 (10 nM) and antibodies (100 nM each), the cells were subjected to LPS (10 ng/ml, L2654, Sigma) and IFNγ (100 u/ml, 485M100/CF, R&D Systems) treatment to achieve activation of macrophages. The next day, Pan02 cells were labeled with CSFE (C34554, Invitrogen) according to manufacturer instructions and co-plated with activated macrophages at 1:4 ratio. Twenty-four hours later macrophages and tumor cells were collected following incubation with TryLE Express™, and analyzed by FACS as described in Example 17. Myeloid cells were identified by rat anti-mouse CD11b BUV395 (M1/70, BD Biosciences), tumor cells were identified as CSFE-positive/CD11b-negative population, live cells were separated from dead cells by DAPI (4',6-diamidino-2-phenylindole) (62247, Thermo Scientific).

As shown in FIG. 32, recombinant GDF15 inhibited macrophage-mediated tumor cell killing (closed triangles). This GDF15-mediated inhibition was reversed by treatment with anti-GDF15 antibodies (open circles and open triangles).

These results demonstrate that treatment with anti-GDF15 antibodies is efficacious in promoting anti-tumorigenic activity of immune cells.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety for all purposes. In the event that one or more of the incorporated literature and similar materials differs from or contradicts this application, including but not limited to defined terms, term usage, described techniques, or the like, this application controls.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An antibody, or antigen binding fragment thereof, that specifically binds to human growth differentiation factor 15 (GDF15), comprising at least one of the following:
   a) a light chain complementarity determining region 1 (LCDR-1) comprising the amino acid sequence of SEQ ID NO:95, a LCDR-2 comprising the amino acid sequence of SEQ ID NO:28, a LCDR-3 comprising the amino acid sequence of SEQ ID NO:9, a heavy chain complementarity determining region 1 (HCDR-1) comprising the amino acid sequence of SEQ ID NO:32, a HCDR-2 comprising the amino acid sequence of SEQ ID NO:165, and a HCDR-3 comprising the amino acid sequence of SEQ ID NO:52;
   b) a LCDR-1 comprising the amino acid sequence of SEQ ID NO:184, a LCDR-2 comprising the amino acid sequence of SEQ ID NO:185, a LCDR-3 comprising the amino acid sequence of SEQ ID NO:186, a HCDR-1 comprising the amino acid sequence of SEQ ID NO:179, a HCDR-2 comprising the amino acid sequence of SEQ ID NO:180, and a HCDR-3 comprising the amino acid sequence of SEQ ID NO:181;
   c) the HCDR-1, HCDR-2, and HCDR-3 amino acid sequences as set forth in the amino acid sequence of SEQ ID NO:166, and the LCDR-1, LCDR-2, and LCDR-3 amino acid sequences as set forth in the amino acid sequence of SEQ ID NO:163;
   d) the amino acid sequence encoded by the insert of the plasmid deposited at the ATCC and having ATCC Accession No. PTA-125038, and the amino acid sequence encoded by the insert of the plasmid deposited at the ATCC and having ATCC Accession No. PTA-125039;
   e) a VH comprising the amino acid sequence of SEQ ID NO:166 and a VL comprising the amino acid sequence of SEQ ID NO:163;
   f) a VH comprising the amino acid sequence of SEQ ID NO:189 and a VL comprising the amino acid sequence of SEQ ID NO:191;
   g) a HC comprising the amino acid sequence of SEQ ID NO:164, and a LC comprising the amino acid sequence of SEQ ID NO:162; or
   h) a HC comprising the amino acid sequence of SEQ ID NO:190, and a LC comprising the amino acid sequence of SEQ ID NO:192.

2. The antibody, or antigen binding fragment thereof, of claim 1(a)-(f), comprising a human Fc domain selected from the group consisting of an Fc domain of IgA1 IgA2, IgD, IgE, IgM, IgG1, IgG2, IgG3, or IgG4.

3. The antibody, or antigen binding fragment thereof, of claim 1, wherein the antibody, or antigen binding fragment thereof, binds human or cynomolgus monkey GDF15 with a KD about or less than a value selected from the group consisting of about 10 nM, 5 nM, 2 nM, 1 nM, 900 pM, 800 pM, 700 pM, 600 pM, 500 pM, 400 pM, 300 pM, 250 pM, 200 pM, 150 pM, 100 pM, 50 pM, 40 pM, 30 pM, 25 pM, 20 pM, 15 pM, and 10 pM.

4. An isolated nucleic acid encoding the antibody, or antigen-binding fragment thereof, of claim 1.

5. An isolated nucleic acid comprising:
   a) the nucleic acid sequence of SEQ ID NO:167, the nucleic acid sequence of SEQ ID NO:168, or both,
   b) the nucleic acid sequence of SEQ ID NO:169, the nucleic acid sequence of SEQ ID NO:170, or both;
   c) the nucleic acid sequence of SEQ ID NO:169, the nucleic acid sequence of SEQ ID NO:170, or both, and wherein the nucleic acid sequence of SEQ ID NO:170 comprises a G at nucleotide number 1344 and/or a T at nucleotide number 1347; or
   d) the nucleic acid sequence of the insert of the plasmid deposited with the ATCC and having the Accession Number PTA-125038, the nucleic acid sequence of the insert of the plasmid deposited with the ATCC and having the Accession Number PTA-125039, or both.

6. A vector comprising the nucleic acid of claim 4.

7. A host cell comprising the vector of claim 6.

8. The host cell of claim 7, wherein said host cell is a mammalian cell selected from the group consisting of a CHO cell, a COS cell, a HEK-293 cell, an NS0 cell, a PER.C6 cell, or an Sp2.0 cell.

9. A method of making an antibody, or antigen binding fragment thereof, comprising culturing the host cell of claim 8 under a condition wherein said antibody, or antigen binding fragment thereof, is expressed by said host cell.

10. A pharmaceutical composition comprising an antibody, or antigen binding fragment thereof, of claim 1, and a pharmaceutically acceptable carrier or excipient.

11. An antibody, or antigen binding fragment thereof, comprising a heavy chain comprising the amino acid sequence of SEQ ID NO:164, and a light chain comprising the amino acid sequence of SEQ ID NO:162.

* * * * *

UNITED STATES PATENT AND TRADEMARK OFFICE
CERTIFICATE OF CORRECTION

| | | |
|---|---|---|
| PATENT NO. | : 11,566,066 B2 | Page 1 of 1 |
| APPLICATION NO. | : 16/541817 | |
| DATED | : January 31, 2023 | |
| INVENTOR(S) | : Beaumont et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this
Seventh Day of January, 2025

Derrick Brent
*Acting Director of the United States Patent and Trademark Office*

SEQUENCE LISTING

```
<160> NUMBER OF SEQ ID NOS: 221

<210> SEQ ID NO 1
<211> LENGTH: 112
<212> TYPE: PRT
<213> ORGANISM: Artificial Sequence
<220> FEATURE:
<223> OTHER INFORMATION: Synthetic Construct

<400> SEQUENCE: 1

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 2
```

```
<211> LENGTH: 345
<212> TYPE: PRT
<213> ORGANISM: Artificial Sequence
<220> FEATURE:
<223> OTHER INFORMATION: Synthetic Construct

<400> SEQUENCE: 2

Gly Cys Lys Pro Cys Ile Cys Thr Val Pro Glu Val Ser Ser Val Phe
1               5                   10                  15

Ile Phe Pro Pro Lys Pro Lys Asp Val Leu Thr Ile Thr Leu Thr Pro
            20                  25                  30

Lys Val Thr Cys Val Val Val Asp Ile Ser Lys Asp Asp Pro Glu Val
        35                  40                  45

Gln Phe Ser Trp Phe Val Asp Asp Val Glu Val His Thr Ala Gln Thr
    50                  55                  60

Gln Pro Arg Glu Glu Gln Phe Asn Ser Thr Phe Arg Ser Val Ser Glu
65                  70                  75                  80

Leu Pro Ile Met His Gln Asp Trp Leu Asn Gly Lys Glu Phe Lys Cys
                85                  90                  95

Arg Val Asn Ser Ala Ala Phe Pro Ala Pro Ile Glu Lys Thr Ile Ser
            100                 105                 110

Lys Thr Lys Gly Arg Pro Lys Ala Pro Gln Val Tyr Thr Ile Pro Pro
        115                 120                 125

Pro Lys Glu Gln Met Ala Lys Asp Lys Val Ser Leu Thr Cys Met Ile
    130                 135                 140

Thr Asp Phe Phe Pro Glu Asp Ile Thr Val Glu Trp Gln Trp Asn Gly
145                 150                 155                 160

Gln Pro Ala Glu Asn Tyr Lys Asn Thr Gln Pro Ile Met Asp Thr Asp
                165                 170                 175

Gly Ser Tyr Phe Val Tyr Ser Lys Leu Asn Val Gln Lys Ser Asn Trp
            180                 185                 190

Glu Ala Gly Asn Thr Phe Thr Cys Ser Val Leu His Glu Gly Leu His
        195                 200                 205

Asn His His Thr Glu Lys Ser Leu Ser His Ser Pro Gly Lys Ile Glu
    210                 215                 220

Gly Arg Met Asp Gly Gly Gly Ser Ala Arg Asn Gly Asp His Cys
225                 230                 235                 240

Pro Leu Gly Pro Gly Arg Cys Cys Arg Leu His Thr Val Arg Ala Ser
                245                 250                 255

Leu Glu Asp Leu Gly Trp Ala Asp Trp Val Leu Ser Pro Arg Glu Val
            260                 265                 270

Gln Val Thr Met Cys Ile Gly Ala Cys Pro Ser Gln Phe Arg Ala Ala
        275                 280                 285

Asn Met His Ala Gln Ile Lys Thr Ser Leu His Arg Leu Lys Pro Asp
    290                 295                 300

Thr Val Pro Ala Pro Cys Cys Val Pro Ala Ser Tyr Asn Pro Met Val
305                 310                 315                 320

Leu Ile Gln Lys Thr Asp Thr Gly Val Ser Leu Gln Thr Tyr Asp Asp
                325                 330                 335

Leu Leu Ala Lys Asp Cys His Cys Ile
            340                 345

<210> SEQ ID NO 3
<211> LENGTH: 332
<212> TYPE: PRT
<213> ORGANISM: Artificial Sequence
```

<220> FEATURE:
<223> OTHER INFORMATION: Synthetic Construct

<400> SEQUENCE: 3

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Asn Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Asn Ser Thr Leu Thr
                165                 170                 175

Val Asp Lys Ser Arg Trp Gln Gln Gly Asn Val Phe Ser Cys Ser Val
            180                 185                 190

Leu His Glu Ala Leu His Ser His Tyr Thr Gln Lys Ser Leu Ser Leu
        195                 200                 205

Ser Pro Lys Gly Ser Glu Asn Leu Tyr Phe Gln Gly Ala Arg Asn Gly
    210                 215                 220

Asp His Cys Pro Leu Gly Pro Gly Arg Cys Cys Arg Leu His Thr Val
225                 230                 235                 240

Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
            260                 265                 270

Arg Ala Ala Asn Met His Ala Gln Ile Lys Thr Ser Leu His Arg Leu
        275                 280                 285

Lys Pro Asp Thr Val Pro Ala Pro Cys Cys Val Pro Ala Ser Tyr Asn
    290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330

<210> SEQ ID NO 4
<211> LENGTH: 345
<212> TYPE: PRT
<213> ORGANISM: Artificial Sequence
<220> FEATURE:
<223> OTHER INFORMATION: Synthetic Construct

<400> SEQUENCE: 4

Gly Cys Lys Pro Cys Ile Cys Thr Val Pro Glu Val Ser Ser Val Phe

```
            1               5                  10                 15
        Ile Phe Pro Pro Lys Pro Lys Asp Val Leu Thr Ile Thr Leu Thr Pro
                        20                 25                 30

Lys Val Thr Cys Val Val Asp Ile Ser Lys Asp Pro Glu Val
                        35                 40                 45

Gln Phe Ser Trp Phe Val Asp Val Glu Val His Thr Ala Gln Thr
                50                 55                 60

Gln Pro Arg Glu Glu Gln Phe Asn Ser Thr Phe Arg Ser Val Ser Glu
        65                 70                 75                 80

Leu Pro Ile Met His Gln Asp Trp Leu Asn Gly Lys Glu Phe Lys Cys
                        85                 90                 95

Arg Val Asn Ser Ala Ala Phe Pro Ala Pro Ile Glu Lys Thr Ile Ser
                        100                105                110

Lys Thr Lys Gly Arg Pro Lys Ala Pro Gln Val Tyr Thr Ile Pro Pro
                        115                120                125

Pro Lys Glu Gln Met Ala Lys Asp Lys Val Ser Leu Thr Cys Met Ile
                        130                135                140

Thr Asp Phe Phe Pro Glu Asp Ile Thr Val Glu Trp Gln Trp Asn Gly
        145                150                155                160

Gln Pro Ala Glu Asn Tyr Lys Asn Thr Gln Pro Ile Met Asp Thr Asp
                        165                170                175

Gly Ser Tyr Phe Val Tyr Ser Lys Leu Asn Val Gln Lys Ser Asn Trp
                        180                185                190

Glu Ala Gly Asn Thr Phe Thr Cys Ser Val Leu His Glu Gly Leu His
                        195                200                205

Asn His His Thr Glu Lys Ser Leu Ser His Ser Pro Gly Lys Ile Glu
        210                215                220

Gly Arg Met Asp Gly Gly Gly Ser Ala Arg Asn Gly Asp Arg Cys
        225                230                235                240

Pro Leu Gly Pro Gly Arg Cys Cys Arg Leu His Thr Val His Ala Ser
                        245                250                255

Leu Glu Asp Leu Gly Trp Ala Asp Trp Val Leu Ser Pro Arg Glu Val
                        260                265                270

Gln Val Thr Met Cys Ile Gly Ala Cys Pro Ser Gln Phe Arg Glu Ala
                        275                280                285

Asn Met His Ala Gln Ile Lys Met Asn Leu His Arg Leu Lys Pro Asp
                        290                295                300

Thr Val Pro Ala Pro Cys Cys Val Pro Ala Ser Tyr Asn Pro Met Val
        305                310                315                320

Leu Ile Gln Lys Thr Asp Thr Gly Val Ser Leu Gln Thr Tyr Asp Asp
                        325                330                335

Leu Leu Ala Lys Asp Cys His Cys Val
                        340                345

<210> SEQ ID NO 5
<211> LENGTH: 345
<212> TYPE: PRT
<213> ORGANISM: Artificial Sequence
<220> FEATURE:
<223> OTHER INFORMATION: Synthetic Construct

<400> SEQUENCE: 5

Gly Cys Lys Pro Cys Ile Cys Thr Val Pro Glu Val Ser Ser Val Phe
        1               5                  10                 15

Ile Phe Pro Pro Lys Pro Lys Asp Val Leu Thr Ile Thr Leu Thr Pro
```

```
            20                  25                  30
Lys Val Thr Cys Val Val Asp Ile Ser Lys Asp Pro Glu Val
        35                  40                  45
Gln Phe Ser Trp Phe Val Asp Asp Val Glu Val His Thr Ala Gln Thr
    50                  55                  60
Gln Pro Arg Glu Glu Gln Phe Asn Ser Thr Phe Arg Ser Val Ser Glu
65                  70                  75                  80
Leu Pro Ile Met His Gln Asp Trp Leu Asn Gly Lys Glu Phe Lys Cys
                85                  90                  95
Arg Val Asn Ser Ala Ala Phe Pro Ala Pro Ile Glu Lys Thr Ile Ser
            100                 105                 110
Lys Thr Lys Gly Arg Pro Lys Ala Pro Gln Val Tyr Thr Ile Pro Pro
        115                 120                 125
Pro Lys Glu Gln Met Ala Lys Asp Lys Val Ser Leu Thr Cys Met Ile
    130                 135                 140
Thr Asp Phe Phe Pro Glu Asp Ile Thr Val Glu Trp Gln Trp Asn Gly
145                 150                 155                 160
Gln Pro Ala Glu Asn Tyr Lys Asn Thr Gln Pro Ile Met Asp Thr Asp
                165                 170                 175
Gly Ser Tyr Phe Val Tyr Ser Lys Leu Asn Val Gln Lys Ser Asn Trp
            180                 185                 190
Glu Ala Gly Asn Thr Phe Thr Cys Ser Val Leu His Glu Gly Leu His
        195                 200                 205
Asn His His Thr Glu Lys Ser Leu Ser His Ser Pro Gly Lys Ile Glu
    210                 215                 220
Gly Arg Met Asp Gly Gly Gly Ser Ala Arg Asn Gly Asp His Cys
225                 230                 235                 240
Pro Leu Gly Pro Gly Arg Cys Cys Arg Leu His Thr Val Arg Ala Ser
                245                 250                 255
Leu Glu Asp Leu Gly Trp Ala Asp Trp Val Leu Ser Pro Arg Glu Val
            260                 265                 270
Gln Val Thr Met Cys Ile Gly Ala Cys Pro Ser Gln Phe Arg Ala Ala
        275                 280                 285
Asn Met His Ala Gln Ile Lys Thr Ser Leu His Arg Leu Lys Pro Asp
    290                 295                 300
Thr Val Pro Ala Pro Cys Cys Val Pro Ala Ser Tyr Asn Pro Met Val
305                 310                 315                 320
Leu Ile Gln Lys Thr Asp Thr Gly Val Ser Leu Gln Thr Tyr Asp Asp
                325                 330                 335
Leu Leu Ala Lys Asp Cys His Cys Ile
            340                 345

<210> SEQ ID NO 6
<211> LENGTH: 214
<212> TYPE: PRT
<213> ORGANISM: Artificial Sequence
<220> FEATURE:
<223> OTHER INFORMATION: Synthetic Construct

<400> SEQUENCE: 6

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val His Ser Tyr
            20                  25                  30
Leu Ala Trp Tyr Gln Gln Lys Pro Gly Gln Ala Pro Arg Leu Leu Ile
```

-continued

```
                35                  40                  45
Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Phe Trp Ser Trp Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

```
Arg Ala Ser Gln Ser Val His Ser Tyr Leu Ala
 1               5                  10
```

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

```
Asp Ala Ser Asn Arg Ala Thr
 1               5
```

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

```
Gln Gln Phe Trp Ser Trp Pro Trp Thr
 1               5
```

<210> SEQ ID NO 10
<211> LENGTH: 107
<212> TYPE: PRT
<213> ORGANISM: Artificial Sequence

```
<220> FEATURE:
<223> OTHER INFORMATION: Synthetic Construct

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 11
<211> LENGTH: 107
<212> TYPE: PRT
<213> ORGANISM: Artificial Sequence
<220> FEATURE:
<223> OTHER INFORMATION: Synthetic Construct

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Trp Pro Trp
                85                  90                  95

Thr Phe Gly Gln Gly Thr Lys Val Glu Ile Lys
            100                 105

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Phe Gly Gln Gly Thr Lys Val Glu Ile Lys Arg
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct

<400> SEQUENCE: 13
```

```
Glu Pro Lys Ser Cys Asp Lys Thr His Thr Cys Pro Pro Cys Pro
1               5                   10                  15
```

<210> SEQ ID NO 14
<211> LENGTH: 110
<212> TYPE: PRT
<213> ORGANISM: Artificial Sequence
<220> FEATURE:
<223> OTHER INFORMATION: Synthetic Construct

<400> SEQUENCE: 14

```
Ala Pro Glu Ala Ala Gly Ala Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 15
<211> LENGTH: 106
<212> TYPE: PRT
<213> ORGANISM: Artificial Sequence
<220> FEATURE:
<223> OTHER INFORMATION: Synthetic Construct

<400> SEQUENCE: 15

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 16
<211> LENGTH: 449
<212> TYPE: PRT
<213> ORGANISM: Artificial Sequence
<220> FEATURE:
<223> OTHER INFORMATION: Synthetic Construct

<400> SEQUENCE: 16

```
Gln Val Gln Leu Val Gln Ser Gly Ala Glu Val Lys Lys Pro Gly Ser
1               5                   10                  15
```

Ser Val Lys Val Ser Cys Lys Ala Ser Gly Tyr Thr Phe Ser Ser Tyr
                20                  25                  30

Asn Ile Ser Trp Val Arg Gln Ala Pro Gly Gln Gly Leu Glu Trp Met
             35                  40                  45

Gly Gly Ile Asn Pro Ile Asn Gly Leu Ala Phe Tyr Asn Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro

-continued

```
              435                 440                 445
Gly

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Gly Tyr Thr Phe Ser Ser Tyr Asn Ile Ser
1               5                  10

<210> SEQ ID NO 18
<211> LENGTH: 17
<212> TYPE: PRT
<213> ORGANISM: Artificial Sequence
<220> FEATURE:
<223> OTHER INFORMATION: Synthetic Construct

<400> SEQUENCE: 18

Gly Ile Asn Pro Ile Asn Gly Leu Ala Phe Tyr Asn Gln Lys Phe Gln
1               5                  10                  15

Gly

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Glu Ala Ile Thr Thr Val Gly Ala Met Asp Tyr
1               5                  10

<210> SEQ ID NO 20
<211> LENGTH: 97
<212> TYPE: PRT
<213> ORGANISM: Artificial Sequence
<220> FEATURE:
<223> OTHER INFORMATION: Synthetic Construct

<400> SEQUENCE: 20

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys

<210> SEQ ID NO 21
<211> LENGTH: 120
<212> TYPE: PRT
```

<213> ORGANISM: Artificial Sequence
<220> FEATURE:
<223> OTHER INFORMATION: Synthetic Construct

<400> SEQUENCE: 21

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Ser Trp Val Arg Gln Ala Pro Gly Gln Gly Leu Glu Trp Met
        35                  40                  45

Gly Gly Ile Asn Pro Ile Asn Gly Leu Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120
```

<210> SEQ ID NO 22
<211> LENGTH: 25
<212> TYPE: PRT
<213> ORGANISM: Artificial Sequence
<220> FEATURE:
<223> OTHER INFORMATION: Synthetic Construct

<400> SEQUENCE: 22

```
Gln Val Gln Leu Val Gln Ser Gly Ala Glu Val Lys Lys Pro Gly Ser
1               5                   10                  15

Ser Val Lys Val Ser Cys Lys Ala Ser
            20                  25
```

<210> SEQ ID NO 23
<211> LENGTH: 14
<212> TYPE: PRT
<213> ORGANISM: Artificial Sequence
<220> FEATURE:
<223> OTHER INFORMATION: Synthetic Construct

<400> SEQUENCE: 23

```
Trp Val Arg Gln Ala Pro Gly Gln Gly Leu Glu Trp Met Gly
1               5                   10
```

<210> SEQ ID NO 24
<211> LENGTH: 32
<212> TYPE: PRT
<213> ORGANISM: Artificial Sequence
<220> FEATURE:
<223> OTHER INFORMATION: Synthetic Construct

<400> SEQUENCE: 24

```
Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 25
<211> LENGTH: 11
<212> TYPE: PRT

```
<213> ORGANISM: Artificial Sequence
<220> FEATURE:
<223> OTHER INFORMATION: Synthetic Construct

<400> SEQUENCE: 25

Trp Gly Gln Gly Thr Leu Val Thr Val Ser Ser
1               5                   10

<210> SEQ ID NO 26
<211> LENGTH: 214
<212> TYPE: PRT
<213> ORGANISM: Artificial Sequence
<220> FEATURE:
<223> OTHER INFORMATION: Synthetic Construct

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Asp Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Asp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Arg Thr Ser Gln Asn Val His Ser Tyr Leu Ala
1               5                   10

<210> SEQ ID NO 28
<211> LENGTH: 7
<212> TYPE: PRT
<213> ORGANISM: Artificial Sequence
```

<220> FEATURE:
<223> OTHER INFORMATION: Synthetic Construct

<400> SEQUENCE: 28

Asp Ala Ser Thr Arg Ala Asp
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Gln Gln Phe Trp Ser Asp Pro Trp Thr
1               5

<210> SEQ ID NO 30
<211> LENGTH: 107
<212> TYPE: PRT
<213> ORGANISM: Artificial Sequence
<220> FEATURE:
<223> OTHER INFORMATION: Synthetic Construct

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Asp Pro Trp
                85                  90                  95

Thr Phe Gly Gln Gly Thr Lys Val Glu Ile Lys
            100                 105

<210> SEQ ID NO 31
<211> LENGTH: 449
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Asp Trp Val Arg Gln Ala Pro Gly Gln Gly Leu Glu Trp Met
        35                  40                  45

Gly Gln Ile Asn Pro Asn Asn Gly Leu Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Gly Tyr Thr Phe Ser Ser Tyr Asn Ile Asp
1               5                   10

<210> SEQ ID NO 33
<211> LENGTH: 17
<212> TYPE: PRT
<213> ORGANISM: Artificial Sequence
<220> FEATURE:
<223> OTHER INFORMATION: Synthetic Construct

<400> SEQUENCE: 33

Gln Ile Asn Pro Asn Asn Gly Leu Ala Phe Tyr Asn Gln Lys Phe Gln
1               5                   10                  15

Gly

<210> SEQ ID NO 34
<211> LENGTH: 120
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Asp Trp Val Arg Gln Ala Pro Gly Gln Gly Leu Glu Trp Met
        35                  40                  45

Gly Gln Ile Asn Pro Asn Asn Gly Leu Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 35
<211> LENGTH: 214
<212> TYPE: PRT
<213> ORGANISM: Artificial Sequence
<220> FEATURE:
<223> OTHER INFORMATION: Synthetic Construct

<400> SEQUENCE: 35

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Lys Thr Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ser Ser Asp Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 11
<212> TYPE: PRT
<213> ORGANISM: Artificial Sequence
<220> FEATURE:
<223> OTHER INFORMATION: Synthetic Construct

<400> SEQUENCE: 36

Arg Thr Ser Gln Ser Val His Ser Tyr Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Asp Ala Lys Thr Arg Ala Asp
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Gln Gln Phe Ser Ser Asp Pro Tyr Thr
1               5

<210> SEQ ID NO 39
<211> LENGTH: 107
<212> TYPE: PRT
<213> ORGANISM: Artificial Sequence
<220> FEATURE:
<223> OTHER INFORMATION: Synthetic Construct

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Val His Ser Tyr
            20                  25                  30

```
Leu Ala Trp Tyr Gln Gln Lys Pro Gly Gln Ala Pro Arg Leu Leu Ile
        35                  40                  45

Tyr Asp Ala Lys Thr Arg Ala Asp Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ser Ser Asp Pro Tyr
                85                  90                  95

Thr Phe Gly Gln Gly Thr Lys Val Glu Ile Lys
            100                 105

<210> SEQ ID NO 40
<211> LENGTH: 449
<212> TYPE: PRT
<213> ORGANISM: Artificial Sequence
<220> FEATURE:
<223> OTHER INFORMATION: Synthetic Construct

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
                20                  25                  30

Asn Ile Asp Trp Val Arg Gln Ala Pro Gly Gln Gly Leu Glu Trp Met
            35                  40                  45

Gly Gln Ile Asn Pro Asn Asn Gly Leu Ile Phe Phe Asn Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Gly Tyr Thr Phe Ser Asp Tyr Asn Ile Asp
1               5                   10

<210> SEQ ID NO 42
<211> LENGTH: 17
<212> TYPE: PRT
<213> ORGANISM: Artificial Sequence
<220> FEATURE:
<223> OTHER INFORMATION: Synthetic Construct

<400> SEQUENCE: 42

Gln Ile Asn Pro Asn Asn Gly Leu Ile Phe Phe Asn Gln Lys Phe Gln
1               5                   10                  15
Gly

<210> SEQ ID NO 43
<211> LENGTH: 11
<212> TYPE: PRT
<213> ORGANISM: Artificial Sequence
<220> FEATURE:
<223> OTHER INFORMATION: Synthetic Construct

<400> SEQUENCE: 43

Glu Val Ile Thr Thr Val Gly Ala Met Asp Tyr
1               5                   10

<210> SEQ ID NO 44
<211> LENGTH: 120
<212> TYPE: PRT
<213> ORGANISM: Artificial Sequence
```

```
<220> FEATURE:
<223> OTHER INFORMATION: Synthetic Construct

<400> SEQUENCE: 44

Gln Val Gln Leu Val Gln Ser Gly Ala Glu Val Lys Pro Gly Ser
1               5                   10                  15

Ser Val Lys Val Ser Cys Lys Ala Ser Gly Tyr Thr Phe Ser Asp Tyr
                20                  25                  30

Asn Ile Asp Trp Val Arg Gln Ala Pro Gly Gln Gly Leu Glu Trp Met
            35                  40                  45

Gly Gln Ile Asn Pro Asn Asn Gly Leu Ile Phe Phe Asn Gln Lys Phe
50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Ile Thr Thr Val Gly Ala Met Asp Tyr Trp Gly Gln
                100                 105                 110

Gly Thr Leu Val Thr Val Ser Ser
            115                 120

<210> SEQ ID NO 45
<211> LENGTH: 214
<212> TYPE: PRT
<213> ORGANISM: Artificial Sequence
<220> FEATURE:
<223> OTHER INFORMATION: Synthetic Construct

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Glu Asn Val His Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Leu Ala Asp Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Asp Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210
```

```
<210> SEQ ID NO 46
<211> LENGTH: 11
<212> TYPE: PRT
<213> ORGANISM: Artificial Sequence
<220> FEATURE:
<223> OTHER INFORMATION: Synthetic Construct

<400> SEQUENCE: 46

Arg Thr Ser Glu Asn Val His Ser Tyr Leu Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Synthetic Construct

<400> SEQUENCE: 47

Asp Ala Ser Asn Leu Ala Asp
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct

<400> SEQUENCE: 48

Gln Gln Phe Trp Ser Asp Pro Tyr Thr
1               5

<210> SEQ ID NO 49
<211> LENGTH: 107
<212> TYPE: PRT
<213> ORGANISM: Artificial Sequence
<220> FEATURE:
<223> OTHER INFORMATION: Synthetic Construct

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Glu Asn Val His Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Leu Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Asp Pro Tyr
                85                  90                  95

Thr Phe Gly Gln Gly Thr Lys Val Glu Ile Lys
            100                 105

<210> SEQ ID NO 50
<211> LENGTH: 449
<212> TYPE: PRT
<213> ORGANISM: Artificial Sequence
<220> FEATURE:
<223> OTHER INFORMATION: Synthetic Construct
```

<400> SEQUENCE: 50

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
                20                  25                  30

Asn Ile Asp Trp Val Arg Gln Ala Pro Gly Gln Gly Leu Glu Trp Met
            35                  40                  45

Gly Gly Ile Asn Pro Ile Asn Gly Leu Ile Phe Phe Asn Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp His Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

```
            405                 410                 415
Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly

<210> SEQ ID NO 51
<211> LENGTH: 17
<212> TYPE: PRT
<213> ORGANISM: Artificial Sequence
<220> FEATURE:
<223> OTHER INFORMATION: Synthetic Construct

<400> SEQUENCE: 51

Gly Ile Asn Pro Ile Asn Gly Leu Ile Phe Phe Asn Gln Lys Phe Gln
1               5                   10                  15

Gly

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct

<400> SEQUENCE: 52

Glu Ala Ile Thr Thr Val Gly Ala Met Asp His
1               5                   10

<210> SEQ ID NO 53
<211> LENGTH: 120
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Asp Trp Val Arg Gln Ala Pro Gly Gln Gly Leu Glu Trp Met
        35                  40                  45

Gly Gly Ile Asn Pro Ile Asn Gly Leu Ile Phe Phe Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp His Trp Gly Gln
            100                 105                 110

Gly Thr Leu Val Thr Val Ser Ser
        115                 120

<210> SEQ ID NO 54
<211> LENGTH: 214
<212> TYPE: PRT
<213> ORGANISM: Artificial Sequence
<220> FEATURE:
<223> OTHER INFORMATION: Synthetic Construct
```

<400> SEQUENCE: 54

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Leu His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Asp Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 55
<211> LENGTH: 11
<212> TYPE: PRT
<213> ORGANISM: Artificial Sequence
<220> FEATURE:
<223> OTHER INFORMATION: Synthetic Construct

<400> SEQUENCE: 55

Arg Ala Ser Gln Asn Leu His Ser Tyr Leu Ala
1               5                   10

<210> SEQ ID NO 56
<211> LENGTH: 107
<212> TYPE: PRT
<213> ORGANISM: Artificial Sequence
<220> FEATURE:
<223> OTHER INFORMATION: Synthetic Construct

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Leu His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Asp Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Phe Trp Ser Asp Pro Tyr
                 85                  90                  95

Thr Phe Gly Gln Gly Thr Lys Val Glu Ile Lys
            100                 105

<210> SEQ ID NO 57
<211> LENGTH: 449
<212> TYPE: PRT
<213> ORGANISM: Artificial Sequence
<220> FEATURE:
<223> OTHER INFORMATION: Synthetic Construct

<400> SEQUENCE: 57

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Ser Asp Tyr
                 20                  25                  30

Asn Met Asp Trp Val Arg Gln Ala Pro Gly Gln Gly Leu Glu Trp Met
             35                  40                  45

Gly Gln Ile Asn Pro Asn Asn Gly Leu Ala Asn Tyr Asn Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ala Ile Thr Thr Val Gly Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 58
<211> LENGTH: 10
<212> TYPE: PRT
<213> ORGANISM: Artificial Sequence
<220> FEATURE:
<223> OTHER INFORMATION: Synthetic Construct

<400> SEQUENCE: 58

Gly Tyr Thr Phe Ser Asp Tyr Asn Met Asp
1               5                   10

<210> SEQ ID NO 59
<211> LENGTH: 17
<212> TYPE: PRT
<213> ORGANISM: Artificial Sequence
<220> FEATURE:
<223> OTHER INFORMATION: Synthetic Construct

<400> SEQUENCE: 59

Gln Ile Asn Pro Asn Asn Gly Leu Ala Asn Tyr Asn Gln Lys Phe Gln
1               5                   10                  15

Gly

<210> SEQ ID NO 60
<211> LENGTH: 120
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Leu Ala Asn Tyr Asn Gln Lys Phe
    50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
             85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 61
<211> LENGTH: 214
<212> TYPE: PRT
<213> ORGANISM: Artificial Sequence
<220> FEATURE:
<223> OTHER INFORMATION: Synthetic Construct

<400> SEQUENCE: 61

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Asn Asp Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 62
<211> LENGTH: 11
<212> TYPE: PRT
<213> ORGANISM: Artificial Sequence
<220> FEATURE:
<223> OTHER INFORMATION: Synthetic Construct

<400> SEQUENCE: 62

Arg Ala Ser Gln Asn Val His Ser Tyr Leu Ala
1               5                   10

<210> SEQ ID NO 63
<211> LENGTH: 9
<212> TYPE: PRT
```

<213> ORGANISM: Artificial Sequence
<220> FEATURE:
<223> OTHER INFORMATION: Synthetic Construct

<400> SEQUENCE: 63

Gln Gln Phe Trp Asn Asp Pro Tyr Thr
1               5

<210> SEQ ID NO 64
<211> LENGTH: 107
<212> TYPE: PRT
<213> ORGANISM: Artificial Sequence
<220> FEATURE:
<223> OTHER INFORMATION: Synthetic Construct

<400> SEQUENCE: 64

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Asn Asp Pro Tyr
                85                  90                  95

Thr Phe Gly Gln Gly Thr Lys Val Glu Ile Lys
            100                 105

<210> SEQ ID NO 65
<211> LENGTH: 449
<212> TYPE: PRT
<213> ORGANISM: Artificial Sequence
<220> FEATURE:
<223> OTHER INFORMATION: Synthetic Construct

<400> SEQUENCE: 65

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Ile Asp Trp Val Arg Gln Ala Pro Gly Gln Gly Leu Glu Trp Met
        35                  40                  45

Gly Gln Ile Asn Pro Asn Asn Gly Leu Ile Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

-continued

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 66
<211> LENGTH: 10
<212> TYPE: PRT
<213> ORGANISM: Artificial Sequence
<220> FEATURE:
<223> OTHER INFORMATION: Synthetic Construct

<400> SEQUENCE: 66

Gly Tyr Thr Phe Thr Asp Tyr Asn Ile Asp
1               5                   10

<210> SEQ ID NO 67
<211> LENGTH: 17
<212> TYPE: PRT
<213> ORGANISM: Artificial Sequence
<220> FEATURE:
<223> OTHER INFORMATION: Synthetic Construct

<400> SEQUENCE: 67
```

```
Gln Ile Asn Pro Asn Gly Leu Ile Phe Tyr Asn Gln Lys Phe Gln
1               5                   10                  15

Gly
```

<210> SEQ ID NO 68
<211> LENGTH: 120
<212> TYPE: PRT
<213> ORGANISM: Artificial Sequence
<220> FEATURE:
<223> OTHER INFORMATION: Synthetic Construct

<400> SEQUENCE: 68

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Ile Asp Trp Val Arg Gln Ala Pro Gly Gln Gly Leu Glu Trp Met
        35                  40                  45

Gly Gln Ile Asn Pro Asn Asn Gly Leu Ile Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120
```

<210> SEQ ID NO 69
<211> LENGTH: 214
<212> TYPE: PRT
<213> ORGANISM: Artificial Sequence
<220> FEATURE:
<223> OTHER INFORMATION: Synthetic Construct

<400> SEQUENCE: 69

```
Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Lys Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ser Ser Asp Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 70
<211> LENGTH: 7
<212> TYPE: PRT
<213> ORGANISM: Artificial Sequence
<220> FEATURE:
<223> OTHER INFORMATION: Synthetic Construct

<400> SEQUENCE: 70

Asp Ala Lys Thr Arg Ala Thr
1               5

<210> SEQ ID NO 71
<211> LENGTH: 107
<212> TYPE: PRT
<213> ORGANISM: Artificial Sequence
<220> FEATURE:
<223> OTHER INFORMATION: Synthetic Construct

<400> SEQUENCE: 71

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Lys Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ser Ser Asp Pro Tyr
                85                  90                  95

Thr Phe Gly Gln Gly Thr Lys Val Glu Ile Lys
            100                 105

<210> SEQ ID NO 72
<211> LENGTH: 449
<212> TYPE: PRT
<213> ORGANISM: Artificial Sequence
<220> FEATURE:
<223> OTHER INFORMATION: Synthetic Construct

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Ile Asp Trp Val Arg Gln Ala Pro Gly Gln Gly Leu Glu Trp Met
        35                  40                  45

Gly Gln Ile Asn Pro Asn Asn Gly Leu Ala Phe Tyr Asn Gln Lys Phe
    50                  55                  60

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Asn Ala Val Tyr Tyr Cys
                 85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 73
<211> LENGTH: 120
<212> TYPE: PRT
<213> ORGANISM: Artificial Sequence
```

```
<220> FEATURE:
<223> OTHER INFORMATION: Synthetic Construct

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Ile Asp Trp Val Arg Gln Ala Pro Gly Gln Gly Leu Glu Trp Met
        35                  40                  45

Gly Gln Ile Asn Pro Asn Asn Gly Leu Ala Phe Tyr Asn Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Asn Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 74
<211> LENGTH: 32
<212> TYPE: PRT
<213> ORGANISM: Artificial Sequence
<220> FEATURE:
<223> OTHER INFORMATION: Synthetic Construct

<400> SEQUENCE: 74

Arg Val Thr Ile Thr Ala Asp Glu Ser Thr Ser Thr Ala Tyr Met Glu
1               5                   10                  15

Leu Ser Ser Leu Arg Ser Glu Asp Asn Ala Val Tyr Tyr Cys Ala Arg
            20                  25                  30

<210> SEQ ID NO 75
<211> LENGTH: 214
<212> TYPE: PRT
<213> ORGANISM: Artificial Sequence
<220> FEATURE:
<223> OTHER INFORMATION: Synthetic Construct

<400> SEQUENCE: 75

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Leu Ala Asp Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ser Asn Asp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 76
<211> LENGTH: 9
<212> TYPE: PRT
<213> ORGANISM: Artificial Sequence
<220> FEATURE:
<223> OTHER INFORMATION: Synthetic Construct

<400> SEQUENCE: 76

```
Gln Gln Phe Ser Asn Asp Pro Trp Thr
1               5
```

<210> SEQ ID NO 77
<211> LENGTH: 107
<212> TYPE: PRT
<213> ORGANISM: Artificial Sequence
<220> FEATURE:
<223> OTHER INFORMATION: Synthetic Construct

<400> SEQUENCE: 77

```
Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Leu Ala Asp Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ser Asn Asp Pro Trp
                85                  90                  95

Thr Phe Gly Gln Gly Thr Lys Val Glu Ile Lys
            100                 105
```

<210> SEQ ID NO 78
<211> LENGTH: 449
<212> TYPE: PRT
<213> ORGANISM: Artificial Sequence
<220> FEATURE:
<223> OTHER INFORMATION: Synthetic Construct

<400> SEQUENCE: 78

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
```

```
            35                  40                  45
Gly Gln Ile Asn Pro Asn Asn Gly Leu Ala Phe Tyr Asn Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ala Ile Thr Thr Val Gly Ala Thr Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 79
<211> LENGTH: 11
<212> TYPE: PRT
<213> ORGANISM: Artificial Sequence
<220> FEATURE:
<223> OTHER INFORMATION: Synthetic Construct

<400> SEQUENCE: 79

Glu Ala Ile Thr Thr Val Gly Ala Thr Asp Tyr
1               5                   10

<210> SEQ ID NO 80
<211> LENGTH: 120
<212> TYPE: PRT
<213> ORGANISM: Artificial Sequence
<220> FEATURE:
<223> OTHER INFORMATION: Synthetic Construct

<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
                20                  25                  30

Asn Met Asp Trp Val Arg Gln Ala Pro Gly Gln Gly Leu Glu Trp Met
            35                  40                  45

Gly Gln Ile Asn Pro Asn Asn Gly Leu Ala Phe Tyr Asn Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Thr Asp Tyr Trp Gly Gln
            100                 105                 110

Gly Thr Leu Val Thr Val Ser Ser
        115                 120

<210> SEQ ID NO 81
<211> LENGTH: 214
<212> TYPE: PRT
<213> ORGANISM: Artificial Sequence
<220> FEATURE:
<223> OTHER INFORMATION: Synthetic Construct

<400> SEQUENCE: 81

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Asn Val His Asn Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Asp Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly

```
                115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
                195                 200                 205
Phe Asn Arg Gly Glu Cys
    210

<210> SEQ ID NO 82
<211> LENGTH: 11
<212> TYPE: PRT
<213> ORGANISM: Artificial Sequence
<220> FEATURE:
<223> OTHER INFORMATION: Synthetic Construct

<400> SEQUENCE: 82

Arg Thr Ser Gln Asn Val His Asn Tyr Leu Ala
1               5                   10

<210> SEQ ID NO 83
<211> LENGTH: 107
<212> TYPE: PRT
<213> ORGANISM: Artificial Sequence
<220> FEATURE:
<223> OTHER INFORMATION: Synthetic Construct

<400> SEQUENCE: 83

Glu Ile Val Leu Thr Gln Ser Pro Ala Thr Leu Ser Leu Ser Pro Gly
1               5                   10                  15
Glu Arg Ala Thr Leu Ser Cys Arg Thr Ser Gln Asn Val His Asn Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Phe Trp Ser Asp Pro Tyr
                85                  90                  95
Thr Phe Gly Gln Gly Thr Lys Val Glu Ile Lys
            100                 105

<210> SEQ ID NO 84
<211> LENGTH: 449
<212> TYPE: PRT
<213> ORGANISM: Artificial Sequence
<220> FEATURE:
<223> OTHER INFORMATION: Synthetic Construct

<400> SEQUENCE: 84

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Ser Ser Tyr
            20                  25                  30
```

```
Asn Ile Asp Trp Val Arg Gln Ala Pro Gly Gln Gly Leu Glu Trp Met
    35                  40                  45

Gly Gln Ile Asn Pro Ile Asn Gly Leu Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
                100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445
```

Gly

<210> SEQ ID NO 85
<211> LENGTH: 17
<212> TYPE: PRT
<213> ORGANISM: Artificial Sequence
<220> FEATURE:
<223> OTHER INFORMATION: Synthetic Construct

<400> SEQUENCE: 85

Gln Ile Asn Pro Ile Asn Gly Leu Ala Phe Tyr Asn Gln Lys Phe Gln
1               5                   10                  15

Gly

<210> SEQ ID NO 86
<211> LENGTH: 120
<212> TYPE: PRT
<213> ORGANISM: Artificial Sequence
<220> FEATURE:
<223> OTHER INFORMATION: Synthetic Construct

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Asp Trp Val Arg Gln Ala Pro Gly Gln Gly Leu Glu Trp Met
        35                  40                  45

Gly Gln Ile Asn Pro Ile Asn Gly Leu Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 87
<211> LENGTH: 214
<212> TYPE: PRT
<213> ORGANISM: Artificial Sequence
<220> FEATURE:
<223> OTHER INFORMATION: Synthetic Construct

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Glu Ser Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Asn Trp Pro Trp
                85                  90                  95

```
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 88
<211> LENGTH: 11
<212> TYPE: PRT
<213> ORGANISM: Artificial Sequence
<220> FEATURE:
<223> OTHER INFORMATION: Synthetic Construct

<400> SEQUENCE: 88

Arg Thr Ser Glu Ser Val His Ser Tyr Leu Ala
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct

<400> SEQUENCE: 89

Gln Gln Phe Trp Asn Trp Pro Trp Thr
1               5

<210> SEQ ID NO 90
<211> LENGTH: 107
<212> TYPE: PRT
<213> ORGANISM: Artificial Sequence
<220> FEATURE:
<223> OTHER INFORMATION: Synthetic Construct

<400> SEQUENCE: 90

Glu Ile Val Leu Thr Gln Ser Pro Ala Thr Leu Ser Leu Ser Pro Gly
1               5                   10                  15
Glu Arg Ala Thr Leu Ser Cys Arg Thr Ser Glu Ser Val His Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Phe Trp Asn Trp Pro Trp
                85                  90                  95
Thr Phe Gly Gln Gly Thr Lys Val Glu Ile Lys
```

<210> SEQ ID NO 91
<211> LENGTH: 449
<212> TYPE: PRT
<213> ORGANISM: Artificial Sequence
<220> FEATURE:
<223> OTHER INFORMATION: Synthetic Construct

<400> SEQUENCE: 91

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gly Ile Asn Pro Asn Asn Gly Leu Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
                    355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 92
<211> LENGTH: 17
<212> TYPE: PRT
<213> ORGANISM: Artificial Sequence
<220> FEATURE:
<223> OTHER INFORMATION: Synthetic Construct

<400> SEQUENCE: 92

Gly Ile Asn Pro Asn Asn Gly Leu Ala Phe Tyr Asn Gln Lys Phe Gln
1               5                   10                  15

Gly

<210> SEQ ID NO 93
<211> LENGTH: 120
<212> TYPE: PRT
<213> ORGANISM: Artificial Sequence
<220> FEATURE:
<223> OTHER INFORMATION: Synthetic Construct

<400> SEQUENCE: 93

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gly Ile Asn Pro Asn Asn Gly Leu Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 94
<211> LENGTH: 214
<212> TYPE: PRT
<213> ORGANISM: Artificial Sequence
<220> FEATURE:
<223> OTHER INFORMATION: Synthetic Construct

<400> SEQUENCE: 94

Glu Ile Val Leu Thr Gln Ser Pro Ala Thr Leu Ser Leu Ser Pro Gly
```

-continued

```
                1               5                  10                  15
        Glu Arg Ala Thr Leu Ser Cys Arg Thr Ser Gln Ser Val His Asn Tyr
                        20                  25                  30

Leu Ala Trp Tyr Gln Gln Lys Pro Gly Gln Ala Pro Arg Leu Leu Ile
                        35                  40                  45

Tyr Asp Ala Ser Thr Arg Ala Asp Gly Ile Pro Ala Arg Phe Ser Gly
                        50                  55                  60

Ser Gly Ser Gly Thr Asp Phe Thr Leu Thr Ile Ser Ser Leu Glu Pro
        65                  70                  75                  80

Glu Asp Phe Ala Val Tyr Tyr Cys Gln Gln Phe Ser Ser Asp Pro Tyr
                        85                  90                  95

Thr Phe Gly Gln Gly Thr Lys Val Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                        130                 135                 140

Lys Val Gln Trp Lys Val Asp Asn Ala Leu Gln Ser Gly Asn Ser Gln
        145                 150                 155                 160

Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                 205

Phe Asn Arg Gly Glu Cys
                        210

<210> SEQ ID NO 95
<211> LENGTH: 11
<212> TYPE: PRT
<213> ORGANISM: Artificial Sequence
<220> FEATURE:
<223> OTHER INFORMATION: Synthetic Construct

<400> SEQUENCE: 95

Arg Thr Ser Gln Ser Val His Asn Tyr Leu Ala
1               5                   10

<210> SEQ ID NO 96
<211> LENGTH: 107
<212> TYPE: PRT
<213> ORGANISM: Artificial Sequence
<220> FEATURE:
<223> OTHER INFORMATION: Synthetic Construct

<400> SEQUENCE: 96

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Val His Asn Tyr
                20                  25                  30

Leu Ala Trp Tyr Gln Gln Lys Pro Gly Gln Ala Pro Arg Leu Leu Ile
                35                  40                  45

Tyr Asp Ala Ser Thr Arg Ala Asp Gly Ile Pro Ala Arg Phe Ser Gly
                50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Phe Ser Ser Asp Pro Tyr
                85                  90                  95

Thr Phe Gly Gln Gly Thr Lys Val Glu Ile Lys
            100                 105

<210> SEQ ID NO 97
<211> LENGTH: 449
<212> TYPE: PRT
<213> ORGANISM: Artificial Sequence
<220> FEATURE:
<223> OTHER INFORMATION: Synthetic Construct

<400> SEQUENCE: 97

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Ile Phe Gly Leu Ala Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 98
<211> LENGTH: 17
<212> TYPE: PRT
<213> ORGANISM: Artificial Sequence
<220> FEATURE:
<223> OTHER INFORMATION: Synthetic Construct

<400> SEQUENCE: 98

Gln Ile Asn Pro Ile Phe Gly Leu Ala Phe Tyr Ala Gln Lys Phe Gln
1               5                   10                  15

Gly

<210> SEQ ID NO 99
<211> LENGTH: 120
<212> TYPE: PRT
<213> ORGANISM: Artificial Sequence
<220> FEATURE:
<223> OTHER INFORMATION: Synthetic Construct

<400> SEQUENCE: 99

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Ile Phe Gly Leu Ala Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Ile Thr Thr Val Gly Ala Met Asp Tyr Trp Gly Gln
            100                 105                 110

Gly Thr Leu Val Thr Val Ser Ser
        115                 120

<210> SEQ ID NO 100
<211> LENGTH: 214
<212> TYPE: PRT
<213> ORGANISM: Artificial Sequence
<220> FEATURE:
<223> OTHER INFORMATION: Synthetic Construct
```

<400> SEQUENCE: 100

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Leu His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Asn Asp Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 101
<211> LENGTH: 11
<212> TYPE: PRT
<213> ORGANISM: Artificial Sequence
<220> FEATURE:
<223> OTHER INFORMATION: Synthetic Construct

<400> SEQUENCE: 101

Arg Thr Ser Gln Ser Leu His Ser Tyr Leu Ala
1               5                   10

<210> SEQ ID NO 102
<211> LENGTH: 9
<212> TYPE: PRT
<213> ORGANISM: Artificial Sequence
<220> FEATURE:
<223> OTHER INFORMATION: Synthetic Construct

<400> SEQUENCE: 102

Gln Gln Phe Trp Asn Asp Pro Trp Thr
1               5

<210> SEQ ID NO 103
<211> LENGTH: 107
<212> TYPE: PRT
<213> ORGANISM: Artificial Sequence
<220> FEATURE:
<223> OTHER INFORMATION: Synthetic Construct -continued

<400> SEQUENCE: 103

```
Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Leu His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Asn Asp Pro Trp
                85                  90                  95

Thr Phe Gly Gln Gly Thr Lys Val Glu Ile Lys
            100                 105
```

<210> SEQ ID NO 104
<211> LENGTH: 449
<212> TYPE: PRT
<213> ORGANISM: Artificial Sequence
<220> FEATURE:
<223> OTHER INFORMATION: Synthetic Construct

<400> SEQUENCE: 104

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Ile Asp Trp Val Arg Gln Ala Pro Gly Gln Gly Leu Glu Trp Met
        35                  40                  45

Gly Gly Ile Asn Pro Asn Asn Gly Leu Ala Phe Phe Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
```

```
                    245                 250                 255
Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 105
<211> LENGTH: 17
<212> TYPE: PRT
<213> ORGANISM: Artificial Sequence
<220> FEATURE:
<223> OTHER INFORMATION: Synthetic Construct

<400> SEQUENCE: 105

Gly Ile Asn Pro Asn Asn Gly Leu Ala Phe Phe Asn Gln Lys Phe Gln
1               5                   10                  15

Gly

<210> SEQ ID NO 106
<211> LENGTH: 120
<212> TYPE: PRT
<213> ORGANISM: Artificial Sequence
<220> FEATURE:
<223> OTHER INFORMATION: Synthetic Construct

<400> SEQUENCE: 106

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Ile Asp Trp Val Arg Gln Ala Pro Gly Gln Gly Leu Glu Trp Met
        35                  40                  45

Gly Gly Ile Asn Pro Asn Asn Gly Leu Ala Phe Phe Asn Gln Lys Phe
    50                  55                  60

Gln Gly Arg Val Thr Ile Thr Ala Asp Glu Ser Thr Ser Thr Ala Tyr
65                  70                  75                  80
```

Met Glu Leu Ser Ser Leu Arg Ser Glu Asp Thr Ala Val Tyr Tyr Cys
            85                  90                  95

Ala Arg Glu Ala Ile Thr Thr Val Gly Ala Met Asp Tyr Trp Gly Gln
        100                 105                 110

Gly Thr Leu Val Thr Val Ser Ser
        115                 120

<210> SEQ ID NO 107
<211> LENGTH: 214
<212> TYPE: PRT
<213> ORGANISM: Artificial Sequence
<220> FEATURE:
<223> OTHER INFORMATION: Synthetic Construct

<400> SEQUENCE: 107

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Lys Asn Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Asp Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 108
<211> LENGTH: 7
<212> TYPE: PRT
<213> ORGANISM: Artificial Sequence
<220> FEATURE:
<223> OTHER INFORMATION: Synthetic Construct

<400> SEQUENCE: 108

Asp Ala Lys Asn Arg Ala Asp
1               5

<210> SEQ ID NO 109
<211> LENGTH: 107
<212> TYPE: PRT

<213> ORGANISM: Artificial Sequence
<220> FEATURE:
<223> OTHER INFORMATION: Synthetic Construct

<400> SEQUENCE: 109

```
Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Lys Asn Arg Ala Asp Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Asp Pro Tyr
                85                  90                  95

Thr Phe Gly Gln Gly Thr Lys Val Glu Ile Lys
            100                 105
```

<210> SEQ ID NO 110
<211> LENGTH: 449
<212> TYPE: PRT
<213> ORGANISM: Artificial Sequence
<220> FEATURE:
<223> OTHER INFORMATION: Synthetic Construct

<400> SEQUENCE: 110

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Ser Trp Val Arg Gln Ala Pro Gly Gln Gly Leu Glu Trp Met
        35                  40                  45

Gly Gln Ile Asn Pro Asn Asn Gly Leu Ala Phe Tyr Asn Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Glu Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

```
Lys Thr His Thr Cys Pro Cys Pro Ala Pro Glu Ala Ala Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 111
<211> LENGTH: 11
<212> TYPE: PRT
<213> ORGANISM: Artificial Sequence
<220> FEATURE:
<223> OTHER INFORMATION: Synthetic Construct

<400> SEQUENCE: 111

Glu Ala Ile Thr Thr Val Gly Ala Met Glu Tyr
1               5                   10

<210> SEQ ID NO 112
<211> LENGTH: 120
<212> TYPE: PRT
<213> ORGANISM: Artificial Sequence
<220> FEATURE:
<223> OTHER INFORMATION: Synthetic Construct

<400> SEQUENCE: 112

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Ser Trp Val Arg Gln Ala Pro Gly Gln Gly Leu Glu Trp Met
        35                  40                  45

Gly Gln Ile Asn Pro Asn Asn Gly Leu Ala Phe Tyr Asn Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ala Ile Thr Thr Val Gly Ala Met Glu Tyr Trp Gly Gln
            100                 105                 110

Gly Thr Leu Val Thr Val Ser Ser
        115                 120

<210> SEQ ID NO 113
<211> LENGTH: 214
<212> TYPE: PRT
<213> ORGANISM: Artificial Sequence
<220> FEATURE:
<223> OTHER INFORMATION: Synthetic Construct

<400> SEQUENCE: 113

Glu Ile Val Leu Thr Gln Ser Pro Ala Thr Leu Ser Leu Ser Pro Gly
1               5                  10                  15

Glu Arg Ala Thr Leu Ser Cys Arg Thr Ser Gln Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Asp Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Phe Trp Asn Asp Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 114
<211> LENGTH: 7
<212> TYPE: PRT
<213> ORGANISM: Artificial Sequence
<220> FEATURE:
<223> OTHER INFORMATION: Synthetic Construct

<400> SEQUENCE: 114

Asp Ala Ser Asn Arg Ala Asp
1               5

<210> SEQ ID NO 115
```

<211> LENGTH: 107
<212> TYPE: PRT
<213> ORGANISM: Artificial Sequence
<220> FEATURE:
<223> OTHER INFORMATION: Synthetic Construct

<400> SEQUENCE: 115

```
Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Asp Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Asn Asp Pro Tyr
                85                  90                  95

Thr Phe Gly Gln Gly Thr Lys Val Glu Ile Lys
            100                 105
```

<210> SEQ ID NO 116
<211> LENGTH: 449
<212> TYPE: PRT
<213> ORGANISM: Artificial Sequence
<220> FEATURE:
<223> OTHER INFORMATION: Synthetic Construct

<400> SEQUENCE: 116

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Ile Ser Trp Val Arg Gln Ala Pro Gly Gln Gly Leu Glu Trp Met
        35                  40                  45

Gly Gln Ile Asn Pro Asn Asn Gly Leu Ile Phe Phe Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Gln Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
```

```
              210                 215                 220
Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
Gly

<210> SEQ ID NO 117
<211> LENGTH: 10
<212> TYPE: PRT
<213> ORGANISM: Artificial Sequence
<220> FEATURE:
<223> OTHER INFORMATION: Synthetic Construct

<400> SEQUENCE: 117

Gly Tyr Thr Phe Thr Ser Tyr Asn Ile Ser
1               5                   10

<210> SEQ ID NO 118
<211> LENGTH: 17
<212> TYPE: PRT
<213> ORGANISM: Artificial Sequence
<220> FEATURE:
<223> OTHER INFORMATION: Synthetic Construct

<400> SEQUENCE: 118

Gln Ile Asn Pro Asn Asn Gly Leu Ile Phe Phe Ala Gln Lys Phe Gln
1               5                   10                  15
Gly

<210> SEQ ID NO 119
<211> LENGTH: 11
<212> TYPE: PRT
<213> ORGANISM: Artificial Sequence
```

```
<220> FEATURE:
<223> OTHER INFORMATION: Synthetic Construct

<400> SEQUENCE: 119

Glu Ala Ile Thr Thr Val Gly Ala Met Asp Gln
1               5                   10

<210> SEQ ID NO 120
<211> LENGTH: 120
<212> TYPE: PRT
<213> ORGANISM: Artificial Sequence
<220> FEATURE:
<223> OTHER INFORMATION: Synthetic Construct

<400> SEQUENCE: 120

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Ile Ser Trp Val Arg Gln Ala Pro Gly Gln Gly Leu Glu Trp Met
        35                  40                  45

Gly Gln Ile Asn Pro Asn Asn Gly Leu Ile Phe Phe Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Gln Trp Gly Gln
            100                 105                 110

Gly Thr Leu Val Thr Val Ser Ser
        115                 120

<210> SEQ ID NO 121
<211> LENGTH: 214
<212> TYPE: PRT
<213> ORGANISM: Artificial Sequence
<220> FEATURE:
<223> OTHER INFORMATION: Synthetic Construct

<400> SEQUENCE: 121

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Glu Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Leu Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 122
<211> LENGTH: 7
<212> TYPE: PRT
<213> ORGANISM: Artificial Sequence
<220> FEATURE:
<223> OTHER INFORMATION: Synthetic Construct

<400> SEQUENCE: 122

Asp Ala Ser Thr Leu Ala Thr
1               5

<210> SEQ ID NO 123
<211> LENGTH: 107
<212> TYPE: PRT
<213> ORGANISM: Artificial Sequence
<220> FEATURE:
<223> OTHER INFORMATION: Synthetic Construct

<400> SEQUENCE: 123

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Glu Asn Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Leu Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Trp Pro Trp
                85                  90                  95

Thr Phe Gly Gln Gly Thr Lys Val Glu Ile Lys
            100                 105

<210> SEQ ID NO 124
<211> LENGTH: 449
<212> TYPE: PRT
<213> ORGANISM: Artificial Sequence
<220> FEATURE:
<223> OTHER INFORMATION: Synthetic Construct

<400> SEQUENCE: 124

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Ile Ser Trp Val Arg Gln Ala Pro Gly Gln Gly Leu Glu Trp Met
        35                  40                  45

Gly Gly Ile Asn Pro Ile Phe Gly Leu Ala Phe Tyr Asn Gln Lys Phe
```

```
                    50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ala Ile Thr Thr Val Gly Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 125
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 125

Gly Tyr Thr Phe Ser Asp Tyr Asn Ile Ser
1               5                   10

<210> SEQ ID NO 126
<211> LENGTH: 17
<212> TYPE: PRT
<213> ORGANISM: Artificial Sequence
<220> FEATURE:
<223> OTHER INFORMATION: Synthetic Construct

<400> SEQUENCE: 126

Gly Ile Asn Pro Ile Phe Gly Leu Ala Phe Tyr Asn Gln Lys Phe Gln
1               5                   10                  15

Gly

<210> SEQ ID NO 127
<211> LENGTH: 120
<212> TYPE: PRT
<213> ORGANISM: Artificial Sequence
<220> FEATURE:
<223> OTHER INFORMATION: Synthetic Construct

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
                20                  25                  30

Asn Ile Ser Trp Val Arg Gln Ala Pro Gly Gln Gly Leu Glu Trp Met
            35                  40                  45

Gly Gly Ile Asn Pro Ile Phe Gly Leu Ala Phe Tyr Asn Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
                100                 105                 110

Gly Thr Leu Val Thr Val Ser Ser
            115                 120

<210> SEQ ID NO 128
<211> LENGTH: 214
<212> TYPE: PRT
<213> ORGANISM: Artificial Sequence
<220> FEATURE:
<223> OTHER INFORMATION: Synthetic Construct

<400> SEQUENCE: 128

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Val Ser Asn Tyr
                20                  25                  30

Leu Ala Trp Tyr Gln Gln Lys Pro Gly Gln Ala Pro Arg Leu Leu Ile
            35                  40                  45

Tyr Asp Ala Lys Asn Arg Ala Thr Gly Ile Pro Ala Arg Phe Ser Gly
```

```
                50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Phe Trp Asn Asp Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 129
<211> LENGTH: 11
<212> TYPE: PRT
<213> ORGANISM: Artificial Sequence
<220> FEATURE:
<223> OTHER INFORMATION: Synthetic Construct

<400> SEQUENCE: 129

Arg Thr Ser Gln Ser Val Ser Asn Tyr Leu Ala
 1               5                  10

<210> SEQ ID NO 130
<211> LENGTH: 7
<212> TYPE: PRT
<213> ORGANISM: Artificial Sequence
<220> FEATURE:
<223> OTHER INFORMATION: Synthetic Construct

<400> SEQUENCE: 130

Asp Ala Lys Asn Arg Ala Thr
 1               5

<210> SEQ ID NO 131
<211> LENGTH: 107
<212> TYPE: PRT
<213> ORGANISM: Artificial Sequence
<220> FEATURE:
<223> OTHER INFORMATION: Synthetic Construct

<400> SEQUENCE: 131

Glu Ile Val Leu Thr Gln Ser Pro Ala Thr Leu Ser Leu Ser Pro Gly
 1               5                  10                  15

Glu Arg Ala Thr Leu Ser Cys Arg Thr Ser Gln Ser Val Ser Asn Tyr
             20                  25                  30

Leu Ala Trp Tyr Gln Gln Lys Pro Gly Gln Ala Pro Arg Leu Leu Ile
         35                  40                  45

Tyr Asp Ala Lys Asn Arg Ala Thr Gly Ile Pro Ala Arg Phe Ser Gly
     50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Phe Trp Asn Asp Pro Trp
                 85                  90                  95

Thr Phe Gly Gln Gly Thr Lys Val Glu Ile Lys
                100                 105

<210> SEQ ID NO 132
<211> LENGTH: 449
<212> TYPE: PRT
<213> ORGANISM: Artificial Sequence
<220> FEATURE:
<223> OTHER INFORMATION: Synthetic Construct

<400> SEQUENCE: 132

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Thr Asp Tyr
                 20                  25                  30

Asn Ile Ser Trp Val Arg Gln Ala Pro Gly Gln Gly Leu Glu Trp Met
             35                  40                  45

Gly Gln Ile Asn Pro Asn Asn Gly Leu Ala Phe Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Phe Ile Thr Thr Val Gly Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 133
<211> LENGTH: 10
<212> TYPE: PRT
<213> ORGANISM: Artificial Sequence
<220> FEATURE:
<223> OTHER INFORMATION: Synthetic Construct

<400> SEQUENCE: 133

Gly Tyr Thr Phe Thr Asp Tyr Asn Ile Ser
1               5                   10

<210> SEQ ID NO 134
<211> LENGTH: 17
<212> TYPE: PRT
<213> ORGANISM: Artificial Sequence
<220> FEATURE:
<223> OTHER INFORMATION: Synthetic Construct

<400> SEQUENCE: 134

Gln Ile Asn Pro Asn Asn Gly Leu Ala Phe Tyr Ala Gln Lys Phe Gln
1               5                   10                  15
Gly

<210> SEQ ID NO 135
<211> LENGTH: 11
<212> TYPE: PRT
<213> ORGANISM: Artificial Sequence
<220> FEATURE:
<223> OTHER INFORMATION: Synthetic Construct

<400> SEQUENCE: 135

Glu Phe Ile Thr Thr Val Gly Ala Met Asp Tyr
1               5                   10

<210> SEQ ID NO 136
<211> LENGTH: 120
<212> TYPE: PRT
<213> ORGANISM: Artificial Sequence
<220> FEATURE:
<223> OTHER INFORMATION: Synthetic Construct

<400> SEQUENCE: 136

Gln Val Gln Leu Val Gln Ser Gly Ala Glu Val Lys Lys Pro Gly Ser
```

```
            1               5                  10                 15
Ser Val Lys Val Ser Cys Lys Ala Ser Gly Tyr Thr Phe Thr Asp Tyr
             20                  25                 30

Asn Ile Ser Trp Val Arg Gln Ala Pro Gly Gln Gly Leu Glu Trp Met
             35                  40                 45

Gly Gln Ile Asn Pro Asn Asn Gly Leu Ala Phe Tyr Ala Gln Lys Phe
         50                  55                 60

Gln Gly Arg Val Thr Ile Thr Ala Asp Glu Ser Thr Ser Thr Ala Tyr
65                  70                  75                 80

Met Glu Leu Ser Ser Leu Arg Ser Glu Asp Thr Ala Val Tyr Tyr Cys
                 85                  90                  95

Ala Arg Glu Phe Ile Thr Thr Val Gly Ala Met Asp Tyr Trp Gly Gln
                100                 105                 110

Gly Thr Leu Val Thr Val Ser Ser
                115                 120

<210> SEQ ID NO 137
<211> LENGTH: 214
<212> TYPE: PRT
<213> ORGANISM: Artificial Sequence
<220> FEATURE:
<223> OTHER INFORMATION: Synthetic Construct

<400> SEQUENCE: 137

Glu Ile Val Leu Thr Gln Ser Pro Ala Thr Leu Ser Leu Ser Pro Gly
1               5                  10                 15

Glu Arg Ala Thr Leu Ser Cys Arg Thr Ser Glu Ser Val Ser Ser Tyr
             20                  25                 30

Leu Ala Trp Tyr Gln Gln Lys Pro Gly Gln Ala Pro Arg Leu Leu Ile
             35                  40                 45

Tyr Asp Ala Lys Thr Arg Ala Asp Gly Ile Pro Ala Arg Phe Ser Gly
         50                  55                 60

Ser Gly Ser Gly Thr Asp Phe Thr Leu Thr Ile Ser Ser Leu Glu Pro
65                  70                  75                 80

Glu Asp Phe Ala Val Tyr Tyr Cys Gln Gln Phe Trp Ser Trp Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
             130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
             195                 200                 205

Phe Asn Arg Gly Glu Cys
         210

<210> SEQ ID NO 138
<211> LENGTH: 11
<212> TYPE: PRT
```

<213> ORGANISM: Artificial Sequence
<220> FEATURE:
<223> OTHER INFORMATION: Synthetic Construct

<400> SEQUENCE: 138

```
Arg Thr Ser Glu Ser Val Ser Ser Tyr Leu Ala
1               5                   10
```

<210> SEQ ID NO 139
<211> LENGTH: 107
<212> TYPE: PRT
<213> ORGANISM: Artificial Sequence
<220> FEATURE:
<223> OTHER INFORMATION: Synthetic Construct

<400> SEQUENCE: 139

```
Glu Ile Val Leu Thr Gln Ser Pro Ala Thr Leu Ser Leu Ser Pro Gly
1               5                   10                  15

Glu Arg Ala Thr Leu Ser Cys Arg Thr Ser Glu Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Lys Thr Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Trp Pro Trp
                85                  90                  95

Thr Phe Gly Gln Gly Thr Lys Val Glu Ile Lys
            100                 105
```

<210> SEQ ID NO 140
<211> LENGTH: 449
<212> TYPE: PRT
<213> ORGANISM: Artificial Sequence
<220> FEATURE:
<223> OTHER INFORMATION: Synthetic Construct

<400> SEQUENCE: 140

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gly Ile Asn Pro Asn Asn Gly Thr Ala Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Gln Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160
```

-continued

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 141
<211> LENGTH: 17
<212> TYPE: PRT
<213> ORGANISM: Artificial Sequence
<220> FEATURE:
<223> OTHER INFORMATION: Synthetic Construct

<400> SEQUENCE: 141

Gly Ile Asn Pro Asn Asn Gly Thr Ala Phe Tyr Ala Gln Lys Phe Gln
1               5                   10                  15

Gly

<210> SEQ ID NO 142
<211> LENGTH: 120
<212> TYPE: PRT
<213> ORGANISM: Artificial Sequence
<220> FEATURE:
<223> OTHER INFORMATION: Synthetic Construct

<400> SEQUENCE: 142

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gly Ile Asn Pro Asn Asn Gly Thr Ala Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Gln Trp Gly Gln
            100                 105                 110

Gly Thr Leu Val Thr Val Ser Ser
        115                 120
```

<210> SEQ ID NO 143
<211> LENGTH: 214
<212> TYPE: PRT
<213> ORGANISM: Artificial Sequence
<220> FEATURE:
<223> OTHER INFORMATION: Synthetic Construct

<400> SEQUENCE: 143

```
Glu Ile Val Leu Thr Gln Ser Pro Ala Thr Leu Ser Leu Ser Pro Gly
1               5                   10                  15

Glu Arg Ala Thr Leu Ser Cys Arg Thr Ser Glu Ser Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Asp Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 144
<211> LENGTH: 107
<212> TYPE: PRT
<213> ORGANISM: Artificial Sequence
<220> FEATURE:
<223> OTHER INFORMATION: Synthetic Construct

<400> SEQUENCE: 144

```
Glu Ile Val Leu Thr Gln Ser Pro Ala Thr Leu Ser Leu Ser Pro Gly
1               5                   10                  15

Glu Arg Ala Thr Leu Ser Cys Arg Thr Ser Glu Ser Val His Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Asp Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Asp Pro Tyr
                85                  90                  95

Thr Phe Gly Gln Gly Thr Lys Val Glu Ile Lys
            100                 105
```

<210> SEQ ID NO 145
<211> LENGTH: 449
<212> TYPE: PRT
<213> ORGANISM: Artificial Sequence
<220> FEATURE:
<223> OTHER INFORMATION: Synthetic Construct

<400> SEQUENCE: 145

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Asp Trp Val Arg Gln Ala Pro Gly Gln Gly Leu Glu Trp Met
        35                  40                  45

Gly Gln Ile Asn Pro Asn Asn Gly Leu Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Ile Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 146
<211> LENGTH: 17
<212> TYPE: PRT
<213> ORGANISM: Artificial Sequence
<220> FEATURE:
<223> OTHER INFORMATION: Synthetic Construct

<400> SEQUENCE: 146

Gln Ile Asn Pro Asn Asn Gly Leu Ala Asn Tyr Ala Gln Lys Phe Gln
1               5                   10                  15

Gly

<210> SEQ ID NO 147
<211> LENGTH: 11
<212> TYPE: PRT
<213> ORGANISM: Artificial Sequence
<220> FEATURE:
<223> OTHER INFORMATION: Synthetic Construct

<400> SEQUENCE: 147

Glu Ala Ile Thr Thr Ile Gly Ala Met Asp Tyr
1               5                   10

<210> SEQ ID NO 148
<211> LENGTH: 120

```
<212> TYPE: PRT
<213> ORGANISM: Artificial Sequence
<220> FEATURE:
<223> OTHER INFORMATION: Synthetic Construct

<400> SEQUENCE: 148

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Asp Trp Val Arg Gln Ala Pro Gly Gln Gly Leu Glu Trp Met
        35                  40                  45

Gly Gln Ile Asn Pro Asn Asn Gly Leu Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Ile Gly Ala Met Asp Tyr Trp Gly Gln
            100                 105                 110

Gly Thr Leu Val Thr Val Ser Ser
        115                 120

<210> SEQ ID NO 149
<211> LENGTH: 214
<212> TYPE: PRT
<213> ORGANISM: Artificial Sequence
<220> FEATURE:
<223> OTHER INFORMATION: Synthetic Construct

<400> SEQUENCE: 149

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Leu Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Lys Asn Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ser Ser Asp Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 150
<211> LENGTH: 11
<212> TYPE: PRT
<213> ORGANISM: Artificial Sequence
<220> FEATURE:
<223> OTHER INFORMATION: Synthetic Construct

<400> SEQUENCE: 150

Arg Ala Ser Gln Ser Leu Ser Ser Tyr Leu Ala
1               5                   10

<210> SEQ ID NO 151
<211> LENGTH: 107
<212> TYPE: PRT
<213> ORGANISM: Artificial Sequence
<220> FEATURE:
<223> OTHER INFORMATION: Synthetic Construct

<400> SEQUENCE: 151

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Leu Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Lys Asn Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ser Ser Asp Pro Tyr
                85                  90                  95

Thr Phe Gly Gln Gly Thr Lys Val Glu Ile Lys
            100                 105

<210> SEQ ID NO 152
<211> LENGTH: 449
<212> TYPE: PRT
<213> ORGANISM: Artificial Sequence
<220> FEATURE:
<223> OTHER INFORMATION: Synthetic Construct

<400> SEQUENCE: 152

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Ile Asp Trp Val Arg Gln Ala Pro Gly Gln Gly Leu Glu Trp Met
        35                  40                  45

Gly Gln Ile Asn Pro Asn Asn Gly Leu Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gln Ile Thr Thr Val Gly Ala Met Asp Tyr Trp Gly Gln
            100                 105                 110
```

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 153
<211> LENGTH: 10
<212> TYPE: PRT
<213> ORGANISM: Artificial Sequence
<220> FEATURE:
<223> OTHER INFORMATION: Synthetic Construct

<400> SEQUENCE: 153

Gly Tyr Thr Phe Thr Ser Tyr Asn Ile Asp
1               5                   10

```
<210> SEQ ID NO 154
<211> LENGTH: 11
<212> TYPE: PRT
<213> ORGANISM: Artificial Sequence
<220> FEATURE:
<223> OTHER INFORMATION: Synthetic Construct

<400> SEQUENCE: 154

Glu Gln Ile Thr Thr Val Gly Ala Met Asp Tyr
1               5                   10

<210> SEQ ID NO 155
<211> LENGTH: 120
<212> TYPE: PRT
<213> ORGANISM: Artificial Sequence
<220> FEATURE:
<223> OTHER INFORMATION: Synthetic Construct

<400> SEQUENCE: 155

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Asn Ile Asp Trp Val Arg Gln Ala Pro Gly Gln Gly Leu Glu Trp Met
            35                  40                  45

Gly Gln Ile Asn Pro Asn Asn Gly Leu Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gln Ile Thr Thr Val Gly Ala Met Asp Tyr Trp Gly Gln
            100                 105                 110

Gly Thr Leu Val Thr Val Ser Ser
        115                 120

<210> SEQ ID NO 156
<211> LENGTH: 214
<212> TYPE: PRT
<213> ORGANISM: Artificial Sequence
<220> FEATURE:
<223> OTHER INFORMATION: Synthetic Construct

<400> SEQUENCE: 156

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val His Asn Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 157
<211> LENGTH: 11
<212> TYPE: PRT
<213> ORGANISM: Artificial Sequence
<220> FEATURE:
<223> OTHER INFORMATION: Synthetic Construct

<400> SEQUENCE: 157

Arg Ala Ser Gln Asn Val His Asn Tyr Leu Ala
1               5                   10

<210> SEQ ID NO 158
<211> LENGTH: 107
<212> TYPE: PRT
<213> ORGANISM: Artificial Sequence
<220> FEATURE:
<223> OTHER INFORMATION: Synthetic Construct

<400> SEQUENCE: 158

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val His Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Trp Pro Trp
                85                  90                  95

Thr Phe Gly Gln Gly Thr Lys Val Glu Ile Lys
            100                 105

<210> SEQ ID NO 159
<211> LENGTH: 449
<212> TYPE: PRT
<213> ORGANISM: Artificial Sequence
<220> FEATURE:
<223> OTHER INFORMATION: Synthetic Construct

<400> SEQUENCE: 159

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30
```

```
Asn Ile Asp Trp Val Arg Gln Ala Pro Gly Gln Gly Leu Glu Trp Met
         35                  40                  45

Gly Gly Ile Asn Pro Ile Phe Gly Leu Ala Phe Tyr Asn Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ala Ile Thr Thr Val Gly Ala Met Asp Pro Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 160
<211> LENGTH: 11
<212> TYPE: PRT
<213> ORGANISM: Artificial Sequence
<220> FEATURE:
<223> OTHER INFORMATION: Synthetic Construct

<400> SEQUENCE: 160

Glu Ala Ile Thr Thr Val Gly Ala Met Asp Pro
1               5                   10

<210> SEQ ID NO 161
<211> LENGTH: 120
<212> TYPE: PRT
<213> ORGANISM: Artificial Sequence
<220> FEATURE:
<223> OTHER INFORMATION: Synthetic Construct

<400> SEQUENCE: 161

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Asp Trp Val Arg Gln Ala Pro Gly Gln Gly Leu Glu Trp Met
        35                  40                  45

Gly Gly Ile Asn Pro Ile Phe Gly Leu Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Pro Trp Gly Gln
            100                 105                 110

Gly Thr Leu Val Thr Val Ser Ser
        115                 120

<210> SEQ ID NO 162
<211> LENGTH: 214
<212> TYPE: PRT
<213> ORGANISM: Artificial Sequence
<220> FEATURE:
<223> OTHER INFORMATION: Synthetic Construct

<400> SEQUENCE: 162

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Val His Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 163
<211> LENGTH: 107
<212> TYPE: PRT
<213> ORGANISM: Artificial Sequence
<220> FEATURE:
<223> OTHER INFORMATION: Synthetic Construct

<400> SEQUENCE: 163

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Val His Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Trp Ser Trp Pro Trp
                85                  90                  95

Thr Phe Gly Gln Gly Thr Lys Val Glu Ile Lys
            100                 105

<210> SEQ ID NO 164
<211> LENGTH: 449
<212> TYPE: PRT
<213> ORGANISM: Artificial Sequence
<220> FEATURE:
<223> OTHER INFORMATION: Synthetic Construct

<400> SEQUENCE: 164

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Asp Trp Val Arg Gln Ala Pro Gly Gln Gly Leu Glu Trp Met
        35                  40                  45

Gly Gly Ile Asn Pro Ile Phe Gly Thr Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Glu Ala Ile Thr Thr Val Gly Ala Met Asp His Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 165
<211> LENGTH: 17
<212> TYPE: PRT
<213> ORGANISM: Artificial Sequence
<220> FEATURE:
<223> OTHER INFORMATION: Synthetic Construct

<400> SEQUENCE: 165
```

```
Gly Ile Asn Pro Ile Phe Gly Thr Ala Phe Tyr Asn Gln Lys Phe Gln
1               5                   10                  15

Gly

<210> SEQ ID NO 166
<211> LENGTH: 120
<212> TYPE: PRT
<213> ORGANISM: Artificial Sequence
<220> FEATURE:
<223> OTHER INFORMATION: Synthetic Construct

<400> SEQUENCE: 166

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Ile Asp Trp Val Arg Gln Ala Pro Gly Gln Gly Leu Glu Trp Met
        35                  40                  45

Gly Gly Ile Asn Pro Ile Phe Gly Thr Ala Phe Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp His Trp Gly Gln
            100                 105                 110

Gly Thr Leu Val Thr Val Ser Ser
        115                 120

<210> SEQ ID NO 167
<211> LENGTH: 321
<212> TYPE: DNA
<213> ORGANISM: Artificial Sequence
<220> FEATURE:
<223> OTHER INFORMATION: Synthetic Construct

<400> SEQUENCE: 167
gaaattgtgc tgacccagag cccggcgacc ctgagcctga gcccgggcga acgcgcgacc      60
ctgagctgcc gcaccagcca gagcgttcat aactatctgg cgtggtatca gcagaaaccg     120
ggccaggcgc cgcgcctgct gatttatgat gcgagcaccc gtgcggatgg cattccggca     180
cgctttagcg gcagcggcag cggcaccgat tttaccctga ccattagcag cctggaaccg     240
gaagattttg cggtgtatta ttgccagcag ttttggagct ggccgtggac ctttggccag     300
ggcaccaaag tggaaattaa a                                                321

<210> SEQ ID NO 168
<211> LENGTH: 360
<212> TYPE: DNA
<213> ORGANISM: Artificial Sequence
<220> FEATURE:
<223> OTHER INFORMATION: Synthetic Construct

<400> SEQUENCE: 168
caggtgcagc tggtgcagag cggcgcggaa gtgaaaaaac cgggcagcag cgtgaaagtg      60
agctgcaaag cgagcggcta cctttagc agctataaca ttgattgggt gcgccaggcg     120
ccgggccagg gcctggaatg gatgggcggt attaacccga ttttggcac cgcattttat     180 aaccagaaat tcagggccg cgtgaccatt accgcggatg aaagcaccag caccgcgtat     240
```

| | |
|---|---|
| atggaactga gcagcctgcg cagcgaagat accgcggtgt attattgcgc acgcgaagcg | 300 |
| attaccaccg tgggcgcgat ggatcattgg ggccagggca ccctggtgac cgtgagcagc | 360 |

<210> SEQ ID NO 169
<211> LENGTH: 642
<212> TYPE: DNA
<213> ORGANISM: Artificial Sequence
<220> FEATURE:
<223> OTHER INFORMATION: Synthetic Construct

<400> SEQUENCE: 169

| | |
|---|---|
| gaaattgtgc tgacccagag cccggcgacc ctgagcctga gcccgggcga acgcgcgacc | 60 |
| ctgagctgcc gcaccagcca gagcgttcat aactatctgg cgtggtatca gcagaaaccg | 120 |
| ggccaggcgc cgcgcctgct gatttatgat gcgagcaccc gtgcggatgg cattccggca | 180 |
| cgctttagcg gcagcggcag cggcaccgat tttaccctga ccattagcag cctgaaaccg | 240 |
| gaagattttg cggtgtatta ttgccagcag ttttggagct ggccgtggac ctttggccag | 300 |
| ggcaccaaag tggaaattaa acgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga aaacacaaa gtctacgcct gcgaagtcac ccatcagggc | 600 |
| ctgagctcgc ccgtcacaaa gagcttcaac aggggagagt gt | 642 |

<210> SEQ ID NO 170
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 170

| | |
|---|---|
| caggtgcagc tggtgcagag cggcgcggaa gtgaaaaaac cgggcagcag cgtgaaagtg | 60 |
| agctgcaaag cgagcggcta tacctttagc agctataaca ttgattgggt gcgccaggcg | 120 |
| ccgggccagg gcctggaatg gatgggcggt attaacccga ttttggcac cgcattttat | 180 |
| aaccagaaat tcagggccg cgtgaccatt accgcggatg aaagcaccag caccgcgtat | 240 |
| atggaactga gcagcctgcg cagcgaagat accgcggtgt attattgcgc acgcgaagcg | 300 |
| attaccaccg tgggcgcgat ggatcattgg ggccagggca ccctggtgac cgtgagcagc | 360 |
| gcgtcgacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagaa agttgagccc | 660 |
| aaatcttgtg acaaaactca cacatgccca ccgtgcccag cacctgaagc cgctggggca | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |

```
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260 cagcaggga acgtcttctc atgctccgtg atgcatgagg ctctgcacaa ccactacacg   1320
cagaagagcc tctccctgtc ccccgga                                      1347
```

<210> SEQ ID NO 171
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa can be S or T
<220> FEATURE:
<221> NAME/KEY: MISC_FEATURE
<222> LOCATION: (6)..(6)
<223> OTHER INFORMATION: Xaa can be S or D

<400> SEQUENCE: 171

```
Gly Tyr Thr Phe Xaa Xaa Tyr Asn Ile Asp
1               5                   10
```

<210> SEQ ID NO 172
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be G or Q
<220> FEATURE:
<221> NAME/KEY: MISC_FEATURE
<222> LOCATION: (5)..(5)
<223> OTHER INFORMATION: Xaa can be I or N
<220> FEATURE:
<221> NAME/KEY: MISC_FEATURE
<222> LOCATION: (6)..(6)
<223> OTHER INFORMATION: Xaa can be F or N
<220> FEATURE:
<221> NAME/KEY: MISC_FEATURE
<222> LOCATION: (8)..(8)
<223> OTHER INFORMATION: Xaa can be T or L
<220> FEATURE:
<221> NAME/KEY: MISC_FEATURE
<222> LOCATION: (10)..(10)
<223> OTHER INFORMATION: Xaa can be F or N
<220> FEATURE:
<221> NAME/KEY: MISC_FEATURE
<222> LOCATION: (11)..(11)
<223> OTHER INFORMATION: Xaa can be Y or F
<220> FEATURE:
<221> NAME/KEY: MISC_FEATURE
<222> LOCATION: (12)..(12)
<223> OTHER INFORMATION: Xaa can be N or A

<400> SEQUENCE: 172

```
Xaa Ile Asn Pro Xaa Xaa Gly Xaa Ala Xaa Xaa Xaa Gln Lys Phe Gln
1               5                   10                  15

Gly
```

<210> SEQ ID NO 173

```
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa can be A or Q
<220> FEATURE:
<221> NAME/KEY: MISC_FEATURE
<222> LOCATION: (6)..(6)
<223> OTHER INFORMATION: Xaa can be V or I
<220> FEATURE:
<221> NAME/KEY: MISC_FEATURE
<222> LOCATION: (11)..(11)
<223> OTHER INFORMATION: Xaa can be H or Y

<400> SEQUENCE: 173

Glu Xaa Ile Thr Thr Xaa Gly Ala Met Asp Xaa
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa can be T or A
<220> FEATURE:
<221> NAME/KEY: MISC_FEATURE
<222> LOCATION: (5)..(5)
<223> OTHER INFORMATION: Xaa can be S or N
<220> FEATURE:
<221> NAME/KEY: MISC_FEATURE
<222> LOCATION: (6)..(6)
<223> OTHER INFORMATION: Xaa can be V or L
<220> FEATURE:
<221> NAME/KEY: MISC_FEATURE
<222> LOCATION: (7)..(7)
<223> OTHER INFORMATION: Xaa can be H or S
<220> FEATURE:
<221> NAME/KEY: MISC_FEATURE
<222> LOCATION: (8)..(8)
<223> OTHER INFORMATION: Xaa can be N or S

<400> SEQUENCE: 174

Arg Xaa Ser Gln Xaa Xaa Xaa Xaa Tyr Leu Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa can be S or K
<220> FEATURE:
<221> NAME/KEY: MISC_FEATURE
<222> LOCATION: (4)..(4)
<223> OTHER INFORMATION: Xaa can be T or N
<220> FEATURE:
<221> NAME/KEY: MISC_FEATURE
<222> LOCATION: (7)..(7)
<223> OTHER INFORMATION: Xaa can be D or T

<400> SEQUENCE: 175

Asp Ala Xaa Xaa Arg Ala Xaa
```

<210> SEQ ID NO 176
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa can be W or S
<220> FEATURE:
<221> NAME/KEY: MISC_FEATURE
<222> LOCATION: (5)..(5)
<223> OTHER INFORMATION: Xaa can be S or N
<220> FEATURE:
<221> NAME/KEY: MISC_FEATURE
<222> LOCATION: (6)..(6)
<223> OTHER INFORMATION: Xaa can be W or D
<220> FEATURE:
<221> NAME/KEY: MISC_FEATURE
<222> LOCATION: (8)..(8)
<223> OTHER INFORMATION: Xaa can be W or Y

<400> SEQUENCE: 176

Gln Gln Phe Xaa Xaa Xaa Pro Xaa Thr
1               5

<210> SEQ ID NO 177
<211> LENGTH: 120
<212> TYPE: PRT
<213> ORGANISM: Artificial Sequence
<220> FEATURE:
<223> OTHER INFORMATION: Synthetic Construct

<400> SEQUENCE: 177

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Asn Asn Gly Leu Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 178
<211> LENGTH: 107
<212> TYPE: PRT
<213> ORGANISM: Artificial Sequence
<220> FEATURE:
<223> OTHER INFORMATION: Synthetic Construct

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr

```
                20                  25                  30
Leu Ala Trp Tyr Gln Gln Lys Pro Gly Lys Ser Pro Lys Leu Leu Ile
            35                  40                  45

Tyr Asp Ala Lys Thr Leu Ala Asp Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Ser Asp Pro Tyr
                85                  90                  95

Thr Phe Gly Gln Gly Thr Lys Leu Glu Ile Lys
            100                 105
```

<210> SEQ ID NO 179
<211> LENGTH: 10
<212> TYPE: PRT
<213> ORGANISM: Artificial Sequence
<220> FEATURE:
<223> OTHER INFORMATION: Synthetic Construct

<400> SEQUENCE: 179

```
Gly Tyr Pro Phe Glu Gly Trp Tyr Ile His
1               5                   10
```

<210> SEQ ID NO 180
<211> LENGTH: 17
<212> TYPE: PRT
<213> ORGANISM: Artificial Sequence
<220> FEATURE:
<223> OTHER INFORMATION: Synthetic Construct

<400> SEQUENCE: 180

```
Trp Asn Asn Pro Arg Thr Gly Leu Thr Asn His Ala Gln Lys Phe Gln
1               5                   10                  15
Gly
```

<210> SEQ ID NO 181
<211> LENGTH: 10
<212> TYPE: PRT
<213> ORGANISM: Artificial Sequence
<220> FEATURE:
<223> OTHER INFORMATION: Synthetic Construct

<400> SEQUENCE: 181

```
Gly Val Gly Ala Asp Ala Ala Phe Asp Ile
1               5                   10
```

<210> SEQ ID NO 182
<211> LENGTH: 119
<212> TYPE: PRT
<213> ORGANISM: Artificial Sequence
<220> FEATURE:
<223> OTHER INFORMATION: Synthetic Construct

<400> SEQUENCE: 182

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Pro Phe Glu Gly Trp
            20                  25                  30

Tyr Ile His Trp Val Lys Gln Arg Pro Gly Gln Gly Leu Glu Trp Met
        35                  40                  45

Gly Trp Asn Asn Pro Arg Thr Gly Leu Thr Asn His Ala Gln Lys Phe
    50                  55                  60
```

```
Gln Gly Lys Val Thr Met Thr Arg Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Val Gly Ala Asp Ala Phe Asp Ile Trp Gly Gln Gly
            100                 105                 110

Thr Thr Leu Thr Val Ser Ser
            115
```

<210> SEQ ID NO 183
<211> LENGTH: 443
<212> TYPE: PRT
<213> ORGANISM: Artificial Sequence
<220> FEATURE:
<223> OTHER INFORMATION: Synthetic Construct

<400> SEQUENCE: 183

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Pro Phe Glu Gly Trp
            20                  25                  30

Tyr Ile His Trp Val Lys Gln Arg Pro Gly Gln Gly Leu Glu Trp Met
        35                  40                  45

Gly Trp Asn Asn Pro Arg Thr Gly Leu Thr Asn His Ala Gln Lys Phe
50                  55                  60

Gln Gly Lys Val Thr Met Thr Arg Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Val Gly Ala Asp Ala Phe Asp Ile Trp Gly Gln Gly
            100                 105                 110

Thr Thr Leu Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
        130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Ala Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
290                 295                 300
```

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Ile Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 184
<211> LENGTH: 16
<212> TYPE: PRT
<213> ORGANISM: Artificial Sequence
<220> FEATURE:
<223> OTHER INFORMATION: Synthetic Construct

<400> SEQUENCE: 184

Arg Ser Ser Gln Ser Leu Leu Trp Lys His Gly Tyr Asn Tyr Leu Asp
1               5                   10                  15

<210> SEQ ID NO 185
<211> LENGTH: 7
<212> TYPE: PRT
<213> ORGANISM: Artificial Sequence
<220> FEATURE:
<223> OTHER INFORMATION: Synthetic Construct

<400> SEQUENCE: 185

Leu Asp Arg Asn Arg Ala His
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic Construct

<400> SEQUENCE: 186

Met Gln Ser Phe Glu Thr Pro Ile Thr
1               5

<210> SEQ ID NO 187
<211> LENGTH: 112
<212> TYPE: PRT
<213> ORGANISM: Artificial Sequence
<220> FEATURE:
<223> OTHER INFORMATION: Synthetic Construct

<400> SEQUENCE: 187

Asp Ile Val Met Thr Gln Ser Pro Ser Ser Leu Ser Val Ser Ala Gly
1               5                   10                  15

```
Glu Lys Val Thr Met Ser Cys Arg Ser Ser Gln Ser Leu Leu Trp Lys
            20                  25                  30

His Gly Tyr Asn Tyr Leu Asp Trp Tyr Gln Gln Lys Pro Gly Gln Pro
        35                  40                  45

Pro Lys Leu Leu Ile Tyr Leu Asp Arg Asn Arg Ala His Gly Val Pro
 50                  55                  60

Asp Arg Phe Thr Gly Ser Gly Ser Gly Thr Asp Phe Thr Leu Thr Ile
 65                  70                  75                  80

Ser Ser Val Gln Ala Glu Asp Leu Ala Val Tyr Tyr Cys Met Gln Ser
                85                  90                  95

Phe Glu Thr Pro Ile Thr Phe Gly Gly Gly Thr Lys Leu Glu Ile Lys
            100                 105                 110
```

<210> SEQ ID NO 188
<211> LENGTH: 219
<212> TYPE: PRT
<213> ORGANISM: Artificial Sequence
<220> FEATURE:
<223> OTHER INFORMATION: Synthetic Construct

<400> SEQUENCE: 188

```
Asp Ile Val Met Thr Gln Ser Pro Ser Ser Leu Ser Val Ser Ala Gly
 1               5                  10                  15

Glu Lys Val Thr Met Ser Cys Arg Ser Ser Gln Ser Leu Leu Trp Lys
            20                  25                  30

His Gly Tyr Asn Tyr Leu Asp Trp Tyr Gln Gln Lys Pro Gly Gln Pro
        35                  40                  45

Pro Lys Leu Leu Ile Tyr Leu Asp Arg Asn Arg Ala His Gly Val Pro
 50                  55                  60

Asp Arg Phe Thr Gly Ser Gly Ser Gly Thr Asp Phe Thr Leu Thr Ile
 65                  70                  75                  80

Ser Ser Val Gln Ala Glu Asp Leu Ala Val Tyr Tyr Cys Met Gln Ser
                85                  90                  95

Phe Glu Thr Pro Ile Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
210                 215
```

<210> SEQ ID NO 189
<211> LENGTH: 119
<212> TYPE: PRT
<213> ORGANISM: Artificial Sequence
<220> FEATURE:
<223> OTHER INFORMATION: Synthetic Construct

<400> SEQUENCE: 189

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Pro Phe Glu Gly Trp
            20                  25                  30

Tyr Ile His Trp Val Lys Gln Arg Pro Gly Gln Gly Leu Glu Trp Met
        35                  40                  45

Gly Trp Asn Asn Pro Arg Thr Gly Leu Thr Asn His Ala Gln Lys Phe
    50                  55                  60

Gln Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Val Gly Ala Asp Ala Ala Phe Asp Ile Trp Gly Gln Gly
            100                 105                 110

Thr Thr Leu Thr Val Ser Ser
        115

<210> SEQ ID NO 190
<211> LENGTH: 443
<212> TYPE: PRT
<213> ORGANISM: Artificial Sequence
<220> FEATURE:
<223> OTHER INFORMATION: Synthetic Construct

<400> SEQUENCE: 190

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Pro Phe Glu Gly Trp
            20                  25                  30

Tyr Ile His Trp Val Lys Gln Arg Pro Gly Gln Gly Leu Glu Trp Met
        35                  40                  45

Gly Trp Asn Asn Pro Arg Thr Gly Leu Thr Asn His Ala Gln Lys Phe
    50                  55                  60

Gln Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Val Gly Ala Asp Ala Ala Phe Asp Ile Trp Gly Gln Gly
            100                 105                 110

Thr Thr Leu Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro

```
225                 230                 235                 240
Pro Lys Pro Lys Asp Val Leu Thr Ile Thr Leu Thr Pro Lys Val Thr
                245                 250                 255

Cys Val Val Ala Ile Ser Lys Asp Pro Glu Val Gln Phe Ser
            260                 265                 270

Trp Phe Val Asp Asp Val Glu Val His Thr Ala Gln Thr Gln Pro Arg
                275                 280                 285

Glu Glu Gln Phe Asn Ser Thr Phe Arg Ser Val Ser Glu Leu Pro Ile
            290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
                355                 360                 365

Phe Pro Glu Asp Ile Thr Val Glu Trp Gln Trp Asn Gly Gln Pro Ala
            370                 375                 380

Glu Asn Tyr Lys Asn Thr Gln Pro Ile Met Asp Thr Asp Gly Ser Tyr
385                 390                 395                 400

Phe Ile Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 191
<211> LENGTH: 112
<212> TYPE: PRT
<213> ORGANISM: Artificial Sequence
<220> FEATURE:
<223> OTHER INFORMATION: Synthetic Construct

<400> SEQUENCE: 191

Asp Ile Val Leu Thr Gln Ser Pro Ser Ser Leu Ser Val Ser Ala Gly
1               5                   10                  15

Glu Lys Val Thr Met Ser Cys Arg Ser Ser Gln Ser Leu Leu Trp Lys
            20                  25                  30

His Gly Tyr Asn Tyr Leu Asp Trp Tyr Gln Gln Lys Pro Gly Gln Pro
        35                  40                  45

Pro Lys Leu Leu Ile Tyr Leu Asp Arg Asn Arg Ala His Gly Val Pro
50                  55                  60

Asp Arg Phe Thr Gly Ser Gly Ser Gly Thr Asp Phe Thr Leu Thr Ile
65                  70                  75                  80

Ser Ser Val Gln Ala Glu Asp Leu Ala Val Tyr Tyr Cys Met Gln Ser
                85                  90                  95

Phe Glu Thr Pro Ile Thr Phe Gly Gly Gly Thr Lys Leu Glu Ile Lys
            100                 105                 110

<210> SEQ ID NO 192
<211> LENGTH: 219
<212> TYPE: PRT
<213> ORGANISM: Artificial Sequence
<220> FEATURE:
<223> OTHER INFORMATION: Synthetic Construct
```

<400> SEQUENCE: 192

```
Asp Ile Val Leu Thr Gln Ser Pro Ser Ser Leu Ser Val Ser Ala Gly
1               5                   10                  15

Glu Lys Val Thr Met Ser Cys Arg Ser Ser Gln Ser Leu Leu Trp Lys
            20                  25                  30

His Gly Tyr Asn Tyr Leu Asp Trp Tyr Gln Gln Lys Pro Gly Gln Pro
        35                  40                  45

Pro Lys Leu Leu Ile Tyr Leu Asp Arg Asn Arg Ala His Gly Val Pro
    50                  55                  60

Asp Arg Phe Thr Gly Ser Gly Ser Gly Thr Asp Phe Thr Leu Thr Ile
65                  70                  75                  80

Ser Ser Val Gln Ala Glu Asp Leu Ala Val Tyr Tyr Cys Met Gln Ser
                85                  90                  95

Phe Glu Thr Pro Ile Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 193
<211> LENGTH: 119
<212> TYPE: PRT
<213> ORGANISM: Artificial Sequence
<220> FEATURE:
<223> OTHER INFORMATION: Synthetic Construct

<400> SEQUENCE: 193

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Glu Gly Trp
            20                  25                  30

Tyr Ile His Trp Val Arg Gln Ala Pro Gly Gln Gly Leu Glu Trp Met
        35                  40                  45

Gly Trp Asn Asn Pro Arg Thr Gly Leu Thr Asn His Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Val Gly Ala Asp Ala Ala Phe Asp Ile Trp Gly Gln Gly
            100                 105                 110

Thr Met Val Thr Val Ser Ser
        115
```

<210> SEQ ID NO 194
<211> LENGTH: 448
<212> TYPE: PRT
<213> ORGANISM: Artificial Sequence
<220> FEATURE:
<223> OTHER INFORMATION: Synthetic Construct

<400> SEQUENCE: 194

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Glu Gly Trp
            20                  25                  30

Tyr Ile His Trp Val Arg Gln Ala Pro Gly Gln Gly Leu Glu Trp Met
        35                  40                  45

Gly Trp Asn Asn Pro Arg Thr Gly Leu Thr Asn His Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Val Gly Ala Asp Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 195
<211> LENGTH: 112
<212> TYPE: PRT
<213> ORGANISM: Artificial Sequence
<220> FEATURE:
<223> OTHER INFORMATION: Synthetic Construct

<400> SEQUENCE: 195

Glu Ile Val Leu Thr Gln Ser Pro Ala Thr Leu Ser Leu Ser Pro Gly
1               5                   10                  15

Glu Arg Ala Thr Leu Ser Cys Arg Ser Ser Gln Ser Leu Leu Trp Lys
            20                  25                  30

His Gly Tyr Asn Tyr Leu Asp Trp Tyr Gln Gln Lys Pro Gly Gln Ala
        35                  40                  45

Pro Arg Leu Leu Ile Tyr Leu Asp Arg Asn Arg Ala His Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Met Gln Ser
                85                  90                  95

Phe Glu Thr Pro Ile Thr Phe Gly Gln Gly Thr Lys Val Glu Ile Lys
            100                 105                 110

<210> SEQ ID NO 196
<211> LENGTH: 219
<212> TYPE: PRT
<213> ORGANISM: Artificial Sequence
<220> FEATURE:
<223> OTHER INFORMATION: Synthetic Construct

<400> SEQUENCE: 196

Glu Ile Val Leu Thr Gln Ser Pro Ala Thr Leu Ser Leu Ser Pro Gly
1               5                   10                  15

Glu Arg Ala Thr Leu Ser Cys Arg Ser Ser Gln Ser Leu Leu Trp Lys
            20                  25                  30

His Gly Tyr Asn Tyr Leu Asp Trp Tyr Gln Gln Lys Pro Gly Gln Ala
        35                  40                  45

Pro Arg Leu Leu Ile Tyr Leu Asp Arg Asn Arg Ala His Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Met Gln Ser
                85                  90                  95

Phe Glu Thr Pro Ile Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125
```

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 197
<211> LENGTH: 444
<212> TYPE: PRT
<213> ORGANISM: Artificial Sequence
<220> FEATURE:
<223> OTHER INFORMATION: Synthetic Construct

<400> SEQUENCE: 197

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Leu Thr Asn Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 198
<211> LENGTH: 443
<212> TYPE: PRT
<213> ORGANISM: Artificial Sequence
<220> FEATURE:
<223> OTHER INFORMATION: Synthetic Construct

<400> SEQUENCE: 198

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Leu Thr Asn Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                    325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
            435                 440

<210> SEQ ID NO 199
<211> LENGTH: 221
<212> TYPE: PRT
<213> ORGANISM: Artificial Sequence
<220> FEATURE:
<223> OTHER INFORMATION: Synthetic Construct

<400> SEQUENCE: 199

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Trp Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Tyr Trp Thr Ser Tyr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro His Thr Phe Gly Gly Gly Thr Lys Val Glu Ile
            100                 105                 110

```
Lys Arg Gly Thr Val Ala Ala Pro Ser Val Phe Ile Phe Pro Pro Ser
            115                 120                 125

Asp Glu Gln Leu Lys Ser Gly Thr Ala Ser Val Val Cys Leu Leu Asn
130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
            210                 215                 220

<210> SEQ ID NO 200
<211> LENGTH: 117
<212> TYPE: PRT
<213> ORGANISM: Artificial Sequence
<220> FEATURE:
<223> OTHER INFORMATION: Synthetic Construct

<400> SEQUENCE: 200

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Leu Thr Asn Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Thr Gly Thr Phe Ala Tyr Trp Gly Gln Gly Thr Leu
            100                 105                 110

Val Thr Val Ser Ser
        115

<210> SEQ ID NO 201
<211> LENGTH: 117
<212> TYPE: PRT
<213> ORGANISM: Artificial Sequence
<220> FEATURE:
<223> OTHER INFORMATION: Synthetic Construct

<400> SEQUENCE: 201

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Trp Pro Gly Ser Ser Leu Thr Asn Tyr Asn Glu Lys Phe
    50                  55                  60

Lys Asn Arg Val Thr Met Thr Arg Asp Thr Ser Thr Ser Thr Val Tyr
```

```
                65                  70                  75                  80
Met Glu Leu Ser Ser Leu Arg Ser Glu Asp Thr Ala Val Tyr Tyr Cys
                    85                  90                  95

Ala Arg Leu Leu Thr Gly Thr Phe Ala Tyr Trp Gly Gln Gly Thr Leu
                100                 105                 110

Val Thr Val Ser Ser
        115

<210> SEQ ID NO 202
<211> LENGTH: 113
<212> TYPE: PRT
<213> ORGANISM: Artificial Sequence
<220> FEATURE:
<223> OTHER INFORMATION: Synthetic Construct

<400> SEQUENCE: 202

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Trp Asp Ser
                20                  25                  30

Gly Asn Gln Lys Asn Phe Leu Thr Trp Tyr Gln Gln Lys Pro Gly Gln
            35                  40                  45

Pro Pro Lys Leu Leu Ile Tyr Trp Thr Ser Tyr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro His Thr Phe Gly Gly Gly Thr Lys Val Glu Ile
                100                 105                 110

Lys

<210> SEQ ID NO 203
<211> LENGTH: 432
<212> TYPE: PRT
<213> ORGANISM: Artificial Sequence
<220> FEATURE:
<223> OTHER INFORMATION: Synthetic Construct

<400> SEQUENCE: 203

Gln Val Gln Leu Val Glu Ser Gly Gly Gly Trp Gln Pro Gly Arg Ser
1               5                   10                  15

Leu Arg Leu Asp Cys Lys Ala Ser Gly Ile Thr Phe Ser Asn Ser Gly
                20                  25                  30

Met His Trp Val Arg Gln Ala Pro Gly Lys Gly Leu Glu Trp Val Ala
            35                  40                  45

Val Arg Trp Tyr Asp Gly Ser Lys Arg Tyr Tyr Ala Asp Ser Val Lys
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Thr Asn Asp Asp Tyr Trp Gly Gln Gly Thr Leu Val Thr Val Ser Ser
                100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Asp Tyr Phe
```

```
                130                 135                 140
Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Thr Tyr Thr
            180                 185                 190

Cys Asn Val Asp His Lys Pro Ser Asn Thr Lys Val Asp Arg Val Glu
        195                 200                 205

Ser Tyr Gly Pro Pro Cys Pro Pro Cys Pro Ala Pro Glu Phe Leu Gly
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Ser Gln Glu
                245                 250                 255

Asp Pro Glu Val Gln Phe Asn Trp Tyr Val Asp Gly Val Glu Val His
                260                 265                 270

Asn Ala Thr Lys Pro Arg Glu Glu Gln Phe Asn Ser Thr Tyr Arg Val
            275                 280                 285

Val Ser Val Leu Thr Val Leu His Gln Asp Trp Leu Asn Gly Lys Glu
        290                 295                 300

Tyr Lys Cys Lys Val Ser Asn Lys Gly Leu Pro Ser Ser Ile Glu Lys
305                 310                 315                 320

Thr Ile Ser Lys Ala Gly Gln Pro Arg Glu Pro Gln Val Tyr Thr Leu
                325                 330                 335

Pro Pro Ser Gln Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Lys Asn Tyr Lys Thr Thr Pro Pro Val Leu Asp
    370                 375                 380

Ser Asp Gly Ser Phe Phe Leu Tyr Ser Arg Leu Thr Val Asp Lys Ser
385                 390                 395                 400

Arg Trp Gln Glu Gly Asn Val Phe Ser Cys Ser Val Met His Glu Ala
                405                 410                 415

Leu His Asn His Tyr Thr Gln Lys Ser Leu Ser Leu Ser Leu Gly Lys
            420                 425                 430

<210> SEQ ID NO 204
<211> LENGTH: 208
<212> TYPE: PRT
<213> ORGANISM: Artificial Sequence
<220> FEATURE:
<223> OTHER INFORMATION: Synthetic Construct

<400> SEQUENCE: 204

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Pro Gly Gln Ala Pro Arg Leu Leu Ile Tyr
            35                  40                  45

Asp Ala Ser Asn Arg Ala Thr Gly Ile Pro Ala Arg Phe Ser Gly Ser
        50                  55                  60

Gly Ser Gly Thr Asp Phe Thr Leu Thr Ile Ser Ser Leu Glu Pro Glu
```

```
                65                  70                  75                  80
Asp Phe Ala Val Tyr Tyr Cys Gln Gln Ser Ser Asn Trp Pro Arg Thr
                    85                  90                  95

Phe Gly Gln Gly Thr Lys Val Glu Ile Arg Thr Val Ala Ala Pro Ser
                100                 105                 110

Val Phe Ile Phe Pro Pro Ser Asp Glu Gln Leu Ser Gly Thr Ala Ser
            115                 120                 125

Val Val Cys Leu Leu Asn Asn Phe Tyr Pro Arg Glu Ala Val Gln Trp
        130                 135                 140

Lys Val Asp Asn Ala Leu Gln Ser Gly Asn Ser Gln Glu Ser Val Thr
145                 150                 155                 160

Glu Gln Asp Ser Asp Ser Thr Tyr Ser Leu Ser Ser Thr Leu Thr Leu
                165                 170                 175

Ser Lys Ala Asp Tyr Glu Lys His Lys Val Tyr Ala Cys Glu Val Thr
            180                 185                 190

His Gln Gly Leu Ser Ser Pro Val Thr Ser Phe Asn Arg Gly Glu Cys
        195                 200                 205

<210> SEQ ID NO 205
<211> LENGTH: 447
<212> TYPE: PRT
<213> ORGANISM: Artificial Sequence
<220> FEATURE:
<223> OTHER INFORMATION: Synthetic Construct

<400> SEQUENCE: 205

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
```

```
                225                 230                 235                 240
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 206
<211> LENGTH: 218
<212> TYPE: PRT
<213> ORGANISM: Artificial Sequence
<220> FEATURE:
<223> OTHER INFORMATION: Synthetic Construct

<400> SEQUENCE: 206

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
```

```
145                 150                 155                 160
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 207
<211> LENGTH: 432
<212> TYPE: PRT
<213> ORGANISM: Artificial Sequence
<220> FEATURE:
<223> OTHER INFORMATION: Synthetic Construct

<400> SEQUENCE: 207

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr Trp Glu Pro Lys Ser Cys Asp
        195                 200                 205

Lys Thr His Thr Cys Pro Pro Cys Pro Ala Pro Glu Leu Leu Gly Gly
    210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser His Glu Asp
                245                 250                 255

Pro Glu Val Lys Phe Asn Trp Tyr Val Asp Gly Val Glu Val His Asn
            260                 265                 270

Ala Lys Thr Lys Pro Arg Glu Glu Gln Tyr Asn Ser Thr Tyr Arg Trp
        275                 280                 285

Ser Val Leu Thr Val Leu His Gln Asp Trp Leu Asn Gly Lys Glu Tyr
```

```
                    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

<210> SEQ ID NO 208
<211> LENGTH: 118
<212> TYPE: PRT
<213> ORGANISM: Artificial Sequence
<220> FEATURE:
<223> OTHER INFORMATION: Synthetic Construct

<400> SEQUENCE: 208

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 209
<211> LENGTH: 108
<212> TYPE: PRT
<213> ORGANISM: Artificial Sequence
<220> FEATURE:
<223> OTHER INFORMATION: Synthetic Construct

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg
                100                 105
```

<210> SEQ ID NO 210
<211> LENGTH: 7
<212> TYPE: PRT
<213> ORGANISM: Artificial Sequence
<220> FEATURE:
<223> OTHER INFORMATION: Synthetic Construct

<400> SEQUENCE: 210

```
Gly Tyr Thr Phe Thr Ser Tyr
 1               5
```

<210> SEQ ID NO 211
<211> LENGTH: 10
<212> TYPE: PRT
<213> ORGANISM: Artificial Sequence
<220> FEATURE:
<223> OTHER INFORMATION: Synthetic Construct

<400> SEQUENCE: 211

```
Gly Tyr Thr Phe Thr Ser Tyr Trp Ile Asn
 1               5                  10
```

<210> SEQ ID NO 212
<211> LENGTH: 5
<212> TYPE: PRT
<213> ORGANISM: Artificial Sequence
<220> FEATURE:
<223> OTHER INFORMATION: Synthetic Construct

<400> SEQUENCE: 212

```
Ser Tyr Trp Ile Asn
 1               5
```

<210> SEQ ID NO 213
<211> LENGTH: 8
<212> TYPE: PRT
<213> ORGANISM: Artificial Sequence
<220> FEATURE:
<223> OTHER INFORMATION: Synthetic Construct

<400> SEQUENCE: 213

```
Asn Ile Tyr Pro Gly Ser Ser Leu
 1               5
```

<210> SEQ ID NO 214
<211> LENGTH: 16
<212> TYPE: PRT
<213> ORGANISM: Artificial Sequence
<220> FEATURE:
<223> OTHER INFORMATION: Synthetic Construct

<400> SEQUENCE: 214

```
Asn Ile Tyr Pro Gly Ser Ser Leu Thr Asn Tyr Asn Glu Lys Phe Lys
 1               5                  10                  15
```

<210> SEQ ID NO 215

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 215

Leu Ser Thr Gly Thr Phe Ala Tyr
1               5

<210> SEQ ID NO 216
<211> LENGTH: 17
<212> TYPE: PRT
<213> ORGANISM: Artificial Sequence
<220> FEATURE:
<223> OTHER INFORMATION: Synthetic Construct

<400> SEQUENCE: 216

Lys Ser Ser Gln Ser Leu Trp Asp Ser Gly Asn Gln Lys Asn Phe Leu
1               5                   10                  15

Thr

<210> SEQ ID NO 217
<211> LENGTH: 7
<212> TYPE: PRT
<213> ORGANISM: Artificial Sequence
<220> FEATURE:
<223> OTHER INFORMATION: Synthetic Construct

<400> SEQUENCE: 217

Trp Thr Ser Tyr Arg Glu Ser
1               5

<210> SEQ ID NO 218
<211> LENGTH: 9
<212> TYPE: PRT
<213> ORGANISM: Artificial Sequence
<220> FEATURE:
<223> OTHER INFORMATION: Synthetic Construct

<400> SEQUENCE: 218

Gln Asn Asp Tyr Phe Tyr Pro His Thr
1               5

<210> SEQ ID NO 219
<211> LENGTH: 117
<212> TYPE: PRT
<213> ORGANISM: Artificial Sequence
<220> FEATURE:
<223> OTHER INFORMATION: Synthetic Construct

<400> SEQUENCE: 219

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Asn Trp Val Arg Gln Ala Pro Gly Gln Gly Leu Glu Trp Met
            35                  40                  45

Gly Asn Ile Tyr Pro Gly Ser Ser Leu Thr Asn Tyr Asn Glu Lys Phe
        50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Leu Ser Thr Gly Thr Phe Ala Tyr Trp Gly Gln Gly Thr Leu
                100                 105                 110

Val Thr Val Ser Ser
            115

<210> SEQ ID NO 220
<211> LENGTH: 113
<212> TYPE: PRT
<213> ORGANISM: Artificial Sequence
<220> FEATURE:
<223> OTHER INFORMATION: Synthetic Construct

<400> SEQUENCE: 220

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Trp Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Tyr Trp Thr Ser Tyr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro His Thr Phe Gly Gly Gly Thr Lys Val Glu Ile
            100                 105                 110

Lys

<210> SEQ ID NO 221
<211> LENGTH: 290
<212> TYPE: PRT
<213> ORGANISM: Artificial Sequence
<220> FEATURE:
<223> OTHER INFORMATION: Synthetic Construct

<400> SEQUENCE: 221

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

-continued

```
Pro Lys Ala Glu Val Ile Trp Thr Ser Ser Asp His Gln Val Leu Ser
            165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
        195                 200                 205
Cys Thr Phe Arg Arg Leu Asp Pro Glu Glu Asn His Thr Ala Glu Leu
    210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
            245                 250                 255
Phe Ile Phe Arg Leu Arg Lys Gly Arg Met Met Asp Val Lys Lys Cys
            260                 265                 270
Gly Ile Gln Asp Thr Asn Ser Lys Lys Gln Ser Asp Thr His Leu Glu
        275                 280                 285
Glu Thr
    290
```